US012098352B2

(12) United States Patent
Nawroth et al.

(10) Patent No.: US 12,098,352 B2
(45) Date of Patent: Sep. 24, 2024

(54) STEM CELL-BASED LUNG-ON-CHIP MODELS

(71) Applicant: EMULATE, INC., Boston, MA (US)

(72) Inventors: Janna Nawroth, Boston, MA (US); Riccardo Barrile, Boston, MA (US); David Conegliano, Boston, MA (US); Remi Villenave, Boston, MA (US); Carolina Lucchesi, Westwood, MA (US); Justin Nguyen, Medford, MA (US); Antonio Varone, West Roxbury, MA (US); Catherine Karalis, Brookline, MA (US); Geraldine Hamilton, Boston, MA (US)

(73) Assignee: EMULATE, INC., Boston, MA (US)

( * ) Notice: Subject to any disclaimer, the term of this patent is extended or adjusted under 35 U.S.C. 154(b) by 1084 days.

(21) Appl. No.: 16/983,850

(22) Filed: Aug. 3, 2020

(65) Prior Publication Data
US 2021/0062129 A1 Mar. 4, 2021

Related U.S. Application Data

(63) Continuation of application No. PCT/US2019/016680, filed on Feb. 5, 2019.
(Continued)

(51) Int. Cl.
*C12M 3/06* (2006.01)
*B01L 3/00* (2006.01)
(Continued)

(52) U.S. Cl.
CPC ........... *C12M 23/16* (2013.01); *B01L 3/5027* (2013.01); *C12N 5/0688* (2013.01);
(Continued)

(58) Field of Classification Search
CPC .... C12M 23/16; C12N 5/0688; C12N 5/0696; C12N 2501/115; C12N 2501/117;
(Continued)

(56) References Cited

U.S. PATENT DOCUMENTS

| 8,647,861 B2 | 2/2014 | Ingber et al. ............. 435/289.1 |
| 2014/0105870 A1* | 4/2014 | Niklason .............. C12N 5/0688 |
| | | 435/325 |

(Continued)

FOREIGN PATENT DOCUMENTS

| WO | WO2010009307 | 7/2009 |
| WO | WO2012118799 | 9/2012 |

(Continued)

OTHER PUBLICATIONS

Bajaj, "Advances and Challenges in Recapitulating Human Pulmonary Systems: At the Cusp of Biology and Materials", 2016, American Chemical Society, 2, 473-488. (Year: 2016).*

(Continued)

*Primary Examiner* — Christine T Mui
*Assistant Examiner* — Kathryn Elizabeth Limbaugh
(74) *Attorney, Agent, or Firm* — Medlen & Carroll, LLP

(57) ABSTRACT

An in vitro microfluidic "organ-on-chip" device is described herein that mimics the structure and at least one function of specific areas of the epithelial system in vivo. In particular, a stem cell-based Lung-on-Chip is described. This in vitro microfluidic system can be used for modeling differentiation of cells on-chip into lung cells, e.g., a lung (Lung-On-Chip), bronchial (Airway-On-Chip; small-Airway-On-Chip), alveolar sac (Alveolar-On-Chip), etc., for use in modeling disease states of derived tissue, i.e. as healthy, pre-disease and diseased tissues. Additionally, stem cells under differentiation protocols for deriving (producing) differentiated lung cells off-chips may be seeded onto microfluidic devices (Continued)

at any desired point during the in vitro differentiation pathway for further differentiation on-chip or placed on-chip before, during or after terminal differentiation.

23 Claims, 51 Drawing Sheets

Specification includes a Sequence Listing.

Related U.S. Application Data

(60) Provisional application No. 62/626,427, filed on Feb. 5, 2018.

(51) Int. Cl.
  *C12N 5/071* (2010.01)
  *C12N 5/074* (2010.01)

(52) U.S. Cl.
  CPC ...... *C12N 5/0696* (2013.01); *C12N 2501/115* (2013.01); *C12N 2501/117* (2013.01); *C12N 2501/119* (2013.01); *C12N 2501/155* (2013.01); *C12N 2501/41* (2013.01); *C12N 2502/1323* (2013.01); *C12N 2502/27* (2013.01); *C12N 2503/04* (2013.01); *C12N 2506/02* (2013.01); *C12N 2513/00* (2013.01); *G01N 2800/12* (2013.01)

(58) Field of Classification Search
  CPC ........ C12N 2501/119; C12N 2501/155; C12N 2501/41; C12N 2502/1323; C12N 2503/04; C12N 2506/02; C12N 2513/00; B01L 3/5027; G01N 2800/12
  See application file for complete search history.

(56) References Cited

U.S. PATENT DOCUMENTS

2014/0342445 A1* 11/2014 Ingber .................... C12M 23/16
                                                                  435/294.1
2016/0243738 A1   8/2016 Katrycz et al.
2017/0285003 A1  10/2017 Hamilton et al.

FOREIGN PATENT DOCUMENTS

| WO | WO2013086486 | 6/2013 |
|----|---|---|
| WO | WO2013086502 | 6/2013 |
| WO | WO2015138032 | 9/2015 |
| WO | WO2015138034 | 9/2015 |
| WO | WO 2017173066 | 10/2017 |
| WO | WO 2019/060783 | 3/2019 |

OTHER PUBLICATIONS

Agustí, et al., "Personalized Respiratory Medicine: Exploring the Horizon, Addressing the Issues. Summary of a Brn-Ajrccm Workshop Held in Barcelona on Jun. 12, 2014." *Am J Respir Crit Care Med*, 191(4):391-401 (2015).
Ahmadi, et al., "Phenotypic Profiling of CFTR Modulators in Patient-Derived Respiratory Epithelia." *NPJ Genom Med*, 2:12 (2017).
Alford and Rannels, "Extracellular Matrix Fibronectin Alters Connexin43 Expression by Alveolar Epithelial Cells." *Am J Physiol Lung Cell Mol Physiol*, 280(4):L680-688 (2001).
Alvarez, et al., "Pulmonary Infectious Diseases in Patients with Primary Immunodeficiency and Those Treated with Biologic Immunomodulating Agents." *Curr Opin Pulm Med*, 17(3):172-179 (2011).
Andreeva, et al., "Regulation of Surfactant Secretion in Alveolar Type IICells." *Am J Physiol Lung Cell Mol Physiol*, 293(2):L259-271 (2007).
Arold, et al., "Variable Stretch Pattern Enhances Surfactant Secretion in Alveolar Type II Cells in Culture." *Am J Physiol Lung Cell Mol Physiol*, 296(4):L574-581 (2009).
Ask and Kolb, "Drug Development for Chronic Lung Disease—Mission Impossible?" *Respirology*, 20(1):13-14 (2015).
Bachofen, et al., "Relations among Alveolar Surface Tension, Surface Area, Volume, and Recoil Pressure." *J Appl Physiol (1985)*, 62(5):1878-1887 (1987).
Balestrini and Niklason, "Extracellular Matrix as a Driver for Lung Regeneration." *Ann Biomed Eng*, 43(3):568-576 (2015) Epub 2014.
Balkissoon, et al., "Chronic Obstructive Pulmonary Disease: A Concise Review." *Med Clin North Am*, 95(6):1125-1141 (2011).
Barkal, et al., "Microbial Volatile Communication in Human Organotypic Lung Models." *Nat Commun*, 8(1):1770 (2017).
Barkauskas, et al., "Type 2 Alveolar Cells Are Stem Cells in Adult Lung." *J Clin Invest*, 123(7):3025-3036 (2013).
Barkauskas, et al., "Lung Organoids: Current Uses and Future Promise." *Development*, 144(6):986-997 (2017).
Barnes, et al., "Chronic Obstructive Pulmonary Disease: Molecular and Cellular Mechanisms." *Eur Respir J*, 22(4):672-688 (2003).
Barrios. "Animal Models of Lung Disease". In Zander D.S. (Ed.), *Molecular Pathology of Lung Diseases*. New York, NY: Springer. pp. 144-149 (2008).
Bartlett, et al., "Mouse Models of Rhinovirus-Induced Disease and Exacerbation of Allergic Airway Inflammation." *Nat Med*, 14(2):199-204 (2008).
Bates, et al., "Recovery of Rat Type II Cell Surfactant Components During Primary Cell Culture." *Am J Physiol Lung Cell Mol Physiol*, 282(2):L267-276 (2002).
Bates, et al., "Animal Models of Asthma." *Am J Physiol Lung Cell Mol Physiol*, 297(3):L401-410 (2009).
Baudoin, et al., "Development of a Renal Microchip for in Vitro Distal Tubule Models." *Biotechnol Prog*, 23(5):1245-1253 (2007).
Bayram, et al., "Comparison of Ciliary Activity and Inflammatory Mediator Release from Bronchial Epithelial Cells of Nonatopic Nonasthmatic Subjects and Atopic Asthmatic Patients and the Effect of Diesel Exhaust Particles in Vitro." *J Allergy Clin Immunol*, 102(5):771-782 (1998).
Bedekar, et al., "Design Software for Application-Specific Microfluidic Devices." *Clin Chem*, 53(11):2023-2026 (2007).
Beebe, et al., "Functional Hydrogel Structures for Autonomous Flow Control inside Microfluidic Channels." *Nature*, 404(6778):588-590 (2000).
Beers and Moodley, "When Is an Alveolar Type 2 Cell an Alveolar Type 2 Cell? A Conundrum for Lung Stem Cell Biology and Regenerative Medicine." *Am J Respir Cell Mol Biol*, 57(1):18-27 (2017).
Bella and Rossmann, "Review: Rhinoviruses and Their iCAM Receptors." *J Struct Biol*, 128(1):69-74 (1999).
Bellin, et al., "Induced Pluripotent Stem Cells: The New Patient?". *Nat Rev Mol Cell Biol*, 13(11):713-726 (2012).
Benam, et al., "Matched-Comparative Modeling of Normal and Diseased Human Airway Responses Using a Microengineered Breathing Lung Chip." *Cell Syst*, 3(5):456-466 e454 (2016A).
Benam, et al., "Small Airway-on-a-Chip Enables Analysis of Human Lung Inflammation and Drug Responses in Vitro." *Nat Methods*, 13(2):151-157 (2016B).
Ben-Yehudah, et al., "Nicotine Exposure During Differentiation Causes Inhibition of N-Myc Expression. " *Respir Res*, 14(1):119 (2013).
Bhatia, et al., "Controlling Cell Interactions by Micropatterning in Co-Cultures: Hepatocytes and 3T3 Fibroblasts." *J Biomed Mater Res*, 34(2):189-199 (1997).
Bhatia, et al., "Effect of Cell-Cell Interactions in Preservation of Cellular Phenotype: Cocultivation of Hepatocytes and Nonparenchymal Cells." *Faseb J*, 13(14):1883-1900 (1999).
Bhatia and Ingber, "Microfluidic Organs-on-Chips." *Nat Biotechnol*, 32(8):760-772 (2014).

(56) References Cited

OTHER PUBLICATIONS

Bhavnani, et al., "Pharmacological and Patient-Specific Response Determinants in Patients with Hospital-Acquired Pneumonia Treated with Tigecycline." *Antimicrob Agents Chemother*, 56(2):1065-1072 (2012).
Birukov, "Cyclic Stretch, Reactive Oxygen Species, and Vascular Remodeling." *Antioxid Redox Signal*, 11(7):1651-1667 (2009).
Bischel, et al., "A Practical Method for Patterning Lumens through ECM Hydrogels Via Viscous Finger Patterning." *J Lab Autom*, 17(2):96-103 (2012).
Blume, et al., "Cellular crosstalk between airway epithelial and endothelial cells regulates barrier functions during exposure to double-stranded RNA." *Immunity, Inflamm. Dis.* 5, 45-56 (2017).
Boei, et al., "Xenobiotic Metabolism in Differentiated Human Bronchial Epithelial Cells." *Arch Toxicol*, 91(5):2093-2105 (2017).
Boers, et al., "No. and Proliferation of Clara Cells in Normal Human Airway Epithelium." *Am J Respir Crit Care Med*, 159(5 Pt 1):1585-1591 (1999).
Borenstein, et al., "Microfabrication Technology for Vascularized Tissue Engineering." *Biomedical Microdevices*, 4(3):167-175 (2002).
Borghardt, et al., "Pharmacometric Models for Characterizing the Pharmacokinetics of Orally Inhaled Drugs." *Aaps J*, 17(4):853-870 (2015).
Bottaro, et al., "Molecular Signaling in Bioengineered Tissue Microenvironments." *Ann N Y Acad Sci*, 961:143-153 (2002).
Bourbon, et al., "Control Mechanisms of Lung Alveolar Development and Their Disorders in Bronchopulmonary Dysplasia." *Pediatr Res*, 57(5 Pt 2):38R-46R (2005).
Bryant and Mostov, "From Cells to Organs: Building Polarized Tissue." *Nat Rev Mol Cell Biol*, 9(11):887-901 (2008).
Burgess, et al., "The Extracellular Matrix—the under-Recognized Element in Lung Disease?". *J Pathol*, 240(4):397-409 (2016).
Butler, et al., "Rapid Expansion of Human Epithelial Stem Cells Suitable for Airway Tissue Engineering." *Am J Respir Crit Care Med*, 194(2):156-168 (2016).
Byrd and Prince, "Animal Models of Respiratory Syncytial Virus Infection." *Clin Infect Dis*, 25(6):1363-1368 (1997).
Cai, et al., "Directed Differentiation of Human Embryonic Stem Cells into Functional Hepatic Cells." *Hepatology*, 45(5):1229-1239 (2007).
Canning and Wright, "Animal Models of Asthma and Chronic Obstructive Pulmonary Disease." *Pulm Pharmacol Ther*, 21(5):695 (2008).
Capulli, et al., "Approaching the in Vitro Clinical Trial: Engineering Organs on Chips." *Lab Chip*, 14(17):3181-3186 (2014).
Chen, et al., "A Three-Dimensional Model of Human Lung Development and Disease from Pluripotent Stem Cells." *Nat Cell Biol*, 19(5):542-549 (2017).
Chiu and Openshaw, "Antiviral B Cell and T Cell Immunity in the Lungs." *Nat Immunol*, 16(1):18-26 (2015).
Christoffersson, et al., "Developing Organ-on-a-Chip Concepts Using Bio-Mechatronic Design Methodology." *Biofabrication*, 9(2):025023 (2017).
Clark, et al., "Fibronectin Mediates Adherence of Rat Alveolar Type II Epithelial Cells Via the Fibroblastic Cell-Attachment Domain." *J Clin Invest*, 77(6):1831-1840 (1986).
Clevers, "Modeling Development and Disease with Organoids." *Cell*, 165(7):1586-1597 (2016).
Click-iT™ Plus TUNEL Assay, Thermo Fisher Scientific Inc., Nov. 6, 2017.
Coultas, et al., "The Epidemiology of Interstitial Lung Diseases." *Am J Respir Crit Care Med*, 150(4):967-972 (1994).
Crosby and Waters, "Epithelial Repair Mechanisms in the Lung." *Am J Physiol Lung Cell Mol Physiol*, 298(6):L715-731 (2010).
Crystal, et al., "Airway Epithelial Cells: Current Concepts and Challenges." *Proc Am Thorac Soc*, 5(7):772-777 (2008).
Cutting. "Cystic Fibrosis Genetics: From Molecular Understanding to Clinical Application." *Nat Rev Genet*, 16(1):45-56 (2015).

D'Amour, et al., "Production of Pancreatic Hormone-Expressing Endocrine Cells from Human Embryonic Stem Cells." *Nat Biotechnol*, 24(11):1392-1401 (2006).
Davies, et al., "Influence of Hemodynamic Forces on Vascular Endothelial Function. In Vitro Studies of Shear Stress and Pinocytosis in Bovine Aortic Cells." *J Clin Invest*, 73(4):1121-1129 (1984).
Davies, "Flow-Mediated Endothelial Mechanotransduction." *Physiol Rev*, 75(3):519-560 (1995).
Daw and Finkelstein, "Lab on a Chip." *Nature*, 442(7101):367-367 (2006).
De Boeck, et al., "CFTR Biomarkers: Time for Promotion to Surrogate End-Point." *Eur Respir J*, 41(1):203-216 (2013).
Dekali, et al., "Assessment of an in Vitro Model of Pulmonary Barrier to Study the Translocation of Nanoparticles." *Toxicol Rep*, 1:157-171 (2014).
Dekkers, et al., "A Functional CFTR Assay Using Primary Cystic Fibrosis Intestinal Organoids." *Nat Med*, 19(7):939-945 (2013).
Dekkers, et al., "Characterizing Responses to CFTR-Modulating Drugs Using Rectal Organoids Derived from Subjects with Cystic Fibrosis." *Sci Transl Med*, 8(344):344ra384 (2016).
DeQuach, et al., "Simple and High Yielding Method for Preparing Tissue Specific Extracellular Matrix Coatings for Cell Culture." *PLoS One*, 5(9):e13039 (2010).
Diez, et al., "Network Analysis in the Investigation of Chronic Respiratory Diseases. From Basics to Application." *Am J Respir Crit Care Med*, 190(9):981-988 (2014).
Dobbs, "Isolation and Culture of Alveolar Type Ii Cells." *Am J Physiol*, 258(4 Pt 1):L134-147 (1990).
Doeing and Solway, "Airway Smooth Muscle in the Pathophysiology and Treatment of Asthma." *J Appl Physiol (1985)*, 114(7):834-843 (2013).
Douville, et al., "Combination of Fluid and Solid Mechanical Stresses Contribute to Cell Death and Detachment in a Microfluidic Alveolar Model." *Lab Chip*, 11(4):609-619 (2011).
Dreyfuss and Saumon, "Ventilator-Induced Lung Injury: Lessons from Experimental Studies." *Am J Respir Crit Care Med*, 157(1):294-323 (1998).
Duffy, et al., "Rapid Prototyping of Microfluidic Systems in Poly(Dimethylsiloxane)." *Anal Chem*, 70(23):4974-4984 (1998).
Dunsmore and Rannels, "Extracellular Matrix Biology in the Lung." *Am J Physiol*, 270(1 Pt 1):L3-27 (1996).
Dvorak, et al., "Do Airway Epithelium Air-Liquid Cultures Represent the in Vivo Airway Epithelium Transcriptome?". *Am J Respir Cell Mol Biol*, 44(4):465-473 (2011).
Dye, et al., "In Vitro Generation of Human Pluripotent Stem Cell Derived Lung Organoids." *Elife*, 4 (2015).
Dye, et al., "A Bioengineered Niche Promotes in Vivo Engraftment and Maturation of Pluripotent Stem Cell Derived Human Lung Organoids." *Elife*, 5 (2016).
Edwards, "Stretch Stimulation: Its Effects on Alveolar Type II Cell Function in the Lung." *Comp Biochem Physiol A Mol Integr Physiol*, 129(1):245-260 (2001).
El-Ali, et al., "Cells on Chips." *Nature*, 442(7101):403-411 (2006).
Elborn. "Cystic Fibrosis." *Lancet*, 388(10059):2519-2531 (2016).
Epstein. "Do Mouse Models of Allergic Asthma Mimic Clinical Disease?". *Int Arch Allergy Immunol*, 133(1):84-100 (2004).
Evans, et al., "The Attenuated Fibroblast Sheath of the Respiratory Tract Epithelial-Mesenchymal Trophic Unit." *Am J Respir Cell Mol Biol*, 21(6):655-657 (1999).
Fang, et al., "Contribution of CFTR to Apical-Basolateral Fluid Transport in Cultured Human Alveolar Epithelial Type II Cells." *Am J Physiol Lung Cell Mol Physiol*, 290(2):L242-249 (2006).
Fatehullah, et al., "Organoids as an in Vitro Model of Human Development and Disease." *Nat Cell Biol*, 18(3):246-254 (2016).
Fehrenbach "Animal Models of Pulmonary Emphysema: A Stereologist's Perspective." *European Respiratory Review*, 15(101):136-147 (2006).
Fidler, et al., "Modulation of Tumor Cell Response to Chemotherapy by the Organ Environment." *Cancer Metastasis Rev*, 13(2):209-222 (1994).
Firth, et al., "Generation of Multiciliated Cells in Functional Airway Epithelia from Human Induced Pluripotent Stem Cells." *Proc Natl Acad Sci USA*, 111(17):E1723-1730 (2014).

(56) References Cited

OTHER PUBLICATIONS

Fisher. "Normal and Pathologic Biochemistry of the Lung." *Environ Health Perspect*, 16:3-9 (1976).
Fishler, et al., "Particle Dynamics and Deposition in True-Scale Pulmonary Acinar Models." *Sci Rep*, 5:14071 (2015).
Flieder and Travis "Pathologic Characteristics of Drug-Induced Lung Disease." *Clin Chest Med*, 25(1):37-45 (2004).
Folch, et al., "Molding of Deep Polydimethylsiloxane Microstructures for Microfluidics and Biological Applications." *J Biomech Eng*, 121(1):28-34 (1999).
Folch and Toner, "Microengineering of Cellular Interactions." *Annu Rev Biomed Eng*, 2:227-256 (2000).
Fonseca, et al., "Experimental Study of Tuberculosis: From Animal Models to Complex Cell Systems and Organoids." *PLoS Pathog*, 13(8):e1006421 (2017).
Forbes, et al., "Challenges in Inhaled Product Development and Opportunities for Open Innovation." *Adv Drug Deliv Rev*, 63(1-2):69-87 (2011).
Forrest. "The Effect of Changes in Lung Volume on the Size and Shape of Alveoli." *J Physiol*, 210(3):533-547 (1970).
Franks, et al., "Resident Cellular Components of the Human Lung: Current Knowledge and Goals for Research on Cell Phenotyping and Function." *Proc Am Thorac Soc*, 5(7):763-766 (2008).
Fredberg, et al., "Airway Smooth Muscle, Tidal Stretches, and Dynamically Determined Contractile States." *Am J Respir Crit Care Med*, 156(6):1752-1759 (1997).
Fredberg and Kamm, "Stress Transmission in the Lung: Pathways from Organ to Molecule." *Annu Rev Physiol*, 68:507-541 (2006).
Fuchs, et al., "Differentiation of Human Alveolar Epithelial Cells in Primary Culture: Morphological Characterization and Synthesis of Caveolin-1 and Surfactant Protein-C." *Cell Tissue Res*, 311(1):31-45 (2003) Epub 2002.
Fujiwara, "Mechanical Stresses Keep Endothelial Cells Healthy: Beneficial Effects of a Physiological Level of Cyclic Stretch on Endothelial Barrier Function." *Am J Physiol Lung Cell Mol Physiol*, 285(4):L782-784 (2003).
Fulcher, et al., "Well-Differentiated Human Airway Epithelial Cell Cultures." *Methods Mol Med*, 107:183-206 (2005).
GBD 2015: Chronic Respiratory Disease Collaborators, "Global, Regional, and National Deaths, Prevalence, Disability-Adjusted Life Years, and Years Lived with Disability for Chronic Obstructive Pulmonary Disease and Asthma, 1990-2015: A Systematic Analysis for the Global Burden of Disease Study 2015." *Lancet Respir Med*, 5(9):691-706 (2017).
Ghaedi, et al., "Human iPS Cell-Derived Alveolar Epithelium Repopulates Lung Extracellular Matrix." *J Clin Invest*, 123(11):4950-4962 (2013).
Gizurarson, "The Effect of Cilia and the Mucociliary Clearance on Successful Drug Delivery." *Biol Pharm Bull*, 38(4):497-506 (2015).
Glasser, et al., "Surfactant Protein-C in the Maintenance of Lung Integrity and Function." J Aller Ther S7:001, 2011.
Gonda. "The Ascent of Pulmonary Drug Delivery." *J Pharm Sci*, 89(7):940-945 (2000).
Gonda. "Systemic Delivery of Drugs to Humans Via Inhalation." *J Aerosol Med*, 19(1):47-53 (2006).
Gonzales, et al., "Differentiation of Human Pulmonary Type II Cells in Vitro by Glucocorticoid Plus Camp." *Am J Physiol Lung Cell Mol Physiol*, 283(5):L940-951 (2002).
Gotoh, et al., "Generation of Alveolar Epithelial Spheroids Via Isolated Progenitor Cells from Human Pluripotent Stem Cells." *Stem Cell Reports*, 3(3):394-403 (2014).
Gould, et al., "Translational Value of Mouse Models in Oncology Drug Development." *Nat Med*, 21(5):431-439 (2015).
Grainge, et al., "Effect of Bronchoconstriction on Airway Remodeling in Asthma." *N Engl J Med*, 364(21):2006-2015 (2011).
Gray, et al., "Mucociliary Differentiation of Serially Passaged Normal Human Tracheobronchial Epithelial Cells." *Am J Respir Cell Mol Biol*, 14(1):104-112 (1996).
Green, et al., "Defense Mechanisms of the Respiratory Membrane." *Am Rev Respir Dis*, 115(3):479-514 (1977).
Green, et al., "Generation of Anterior Foregut Endoderm from Human Embryonic and Induced Pluripotent Stem Cells." *Nat Biotechnol*, 29(3):267-272 (2011).
Greshock, et al., "Cancer Cell Lines as Genetic Models of Their Parent Histology: Analyses Based on Array Comparative Genomic Hybridization." *Cancer Res*, 67(8):3594-3600 (2007).
Griesenbach and Boyd, "Pre-Clinical and Clinical Endpoint Assays for Cystic Fibrosis Gene Therapy." *J Cyst Fibros*, 4(2):89-100 (2005).
Griffith and Swartz, "Capturing Complex 3d Tissue Physiology in Vitro." *Nat Rev Mol Cell Biol*, 7(3):211-224 (2006).
Guseh, et al., "Notch Signaling Promotes Airway Mucous Metaplasia and Inhibits Alveolar Development." *Development*, 136(10):1751-1759 (2009).
Hanania, et al., "Efficacy and Safety of Lebrikizumab in Patients with Uncontrolled Asthma (Lavolta I and Lavolta Ii): Replicate, Phase 3, Randomised, Double-Blind, Placebo-Controlled Trials." *Lancet Respir Med*, 4(10):781-796 (2016).
Harayama, et al., "Establishment of LC-MS Methods for the Analysis of Palmitoylated Surfactant Proteins." *J Lipid Res*, 56(7):1370-1379 (2015).
Hassell, et al., "Human Organ Chip Models Recapitulate Orthotopic Lung Cancer Growth, Therapeutic Responses, and Tumor Dormancy In vitro." *Cell Rep*, 21(2):508-516 (2017).
Hassell, et al., "Human Organ Chip Models Recapitulate Orthotopic Lung Cancer Growth, Therapeutic Responses, and Tumor Dormancy In vitro." *Cell Rep*, 23(12):3698 (2018).
Hastings, et al., "Mechanisms of Alveolar Protein Clearance in the Intact Lung." *Am J Physiol Lung Cell Mol Physiol*, 286(4):L679-689 (2004).
Hawkins and Kotton, "Embryonic and Induced Pluripotent Stem Cells for Lung Regeneration." *Ann Am Thorac Soc*, 12 Suppl 1:S50-53 (2015).
Hawkins, et al., "Prospective Isolation of Nkx2-1-Expressing Human Lung Progenitors Derived from Pluripotent Stem Cells." *J Clin Invest*, 127(6):2277-2294 (2017).
Hawn, et al., "Host-Directed Therapeutics for Tuberculosis: Can We Harness the Host?". *Microbiol Mol Biol Rev*, 77(4):608-627 (2013).
Hermanns, et al., "Lung Epithelial Cell Lines in Coculture with Human Pulmonary Microvascular Endothelial Cells: Development of an Alveolo-Capillary Barrier in Vitro." *Lab Invest*, 84(6):736-752 (2004).
Herriges and Morrisey, "Lung Development: Orchestrating the Generation and Regeneration of a Complex Organ." *Development*, 141(3):502-513 (2014).
Hiemstra, et al., "Human Lung Epithelial Cell Cultures for Analysis of Inhaled Toxicants: Lessons Learned and Future Directions." *Toxicol In Vitro*, 47:137-146 (2018).
Hirst, "Airway Smooth Muscle as a Target in Asthma." *Clin Exp Allergy*, 30 Suppl 1:54-59 (2000).
Holgate, et al., "Drug Development for Airway Diseases: Looking Forward." *Nat Rev Drug Discov*, 14(6):367-368 (2015).
Holliday and Speirs, "Choosing the Right Cell Line for Breast Cancer Research." *Breast Cancer Res*, 13(4):215 (2011).
Holmes, et al., "Animal Models of Asthma: Value, Limitations and Opportunities for Alternative Approaches." *Drug Discov Today*, 16(15-16):659-670 (2011).
Holtzman, et al., "The Role of Airway Epithelial Cells and Innate Immune Cells in Chronic Respiratory Disease." *Nat Rev Immunol*, 14(10):686-698 (2014).
Hu, et al., "A One-Step Strategy for Ultra-Fast and Low-Cost Mass Production of Plastic Membrane Microfluidic Chips." *Lab Chip*, 16(20):3909-3918 (2016).
Huang, et al., "The in Vitro Generation of Lung and Airway Progenitor Cells from Human Pluripotent Stem Cells." *Nat Protoc*, 10(3):413-425 (2015).
Hughes, et al., "The Costs of Using Unauthenticated, over-Passaged Cell Lines: How Much More Data Do We Need?" *Biotechniques*, 43(5):575, 577-578, 581-572 passim (2007).
Huh, et al., "Reconstituting Organ-Level Lung Functions on a Chip." *Science*, 328(5986):1662-1668 (2010).
Huh, et al., "From 3D Cell Culture to Organs-on-Chips." *Trends Cell Biol*, 21(12):745-754 (2011).

(56) References Cited

OTHER PUBLICATIONS

Huh, et al., "A Human Disease Model of Drug Toxicity-Induced Pulmonary Edema in a Lung-on-a-Chip Microdevice." *Sci Transl Med*, 4(159):159ra147 (2012A).
Huh, et al., Microengineered physiological biomimicry: Organs-on-Chips, *Lab Chip* 12, 2156 (2012B).
Huh, et al., "Microfabrication of Human Organs-on-Chips." *Nat Protoc*, 8(11):2135-2157 (2013).
Huh, "A Human Breathing Lung-on-a-Chip." *Ann Am Thorac Soc*, 12 Suppl 1(Suppl 1):S42-44 (2015).
Hukkanen, et al., "Expression and Regulation of Xenobiotic-Metabolizing Cytochrome P450 (CYP) Enzymes in Human Lung." *Crit Rev Toxicol*, 32(5):391-411 (2002).
Hussell and Bell, "Alveolar Macrophages: Plasticity in a Tissue-Specific Context." *Nat Rev Immunol*, 14(2):81-93 (2014).
Hutchinson, et al., "Increasing Global Mortality from Idiopathic Pulmonary Fibrosis in the Twenty-First Century." *Ann Am Thorac Soc*, 11(8):1176-1185 (2014).
Iwasaki, et al., "Early Local Immune Defenses in the Respiratory Tract." *Nat Rev Immunol*, 17(1):7-20 (2017).
Jacob, et al., "Differentiation of Human Pluripotent Stem Cells into Functional Lung Alveolar Epithelial Cells." *Cell Stem Cell*, 21(4):472-488 e410 (2017).
Jain, et al., "Assessment of Whole Blood Thrombosis in a Microfluidic Device Lined by Fixed Human Endothelium." *Biomed Microdevices*, 18(4):73 (2016).
Jain, et al., "Primary Human Lung Alveolus-on-a-Chip Model of Intravascular Thrombosis for Assessment of Therapeutics." *Clin Pharmacol Ther*, 103(2):332-340 (2018).
Jang, et al., "Development of an Osteoblast-Based 3d Continuous-Perfusion Microfluidic System for Drug Screening." *Anal Bioanal Chem*, 390(3):825-832 (2008).
Jang and Suh, "A Multi-Layer Microfluidic Device for Efficient Culture and Analysis of Renal Tubular Cells." *Lab Chip*, 10(1):36-42 (2010).
Jemal, et al., "Cancer Statistics, 2005." *CA Cancer J Clin*, 55(1):10-30 (2005).
Kadzik and Morrisey, "Directing Lung Endoderm Differentiation in Pluripotent Stem Cells." *Cell Stem Cell*, 10(4):355-361 (2012).
Kaihara, et al., "Silicon Micromachining to Tissue Engineer Branched Vascular Channels for Liver Fabrication." *Tissue Eng*, 6(2):105-117 (2000).
Katt, et al., "In Vitro Tumor Models: Advantages, Disadvantages, Variables, and Selecting the Right Platform." *Front Bioeng Biotechnol*, 4:12 (2016).
Kendall and Feghali-Bostwick "Fibroblasts in Fibrosis: Novel Roles and Mediators." *Front Pharmacol*, 5:123 (2014).
Kerem, et al., "Identification of the Cystic Fibrosis Gene: Genetic Analysis." *Science*, 245(4922):1073-1080 (1989).
Khademhosseini, et al., "Microscale Technologies for Tissue Engineering and Biology." *Proceedings of the National Academy of Sciences of the United States of America*, 103(8):2480-2487 (2006).
Killion, et al., "Orthotopic Models Are Necessary to Predict Therapy of Transplantable Tumors in Mice." *Cancer Metastasis Rev*, 17(3):279-284 (1998).
Kimura, et al., "The T/EBP Null Mouse: Thyroid-Specific Enhancer-Binding Protein Is Essential for the Organogenesis of the Thyroid, Lung, Ventral Forebrain, and Pituitary." *Genes Dev*, 10(1):60-69 (1996).
Kitterman, "The Effects of Mechanical Forces on Fetal Lung Growth." *Clin Perinatol*, 23(4):727-740 (1996).
Kling, et al., "Challenges and Future in Vaccines, Drug Development, and Immunomodulatory Therapy." *Ann Am Thorac Soc*, 11 Suppl 4(Suppl 4):S201-210 (2014).
Konar, et al., "Lung-on-a-Chip Technologies for Disease Modeling and Drug Development." *Biomed Eng Comput Biol*, 7(Suppl 1):17-27 (2016).
Konishi, et al., "Directed Induction of Functional Multi-Ciliated Cells in Proximal Airway Epithelial Spheroids from Human Pluripotent Stem Cells." *Stem Cell Reports*, 6(1):18-25 (2016).
Kopf, et al., "The Development and Function of Lung-Resident Macrophages and Dendritic Cells." *Nat Immunol*, 16(1):36-44 (2015).
Kopp, et al., "Chemical Amplification: Continuous-Flow Pcr on a Chip." *Science*, 280(5366):1046-1048 (1998).
Koval, et al., "Extracellular Matrix Influences Alveolar Epithelial Claudin Expression and Barrier Function." *Am J Respir Cell Mol Biol*, 42(2):172-180 (2010).
Lam, et al., "Microfeature Guided Skeletal Muscle Tissue Engineering for Highly Organized 3-Dimensional Free-Standing Constructs." *Biomaterials*, 30(6):1150-1155 (2009).
Lancaster and Knoblich, "Organogenesis in a Dish: Modeling Development and Disease Using Organoid Technologies." *Science*, 345(6194):1247125 (2014).
Landrigan, et al., "The Lancet Commission on Pollution and Health." *Lancet*, 391(10119):462-512 (2018).
Langer and Vacanti, "Tissue Engineering." *Science*, 260(5110):920-926 (1993).
Lavelle, et al., "Animal Models of Cystic Fibrosis Pathology: Phenotypic Parallels and Divergences." *Biomed Res Int*, 2016:5258727 (2016).
Leclerc, et al., "Cell Culture in 3-Dimensional Microfluidic Structure of PDMS (Polydimethylsiloxane)." *Biomedical Microdevices*, 5(2):109-114 (2003).
Lee, et al., "An Artificial Liver Sinusoid with a Microfluidic Endothelial-Like Barrier for Primary Hepatocyte Culture." *Biotechnol Bioeng*, 97(5):1340-1346 (2007).
Lee, et al., "Lung Stem Cell Differentiation in Mice Directed by Endothelial Cells Via a BMP4-NFATc1-Thrombospondin-1 Axis." *Cell*, 156(3):440-455 (2014).
Leist and Hartung, "Reprint: Inflammatory Findings on Species Extrapolations: Humans Are Definitely No 70-Kg Mice." *Altex*, 30(2):227-230 (2013).
Lerner, et al., "The Innate Immune Response in Human Tuberculosis." *Cell Microbiol*, 17(9):1277-1285 (2015).
Levesque, et al., "Vascular Endothelial Cell Proliferation in Culture and the Influence of Flow." *Biomaterials*, 11(9):702-707 (1990).
Liu, et al., "Mechanical Force-Induced Signal Transduction in Lung Cells." *Am J Physiol*, 277(4):L667-683 (1999).
Liu, et al., "Species-Specific Differences in Mouse and Human Airway Epithelial Biology of Recombinant Adeno-Associated Virus Transduction." *Am J Respir Cell Mol Biol*, 34(1):56-64 (2006).
Liu, et al., "Feedback Amplification of Fibrosis through Matrix Stiffening and Cox-2 Suppression." *J Cell Biol*, 190(4):693-706 (2010).
Liu, et al., "The Development of Models for the Evaluation of Pulmonary Drug Disposition." *Expert Opin Drug Metab Toxicol*, 9(4):487-505 (2013).
Livraghi and Randell ,"Cystic Fibrosis and Other Respiratory Diseases of Impaired Mucus Clearance." *Toxicol Pathol*, 35(1):116-129 (2007).
Lo, et al., "Reduced Suppressive Effect of Beta2-Adrenoceptor Agonist on Fibrocyte Function in Severe Asthma." *Respir Res*, 18(1):194 (2017).
Low and Tagle, "Microphysiological Systems ("Organs-on-Chips") for Drug Efficacy and Toxicity Testing." Clinical and Translational Science, 10(4):237-239. 2017.
Lu, et al., "Extracellular Matrix Degradation and Remodeling in Development and Disease." *Cold Spring Harb Perspect Biol*, 3(12) (2011). a005058-a005058.
Lucas, et al., "Regulators of Endothelial and Epithelial Barrier Integrity and Function in Acute Lung Injury." *Biochem Pharmacol*, 77(12):1763-1772 (2009).
Mahler, et al., "Characterization of a Gastrointestinal Tract Microscale Cell Culture Analog Used to Predict Drug Toxicity." *Biotechnol Bioeng*, 104(1):193-205 (2009).
Mahon and Hafner, "Immune Cell Regulatory Pathways Unexplored as Host-Directed Therapeutic Targets for Mycobacterium Tuberculosis: An Opportunity to Apply Precision Medicine Innovations to Infectious Diseases." *Clin Infect Dis*, 61Suppl 3(Suppl 3):S200-216 (2015).
Maiuri, et al., "Strategies for the Etiological Therapy of Cystic Fibrosis." *Cell Death Differ*, 24(11):1825-1844 (2017).

(56) References Cited

OTHER PUBLICATIONS

Malavia, et al., "Airway Epithelium Stimulates Smooth Muscle Proliferation." *Am J Respir Cell Mol Biol*, 41(3):297-304 (2009).
Manz, et al., "Miniaturized Total Chemical Analysis Systems: A Novel Concept for Chemical Sensing." *Sensors and Actuators B: Chemical*, 1(1):244-248 (1990).
Martin and Ramos-Barbón, "Airway Smooth Muscle Growth from the Perspective of Animal Models." *Respir Physiol Neurobiol*, 137(2-3):251-261 (2003).
Martinez, et al., "Idiopathic Pulmonary Fibrosis." *Nat Rev Dis Primers*, 3:17074 (2017).
Mason and Williams, "Phospholipid Composition and Ultrastructure of A549 Cells and Other Cultured Pulmonary Epithelial Cells of Presumed Type Ii Cell Origin." *Biochim Biophys Acta*, 617(1):36-50 (1980).
Matrosovich, et al., "Human and Avian Influenza Viruses Target Different Cell Types in Cultures of Human Airway Epithelium." *Proc Natl Acad Sci U S A*, 101(13):4620-4624 (2004).
Matsuno "Drug-Induced Interstitial Lung Disease: Mechanisms and Best Diagnostic Approaches." *Respir Res*, 13(1):39 (2012).
McCauley, et al., "Efficient Derivation of Functional Human Airway Epithelium from Pluripotent Stem Cells Via Temporal Regulation of Wnt Signaling." *Cell Stem Cell*, 20(6):844-857 e846 (2017).
McCracken, et al., "Diagnosis and Management of Asthma in Adults: A Review." *Jama*, 318(3):279-290 (2017).
McCulley, et al., "The Pulmonary Mesenchyme Directs Lung Development." *Curr Opin Genet Dev*, 32:98-105 (2015).
McDonald and Whitesides, "Poly(Dimethylsiloxane) as a Material for Fabricating Microfluidic Devices." *Acc Chem Res*, 35(7):491-499 (2002).
Mercer and Crapo, "Spatial Distribution of Collagen and Elastin Fibers in the Lungs." *J Appl Physiol (1985)*, 69(2):756-765 (1990).
Metzger, et al., "The Branching Programme of Mouse Lung Development." *Nature*, 453(7196):745-750 (2008).
Mitzner, "Mechanics of the Lung in the 20th Century." *Comprehensive Physiology*, (John Wiley & Sons, Inc., Hoboken, NJ, USA). pp. 2009-2027. 2011.
Montiel-Gonzalez, et al., "Correction of Mutations within the Cystic Fibrosis Transmembrane Conductance Regulator by Site-Directed RNA Editing." *Proc Natl Acad Sci U S A*, 110(45):18285-18290 (2013).
Morgan, et al., "Nutrition of Animal Cells in Tissue Culture; Initial Studies on a Synthetic Medium." *Proc Soc Exp Biol Med*, 73(1):1-8 (1950).
Morgan, et al., "The Nutrition of Animal Tissues Cultivated in Vitro. I. A Survey of Natural Materials as Supplements to Synthetic Medium 199." *J Natl Cancer Inst*, 16(2):557-567 (1955).
Morrisey and Hogan, "Preparing for the First Breath: Genetic and Cellular Mechanisms in Lung Development." *Dev Cell*, 18(1):8-23 (2010).
Mou, et al., "Dual SMAD Signaling Inhibition Enables Long-Term Expansion of Diverse Epithelial Basal Cells." *Cell Stem Cell*, 19(2):217-231 (2016).
Mullane, "The Increasing Challenge of Discovering Asthma Drugs." *Biochem Pharmacol*, 82(6):586-599 (2011).
Murry and Keller, "Differentiation of Embryonic Stem Cells to Clinically Relevant Populations: Lessons from Embryonic Development." *Cell*, 132(4):661-680 (2008).
Nalayanda, et al., "Characterization of Pulmonary Cell Growth Parameters in a Continuous Perfusion Microfluidic Environment." *Exp Lung Res*, 33(6):321-335 (2007).
Namati, et al., "Alveolar Dynamics During Respiration: Are the Pores of Kohn a Pathway to Recruitment?". *Am J Respir Cell Mol Biol*, 38(5):572-578 (2008).
Nathan and Meyer, "IPF Clinical Trial Design and Endpoints." *Curr Opin Pulm Med*, 20(5):463-471 (2014).
Nawroth and Parker, "Design Standards for Engineered Tissues." *Biotechnol Adv*, 31(5):632-637 (2013).
Nemery, et al., "Interstitial Lung Disease Induced by Exogenous Agents: Factors Governing Susceptibility." *Eur Respir J Suppl*, 32:30s-42s (2001).
Nemunaitis, et al., "Granulocyte-Macrophage Colony-Stimulating Factor Gene-Modified Autologous Tumor Vaccines in Non-Small-Cell Lung Cancer." *J Natl Cancer Inst*, 96(4):326-331 (2004).
Nesmith, et al., "Human Airway Musculature on a Chip: An in Vitro Model of Allergic Asthmatic Bronchoconstriction and Bronchodilation." *Lab Chip*, 14(20):3925-3936 (2014).
Nieman, et al., "Physiology in Medicine: Understanding Dynamic Alveolar Physiology to Minimize Ventilator-Induced Lung Injury." *J Appl Physiol (1985)*, 122(6):1516-1522 (2017).
Nikolić, et al., "Human Embryonic Lung Epithelial Tips Are Multipotent Progenitors That Can Be Expanded in Vitro as Long-Term Self-Renewing Organoids." *Elife*, 6 (2017).
Noble, et al., "Pulmonary Fibrosis: Patterns and Perpetrators." *J Clin Invest*, 122(8):2756-2762 (2012).
Ochoa, et al., "Cyclic Stretch Affects Pulmonary Endothelial Cell Control of Pulmonary Smooth Muscle Cell Growth." *American Journal Of Respiratory Cell And Molecular Biology*, 39(1):105-112 (2008).
Ogi and Aruga, "Immunological Monitoring of Anticancer Vaccines in Clinical Trials." *Oncoimmunology*, 2(8):e26012 (2013).
Olin and Wechsler, "Asthma: Pathogenesis and Novel Drugs for Treatment." *BMJ*, 349:g5517 (2014).
Olsen, et al., "Extracellular Matrix-Driven Alveolar Epithelial Cell Differentiation in Vitro." *Exp Lung Res*, 31(5):461-482 (2005).
Ordoñez, et al., "Mild and Moderate Asthma Is Associated with Airway Goblet Cell Hyperplasia and Abnormalities in Mucin Gene Expression." *Am J Respir Crit Care Med*, 163(2):517-523 (2001).
Park, et al., "Microfabricated Grooved Substrates as Platforms for Bioartificial Liver Reactors." *Biotechnol Bioeng*, 90(5):632-644 (2005).
Park, et al., "Microfluidic Culture Platform for Neuroscience Research." *Nat Protoc*, 1(4):2128-2136 (2006).
Parker, et al., "A 3-D Well-Differentiated Model of Pediatric Bronchial Epithelium Demonstrates Unstimulated Morphological Differences between Asthmatic and Nonasthmatic Cells." *Pediatr Res*, 67(1):17-22 (2010).
Patton, et al., "The Lungs as a Portal of Entry for Systemic Drug Delivery." *Proc Am Thorac Soc*, 1(4):338-344 (2004).
Persson, "Con: Mice Are Not a Good Model of Human Airway Disease." *Am J Respir Crit Care Med*, 166(1):6-7; discussion 8 (2002).
Pier, "The Challenges and Promises of New Therapies for Cystic Fibrosis." *J Exp Med*, 209(7):1235-1239 (2012).
Pilewski and Frizzell, "Role of CFTR in Airway Disease." *Physiol Rev*, 79(1 Suppl):S215-255 (1999).
Pirofski and Casadevall, "The Damage-Response Framework of Microbial Pathogenesis and Infectious Diseases." *Adv Exp Med Biol*, 635:135-146 (2008).
Powers, et al., "A Microfabricated Array Bioreactor for Perfused 3D Liver Culture." *Biotechnol Bioeng*, 78(3):257-269 (2002).
Proietti and Antunes, "Sensitivity, Specificity and Positive Predictive Value of Selected Clinical Signs and Symptoms Associated with *Schistosomiasis mansoni.*" *Int J Epidemiol*, 18(3):680-683 (1989).
Quake and Scherer, "From Micro- to Nanofabrication with Soft Materials." *Science*, 290(5496):1536-1540 (2000).
Raez, et al., "Lung Cancer Immunotherapy." *Clin Med Res*, 3(4):221-228 (2005).
Raghu, et al., "Idiopathic Pulmonary Fibrosis: Clinically Meaningful Primary Endpoints in Phase 3 Clinical Trials." *Am J Respir Crit Care Med*, 185(10):1044-1048 (2012).
Ramasamy, et al., "Regulation of Tissue Morphogenesis by Endothelial Cell-Derived Signals." *Trends Cell Biol*, 25(3):148-157 (2015).
Ramos, et al., "Fibroblasts from Idiopathic Pulmonary Fibrosis and Normal Lungs Differ in Growth Rate, Apoptosis, and Tissue Inhibitor of Metalloproteinases Expression." *Am J Respir Cell Mol Biol*, 24(5):591-598 (2001).
Rasmussen and Racaniello, "Selection of Rhinovirus 1A Variants Adapted for Growth in Mouse Lung Epithelial Cells." *Virology*, 420(2):82-88 (2011).

(56) References Cited

OTHER PUBLICATIONS

Ratjen and Döring, "Cystic Fibrosis." *Lancet*, 361(9358):681-689 (2003).
Renzoni, et al., "Pathogenesis of Idiopathic Pulmonary Fibrosis: Review of Recent Findings." *F1000Prime Rep*, 6:69 (2014).
Riordan, et al., "Identification of the Cystic Fibrosis Gene: Cloning and Characterization of Complementary DNA." *Science*, 245(4922):1066-1073 (1989).
Roan and Waters, "What Do We Know About Mechanical Strain in Lung Alveoli?" *Am J Physiol Lung Cell Mol Physiol*, 301(5):L625-635 (2011).
Robinton and Daley, "The Promise of Induced Pluripotent Stem Cells in Research and Therapy." *Nature*, 481(7381):295-305 (2012).
Rock, et al., "Basal Cells as Stem Cells of the Mouse Trachea and Human Airway Epithelium." *Proc Natl Acad Sci USA*, 106(31):12771-12775 (2009).
Ross, et al., "Transcriptional Profiling of Mucociliary Differentiation in Human Airway Epithelial Cells." *Am J Respir Cell Mol Biol*, 37(2):169-185 (2007).
Rozmahel, et al., "Modulation of Disease Severity in Cystic Fibrosis Transmembrane Conductance Regulator Deficient Mice by a Secondary Genetic Factor." *Nat Genet*, 12(3):280-287 (1996).
Ryu, et al., "Idiopathic Pulmonary Fibrosis: Evolving Concepts." *Mayo Clin Proc*, 89(8):1130-1142 (2014).
Saetta, et al., "Goblet Cell Hyperplasia and Epithelial Inflammation in Peripheral Airways of Smokers with Both Symptoms of Chronic Bronchitis and Chronic Airflow Limitation." *Am J Respir Crit Care Med*, 161(3 Pt 1):1016-1021 (2000).
Safdar, et al., "Inhaled Therapeutics for Prevention and Treatment of Pneumonia." *Expert Opin Drug Saf*, 8(4):435-449 (2009).
Sakai and Tager, "Fibrosis of Two: Epithelial Cell-Fibroblast Interactions in Pulmonary Fibrosis." *Biochim Biophys Acta*, 1832(7):911-921 (2013).
Sanchez-Esteban, et al., "Mechanical Stretch Promotes Alveolar Epithelial Type Ii Cell Differentiation." *J Appl Physiol (1985)*, 91(2):589-595 (2001).
Sandberg, et al., "Altered Lung Development after Prenatal Nicotine Exposure in Young Lambs." *Pediatr Res*, 56(3):432-439 (2004).
Schwaiblmair, et al., "Drug Induced Interstitial Lung Disease." *Open Respir Med J*, 6:63-74 (2012).
Schwank, et al., "Functional Repair of Cftr by Crispr/Cas9 in Intestinal Stem Cell Organoids of Cystic Fibrosis Patients." *Cell Stem Cell*, 13(6):653-658 (2013).
Seeger-Nukpezah and Golemis, "The Extracellular Matrix and Ciliary Signaling." *Curr Opin Cell Biol*, 24(5):652-661 (2012).
Sekhon, et al., "Prenatal Nicotine Increases Pulmonary Alpha7 Nicotinic Receptor Expression and Alters Fetal Lung Development in Monkeys." *J Clin Invest*, 103(5):637-647 (1999).
Sekhon, et al., "Prenatal Nicotine Exposure Increases Connective Tissue Expression in Foetal Monkey Pulmonary Vessels." *Eur Respir J*, 23(6):906-915 (2004).
Sellgren, et al., "A Biomimetic Multicellular Model of the Airways Using Primary Human Cells." *Lab Chip*, 14(17):3349-3358 (2014).
Seo, et al., "A Microengineered Model of Rbc Transfusion-Induced Pulmonary Vascular Injury." *Sci Rep*, 7(1):3413 (2017).
Serini, et al., "The Fibronectin Domain Ed-a Is Crucial for Myofibroblastic Phenotype Induction by Transforming Growth Factor-Beta1." *J Cell Biol*, 142(3):873-881 (1998).
Serra, et al., "Pluripotent Stem Cell Differentiation Reveals Distinct Developmental Pathways Regulating Lung- Versus Thyroid-Lineage Specification." *Development*, 144(21):3879-3893 (2017).
Shanker, et al., "Drug Resistance in Lung Cancer." *Lung Cancer (Auckl)*, 1:23-36 (2010).
Sharma, et al., "The Genomic Origins of Asthma." *Thorax*, 69(5):481-487 (2014).
Shin, et al., "Understanding Asthma Using Animal Models." *Allergy Asthma Immunol Res*, 1(1):10-18 (2009).
Shirure and George "Design Considerations to Minimize the Impact of Drug Absorption in Polymer-Based Organ-on-a-Chip Platforms." *Lab Chip*, 17(4):681-690 (2017).

Sin, et al., "The Design and Fabrication of Three-Chamber Microscale Cell Culture Analog Devices with Integrated Dissolved Oxygen Sensors." *Biotechnol Prog*, 20(1):338-345 (2004).
Snoeck, "Modeling Human Lung Development and Disease Using Pluripotent Stem Cells." *Development*, 142(1):13-16 (2015).
Somers, et al., "Generation of Transgene-Free Lung Disease-Specific Human Induced Pluripotent Stem Cells Using a Single Excisable Lentiviral Stem Cell Cassette." *Stem Cells*, 28(10):1728-1740 (2010).
Spagnolo, et al., "Rare Lung Disease and Orphan Drug Development." *Lancet Respir Med*, 1(6):479-487 (2013).
Spence, et al., "Directed Differentiation of Human Pluripotent Stem Cells into Intestinal Tissue in Vitro." *Nature*, 470(7332):105-109 (2011).
Stiemsma and Turvey, "Asthma and the Microbiome: Defining the Critical Window in Early Life." *Allergy Asthma Clin Immunol*, 13:3 (2017).
Stucki, et al., "A Lung-on-a-Chip Array with an Integrated Bio-Inspired Respiration Mechanism." *Lab Chip*, 15(5):1302-1310 (2015).
Sukriti, et al., "Mechanisms Regulating Endothelial Permeability." *Pulm Circ*, 4(4):535-551 (2014).
Sung, et al., "Using Physiologically-Based Pharmacokinetic-Guided "Body-on-a-Chip" Systems to Predict Mammalian Response to Drug and Chemical Exposure." *Exp Biol Med (Maywood)*, 239(9):1225-1239 (2014).
Swain, et al., "Assessment of Cell Line Models of Primary Human Cells by Raman Spectral Phenotyping." *Biophys J*, 98(8):1703-1711 (2010).
Tanabe, et al., "Mechanical Stretch Augments PDGF Receptor Beta Expression and Protein Tyrosine Phosphorylation in Pulmonary Artery Tissue and Smooth Muscle Cells." *Mol Cell Biochem*, 215(1-2):103-113 (2000).
Tanjore, et al., "Contribution of Epithelial-Derived Fibroblasts to Bleomycin-Induced Lung Fibrosis." *Am J Respir Crit Care Med*, 180(7):657-665 (2009).
Tata, et al., "Dedifferentiation of Committed Epithelial Cells into Stem Cells in Vivo." *Nature*, 503(7475):218-223 (2013).
Teijaro, et al., "Endothelial Cells Are Central Orchestrators of Cytokine Amplification During Influenza Virus Infection." *Cell*, 146(6):980-991 (2011).
Thorne and Adamson, "A Review of in Vitro Cigarette Smoke Exposure Systems." *Exp Toxicol Pathol*, 65(7-8):1183-1193 (2013).
Tomos, et al., "Extracellular Matrix Remodeling in Idiopathic Pulmonary Fibrosis. It Is the 'Bed' That Counts and Not 'the Sleepers'." *Expert Rev Respir Med*, 11(4):299-309 (2017).
Tsuda, et al., "Particle transport and deposition: basic physics of particle kinetics." *Comprehensive Physiology*, (John Wiley & Sons, Inc., Hoboken, NJ, USA), pp. 1437-1471. 2013.
Witherden, et al., "Primary Human Alveolar Type II Epithelial Cell Chemokine Release: Effects of Cigarette Smoke and Neutrophil Elastase." *Am J Respir Cell Mol Biol*, 30(4):500-509 (2004).
Vanfleteren, et al., "Moving from the Oslerian Paradigm to the Post-Genomic Era: Are Asthma and COPD Outdated Terms?" *Thorax*, 69(1):72-79 (2014).
Villenave, et al., "Severe Asthma on-Chip: A Novel Platform Enables Study of Viral-Induced Exacerbations in Asthma and Drug Response in Vitro." *European Respiratory Journal*, 50(suppl 61):PA4136 (2017).
Vining and Mooney, "Mechanical Forces Direct Stem Cell Behaviour in Development and Regeneration." *Nat Rev Mol Cell Biol*, 18(12):728-742 (2017).
Wade, et al., "Gene Induction During Differentiation of Human Pulmonary Type II Cells in Vitro." *Am J Respir Cell Mol Biol*, 34(6):727-737 (2006).
Wang, et al., "Differentiated Human Alveolar Epithelial Cells and Reversibility of Their Phenotype in Vitro." *Am J Respir Cell Mol Biol*, 36(6):661-668 (2007).
Waters, et al., "Mechanobiology in Lung Epithelial Cells: Measurements, Perturbations, and Responses." *Compr Physiol*, 2(1):1-29 (2012).
Weeber, et al., "Tumor Organoids as a Pre-Clinical Cancer Model for Drug Discovery." *Cell Chem Biol*, 24(9):1092-1100 (2017).

(56) References Cited

OTHER PUBLICATIONS

White and Martin, "Chlorine Gas Inhalation: Human Clinical Evidence of Toxicity and Experience in Animal Models." *Proc Am Thorac Soc*, 7(4):257-263 (2010).
Whitesides, et al., "Soft Lithography in Biology and Biochemistry." *Annu Rev Biomed Eng*, 3:335-373 (2001).
Whitsett, et al., "Alveolar Surfactant Homeostasis and the Pathogenesis of Pulmonary Disease." *Annu Rev Med*, 61:105-119 (2010).
Wikswo, et al., "Engineering Challenges for Instrumenting and Controlling Integrated Organ-on-Chip Systems." *IEEE Trans Biomed Eng*, 60(3):682-690 (2013).
Williamson, et al., "The Future of the Patient-Specific Body-on-a-Chip." *Lab Chip*, 13(18):3471-3480 (2013).
Wirtz and Dobbs, "The Effects of Mechanical Forces on Lung Functions." *Respir Physiol*, 119(1):1-17 (2000).
Wolters, et al., "Pathogenesis of Idiopathic Pulmonary Fibrosis." *Annu Rev Pathol*, 9:157-179 (2014).
Wong, et al., "Directed Differentiation of Human Pluripotent Stem Cells into Mature Airway Epithelia Expressing Functional CFTR Protein." *Nat Biotechnol*, 30(9):876-882 (2012).
Wong, et al., "Efficient Generation of Functional CFTR-Expressing Airway Epithelial Cells from Human Pluripotent Stem Cells." *Nat Protoc*, 10(3):363-381 (2015).
Woodruff, et al., "Genome-Wide Profiling Identifies Epithelial Cell Genes Associated with Asthma and with Treatment Response to Corticosteroids." *Proc Natl Acad Sci U S A*, 104(40):15858-15863 (2007).
Wouters, et al., "Systemic and Local Inflammation in Asthma and Chronic Obstructive Pulmonary Disease: Is There a Connection?" *Proc Am Thorac Soc*, 6(8):638-647 (2009).
Wu, et al., "Direct-Write Assembly of Biomimetic Microvascular Networks for Efficient Fluid Transport." *Soft Matter*, 6(4):739-742 (2010).
Wu, et al., "Omnidirectional Printing of 3D Microvascular Networks." *Adv Mater*, 23(24):H178-183 (2011).
Xu, et al., "Single-Cell RNA Sequencing Identifies Diverse Roles of Epithelial Cells in Idiopathic Pulmonary Fibrosis." *JCI Insight*, 1(20):e90558 (2016).
Yaddanapudi, et al., "Cancer Vaccines: Looking to the Future." *Oncoimmunology*, 2(3):e23403-e23403 (2013).
Yamamoto, et al., "Long-Term Expansion of Alveolar Stem Cells Derived from Human iPS Cells in Organoids." *Nat Methods*, 14(11):1097-1106 (2017).
Zielenski, "Genotype and Phenotype in Cystic Fibrosis." *Respiration*, 67(2):117-133 (2000).
Batenburg, et al., "Pre-Translational Regulation by Glucocorticoid of Fatty Acid and Phosphatidylcholine Synthesis in Type II Cells from Fetal Rat Lung." FEBS Letters. 307(2):164-168. 1992.
Waghray, et al., "Tips from the Embryonic Lung." Elife. 6(2):1-3. 2017.

\* cited by examiner

Layer-by-layer

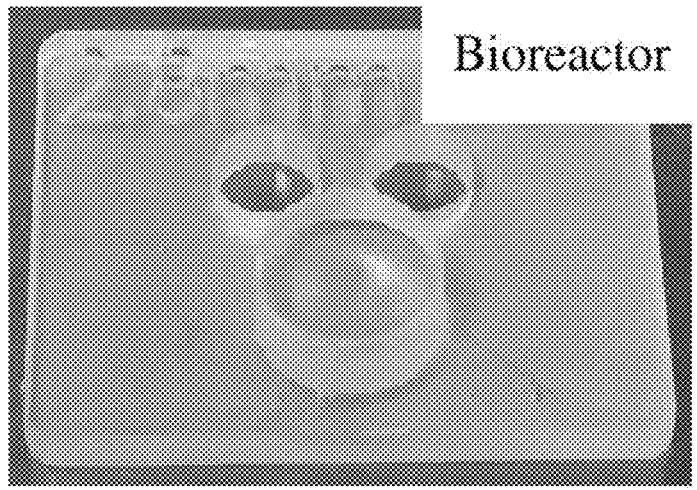
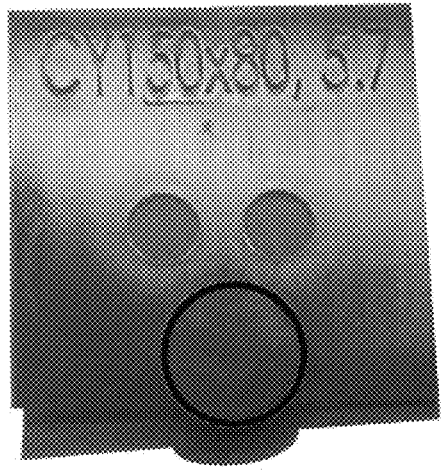
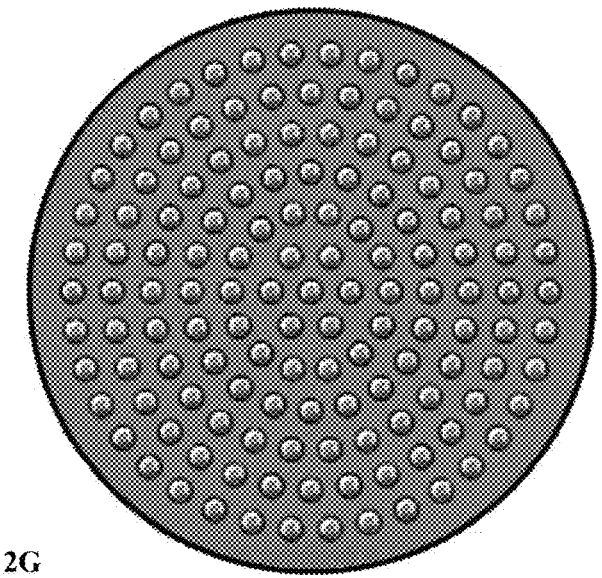
FIG. 2G

Collagen I

Collagen IV – Fibronectin - Laminin

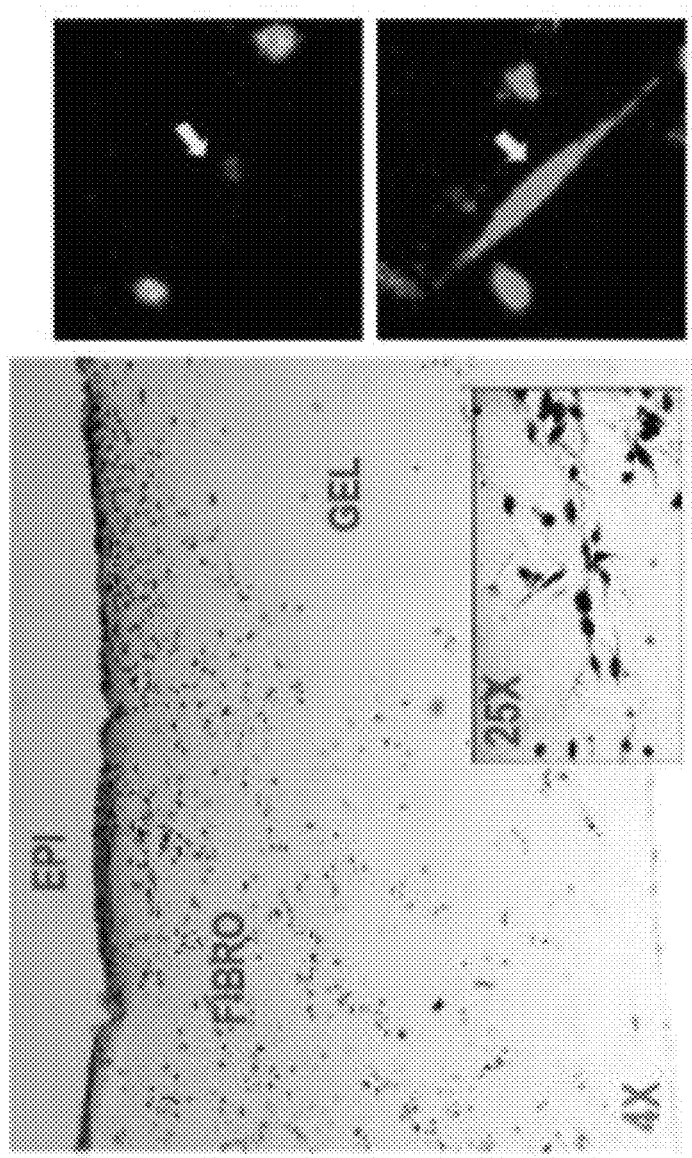
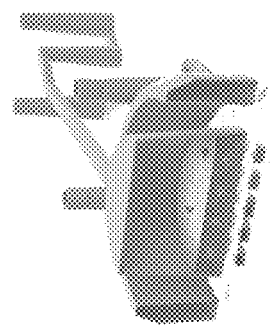
FIG. 10B

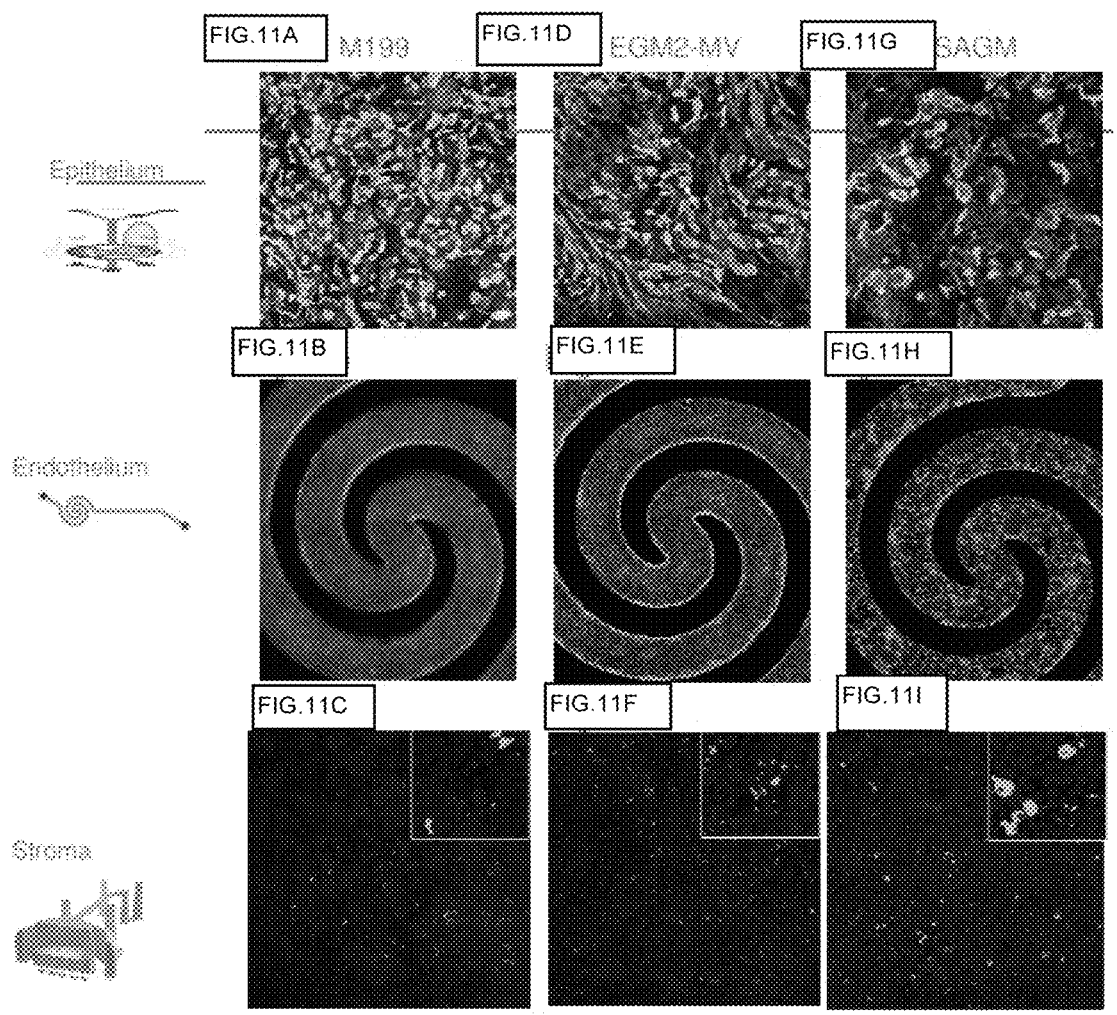

Fig. 14
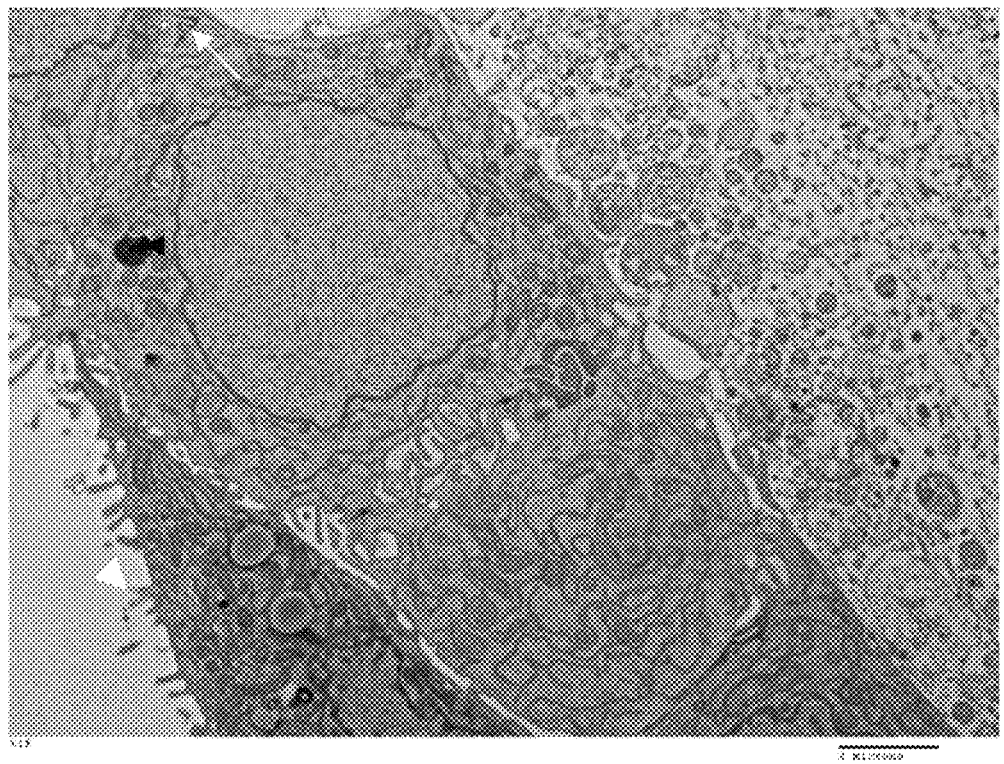
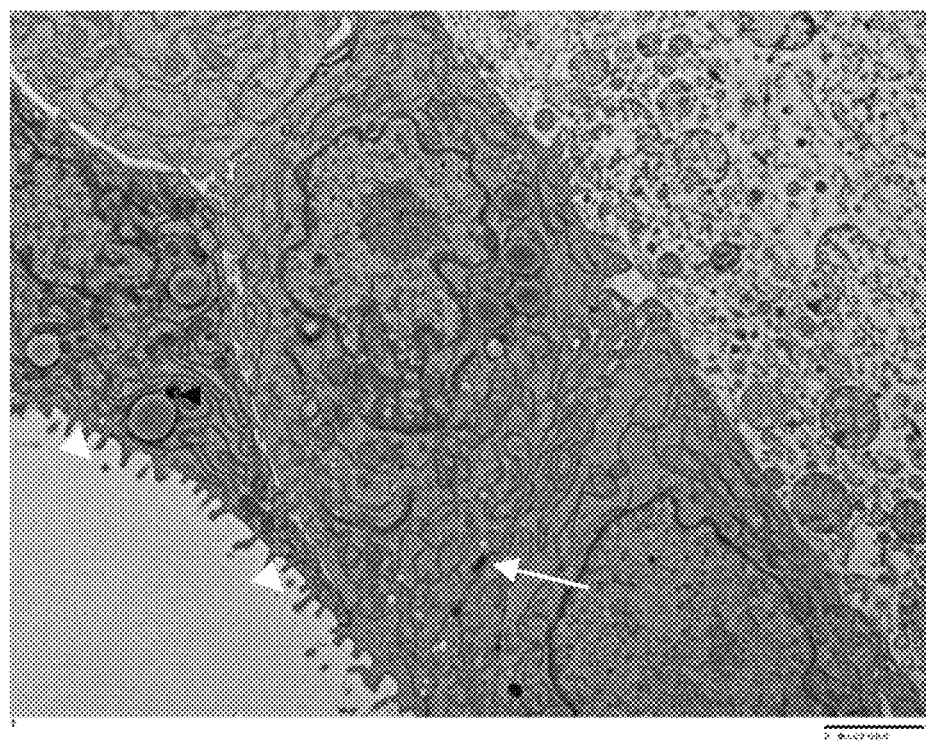

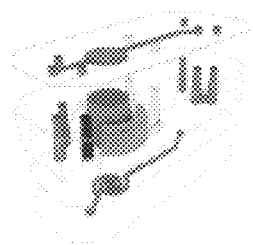
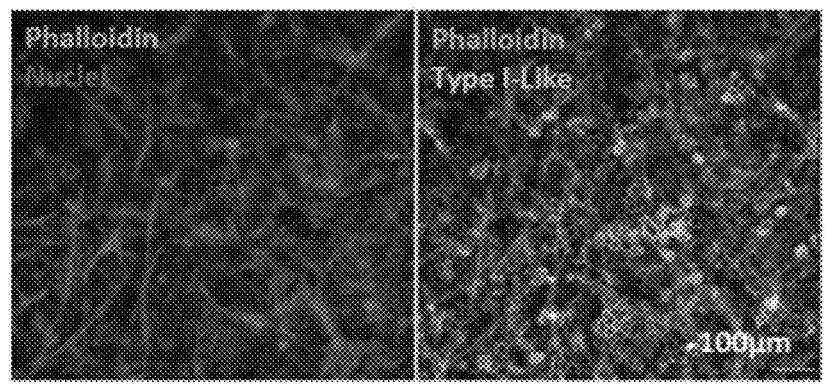
Fig. 18A    Fig. 18B
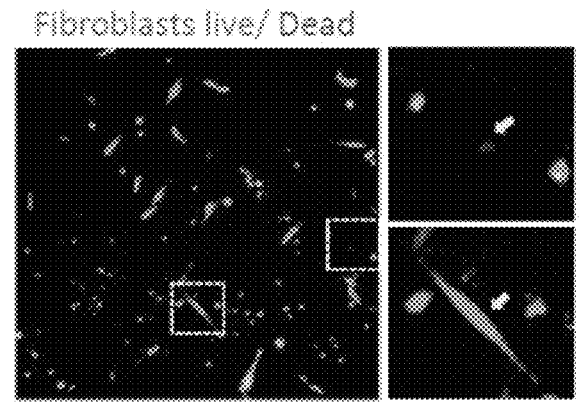
Fig. 18C

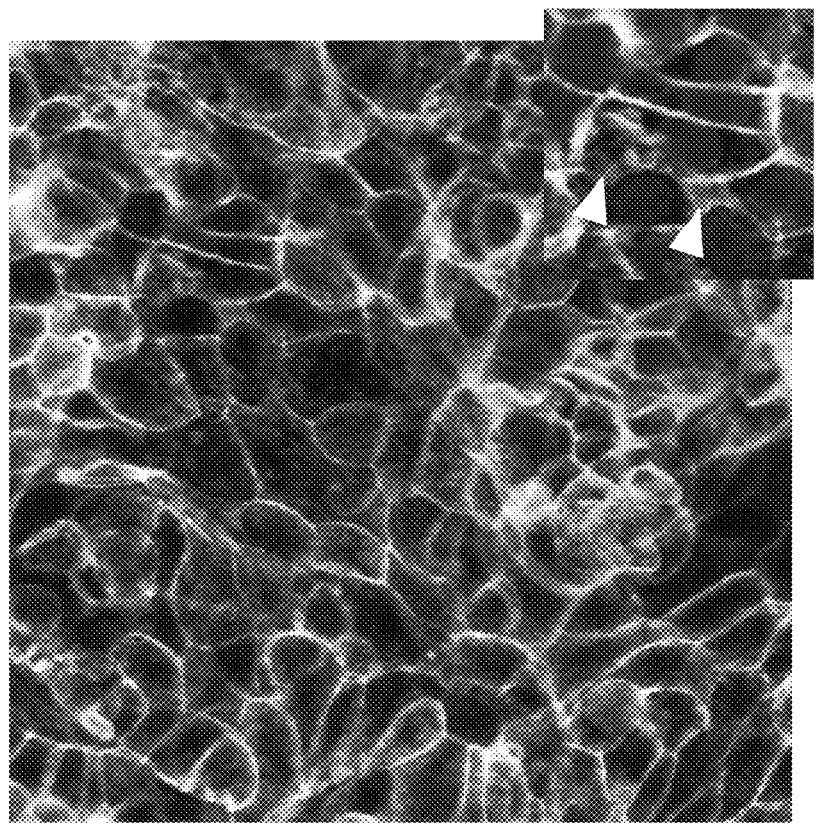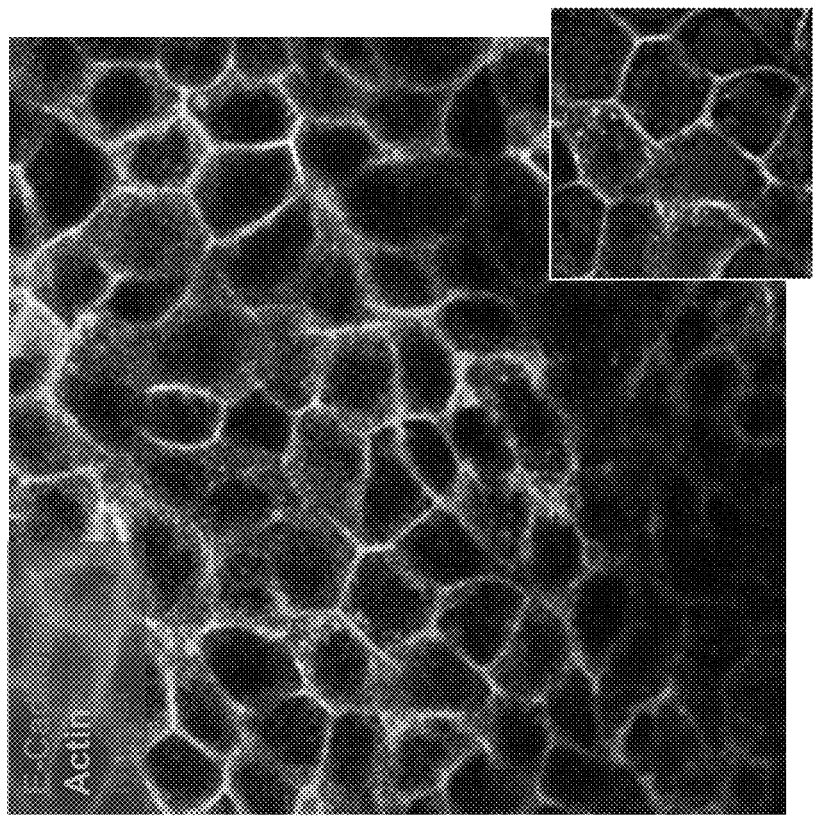
FIG. 25

STEM CELL-BASED LUNG-ON-CHIP MODELS

CROSS-REFERENCE TO RELATED APPLICATIONS

This application is a Continuation of, and claims priority to, PCT Patent Application Serial No. PCT/US2019/016680, filed Feb. 5, 2019, which claims priority to Provisional Application Ser. No. 62/626,427 filed on Feb. 5, 2018, the contents of which are incorporated herein in their entirety.

A Sequence Listing has been submitted in an ASCII text file named "19284.txt" created on Nov. 16, 2020, consisting of 16,822 bytes, the entire content of which is herein incorporated by reference.

FIELD OF THE INVENTION

An in vitro microfluidic "organ-on-chip" device is described herein that mimics the structure and at least one function of specific areas of the epithelial system in vivo. In particular, a stem cell-based Lung-on-Chip is described. This in vitro microfluidic system can be used for modeling differentiation of cells on-chip into lung cells, e.g., a lung (Lung-On-Chip), bronchial (Airway-On-Chip; small-Airway-On-Chip), alveolar sac (Alveolar-On-Chip), etc., for use in modeling disease states of derived tissue, i.e. as healthy, pre-disease and diseased tissues. Additionally, stem cells under differentiation protocols for deriving (producing) differentiated lung cells off-chips may be seeded onto microfluidic devices at any desired point during the in vitro differentiation pathway for further differentiation on-chip or placed on-chip before, during or after terminal differentiation. Additionally, these microfluidic "stem cell-based Lung-on-Chip" allow identification of cells and cellular derived factors driving disease states in addition to drug testing for diseases, infections and for reducing inflammation effecting lung alveolar and/or epithelial regions. Further, fluidic devices are provided seeded with primary alveolar cells for use in providing a functional Type II and Type I cell layer, wherein Type II cells express and secrete surfactants, such as Surfactant B (Surf B; SP-B) and Surfactant C (Surf C; SP-C), which were detectable at the protein level by antibody staining in Type II cells. Such devices and cells have a number of uses, including but not limited to for use under inflammatory conditions, in drug development and testing, and for individualized (personalized) medicine. Moreover, an ALI-M was developed for supporting multiple cell types in co-cultures with functional Type II and Type I cells.

BACKGROUND

Pathologies of the respiratory system such as lung infections and chronic airway diseases are among the leading causes of morbidity and death, killing one in six people worldwide. Development of more effective treatments is hindered by the lack of preclinical models of the human lung that can capture the highly heterogeneous disease phenotypes and drug responses observed in patients.

What is needed are preclinical models of the human lung that can capture the highly heterogeneous disease phenotypes and drug responses observed in patients.

SUMMARY OF THE INVENTION

An in vitro microfluidic "organ-on-chip" device is described herein that mimics the structure and at least one function of specific areas of the epithelial system in vivo. In particular, a stem cell-based Lung-on-Chip is described. This in vitro microfluidic system can be used for modeling differentiation of cells on-chip into lung cells, e.g., a lung (Lung-On-Chip), bronchial (Airway-On-Chip; small-Airway-On-Chip), alveolar sac (Alveolar-On-Chip), etc., for use in modeling disease states of derived tissue, i.e. as healthy, pre-disease and diseased tissues. Additionally, stem cells under differentiation protocols for deriving (producing) differentiated lung cells off-chips may be seeded onto microfluidic devices at any desired point during the in vitro differentiation pathway for further differentiation on-chip or placed on-chip before, during or after terminal differentiation. Additionally, these microfluidic "stem cell-based Lung-on-Chip" allow identification of cells and cellular derived factors driving disease states in addition to drug testing for diseases, infections and for reducing inflammation effecting lung alveolar and/or epithelial regions. Further, fluidic devices are provided seeded with primary alveolar cells for use in providing a functional Type II and Type I cell layer, wherein Type II cells express and secrete surfactants, such as Surfactant B (Surf B; SP-B) and Surfactant C (Surf C; SP-C), which were detectable at the protein level by antibody staining in Type II cells. The devices and cells may be used for a number of purposes, including but not limited to, for use under inflammatory conditions, in drug development and testing, and for individualized (personalized) medicine. Moreover, an ALI-M was developed for supporting multiple cell types in co-cultures with functional Type II and Type I cells.

One advantage of using stem cells in organs on chips is not only to capture patient specific phenotypes but also to have the ability to have all the cells inside a chip coming from the same patient, e.g. the same source. This is important when immune cells are used on the chip that recognizes nonself. Co-culturing immune cells from one patient with epithelial cells from another patient may induce an immune response and lead to cell destruction merely because cells are not compatible. Stem cell bring a solution to this issue as all cells can be derived from the same patient, thus being compatible.

The use of lung tissue for providing primary cells bring another solution to this issue as blood, PBMCs, etc., skin fibroblasts, etc., can also be derived from the same patient's fluids and tissue(s), thus being immunologically compatible. As examples, primary cells may be isolated from and/or derived from isolated populations obtained from lobectomies, resected lung tissue, Bronchoalveolar lavage (BAL), etc., to create one embodiment of an Alveolar-Chip as a Patient-Chip (Patient lung-chip; alveolar-lung chip). Thus, in some embodiments, primary cell populations may be obtained as any one or more of endothelial cells, epithelial cells (alveolar cells and precursors) fibroblasts, tissue macrophages, lung tissue macrophages, blood cells, e.g. PBMCs, white blood cells isolated from blood, e.g. neutrophils, monocytes, lymphocytes, etc.

The present invention contemplates, in one embodiment, a microfluidic device comprising at least one microfluidic channel and a population of living cells positioned in at least a region of said microfluidic fluid channel, at least a portion of said cells capable of differentiating into terminally differentiated lung parenchyma cells. In one embodiment, said population of cells is selected from the group consisting of, organ-restricted adult stem cells (aSCs), embryonic stem cells (ESCs), pluripotentent stem cells (PSCs), induced pluripotentent stem cells (iPSCs), primary fetal alveolar cells, organoids and stem cells isolated from lung parenchyma biopsies (or cells derived from any of these cell types listed herein or found in lung biopsies). In one embodiment, said population of cells are partially differentiated into progenitor cells. In one embodiment, said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere.

It is not intended that the present invention be limited to a particular microfluidic device with particular features. In one embodiment, the device further comprises a membrane in said at least one fluid channel, said population of living cells positioned in at least a region of said membrane (see 1840 FIGS. 2B and 2E). In one embodiment, the microfluidic device has ports and channels in fluidic communication (see 211, 221, etc., FIG. 1A-B and black dots FIG. 2C). In one embodiment, the microfluidic device is a closed-top device (see FIG. 1A-C). In another embodiment, the microfluidic device is an open-top device (see FIGS. 2A-F and 2H and 2I) with chambers for the cells (see FIG. 3A-C). In one embodiment, the microfluidic device has an air interface (see FIG. 2H) and contains additional cells (e.g. endothelial cells) (see FIG. 3B).

The present invention contemplates, in another embodiment, a microfluidic device comprising at least one microfluidic channel and a population of living human stem cells positioned in at least a region of said microfluidic fluid channel, at least a portion of said cells capable of differentiating into terminally differentiated lung parenchyma cells. While not intending to be limited to the particular type or source of stem cells, in one embodiment, said population of stem cells is selected from the group consisting of stem cells isolated from lung parenchyma biopsies, organ-restricted adult stem cells (aSCs), embryonic stem cells (ESCs), pluripotentent stem cells (PSCs), induced pluripotentent stem cells (iPSCs), and organoids.

In one embodiment, organoids are used. While not intending to limit the source, in a preferred embodiment said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere.

It is not intended that the present invention be limited to a particular microfluidic device with particular features. In one embodiment, the device further comprises a membrane in said at least one fluid channel, said population of living human stem cells positioned in at least a region of said membrane. In one embodiment, the microfluidic device has ports and channels in fluidic communication (see 211, 221, etc., FIG. 1A-B and black dots FIG. 2C). In one embodiment, the microfluidic device is a closed-top device (see FIG. 1A-C). In another embodiment, the microfluidic device is an open-top device (see FIGS. 2A-F and 2H and 2I) with chambers for the cells (see FIG. 3A-C). In one embodiment, the microfluidic device has an air interface (see FIG. 2H) and contains additional cells (e.g. endothelial cells) (see FIG. 3B).

It is not intended that the stem cells be completely undifferentiated. In one embodiment, said population of stem cells are (or a portion thereof is) partially differentiated into progenitor cells. In one embodiment, said progenitor cell population comprises SOX17+ cells. In one embodiment, said progenitor cell population comprises NKX2-1+ cells. In one embodiment, said progenitor cells are selected from the group consisting of proximal progenitor cells and distal progenitor cells. In one embodiment, said progenitor cells comprise SOX9+ cells. In one embodiment, said progenitor cells comprise SOX2+ cells.

As noted above, the stem cells are capable of differentiating into terminally differentiated lung parenchyma cells. It is not intended that the present invention be limited to a particular type of terminally differentiated lung cell. In one embodiment, said terminally differentiated lung parenchyma cells are selected from the group consisting of alveolar type I cells, alveolar type II cells, alveolar duct cells, ciliated epithelial cells, basal cells, goblet cells, and club cells.

The starting stem cell population, as noted previously, can contain partially differentiated cells. However, in one embodiment, said population of stem cells does not contain a terminally differentiated lung parenchyma cell.

In one embodiment, said membrane comprises one or more types of extracellular matrix proteins attached to said membrane. In one embodiment, said cells are positioned at an air-liquid interface (ALI).

The present invention also contemplates methods involving stem cells on chips. The present invention contemplates, in one embodiment, a method comprising: a) providing; i) a population of living cells, wherein at least a portion of said cells have the capability to differentiate into a terminally differentiated lung parenchyma cell; ii) a microfluidic device comprising at least one microfluidic channel; b) introducing said cells into said at least one microfluidic channel under conditions such that said cells are positioned in at least a region of said microfluidic device so as to create positioned cells; and c) exposing said positioned cells to conditions that cause at least a portion of said cells to differentiate into terminally differentiated lung parenchyma cells.

It is not intended that the present invention be limited to a particular microfluidic device with particular features. In one embodiment, the device further comprises a membrane in said at least one fluid channel, said population of living cells positioned in at least a region of said membrane. In one embodiment, the microfluidic device has ports and channels in fluidic communication (see 211, 221, etc., FIG. 1A-B and black dots FIG. 2C). In one embodiment, the microfluidic device is a closed-top device (see FIG. 1A-C). In another embodiment, the microfluidic device is an open-top device (see FIGS. 2A-F and 2H and 2I) with chambers for the cells (see FIG. 3A-C). In one embodiment, the microfluidic device has an air interface (see FIG. 2H) and contains additional cells (e.g. endothelial cells) (see FIG. 3B).

In one embodiment, microfluidic device further comprises a membrane positioned in at least a region of said microfluidic device (see 208 FIG. 1B; see 1840 FIGS. 2B and 2E), said cells positioned after step b) on at least a region of said membrane.

It is not intended that the present invention be limited to the source of type of cells. However, in one embodiment, said population of cells of step a) is selected from the group consisting of organ-restricted adult stem cells (aSCs), embryonic stem cells (ESCs), pluripotentent stem cells (PSCs), induced pluripotentent stem cells (iPSCs), organoids and stem cells isolated from lung parenchyma biopsies (or cells derived from one of these sources). In one embodiment, the cells are mammalian stem cells, e.g. human stem cells.

In one embodiment, the cells are in or from an organoid. In one embodiment, said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere. In one embodiment, said population of cells of step a) are partially differentiated into progenitor cells.

In another embodiment, the present invention contemplates a method comprising: a) providing; i) a population of living stem cells, wherein at least a portion of said cells have the capability to differentiate into a terminally differentiated lung parenchyma cell; ii) a microfluidic device comprising at least one microfluidic channel; b) introducing said cells into said at least one microfluidic channel under conditions such that said cells are positioned in at least a region of said microfluidic device so as to create positioned cells; and c) exposing said positioned cells to conditions that cause at least a portion of said cells to differentiate into terminally differentiated lung parenchyma cells. In one embodiment, said microfluidic device further comprises a membrane positioned in at least a region of said microfluidic device, said cells positioned after step b) on at least a region of said membrane. It is not intended that the present invention be limited to a particular microfluidic device with particular features. In one embodiment, the device further comprises a membrane in said at least one fluid channel, said population of living human stem cells positioned in at least a region of said membrane. In one embodiment, the microfluidic device has ports and channels in fluidic communication (see FIGS. 1A-C). In one embodiment, the microfluidic device is a closed-top device (see FIGS. 1A-C). In another embodiment, the microfluidic device is an open-top device (see FIGS. 2A-I) with chambers for the cells. In one embodiment, the microfluidic device has an air interface (see FIG. 3B) and contains additional cells (e.g. endothelial cells).

As previously noted, it is not intended that the present invention be limited to the particular source or type of stem cells. In one embodiment, said population of stem cells of step a) is selected from the group consisting of stem cells isolated from lung parenchyma biopsies, organ-restricted adult stem cells (aSCs), embryonic stem cells (ESCs), pluripotent stem cells (PSCs), induced pluripotentent stem cells (iPSCs), and organoids.

In one embodiment, organoids are used. It is not intended that the present invention be limited to the source or type of organoid. However, in one embodiment said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere.

It is not intended that the stem cells be completely undifferentiated, i.e. they may have progressed in the early part of the differentiation pathway. In one embodiment said population of stem cells of step a) are partially differentiated into progenitor cells. In one embodiment, said progenitor cell population comprises SOX17+ cells. In one embodiment, said progenitor cell population comprises NKX2-1+ cells. In one embodiment, said progenitor cells are selected from the group consisting of proximal progenitor cells and distal progenitor cells. In one embodiment, said progenitor cells comprise SOX9+ cells. In one embodiment, said progenitor cells comprise SOX2+ cells.

As noted above, step c) involves exposing said positioned cells to conditions that cause at least a portion of said cells to differentiate into terminally differentiated lung parenchyma cells. It is not intended that the present invention be limited to the type of terminally differentiated lung cell. In one embodiment, said terminally differentiated lung parenchyma cells of step c) are selected from the group consisting of alveolar type I cells, alveolar type II cells, ciliated epithelial cells, basal cells, goblet cells, and club cells.

In one embodiment, said population of stem cells of step a) does not contain a terminally differentiated lung parenchyma cell.

In one embodiment, at least a portion of said terminally differentiated lung parenchyma cells of step c) has at least one characteristic of a disease selected from the group consisting of cystic fibrosis, congenital pediatric lung diseases, inflammatory diseases of the lung, pulmonary fibrosis, lung cancer, and pulmonary infectious disease.

In one embodiment, at least a portion of said terminally differentiated lung parenchyma cell of step c) has at least one characteristic of a disease selected from the group consisting of emphysema, bronchitis, asthma, severe asthma, and chronic bronchitis.

In one embodiment, said conditions comprise exposing said positioned cells to one or more agents. In one embodiment, said one or more agents is selected from the group consisting of Activin A, a TGFbeta signaling inhibitor, a BMP signaling inhibitor, a BMP signaling inducer, a fibroblast growth factor (FGF) signaling inducer, a FGF4 signaling inducer, a Wnt signaling inducer, a Wnt signaling inhibitor, retinoic acid, a glucocorticoid, a Hedgehog pathway activator, and an EGF signaling inducer. In one embodiment, combinations of such agents are used (as described in the Examples below).

The present invention contemplates additional methods, including testing methods and treatment methods based on testing results from the chip assays. In one embodiment, the present invention contemplates a method comprising: a) providing i) a microfluidic device comprising at least one microfluidic channel and a membrane, ii) a plurality of organoids comprising lung cells; and b) seeding said organoids onto said fluidic device under conditions that promote cell attachment to said membrane. In one embodiment, said membrane is coated with extracellular matrix. In one embodiment, said cell attachment results in formation of a cell layer. In one embodiment, said culturing is under flow. In one embodiment, the method further comprises breaking apart said one or more organoids prior to seeding. In one embodiment, said lung cells comprise alveolar epithelial cells. In one embodiment, said lung cells comprise airway epithelial cells. In one embodiment, said one or more organoids are derived from a biopsy. In one embodiment, said biopsy is obtained from a patient having at least one symptom associated with reduced ion channel function. In one embodiment, said biopsy is obtained from a patient having or suspected of having cystic fibrosis. In one embodiment, said organoid is derived from a stem-cell.

In yet another embodiment, the present invention contemplates a method comprising: a) providing; i) a microfluidic device comprising at least one microfluidic channel and a membrane, and ii) a plurality of cells having DNA comprising at least one cystic fibrosis transmembrane conductance regulator (CFTR) gene having a mutation; and b) seeding said cells onto said fluidic device under conditions that promote cell attachment to said membrane. In one embodiment, said membrane is coated with extracellular matrix. In one embodiment, said cell attachment results in formation of a cell layer. In one embodiment, said culturing is under flow. In one embodiment, said gene mutation results in a change in function of a CFTR protein encoded by said CFTR gene. In one embodiment, said cells are derived from stem-cells prior to said seeding in step b. In one embodiment, said cells are differentiated into lung cells after said seeding in step b. In one embodiment, the method further comprises the step of adding at least a first agent. In one embodiment, said first agent comprises a drug. In one embodiment, after adding said first agent a change in said cells is observed. In one embodiment, said observing comprises measuring transport of water. In one embodiment, said observing comprises swelling of said cells. In one embodiment, said cells form a lung organoid. In one embodiment, said microfluidic chip is seeded with a plurality of lung organoids. In one embodiment, said lung organoid comprise alveolar epithelial cells. In one embodiment, said lung organoid comprise airway epithelial cells. In one embodiment, the method further comprises the step of adding at least a first agent. In one embodiment, said first agent comprises a test drug. In one embodiment, after adding said first agent a change in said organoid is observed. In one embodiment, said change comprises swelling of said organoid. In one embodiment, said observing comprises measuring transport of water. In one embodiment, said change comprises a change in organoid size selected from the group consisting of a change in organoid surface area, a change in organoid diameter and a change in content of the organoid. In one embodiment, said observing is done microscopically.

In yet another embodiment, the present invention contemplates a method comprising: a) providing i) first and second microfluidic devices each comprising at least one microfluidic channel and a membrane, and ii) a first plurality of cells derived from a patient suspected of having a condition reducing ion channel function; and ii) a second plurality of cells derived from a patient that does not have reduced ion channel function, and b) seeding said first cells into said first microfluidic device and said second cells into said second microfluidic device, wherein said seeding is done under conditions that promote cell attachment to said membrane, c) adding an agent to said first and second microfluidic devices, and d) comparing swelling of said cells derived from a patient suspected of having a condition reducing ion channel function to cells derived from a patient that does not have reduced ion channel function. In one embodiment, said agent is forskolin. In one embodiment, said cells form a lung organoid. In one embodiment, said microfluidic chip is seeded with cells from a lung organoids. In one embodiment, said organoid comprise alveolar epithelial cells. In one embodiment, said organoid comprise airway epithelial cells. In one embodiment, said agent induces decreased swelling in said cells derived from a patient suspected of having a condition reducing ion channel function compared to swelling induced in said cells derived from a patient that does not have reduced ion channel function. In one embodiment, said cells derived from a patient suspected of having a condition reducing ion channel function respond by increased swelling. In one embodiment, said swelling response of said organoid derived from a patient suspected of having a condition reducing ion channel function is used for making a clinical choice of administering said drug to said patient. In one embodiment, the method further comprises e) administering a drug in therapeutic amounts to said patient for reducing a symptom associated with a reduced ion channel function. In one embodiment, comparing comprises measuring said swelling of said cells by confocal live cell microscopy.

The present invention contemplates, in one embodiment, an air-liquid interface culture medium (ALI-M/M199) comprising a mixture of M199 medium, fetal calf serum, Epidermal Growth Factor (EGF), Keratinocyte Growth Factor (KGF), Vascular Endothelial Cell Growth Factor (VEGF), cyclic monophosphate cyclic adenosine monophosphate (cAMP), Dexamethasone, and heparin sodium salt. In one embodiment, said culture medium further comprises retinoic acid. In one embodiment, said fetal calf serum is heat inactivated; said EGF is at least a portion of a human recombinant protein; said KGF is a human recombinant FGF-7 HEK cell-derived protein; said VEGF is a human recombinant VEGF-165 protein; said cAMP is 8-bromo-cyclicAMP; and said heparin sodium salt is from porcine intestinal mucosa. In one embodiment, said fetal calf serum is 5%-0.5% of said medium.

The present invention contemplates, in one embodiment, a method, comprising: a) providing; i) a microfluidic device comprising a surface and ii) a population of living cells, wherein at least a portion of said cells have the capability to differentiate into functional Type II lung parenchyma cells; b) introducing said cells into said microfluidic device such that said cells are positioned on said surface of said microfluidic device so as to create positioned cells; and c) exposing said positioned cells to conditions that cause at least a portion of said cells to differentiate into functional Type II lung parenchyma cells secreting at least one surfactant protein. In one embodiment, said surfactant protein is surfactant B. In one embodiment, said surfactant protein is surfactant C. In one embodiment, said surfactant C is secreted in amounts greater than 25 ng/ml. In one embodiment, said surfactant C is secreted in amounts between 30-100 ng/ml. In one embodiment, said amount is secreted daily from day 9 to day 15 of culture after introducing said living cells into said microfluidic device. In one embodiment, said method further comprises the step of d) detecting said surfactant at the protein level. In one embodiment, said detecting is by antibody staining. In one embodiment, said surface of said microfluidic device comprises a surface of a microfluidic channel, said microfluidic channel in fluid communication with a source of fluid. In one embodiment, wherein said step c) said positioned cells are exposed to an air-liquid interface. In one embodiment, said surface of said microfluidic device comprises a surface of a chamber, said chamber comprising a stroma area or layer. In one embodiment, said stroma area or layer comprises fibroblast cells. In one embodiment, said stroma area or layer is located adjacent to a spiral channel, wherein said stroma area is separated from the spiral channel by a stretchable membrane. In one embodiment, said spiral channel comprises a confluent layer of endothelial cells. In one embodiment, said spiral channel has an input port and an output port for collecting effluent fluid. In one embodiment, said population of living cells comprises primary alveolar cells. In one embodiment, said population of living cells comprises fetal alveolar cells.

Definitions

As used herein, "cell" refers to any eukaryotic or prokaryotic cell (e.g., bacterial cells such as bacteria (e.g. *E. coli*), fungal, (e.g. yeast), mammalian cells, avian cells, amphibian cells, plant cells, fish cells, and insect cells. Examples of mammalian cells include but are not limited to parenchymal cell types, e.g. epithelial cells of the lung, epithelial cells of the skin and epithelial cells of the urogenital tract.

As used herein, "stem cell" refers to an undifferentiated cell of a multicellular organism capable of giving rise (i.e. through cell division) to more daughter cells of the same stem cell type, and after one or more differentiation steps into other types of daughter cells, over the course of subsequent cell divisions during differentiation. A stem cell may be partially differentiated, i.e. in the early stage of the differentiation pathway. A stem cell may be a primordial germ stem cell, such as stem cells that produce eggs or sperm, an embryonic stem cell (i.e. pluripotent) capable of producing each and every cell of a multicellular organism, pluripotent stem cells induced in cultures of cells by reprogramming a cell population to loose differentiation features to appear more stem-like (i.e. de-differentiate) while gaining the capability to re-differentiate into the same (as in adult organ stem cells) or differentiate into a cell type that was not present in the initial cell population (as in reprogrammed stem cell population, e.g. transgenically introducing and expressing "reprogramming factors" such as Yamanaka factors, i.e. transcription factors Oct4 (Pou5f1), Sox2, cMyc, and Klf4. As one example, induced PSCs, iPSCs, are created from differentiated cells using "reprogramming factors" such that patient specific iPS cells may be created and used as described herein for providing patient group specific and individual patient specific cells. An adult stem cell, such as an organ stem cell isolated from an organ tissue, such as a biopsied tissue, is considered to be more differentiated along a differentiation pathway towards a "terminally differentiated" parenchymal cell of that organ.

In contrast, the majority of terminally differentiated cells loose the capability for further cell division or differentiation. There are exceptions. For example, in some cases a cell considered to be terminally differentiated may be capable of further division as with the case of alveolar II cells, which may be capable of dividing to provide more Type II cells (i.e. self renew, acting as adult stem cells), e.g. in response to lung tissue damage, and dedifferentiate into Type I-like cells or capable of altering a function such as by producing more Type I-like cells.

As used herein, "progenitor cell" in reference to a cell of a multicellular organism refers to a stem cell that has undergone partial differentiation, e.g. one or more differentiation steps but not yet a terminally differentiated cell, i.e. is capable of additional maturation steps prior to terminally differentiation.

As used herein, "differentiation" in reference to a cell of a multicellular organism refers to at least one step in a multistep differentiation process over time by which subsequent generations of cells, i.e. daughter cells, change to become less similar to the starting cell and become more similar to a more differentiated or mature (i.e. specialized or terminally differentiated) cell, e.g. a lung parenchymal cell.

As used herein, "agent" refers to a chemical molecule or biological molecule that produces a specified effect on a cell or cell population, when used either alone or in combination with other agents, e.g. differentiation agents, maturation agents, drugs, etc.

As used herein, "parenchyma" refers in general to functional cells or parts of an organ that may also be referred to descriptively as "parenchymal". As one example, in brain tissue, "parenchyma" refers to the functional tissue comprising at least two types of "parenchyma cells", i.e. brain cells, e.g. neurons and glial cells. As another example, parenchyma cells of the lung or "lung parenchyma" refers to lung tissue outside of the circulation system involved with gas exchange, including but not limited to alveoli and respiratory bronchioles (i.e. small bronchial tubes leading to and inside of alveolar sacs). As yet another example, in cancer, parenchyma refers to the cancerous cells and/or cancer tissue (i.e. tumor). In yet another example, "epithelial tissue" and "epithelial cells" are considered parenchyma, e.g. epithelial cells of the lung including but not limited to alveolar epithelial cells, airway epithelial cells, etc., epithelial cells of the skin including but not limited to keratinocytes.

In contrast, as used herein, the terms "stromal" and "stroma" refers in general to structural (i.e. supportive) tissue, i.e. stromal tissue" of organs, e.g. connective tissues, including but not limited to ECM, blood vessels, nerves, ducts, for supporting parenchyma cells i.e. nutritionally, immunologically, etc. or providing a frame for holding together parenchyma cells as an organ. Stromal cells, including cells capable of secreting connective tissue, e.g. collagen, elastin, reticular fibers, etc., include but not limited to, for examples, bone marrow derived Mesenchymal stem cells, fibroblasts, myofibroblasts, mural cells (pericytes) of the vasculature, etc. Such cells may be found in or near sites of inflammation, such as in or near the lamina propria in vivo, e.g. mucosa, submucosa, etc. and may also include "multipotent stromal cells" or "mesenchymal stromal cells" or "MSCs" found in both in the mucosal region, e.g. in lamina propria-derived cell populations and in submucosal regions, etc., In some embodiments, stromal cells are contemplated for use in microfluidic devices of the present inventions. In some embodiments, "stromal cells" are contemplated for use after isolation from lamina propria-derived cells. In some embodiments, stromal cells are contemplated for use derived from regions that do not include lamina propria. In some embodiments, stromal cells are contemplated for use that are a mixture of LP-derived and non-LP-derived cells, e.g. when biopsy tissue used for isolating cells includes both mucosa and submucosal cells. In some embodiments, stromal cells are isolated from healthy and diseased individuals, and/or from different sites within the same individual. For example, stromal cells may be derived from (e.g. isolated from) an in vivo site of cancer vs. derived from an in vivo healthy looking site, or from a cultured cell line.

As used herein, "airway" refers in general to the bronchial system, e.g. lined with bronchial epithelial cells and other cells observed to be present in vivo, including but not limited to endothelial cells.

As used herein, "lung" cells refers in general to cells found in the lower parts of the bronchial system and alveolar sacs in vivo, e.g. pneumocytes (alveolar cells), Type I, Type II, and precursor cells, ductal cells, stromal cells, endothelial cells, alveolar macrophages (or dust cells), etc.

The terms, "Organ-On-Chip" and the like, i.e. "—On-Chip" or "chip" refers to a "microfluidic device" for modeling any one or more types of tissue, including but not limited to the lung, airway, skin, etc. An "Organ-On-Chip" device is not limited to modeling any particular organ. In fact, "Organ-On-Chip" refers to a "microfluidic device" for modeling any one or more subtypes of airway tissue, skin, brain etc.

As used herein, "fluid" refers to gas or a liquid. Culture media is a fluid that can provide nutrients to cells. "Fluidity" of a substance refers to a capability to flow. As opposed to "viscosity" in reference to a fluid, referring to a measure of a resistance to flowing.

As used herein, a "fluidic device" refers to a capable of having defined manipulation of the working fluid by active components. For example, a "microfluidic device" includes such components as micropumps, microvalves, etc.

As used herein, "microfluidic" relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels. In some embodiments, exemplary flow rates are 30 ul per hour; 60 ul per hour; 150 ul per hour.

As used herein, "channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

As used herein, "fluidically connected" refers to two or more components connected such that a fluid or at least a portion of a fluid can directly or indirectly pass or flow from one component to a second component. Without limitations, two or more components can be fluidically connected together, for example, using one or more fluid-transfer connecting means (e.g., adaptors, tubing, splitters, valves, and/or channels) between the two or more components. For example, two or more components can be fluidically connected by connecting an outlet of one component to an inlet of another component using tubing, a conduit, a channel, piping or any combinations thereof. In other embodiments, two or more components can be fluidically connected together with one or more other connecting means (e.g., devices, systems, and/or modules that can perform an additional function other than fluid transfer, e.g., but not limited to, trapping air bubbles, filtration, signal detection, and/or imaging) are present between the two or more components.

As used herein, "removable top" refers to a cover that is capable of being removed from a device preferably without using screws (or the like) and that is not a molded part of a device.

As used herein, "perfusing" in relation to a fluidic device refers to introducing fluid into the device. As an example of perfusing a device containing cells, perfusing the device is supplying or treating cells or tissues with a fluid. As an example, fluid flowing through a fluidic device in contact with cells is also referred to as perfusing.

As used herein, "membrane" generally refers to a layer that can support the growth of cells. Examples of membranes include but are not limited to a semi-permeable membrane, a porous membrane, etc.

As used herein, the term "porous" generally refers to a material that is permeable or selectively permeable. The term "permeable" as used herein means a material that permits passage of a fluid (e.g., liquid or gas), a molecule, and/or a whole living cell. The term "selectively permeable" as used herein refers to a material that permits passage of one or more target group or species, but acts as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In accordance with some embodiments of the invention, a selectively-permeable membrane can allow certain cell types to pass therethrough but not other cell types.

As used herein, the term "culture" refers to a composition, whether liquid, gel, or solid, which contains one or more microorganisms and/or one or more cells.

As used herein, "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, "culture media" and "cell culture media" and "culture medium" refer to media that are suitable to support maintenance and/or growth of cells in vitro (i.e., cell cultures). Cultured cells include primary cultured cells and cell lines.

As used herein "cultured" or "cultures" refers to cells "grown" or "expanded" or "maintained" in culture medium.

As used herein, "gel" refers to a jelly-like substance and the process of solidifying a solution of gel particles into a gel, e.g. to form a gel. A gel is typically fluid permeable, e.g. water impermeable.

As used herein, "microorganism" refers to any organism of microscopic or ultramicroscopic size including, but not limited to, viruses, bacteria, and protozoa.

A "primary cell" refers to a cell that is directly obtained from a tissue or organ of an animal whether or not the cell is in culture.

A "derived cell" refers to a cell that is a descendant of a cell type, such as a cell derived from a primary cell, e.g. an alveolar cell on chip derived from an isolated primary cell, a cell derived from an embryonic stem cell, e.g. a iPSC-derived cell, etc.

A "cultured cell" refers to a cell which has been maintained and/or propagated in vitro.

As used herein, "morphology" in reference to a cell refers to a visual form of a cell, such as a cell that appears to have a migratory morphology or morphologic form, e.g. elongated or flat cell shape, i.e. a macrophage, vs. a cell that appears to be non-migratory, e.g. having a rounded cell shape, i.e. a monocyte.

As used herein, "phenotype" refers to observable characteristics of an individual resulting from the interaction of its genotype with the environment, including but not limited to a disease phenotype, a healthy phenotype. A phenotype may refer to "inflamed" tissue or "non-inflamed" tissue.

As used herein, "agent" or "compound" refers to a substance and preferably a test substance, such as a small molecule, drug, cytokine, etc.

As used herein, the term "biopsy" refers to a sample of the tissue that is removed from a body, either as a solid or fluid (in liquid form, such as by lavaging or rinsing out cells, e.g. a respiratory bronchoalveolar lavage (e.g. BAL) or lung sample, or as a blood sample) for obtaining biopsy-derived cells or lavage-derived cells, respectively.

As used herein, the term "irritant" refers to a stimulus or agent that induces the state of irritation in an epithelial lining, for example, a bacterial toxin or an allergen that causes activation of resident mononuclear white blood cells, leukocytes, lymphocytes, etc. that in turn triggers activation of resident immune cells any of which may induce irritation.

As used herein, the term "irritation" refers to initiation of inflammation. By way of example only, this may be due to an allergy or damage to epithelial cells in the lining of the respiratory system.

As used herein, the term "inflammation" refers to an in vivo physical condition in which a part of tissue in a body may become reddened, swollen (enlarged), or damaged (ulcerated) especially as a reaction to injury or an irritant. Areas of inflammation can have increased blood flow and capillary permeability, i.e. changes in endothelial cells lining capillaries resulting in capillary dilation and leukocyte infiltration into the irritated and/or inflamed tissues, along with activated immune cells, including white blood cells, leukocytes, lymphocytes, etc., including substances produced by activated immune cells. Inflammation may occur suddenly (acute) or gradually over time (chronic). Inflammation may be local, i.e. in one location as a "patch" or "spot" or may be in several areas as numerous patches, including ulcers, or contiguous involving a large area of tissue.

BRIEF DESCRIPTION OF THE DRAWINGS

FIG. 2G shows photographs of exemplary embodiments of a 3D printed stamps and inserts with the positive shape of a well, as one example of a specified different height as a stamp, e.g. for use in a 2.8 mm bioreactor. This stamp provides an insert that fit within the chamber.

FIG. 3A Overview of Epithelial surface (upper channel) showing exemplary primary adult human alveolar epithelial cells seeded on ECM made of Collagen IV, Fibronectin and Laminin.

FIG. 3B Overview of Vascular compartment (lower channel) showing exemplary primary adult microvascular endothelial cells are seeded on ECM made of Collagen IV and Fibronectin.

FIG. 3C is an expanded side view of tridimensional stoma showing exemplary primary adult human fibroblasts embedded within the stromal compartment.

FIG. 5A By measuring the displacement of the beads we can estimate the percentage of strain that cells feel on-chip when breathing motion is applied.

FIG. 5B Beads are displaced when vacuum is applied to the later chambers of the chip.

FIG. 6A Laminar flow is the normal condition for blood flow throughout most of the circulatory system in the body. It is characterized by concentric layers of blood moving in parallel down the length of a blood vessel.

FIG. 6B Round shape commonly used for Petri dish and 2D cell culture and some organ-on-chip company (Tissues).

FIG. 7A Type II cells expressing low levels of ABCA3 along with much higher levels of Surfactant B. Although higher levels of these markers for Type II cells were induced by I-FN-E, as shown in FIG. 7B, I-FN-E, induced much lower levels of PDPN, a biomarker for Type I cells.

FIG. 7B Type I cells expressed the highest levels of PDPN and other biomarkers when cultured on Coll IV, Fibronectin and Laminin. The combination of Collagen IV, Fibronectin and Laminin promotes the expression and clear segregation of both Type I/Type II cell markers.

FIG. 8A shows immunofluorescent micrographs of cells cultured on, left to right, Coll I vs. Coll IV vs. Coll IV-FN-L. HTI-56 (Type I-Like cells) (red) and HTII-280 (Type II cells) (green). Overlapping colors appear yellow.

FIG. 8B shows a chart comparing a percentage of non-overlapping signal (%) of Type I-like and Type II-like Biomarkers vs. ECM compositions (left to right): Coll I, Laminin, Fibronectin, Coll IV, Gelatin, Elastin, Coll IV-FN-L.

FIG. 9A cells cultured on Collagen I coated surfaces show Irregular cell morphology and large Type I/Type II overlap area (yellow) indicate poor cell differentiation.

FIG. 9B cells cultured on Collagen IV-Fibronectin-Laminin promotes the segregation of both Type I/Type II cell markers on different cell populations.

FIG. 10A-D Viability of the fibroblasts in different media was tested by caspase 3/7 and quantified per field of view.

FIG. 10A Type II (green) and Type I cells cultured in SAGM.

FIG. 10B schematic of chip (left) showing a light microscopic image of Touldine blue stained cross section of epithelial and stroma areas. Inset show a higher magnified area of the stroma region.

FIG. 10C SAGM increases percent of fibroblast apoptosis (per field of view) on Day 10.

FIG. 10D EMG2-MV increases percent of alveolar apoptotic cells (per field of view) on Day 10. Effect of different media compositions on cell viability and maintenance of tissue-specific markers.

FIG. 11A-I shows immunofluorescent images of cells stained for epithelium HTI Type I (colored red) and Type II HTII biomarkers (colored green); FIG. 11B, E, H endothelial cells (colored green) in addition to FIG. 11C, F, I fibroblast cells in the stroma area where nuclei are colored blue and turquoise colored apoptotic identified by caspase antibodies. FIG. 11A, B, C. ALI-M/M199. FIG. 11D, E, F EGM-2MV: gold standard for growing endothelial cells. EGM-2MV shows negative effects (EMT and lack of differentiation) on morphology of the epithelium that is confirmed by the apoptosis staining (FIG. 11C, F, I). FIG. 11G, H, I SAGM: gold standard for growing epithelial cells however SAGM induces death of endothelial cells (FIG. 11H).

FIG. 14 shows a transmission electron microscope image of Type II-like cells containing vesicles filled with presumable surfactant protein (black arrows) and numerous microvilli (white arrowheads). White arrow points to a tight junction between cells.

FIG. 15A shows double staining for VE-Cadherin (red) and DAPI stained nuclei (blue).

FIG. 15B shows double staining for PECAM-1 (DC31) (green) and DAPI stained nuclei (blue).

FIG. 15C shows double staining for VWF (pink) and DAPI stained nuclei (blue).

FIG. 15D shows a merged image of FIG. 15A-C showing endothelial cells with outlined by PECAM-1 (DC31) (green).

FIG. 16B shows fibroblasts cultured in SAGM. Lower inset shows a higher magnification of stained fibroblasts. The lower bar is a z-stack showing fibroblasts in the epithelial layer along with some Type II cells and few Type I cells.

FIG. 16C shows fibroblasts cultured in EGM2. Inset shows a higher magnification of activated-elongated fibroblasts. The lower bar is a z-stack showing fibroblasts in the epithelial layer along with many Type II cells and few Type I cells.

FIG. 16D shows fibroblasts cultured in ALI-M/M199. Inset shows a higher magnification of stained fibroblasts. The lower bar is a z-stack showing fibroblasts in the stroma area below many Type II cells and many Type I cells.

FIG. 17A Left: immunofluorescent image of a fibroblast cell (pink) in relation to Type I (red) cells. Type II cells are stained and colored green. Nuclei are stained and colored blue. The upper bar is a representative z-stack showing a fibroblast extending into the epithelial layer next to a Type I cells. Middle: the same image as on the left but with the red Type I cells removed showing fibroblasts next to nuclei of uncolored cells further supporting the observation that the fibroblasts are contacting mainly the Type I cells. Type II cells are stained green. Right: image from a Supplementary Movie 2: showing that fibroblasts protruding towards the alveolar epithelium.

FIG. 17B shows a brightfield image of an H&E stained cross section of an embedded epithelial layer showing a stoma area.

FIG. 17C shows that relative gene expression of biomarkers for Type I and Type II cells are increased in co-cultures containing fibroblasts, including Type I biomarkers HOPX and AQP5 and surprisingly showing a major increase in Surfactant B expression of Type II cells.

FIG. 17D stretching of the membrane enhances Type II biomarkers but not Type I biomarkers.

FIG. 18A-B fluorescent micrographs show fibroblast morphology and viability in the stretchable open top device.

FIG. 18A Schematic of open top device. Fluorescent micrographs of immunostained cells. Phalloidin (pink) staining of F-actin expressed by fibroblasts in the stroma area. FIG. 18B Type I-like cells (green). Stained nuclei colored blue.

FIG. 18C live (green)/dead (red) staining of fibroblasts.

FIG. 20A microfluidic device (chip) ALI-M/M199 (grey); and microfluidic device (chip) (3+3) & (6+3) (gold). Transwell cells incubated in SAGM with 2% fetal calf serum (blue); Transwell cells incubated in ALI-M/M199 (boosted) (orange).

FIG. 20B ALI-M/M199 (boosted) showing exemplary fluorescent microscope images of immunostained biomarkers of functional Type II cells: Surfactant protein B (SP-B) (red); T1-α (red); Surfactant protein C (SP-C) (green); Na+/K+ pump (red); E-cadherin (green); epithelial sodium channels (αENaC) (red) located on the apical membrane of epithelial cells: co-staining of one cell: ABCA3 left (green) and LAMP3 right (red); ZO-1 (tight junctions) (red). Nuclei are colored blue in some images.

FIG. 21A (right panel) shows induction of alpha smooth muscle Actin (alpha-SMA) (green) and lack of ICAM-1 (red) compared to vehicle treatment (left panel). E-cadherin is shown in pink.

FIG. 21B left chart shows quantitation of alpha-SMA+ nuclei between vehicle (left) and TGF-β1 induced (right). Right chart shows number of DAPI stained cells per field of view.

FIG. 21C left chart shows 2^ddCT fold changes in alpha-SMA RNA expression measured by qRT-PCR (normalized to control) in relation to alpha-SMA+ nuclei in the epithelium at 24 and 72 hours over low amounts of TGF-β1. Right chart shows 2^ddCT fold changes (normalized to control) in relation to alpha-SMA+ nuclei in the endothelium at 24 and 72 hours over low amounts of TGF-β1.

FIG. 22A Effect of LPS on Vascular Expression of ICAM1. Left panel shows intercellular adhesion molecule-1 (ICAM1) (red) induction in co-cultures of Epithelium/Fibroblasts/Vasculature. Middle panel shows ICAM1 (red) induction in co-cultures of Epithelium/Vasculature. Right panel shows little ICAM1 (red) induction in co-cultures of Fibroblasts/Vasculature without epithelium. Representative images (20×) of endothelial cells (HMECs) lining the vascular surface of the Chip fixed and stained for ICAM1 (red) at 24 h post LPS treatment of the alveolar epithelial compartment. Nuclei are colored blue.

FIG. 22B shows secretion of exemplary pro-inflammatory cytokines in the co-presence of epithelial cells. IL-6, il-8 and MCP-1 have 40-90 fold increases in relation to untreated controls.

FIG. 22C Detection of exemplary Lung-Specific Cytokines and Chemokines, IL-6; IL-8; MCP-1 and RANTES, in response to LPS stimulation. Co-cultures of Epithelium/Fibroblasts/Vasculature induced higher levels of cytokines than co-cultures of Epithelium/Vasculature; Fibroblasts/Vasculature or Vasculature alone.

FIG. 25 shows exemplary fluorescent imaging of biomarker staining where $H_2O_2$ (48 h) treatment induces redistribution of E-Cadherin. Control left panel, $H_2O_2$ (10 mM) (48 h) treatment right panel. E-cadherin (green) actin (pink) and nuclei blue.

FIG. 26A Exemplary Dextrin leakage into the alveolar side in response to $H_2O_2$ 48 hours alone, GSK alone, or $H_2O_2$ in combination with GSK FIG. 26B Exemplary Dextrin leakage into the alveolar side in response to H₂O₂ 48 hours in combination with one of the small molecules: GSK, JQ1 and Bardoxolone—pink bars. Pretreatment levels blue bars.

FIG. 26C Exemplary Dextrin leakage into the alveolar side over time, 0-48 hours.

FIG. 26D Exemplary H₂O₂ and GSK induced changes in gene expression of NQO1; SRXN1 and ICAM1.

FIG. 26E Exemplary lactate dehydrogenase (LDH) release measured in effluent in response to H₂O₂ and small molecules: GSK, JQ1 and Bardoxolon.

FIG. 26F Exemplary lactate dehydrogenase (LDH) release measured in effluent over time, 0-48 hours.

GENERAL DESCRIPTION OF THE INVENTION

Figure 1A:
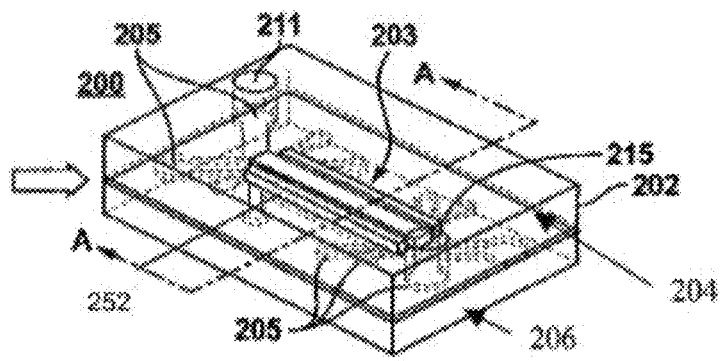
FIG. 1A Illustrates a perspective view of a microfluidic device with microfluidic channels in accordance with an embodiment.

An in vitro microfluidic "organ-on-chip" device is described herein that mimics the structure and at least one function of specific areas of the epithelial system in vivo. In particular, a stem cell-based Lung-on-Chip is described. This in vitro microfluidic system can be used for modeling differentiation of cells on-chip into lung cells, e.g., a lung (Lung-On-Chip), bronchial (Airway-On-Chip; small-Airway-On-Chip), alveolar sac (Alveolar-On-Chip), etc., for use in modeling disease states of derived tissue, i.e. as healthy, pre-disease and diseased tissues. Additionally, stem cells under differentiation protocols for deriving (producing) differentiated lung cells off-chips may be seeded onto microfluidic devices at any desired point during the in vitro differentiation pathway for further differentiation on-chip or placed on-chip before, during or after terminal differentiation. Additionally, these microfluidic "stem cell-based Lung-on-Chip" allow identification of cells and cellular derived factors driving disease states in addition to drug testing for diseases, infections and for reducing inflammation effecting lung alveolar and/or epithelial regions. Further, fluidic devices are provided seeded with primary alveolar cells for use in providing a functional Type II and Type I cell layer, wherein Type II cells express and secrete surfactants, such as Surfactant B (Surf B; SP-B) and Surfactant C (Surf C; SP-C), which were detectable at the protein level by antibody staining in Type II cells. A number of uses are contemplated, including but not limited to, for use under inflammatory conditions, in drug development and testing, and for individualized (personalized) medicine. Moreover, an ALI-M was developed for supporting multiple cell types in co-cultures with functional Type II and Type I cells.

Therefore, the merger of at least two complementary frontier technologies, microfluidic chips and human stem cell engineering, are contemplated to deliver urgently needed in vitro platforms.

Organs-on-Chips, microengineered biomimetic vascularized tissue platforms, mimic the mechanochemical environment and physiological functions of human organs while concurrent advances in generating and differentiating human stem cells promise a renewable supply of patient-specific cells for personalized and precision medicine. Here, we discuss the challenges of modeling human lungs in vitro, evaluate past and current in vitro models including Organs-on-Chips, review the current status of using human pluripotent lung stem cells for in vitro lung tissue modeling, explore in depth how stem-cell based Lung-on-Chips can advance disease modeling and drug testing, and present a practical guide to engineering stem cell based-Lung-on-Chips.

I. Introduction

The lungs constitute the largest tissue interface between the human body and its environment. Exposed to an average of seven liters of inhaled air per minute, lungs are in direct contact with countless noxious particles, viral or bacterial pathogens, hazardous chemicals or toxic gases. As formulated by Green et al, "Each day a surface as large as a tennis court is exposed to a volume of air and contaminants that would fill a swimming pool" (1). Not surprisingly then, lungs are affected by numerous deadly acute and chronic conditions that constitute an immense global health burden. Indeed, respiratory diseases are directly responsible for one in six deaths worldwide (2), while chronic respiratory conditions affect more than one billion people worldwide (3). Among all respiratory diseases, five account for the majority of morbidity and mortality worldwide: chronic obstructive pulmonary disease (COPD), asthma, acute respiratory infections, tuberculosis, and lung cancer (4). Recent reports suggest that onset or aggravation of respiratory disease caused by air pollution, including household air, ambient particulate and ozone, is responsible for 6.5 million deaths annually, a number likely to increase even further in the future (5). It is therefore urgent to develop new tools to study respiratory diseases, understand the underlying mechanisms, and find new therapeutic strategies in order to reduce the health burden caused by lung diseases.

Studying lung diseases and assessing drug efficacy and toxicity involves physiologically relevant models that faithfully recapitulate human lung tissue. While animals, especially rodents, have provided seminal insight into lung physiology and pathophysiology, they are limited in recapitulating the development, structure, disease symptoms, and responses of the human respiratory system, providing a strong rationale for developing and investigating human in vitro lung models for disease modeling, drug discovery, and drug testing (6, 7). For instance, the timing of lung developmental events differs markedly between mice and humans. The prenatal saccular stage, in which alveolar sacs with distinguishable alveolar cell types form and surfactant secretion begins, takes place relatively earlier, and postnatal differentiation of immature saccules continues for a relatively longer time in humans compared to mice. This different pace of development results in a greater degree of branching and complexity of human distal lung structures including respiratory bronchioles, alveolar ducts and associated alveoli. Cellular composition also differs between mouse and human lung. For example, in the mouse airways, mucus-producing goblet cells are rare and secretory club cells (also known as Clara cells) are abundant, whereas the opposite is found in human airways (8). Further, many gene mutations induce different, if any, respiratory symptoms in mice compared to humans (9). Taken together, these fundamental differences demonstrate that animals are imperfect models for a range of human lung diseases and their drug treatment, necessitating the need for better preclinical models of human lung physiology.

In the past 10 years, advances in tissue engineering and soft lithography techniques have converged to give rise to Organs-on-Chips, miniaturized microfluidic cell culture platforms that recreate functional and micro-environmental features of human organs in vitro (10). The idea here is not to rebuild an entire human lung with its intricate architecture, which remains technically impossible at this time and would also greatly complicate the experimental manipulation, analysis and interpretation of the engineered system. Rather, the promise and great benefit of Organs-on-Chips lies in their ability to recreate well-defined functional units of the lung, such as, the alveolar epithelium-blood capillary interface, or the mucociliary barrier of the small airways. Each specific Lung-on-Chip model can be used to isolate, amplify, and systematically combine specific cellular and acellular components of the tissue and dissect their interaction and individual roles in health and disease processes.

Concurrent with the advances in Organs-on-Chips technology, the field of developmental biology has made tremendous progress towards efficient culture and differentiation of stem cell-derived human lung tissue in the form of spheroids or organoids (11). While stem cell technology enables precise modeling of virtually any human tissue, and long term cultures of patient-derived cells, Organs-on-Chips provide the cell microenvironment, biomechanical forces, vascular circulation of immune cells, and sampling capabilities that organoids lack. Thus, as described herein, combining both technologies is contemplated to create an advanced model of human lung tissue to study lung development and pathophysiology, evaluate drugs pharmacodynamics and pharmacokinetics (PK/PD), and discover new diagnostics and therapeutics.

The purpose of the following is to provide a survey of existing state-of-the-art Organs-on-Chip platforms that model human lung tissue and contemplate how this innovative technology can be converged with the field of lung stem cells to establish highly relevant models of lung development, respiratory diseases and drug PK/PD modeling (pharmacokinetic/pharmacodynamic modeling). Pharmacokinetic/pharmacodynamic modeling refers to techniques that combines pharmacologic disciplines of pharmacokinetics and pharmacodynamics.

II. Modeling Human Lung Alveolus Pathophysiology On-Chip

In general, several attempts were made to develop and characterize a functional alveolus unit on-Chip (61, 68, 69, 99, 100). These attempts aimed at recapitulating the alveolar-capillary interface by recreating the boundary between the lung's air sacs and its capillaries within a microfluidic system.

Some of the systems discussed herein include a closed chip design: a microfluidic chamber divided longitudinally into two parallel channels by a flexible, ECM-coated porous membrane that mimics the alveolar interstitium. Such designs support the growth of human alveolar (A549 cell lines (45, 61, 99) or primary (68, 69, 100)) epithelial cells at an air-liquid interface, while human pulmonary microvascular endothelial cells (HMVECs) or umbilical vein endothelial cells (HUVECs) line the opposite side of the same membrane and are exposed to flowing culture medium.

The use of elastic materials for membrane and chip housing enables linear or 3D cyclic stretch that mimics motions of a breathing lung and influences cell behavior (64-66). These platforms were applied to replicate diseases of the lungs; investigate mechanical stress and cell damage; explore immune cells recruitment and extravasation; and test drug efficacy and toxicity.

The first alveolus-on-a-chip, originally called "Lung-on-a-chip" was used to mimic complex physiological mechanisms such as diapedesis of circulating human primary neutrophils following stimulation of the alveolar epithelium with TNF-α or infection with a strain of E. coli (61). In this disease model of bacterial infection of the lung, the endothelium situated underneath the alveolar epithelium becomes activated, as indicated by a rapid increased expression of the adhesion molecule ICAM-1, and promotes adhesion and extravasation of perfused neutrophils. Because Organs-on-Chips are made of PDMS, a transparent polymer, the whole physiological process can be observed by real time, high resolution microscopy (61).

Similarly, the "Lung-on-a-chip" recapitulated silica nanoparticle-induced toxicity and uncovered a role of breathing motions in production of reactive oxygen species (ROS) as well as the cellular uptake of nanoparticles and their transport across both cell layers into the vascular channel (61). Another application of the original "Lung-on-a-chip" includes replication of human pulmonary edema through IL-2-induced lung toxicity (45). IL-2 was shown to induce limited pulmonary vascular leakage into the air channel under static conditions whereas physiological breathing motions increased vascular permeability. Furthermore, IL-2-induced toxicity could be pharmacologically inhibited by a TRPV4 inhibitor (45).

Another model of the lung alveolar epithelium on-chip, was applied to investigate the effects of mechanical strain and surface tension (propagation of the air-liquid interface) on cell death in A549 and murine primary airway epithelium (99). Whereas the original Lung-on-a-chip recapitulates a linear stretch, this alternative design contains a circular stretchable diaphragm whose downward deflection enables a 3-dimensional stretch of its tissue lining.

More recently, efforts were made to increase the chip's physiological relevance by using human primary alveolar epithelial cells and endothelial cells instead of cell lines. Stucki et al. designed another version of an alveolus-on-a-chip that also supports a 3D cyclic deformation (68). This study found that stretch affects barrier permeability and increases the metabolic activity of primary alveolar epithelial cells and the release of inflammatory markers compared to static conditions.

A complex model of intravascular thrombosis utilizing human primary alveolar epithelial and human umbilical vascular endothelial cells was also developed to assess antithrombic therapeutics (69). In this model, the insides of the vascular channel are coated with ECM then seeded with endothelial cells to prevent the perfused human whole blood from clotting. The study shows that treatment of the alveolar lumen of the epithelium-endothelium co-culture with lipopolysaccharides (LPS), molecules also known as lipoglycans and endotoxins and found in the outer membrane of Gram-negative bacteria, triggered thrombotic events. Conversely, LPS stimulation of endothelial cells alone did not lead to blood clot formation, thus recapitulating the tissue-tissue interface in a model of inflammation-mediated thrombosis.

A model of lung cancer was developed in an alveolus-on-a-chip (100). The model features an epithelium-endothelium interface with small proportion of non-small cell lung cancer tumor cells in the alveolar space that was used to investigate the influence of the bio-mechanical microenvironment on tumor cell growth and migration. The study shows that cyclic stretch limits tumor cells' invasion of the vascular compartment in addition to reducing the efficacy of the widely used class of cancer drugs, i.e. Tyrosine Kinase inhibitors, suggesting that local microenvironment cues may influence cancer cells growth and drug activity.

However, in most cases alveolus cultures, including cultures in other types of fluidic devices, derived from adult primary cells do not live long enough for experiments, such as for drug testing, cancer modeling, etc. In fact, typically primary alveolar cell populations comprising primarily Type II cells either degrade within a week and/or differentiate into terminally differentiated Type I cells, then die. In fact, under most culture conditions, primary Type II cells tend to spontaneously differentiate into Type I cells so it is difficult to produce or maintain surfactant-producing human Type II cells in culture. Because functions of Type II alveolar cells include self-renewal and production/regulation/secretion of surfactant proteins, the lack of viable Type II cells over longer culture time periods further limits the use of previously published and described Transwell and fluidic systems.

The ability to develop in vitro models that recapitulate human lung function would greatly advance the understanding of the mechanisms that underlie alveolus response to stimuli and facilitate the establishment of disease models to guide therapeutic discovery. Unfortunately, despite multiple methods for isolating human alveolar type II cells are published in literature (since the first report of the isolation of a surfactant-producing epithelial cell from lung of a rodent by Kikkawa and Yoneda, "The type II epithelial cell of the lung. I. Method of isolation." Lab Invest, 30(1): 76-84, 1974) there is limited success in creating functional human alveolus model that maintains alveolar functions, a differentiated alveolar phenotype, and the production of surfactant C. Some in vitro examples are described (PubMed reference indicators: PMID: 17255555; PMID: 6243488; PMID: 16143588; PMID: 12483282).

Current models, in addition of lacking cell specificity, have limited control over tissue structure and functions and failed to form a functional endothelium-lined vasculature that is needed for alveolar epithelium-endothelium barrier studies. Furthermore, it remains unclear which signals within the cellular microenvironment contribute more specifically to alveolar lineage specification and maturation, and as a result there is still no practical methods for providing populations of mature, functional, alveolar pneumocytes available for the development of in vitro models of human alveolar function.

Therefore, the lack of repeatable and reliable cultures of lung tissue as differentiated and functional human pneumocytes that survive for long-term culture, in particular in fluidic devices, is a significant limitation for use of in vitro human alveolar models to study alveolar functions, including but not limited to drug testing or regenerative medicine in relation to alveolar diseases. In part, further limitations are present because fluidic devices lack a stroma area for co-culturing additional stromal cell type(s) with epithelium, alveolar cells, and endothelium.

In part to overcome limitations of existing systems for growing primary alveolar cell cultures for simulating human in vivo human lung tissue, an open top stretchable fluidic device, including a stroma area for additional cell types, was developed for use with lung cells as an Alveolus-Chip. Specifically, embodiments of a microfluidic devices as an Alveolus-Chip enables long living cultures, at least 2-3 weeks, comprising functional Type II cells producing and secreting surfactant proteins in addition to providing populations of viable Type I cells. In fact, microfluidic Alveolus-Chip cultures produce surprisingly produce high enough levels of surfactant lipoprotein to measure surfactant at the protein level, e.g. by immunohistochemistry; ELIZA; HPLC purification and LCM/MS/MS analysis, in addition to electron microscope observation of multilammelar bodies presumably containing surfactant proteins. Moreover, in some embodiments, it appears that embodiments of a healthy Alveolus-Chip comprise cellular ratios of Type II to Type I cells in vitro approximating those ratios found in healthy human lung tissue in vivo.

Embodiments of an Alveolus-Chip comprise a transparent medical grade Polydimethylsiloxane (PDMS) microfluidic platform that possesses open-top capability created utilizing microchip manufacturing methods. It contains a continuously perfused hollow microchannels lined with living endothelial cells, which interface through a porous transparent elastic membrane with a stretchable chamber where is deposited a lung recreated stroma (3D collagen I hydrogel and Lung ECM in which are embedded lung fibroblasts). The recreated stroma serves as a scaffold for alveolar cells, which are seeded on the top of the 3D hydrogel in direct contact with fibroblasts.

This platform simulates the alveolar overall architectures by mimicking to the highest degree reached so far the tissue-tissue interfaces, chemical gradients, mechanical cues, and vascular perfusion occurring in the body and producing levels of tissue and organ functionality not achievable with other conventional 2D or 3D culture systems (PMID: 29925009; PMID: 2509388).

Alveolus-Chip supports dynamic fluid flow over cells attached to the surface of fluidic devices, a characteristic that has favorable implications in testing therapeutics in a pharmacologically relevant context. Using this platform, it is possible to study how pharmacological active compounds and therapeutics actively or passively across an endothelial barrier under flow, which is information that is contemplated for use to understand drug pharmacokinetics. In addition, since the Alveolus-Chip platform offers the possibility to flow human whole blood or circulating immune cells isolated from blood through the endothelium-lined channels, it also allows to investigate immune recruitment, collect cytokines and study pharmacokinetics under more physiological relevant conditions compared to a static culture system.

Simultaneous modulation of few signaling pathways that have been implicated in alveolar development enables the rapid and efficient adult primary alveolar cell conversion into more terminally differentiated cells that exhibit morphological, molecular and functional characteristics of mature adult alveolar pneumocytes.

By co-culturing the adult alveolar type II cell on a stroma layer (collagen I gel/Lung ECM with embedded lung fibroblasts) in contact with the endothelium in an organ-chip microfluidic device, we also developed a functional microfluidic device that mimics the tissue-tissue interface and some of the mechanical properties of the alveolar epithelium/capillary interface.

It also recapitulates some of the stromal interaction happening in the lung thus we contemplate using an Alveolar chip to study lung induced injury and other disfunctions in vitro. This model we named human Alveolus-Chip could offer a new way to study alveolar function, toxicity and mechanisms of alveolar disease in vitro.

Furthermore, a method for culturing and differentiating primary adult human alveolar cells is described herein, using an open top stretchable fluidic device, including a stroma area. Alveolar cells cultured as described herein using a fluidic device, express markers of the mature phenotype (Type I, Type II, Surfactant B, surfactant C, Aquaporin 5, Podoplanin, ABCA3 and Lamp-3) and exhibit the ability to hold air-liquid interface for more than 10 days, when co-cultured with primary human lung microvascular endothelial cells and primary adult lung fibroblasts.

We also show through H&E, Immunofluorescence, SEM and TEM that alveolar cells produce junctions, basement-membrane collagen, lamellar body and recapitulate the natural tissue-tissue interface of the alveolus, as well. We further validated the capability of the system to predict human responses by testing several classes of pharmaceutical compounds such as small molecule (GSK, JQ1 and Bardoxolone), gluco-corticosteroid(s), and cytokine (TGF-β) in a dose response fashion. The results of our study using organ-chips suggest that this approach permits to more closely mimic the human lung organ-specific physiology and to generate response to drug predictive of the response in vivo. Our approach based on better mimicking human organ microenvironment allowed to enhance alveolar cell differentiation and recreate functions of the alveolus. We also hypothesize that improving tissue organization applying this new technology to other organ might enable the development of novel in vitro models, that in a future not too far could potentially serve as replacements for animals use in drug discovery and toxin testing, may facilitate drug development and be applied in personalized-medicine applications.

A. Cell Sources.

One challenge in developing in vitro alveolar model is identify a cell source that is representative of the alveolar microenvironment. Unfortunately, static 2D cultures used to purify and expand cells often select specific pneumocyte subpopulation which exhibit dramatically different levels of growth and differentiation from the normal population of the lung which they are derived from. Consequently, growth properties, dynamic of differentiation and drug responses significantly differ based on the organ-specific microenvironment cells are derived from and/or depending on the specific technique has been used to isolate them. As a result, most drug development programs result in discovery of therapeutics that act efficiently only on the specific subpopulation which might not be representative of the entire organ, i.e. may have desired effects upon epithelial cells while detrimental to endothelium, and not being effective when tested in vivo. On the other side, the use of in vivo animal models resulted extremely difficult and expensive for testing drugs, and in more than 90% of the case unpredictive of the human response mostly because of interspecies differences (altered progression of disease, difference in metabolism and execration of toxin/metabolites, difference in toxicity and efficacy of pharmaceuticals). Furthermore, current limitations in imaging and chemical analysis limit the capability to monitor specific tissue and/or in situ cell behavior in vivo animal models.

The lung consists of 4 major biological distinct components: trachea, bronchi, bronchioles and alveoli as tiny air sacs. These air sacs are where air-exchange occurs between red blood cells in nearby capillaries and alveolar cells (also known as pneumocytes) that form an epithelial layer providing a cellular barrier between body tissues and air (i.e. gases, mainly $O_2$ and $Co_2$ along with whatever else is breathed into the alveolar areas) in the lung. The alveolar surface exposed to the gaseous environment is lined by two distinct type of epithelial cells: alveolar type I (ATI) which phenotypically looks like squamous epithelial cells that cover appreciatively 93-97% of human epithelial lung surface and alveolar type II (ATII) cells which are cuboidal epithelial cell producing surfactants, and are progenitor cells for providing terminally differentiated alveolar type I cells (PMID: 12483282).

In other words, these two cells types form the blood-air barrier through which circulating blood gets enriched with oxygen (or other gases) breathed into the air sacs. The alveolar capillaries are encased by stroma, which is populated with highly differentiated/specialized mesenchymal cell types, such as fibroblasts, that constitutes a major proportion of the lung mass/stroma. Indeed, most acquired and hereditary forms of lung disease, as well as some drug toxicities, are characterized by fibroblast loss or dysfunction, which results in Idiopathic Pulmonary Fibrosis (IPF), Chronic obstructive pulmonary disease (COPD) and other type of lung degeneration (PMID: 19556518).

Thus, in some embodiments, lung chips described and/or referenced herein are contemplated to be used with stem cells for providing stem cell-based microfluidic lung chips. In some embodiments, stem cells are embryonic stem cells. In some embodiments, stem cells are adult stem cells; such as alveolar epithelial type II (AT2) cells that function as tissue stem cells in the lung. In some embodiments, lung chips described and/or referenced herein are used with primary alveolar cells, including but not limited to human primary alveolar cells derived from induced pluripotent stem cells (including cell lines) (iPSC) or other types of stem cells, e.g. as early lung progenitor cells, human primary alveolar cells isolated from biopsies, human primary alveolar cells derived from cultures of human primary alveolar cells, passaged human primary alveolar cells, i.e. from cultures of human primary alveolar cells, etc. In preferred embodiments, human primary alveolar cells preferably include alveolar epithelial type II (AT2) cells.

B. Open-Top Stretchable Chip.

Open-Top functionality-Compartmentalization for visualization: To mimic the topography of the natural human pneumocyte stromal capillary wall the openable Open-Top lid design allows deposition of a collagen I hydrogel with embedded fibroblast, e.g. by a 200 μl pipette. To facilitate optical confinement of the epithelial cells, the gel is cast within a stamp forming a flat gel containing embedded fibroblasts. Additionally, the use of a stamp for molding the hydrogel allows for easier the imaging of the system. Example shown in FIG. 2G.

A multifunctional microfluidic device that recapitulates some of the fundamental structural, functional and mechanical properties of a three-dimensional cross-section of the human lung epithelium-stroma-capillary endothelial (pneumocyte stromal capillary) wall using a previously published organ-on-a-chip fabrication protocol.

One embodiment of a microfluidic device is composed of a flexible poly(dimethylsiloxane) (PDMS) elastomer and contains two opposed, parallel microchannels, a top fluidic channel 200 μm height×600 μm width with variable geometry, and a bottom spiraled shaped channel 400 μm height× 600 μm width which is separated from a circular chamber (stroma compartment) by a porous flexible PDMS membrane (50 μm thick and 7 μm diameter pores with 40 μm spacing) (examples shown in FIG. 2C-F).

Figure 2A:
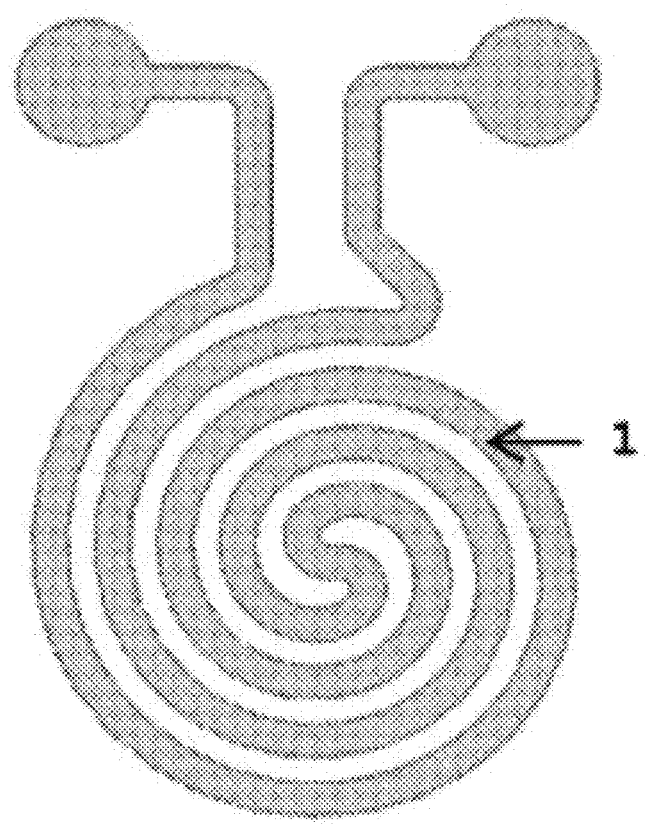
FIG. 2A shows a schematic of one-embodiment of spiral microfluidic channels 1851 in an open top device 1800 shown in FIG. 2D.
Figure 2B:
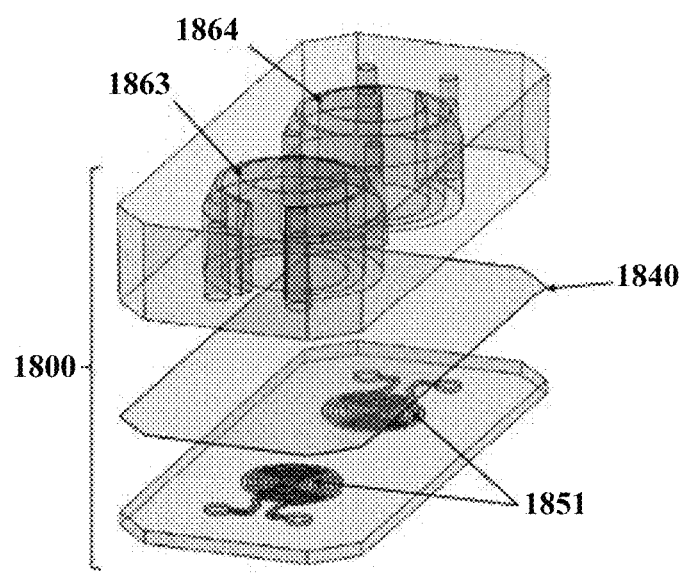
FIG. 2B Illustrates an exploded view of one-embodiment of an open top device 1800 a top chamber 1863 and 1864 and ports and a microfluidic channel in a bottom piece 1851, separated by a membrane 1840 as described herein.
Figure 2C:
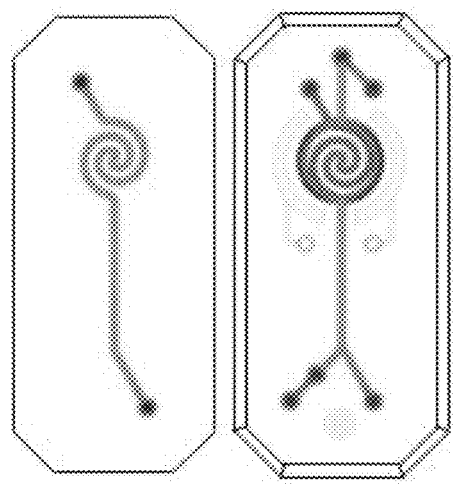
FIG. 2C shows a schematic of one-embodiment (top view) of chip 1800 with a single chamber showing one embodiment of lower channel 1851 (left) and a combined view of an upper (blue) and lower channel (red). Black dots represent inlet and outlet ports.
Figure 2D:
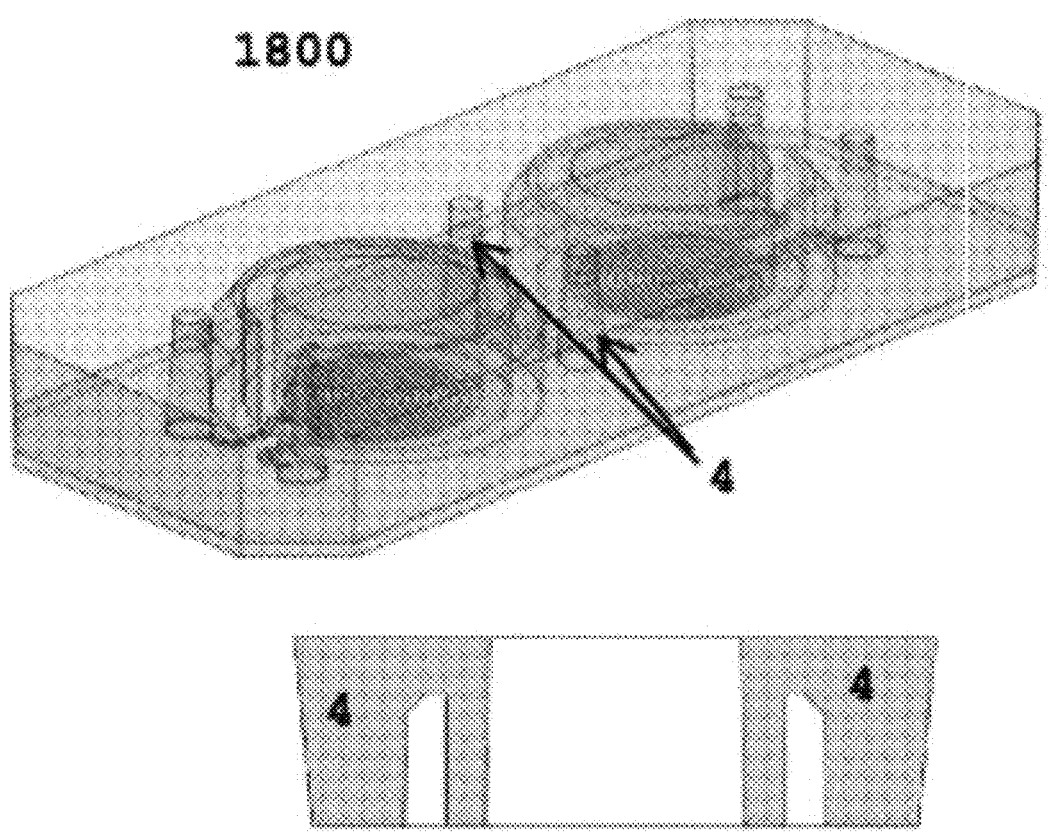
FIG. 2D shows a schematic of one-embodiment of chip 1800 where arrows point to optional vacuum chambers 4, as shown in cross section in the lower schematic.
Figure 2E:
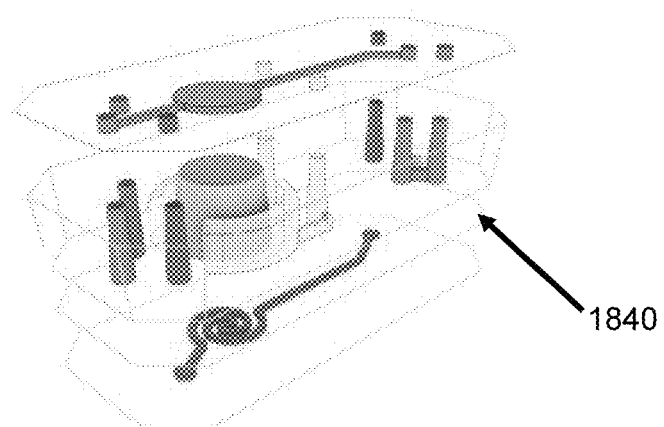
FIG. 2E Illustrates an exploded (layer by layer) view of one-embodiment of an open top device as shown in FIG. 2C, showing membrane 1840.
Figure 2F:
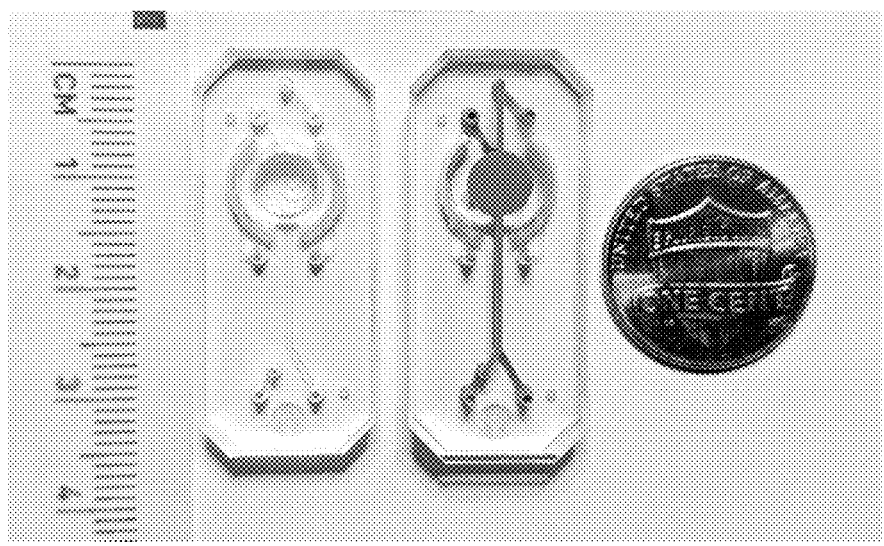
FIG. 2F shows a photograph of one embodiment of an actual open top chip, cm scale on the left, actual chip in the middle with one view showing an overlay of an upper channel (blue) and lower channel (red), with respect to a US Penny for size.
Figure 2H:
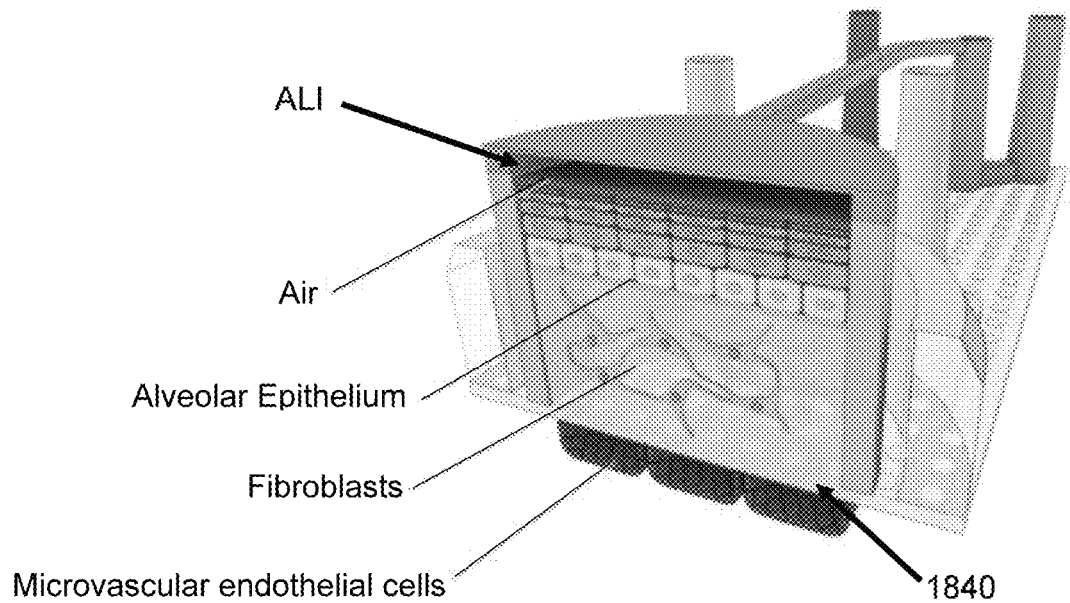
FIG. 2H shows an exemplary schematic of one embodiment of a 3D Alveolus Lung On-Chip as an open top microfluidic chip demonstrating an air layer on top of an alveolar epithelium layer overlaying a stromal area, including fibroblasts, in an upper channel with microvascular endothelial cells in a lower channel, e.g. showing a cut away view of multiple areas (rectangles) as part of one spiral channel.
Figure 2I:
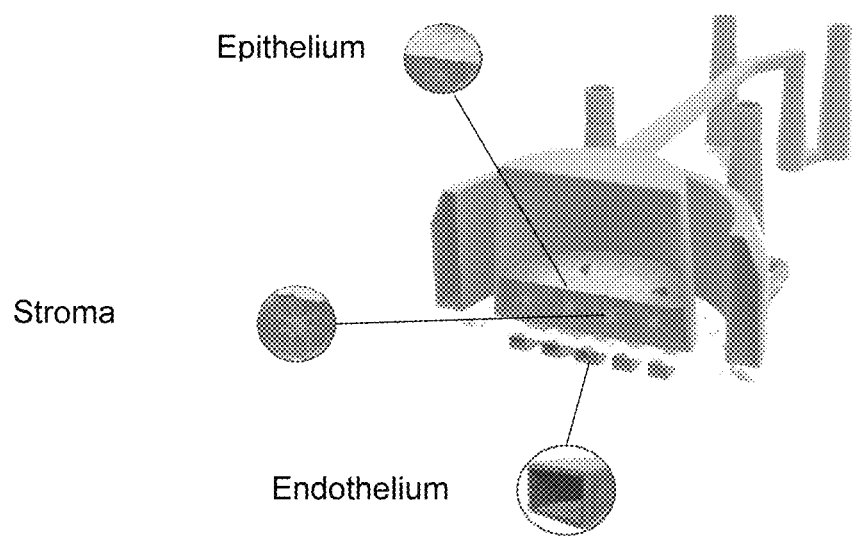
FIG. 2I shows an exemplary schematic of one embodiment of a 3D Alveolus Lung On-Chip as an open top microfluidic chip demonstrating an air layer on top of an alveolar epithelium layer overlaying a stroma area, including fibroblasts (pink), in an upper channel with microvascular endothelial cells in a lower channel, e.g. showing a cut away view of multiple areas (rectangles) as part of one spiral channel.

In preferred embodiments, a stroma compartment (area) is filled with collagen I hydrogel (and/or other different lung ECM components) where primary lung fibroblasts are embedded (recreated or artificial or simulated lung stroma) (FIGS. 2H and 2I).

We cultured pneumocytes on top of (or alternatively on direct contact with) the recreated lung stroma that was coated with a mix of the Collagen IV-Fibronectin-Laminin (Col IV-Fib-Lam) or other components of the basal lamina. Instead, primary human lung endothelial cells were cultured inside the entire bottom channel. The spiraled section/portion of the bottom channel interacts directly with the basal side of the recreated stroma (opposite side of the hydrogel) by the PDMS porous membrane recreating the lung epithelium-stoma-capillary endothelium interface (FIGS. 2H and 2I).

Figure 6A:
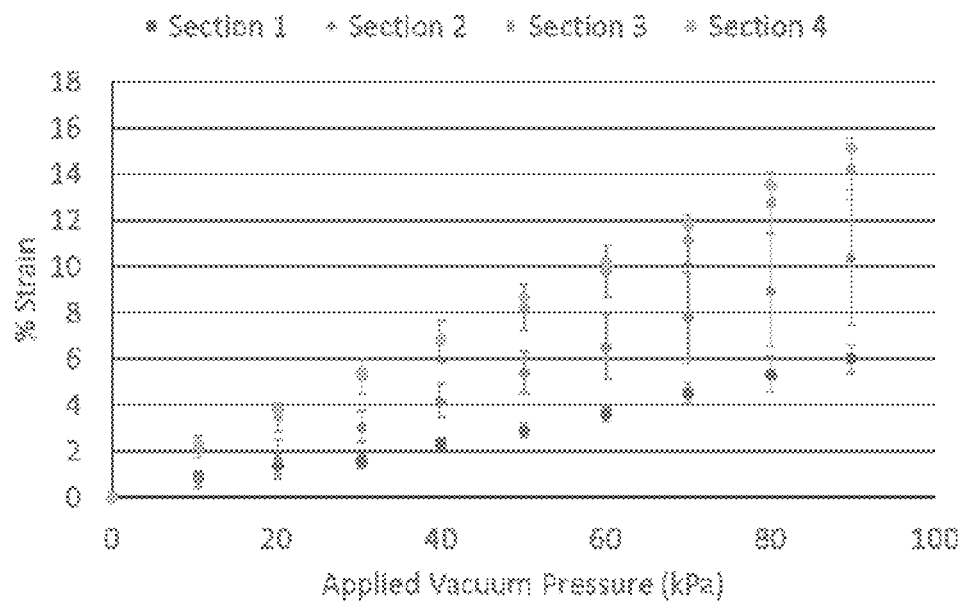
FIG. 6A-B Open-Top Alveolus-Chip Incorporates A Vascular Compartment Designed to Provide Constant Laminar Flow. Spiral shape of the vascular compartment of the Open-Top Chip is design to maintain laminar flow along the entire length of the chamber, a parameter required to perfuse blood or blood cells (such as PBMC) under physiological relevant and in some embodiments, under conditions that does not activate endothelial cells.
Figure 6B:
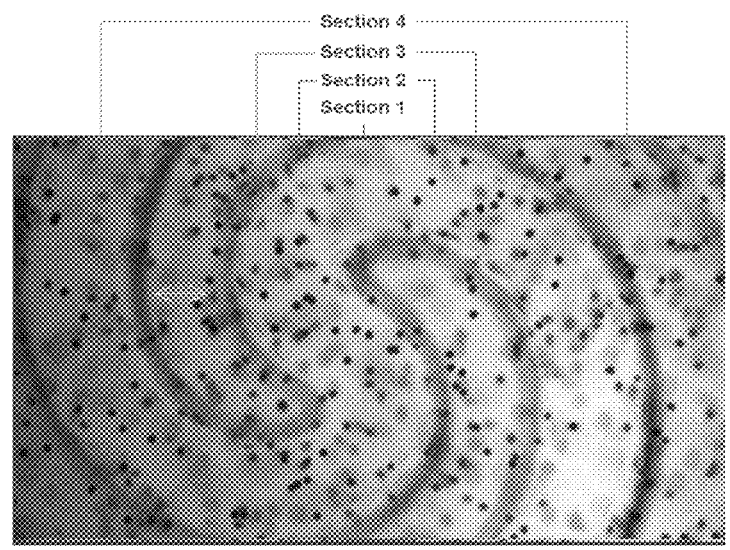

PDMS porous membrane has primarily structural function to physically contain the hydrogel in place. We opted for a spiraled shaped vascular compartment of the Open-Top Chip to maximize the area of fluid in contact with the recreated stroma and simultaneously maintain laminar flow along the entire length of the chamber, a parameter required to perfuse blood or blood cells (such as PBMCs) under physiological relevant and not activating conditions. The spiral-geometry of the vascular chamber allows fine control of the wall-shear rate along the entire endothelial compartment differently from other geometry (FIG. 6A-B).

In the Open-Top Chip we opted for a spiraled shaped vascular compartment for two main reasons: first, the spiraled shape maximizes the area of PDMS porous membrane in contact with the recreated stroma and second it permits to maintain a laminar flow along the entire length of the channel. This spiral shape additionally allows for perfusion (flow) of blood or blood cells (such as peripheral blood mononuclear cell (PBMC) refers to any peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei) under physiological relevant and not activating conditions. The spiral-geometry of the vascular chamber allows fine control of the wall-shear rate along the entire endothelial compartment differently from other geometry (FIG. 5A).

Figure 5A:
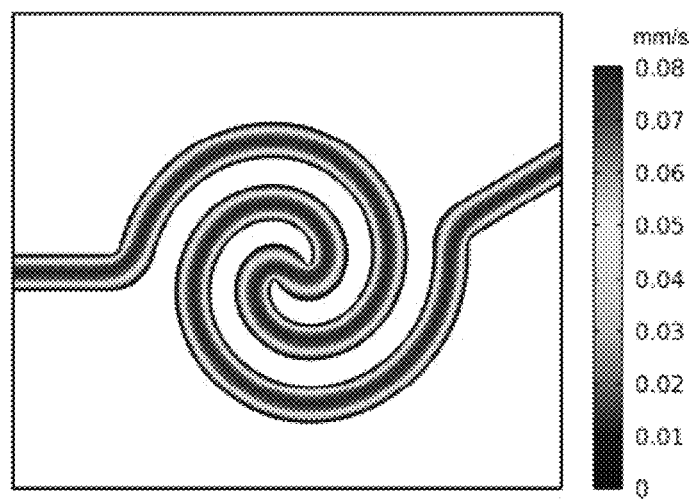
FIG. 5A-B Open-Top Alveolus-Chip Incorporates Stretchable Open-Top Design: Pneumatic Stretching Optimization. By measuring the displacement of the beads we can estimate the percentage of strain that cells feel on-chip when breathing motion is applied.
Figure 5B:
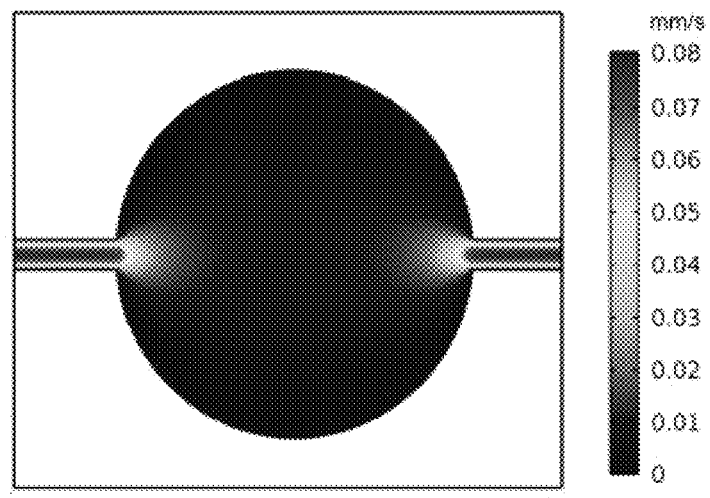

FIG. 5A-B Open-Top Alveolus-Chip Incorporates A Vascular Compartment Designed to Provide Constant Laminar Flow. Spiral shape of the vascular compartment of the Open-Top Chip is design to maintain laminar flow along the entire length of the chamber, a parameter required to perfuse blood or blood cells (such as PBMC) under physiological relevant and in some embodiments, under conditions that does not activate endothelial cells.

FIG. 5A Laminar flow is the normal condition for blood flow throughout most of the circulatory system in the body. It is characterized by concentric layers of blood moving in parallel down the length of a blood vessel. A heat map of flow rate mm/s is shown at the right.

FIG. 5B Round shape commonly used for Petri dish; 2D cell culture and some organ-on-chip company (tissues), also showing a heat map of flow rate mm/s when a round shape is used with inlet and outlet ports in an open top fluidic device, such as described herein.

C. An Open-Top Alveolus-Chip Incorporates Mechanical Stretching and Vascular Fluid Flow.

The role of mechanical forces acting on alveolar cell (epithelial, endothelial and mesenchymal cells) during respiration has been controversially discussed, with no uniquely accepted theory about their biological and physiological relevance. Much of the uncertainty about physiological role of mechanical forces acting on alveolar cell is due to technical difficulties (such as limited imaging and sampling systems, small size of the alveolar cell and relatively large cell displacement during breathing) in analyzing the phenomenon. Therefore, most of the information about Alveolar/lung mechanics has been largely inferred from results of pulmonary functional tests and static histopathology, which although have improved our understanding of lung are not specific. However, along the scientific world there is a common agreed hypothesis that mechanical forces have a role in cell behavior, and therefore to better understanding alveolar based diseases and dysfunctions more direct evidence about alveolar mechanics is needed.

Figure 1B:
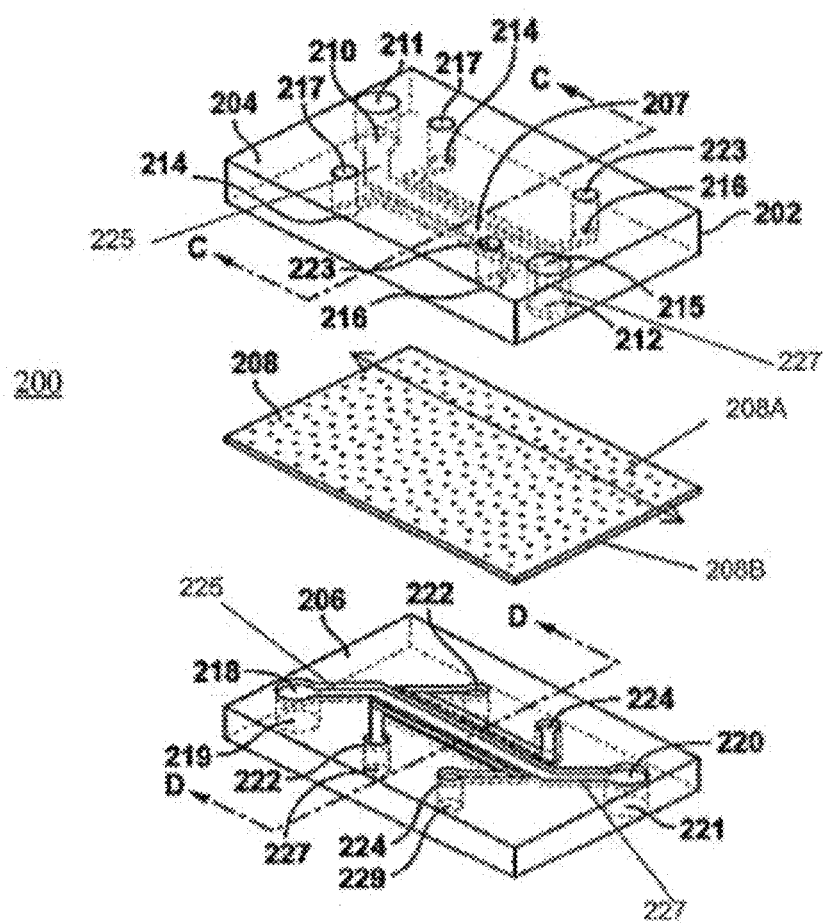
FIG. 1B Illustrates an exploded view of the device 200 in accordance with an embodiment, showing a microfluidic channel in a top piece 207 and a microfluidic channel in a bottom piece, separated by a membrane 208.
Figure 1C:
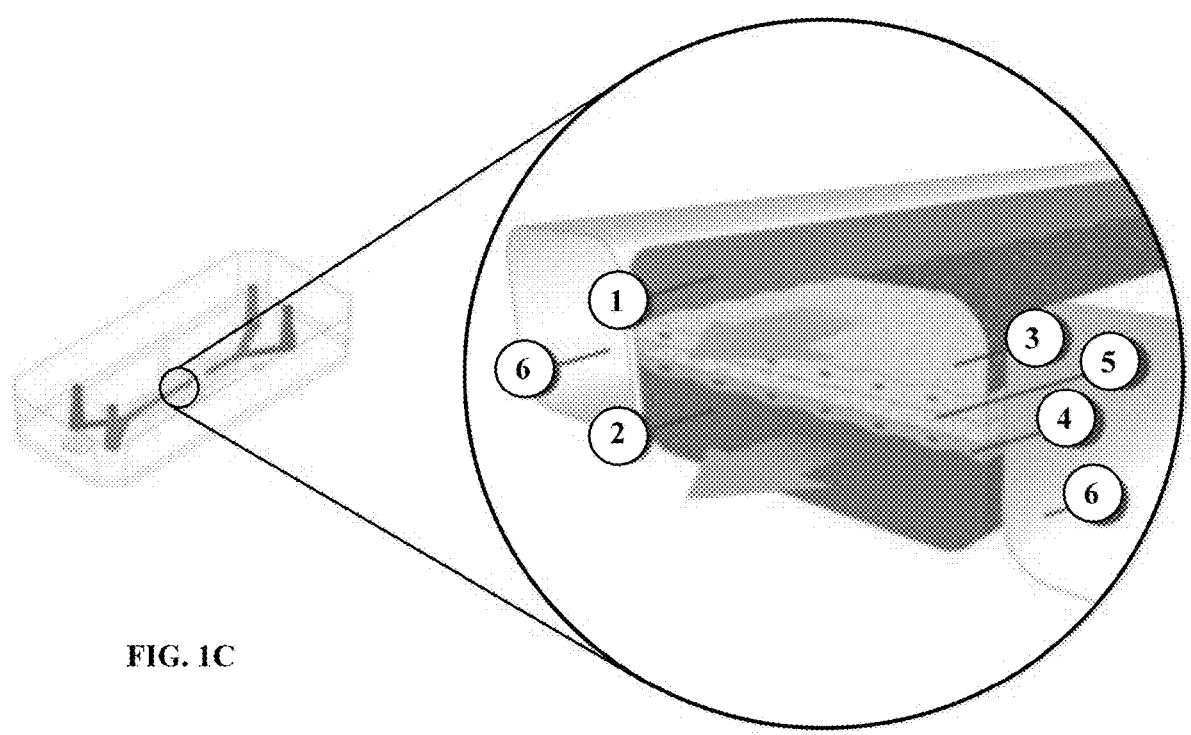
FIG. 1C shows cells in relation to device parts in a closed top chip, e.g. upper and lower channels and optional vacuum chamber. 1. Air channel; 2. Vascular channel (lower); 3. Lung tissue (e.g. epithelial cells); 4. Capillaries (e.g. endothelial cells); 5. Membrane; and 6. Vacuum Channels.

Thus, embodiments of closed top fluidic devices were configured for simulated breathing motions, see FIG. 1C. Additional descriptions are provided herein.

Embodiments of Open top fluidic devices comprising a stroma compartment were also configured for simulating breathing motions. Thus, in one embodiment, within the circular chamber both stroma and epithelium undergo mechanical stretching (e.g. breathing motion). Specifically, to model the cyclic mechanical strain observed in living alveoli (repetitive stretching/relation cycle to which alveolar cells undergo during breathing) we also incorporated two curved shaped hollow vacuum chambers on either sides of the stromal compartment (FIGS. 2H and 2I). The vacuum chambers were specifically designed to generate a deformation liner proportional to the intensity of the applied suction (negative pressure). When negative pressure in the range 0 to 90 KPa is applied the system, it generates a corresponding percentage of strain in the range of 0 and 17% strain (defined as displacement between beads/particles in the hydrogel body mass relative to a reference length in a specific plane, respectively. This range was chosen specifically because there is a quasi-linear dependence between the amount of suction applied and the intensity of stretching generated. A module produced in house allowed to produce suction cycle of 0.2 Hz which generated in turn a cyclic stretching/relaxation cycles of 5 seconds on the adherent epithelial cell monolayer and on the fibroblasts embedded into the collagen I hydrogel scaffold (S1), see FIG. 2D vacuum chambers (4), are used to mimic breathing by stretching the membrane 1840.

Stretching. To model the cyclic mechanical strain observed in living alveoli (repetitive stretching/relation cycle to which alveolar cells undergo during breathing) two curved shaped hollow vacuum chambers were incorporated into an open top fluidic device, located on both sides of the stromal compartment (FIGS. 2H and 2I)).

A cyclic suction (negative pressure) cycle of 0.2 Hz at 50 kPa was applied that produced a cyclic stretching/relaxation cycles of 5% strain in section 2 of the fluidic device. Strain refers to displacement between beads/particles in the hydrogel body mass relative to a reference length in a specific plane—maybe let ask Josiah for a better definition) on the adherent epithelial cell monolayer and on the fibroblasts embedded into the collagen I hydrogel scaffold (S1).

Specific parameters were chosen to define percentage of strain and cycle frequency based on recently published papers [PMID: 28385915: paragraph PATHOPHYSIOLOGY OF VILI Recruitment/derecruitment. Normal alveoli are stable and do not have marked changes in volume with each tidal breath (4-6% change with each cycle;); PMID: 11457769; PMID: 18096874] which identified the natural range of stretching/relaxation of the lung as 4-6% strain at 0.2 Hz. As shown herein, increasing applied vacuum (negative) pressure from around 30 to 90 kPa induced an increase in stretching from around 5%-16%. See, FIG. 6A-B.

FIG. 6A-B Open-Top Alveolus-Chip Incorporates Stretchable Open-Top Design: Pneumatic Stretching Optimization. By measuring the displacement of the beads we can estimate the percentage of strain that cells feel on-chip when breathing motion is applied.

FIG. 6A By measuring the displacement of the beads, provides an estimate of the percentage of strain that cells feel on-chip when breathing motion is applied.

FIG. 6B Beads are displaced when vacuum is applied to the later chambers of the chip. Yellow arrowheads point to an exemplary bead displacement.

D. Differentiation of Adult Alveolar Cells into Pneumocytes: Contribution of ECM.

Although it remains problematic to direct alveolar pluripotent cell differentiation into specific cell types, and/or specific ratios of the cell types, in a robust manner, there is increasing evidence that multiple factors within the tissue microenvironment, including cell-cell interactions, timing of exposure to soluble growth factors, exposure to air and physicochemical properties of the extracellular matrix (ECM) can affect alveolar cell fate terminal differentiation. We therefore explored whether chemically defined soluble factors and insoluble ECM signals and mechanical stimuli can promote the differentiation of adult alveolar cells into more mature terminally differentiated alveolar cells. To avoid the inherent heterogeneity associated with adult alveolar stem cell differentiation methods and to develop a method more easily integrated with microfluidic organ-chip technology, we chose to use adherent cell monolayer cultures.

1. Viability/Differentiation in Relation to ECM.

Previous studies showed that ECM promotes and/or enhance alveolar epithelial cell differentiation. To confirm that the commercial source of freshly isolated alveolar epithelial cells which are reported to be isolated from normal human lung tissue and be passage 1 were equally sensitive to extracellular matrix composition, we measured the ability of these cells to up-regulate genes encoding biomarkers of the alveolar epithelial type I and type II phenotype when cultured on a collagen I hydrogel coated with different ECMs.

We examined surfaces functionalized with various combinations of laminin, Collagen IV, a Fibronectin fragment, overlaying a type I collagen gel with embedded fibroblast for their ability to support alveolar cell adhesion, including under low serum and/or serum-free conditions. Alveolar cells are able to attach to a variety of ECMS, including collagen 1.

These studies revealed that whereas alveolar cells adhered to type I collagen, surfaces coated with collagen IV, fibronectin, laminin fragment were each effective for attachment and propagation of alveolar cells. We used a combination of collagen IV, fibronectin, laminin for subsequent studies based on its higher cell-binding efficiency and the ability of this coating to stimulate higher expression of markers according to mRNA analysis.

Specifically, combinations of ECM (gelatin, laminin, type I and IV collagen, fibronectin, elastin, matrigel and lung ECM and a mixture of Collagen IV, Fibronectin and Laminin, etc. were for culturing alveolar cells in open top fluidic devices. Laminins, Collagen IV and Fibronectin are widely expressed in the alveolar basement membrane during development and functional maturation of the lung.

Figures 7A, 7B:
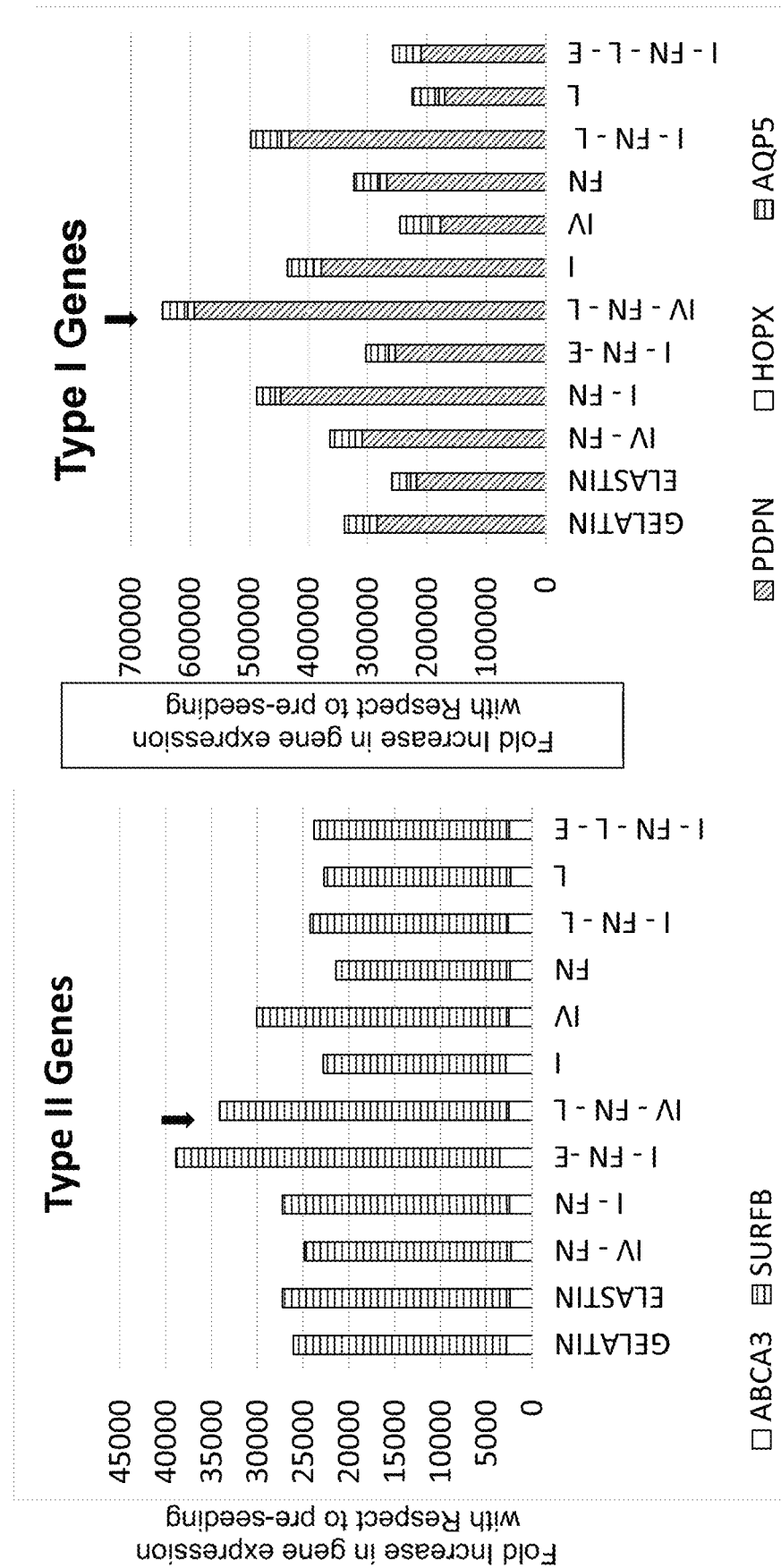
FIG. 7A-B Gene expression data confirms that the combination of Coll IV, Fibronectin and Laminin supports expression of both Type I and Type II pneumocytes better than other combinations tested during the development of the present inventions. QPCR was used to measure fold increasing in gene expression with respect to expression in cells prior to seeding.

Quantitative PCR analysis revealed that the type IV collagen, fibronectin and laminin mixture induce upregulation of both Type I and Type II pneumocyte gene better than any other combination tested (FIG. 7A-B). Noteworthy, in absolute the collagen I, fibronectin, elastin mixture resulted to be the stronger enhancer of type II phenotype, at least, among the tested combination of ECM, however because it has poor enhancement of the type I phenotype genes, we decided to opt for the type IV collagen, fibronectin and laminin mixture as basal coating for this model. In general, these results confirmed that alveolar epithelial cells were sensitive to extracellular matrix composition in the biological culture model and that behave similarly to what has been reported previously in literature.

2. Gene Expression of BioMarkers for Surface Epithelial Cells of the Alveoli, i.e. Pneumocytes.

Expression of Type I biomarkers was evaluated (e.g. ABCA3 and SURFB) and Type II biomarkers (e.g. PDPN, HOPX and AQP5). Some of the biomarkers were Selected from previously reported literature papers (Olsen, et al, "Extracellular matrix-driven alveolar epithelial cell differentiation in vitro." Exp Lung Res 31(5):461-82 (2005); Balestrini, et al, "Extracellular matrix as a driver for lung regeneration." Ann Biomed Eng., 43(3):568-76. (2015:Epub 2014 Oct. 25); Am J Respir Cell Mol Biol. 2010 February; 42(2):172-80. doi: 10.1165/rcmb.2008-0270OC. Epub 2009; Koval, et al, "Extracellular matrix influences alveolar epithelial claudin expression and barrier function." Am J Respir Cell Mol Biol. 42(2): 172-80 (2010:Epub 2009). See, Table 1.

Epithelial cells seeded on an ECM mixture of collagen IV, laminin and fibronectin expressed markers of either type I and type II alveolar pneumocytes, including Aquaporin 5, podoplanin (type I) and ABCA3 and Surfactant B (type II). Additional information on exemplary biomarkers are shown in Table 1.

Gene expression data confirms that the combination of Coll IV, Fibronectin and Laminin supports expression of both Type I and Type II biomarkers at higher levels than other combinations that were tested.

FIG. 7A-B Gene expression data confirms that the combination of Coll IV, Fibronectin and Laminin supports expression of biomarkers for both Type I and Type II pneumocytes better than other combinations tested during the development of the present inventions. QPCR was used to measure fold increasing in gene expression with respect to expression in cells prior to seeding.

FIG. 7A Type II cells expressing low levels of ABCA3 along with much higher levels of Surfactant B. Although higher levels of these markers for Type II cells were induced by I-FN-E, as shown in FIG. 7B, I-FN-E, induced much lower levels of PDPN, a biomarker for Type I cells.

FIG. 7B Type I cells expressed the highest levels of PDPN and other biomarkers when cultured on Coll IV, Fibronectin and Laminin.

Furthermore, effects of ECM Composition on Epithelial Cells were shown by a comparative capability for providing distinct and identifiable populations of Type II and Type I cells, although some overlap would be predicted when transition of Type II to terminally differentiated Type I cells was occurring.

The combination of Collagen IV, Fibronectin and Laminin promotes the expression and clear segregation of both Type I/Type II cell markers.

Figure 8A:
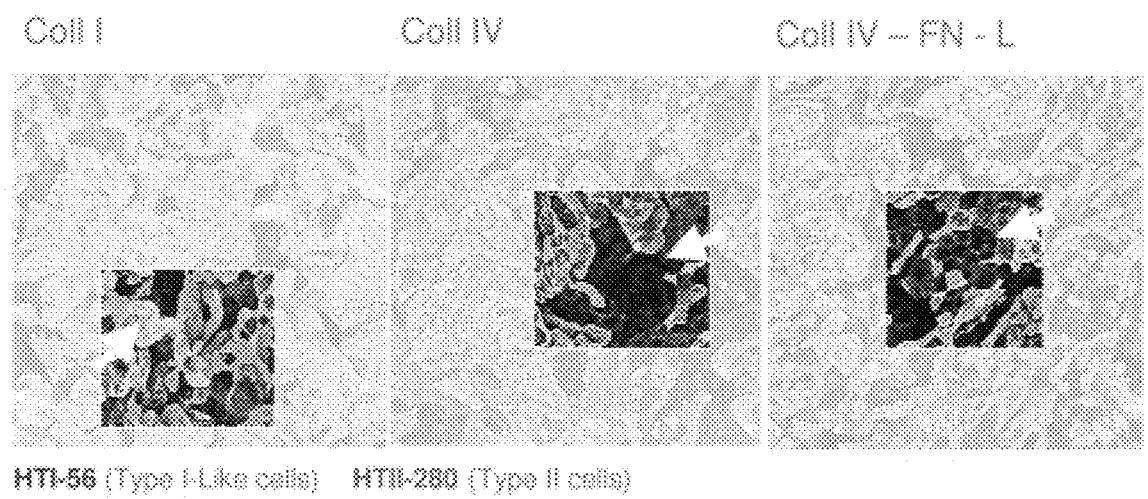
FIG. 8A-B—Effect of ECM Composition on Epithelial Cells: segregation of Type II vs. Type I cells cultured on different ECM.
Figure 8B:
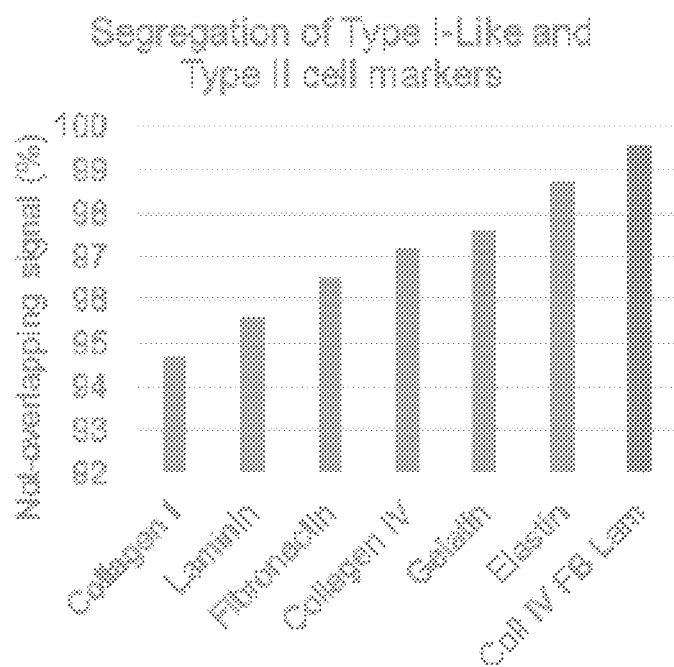

FIG. 8A-B Effect of ECM Composition on Epithelial Cells: segregation of Type II vs. Type I cells cultured on different ECM.

FIG. 8A shows immunofluorescent micrographs of cells cultured on, left to right, Coll I vs. Coll IV vs. Coll IV-FN-L. HTI-56 (Type I-Like cells) (red) and HTII-280 (Type II cells) (green). Overlapping biomarkers/colors appear yellow.

FIG. 8B shows a chart comparing a percentage of non-overlapping signal (%) of Type I-like and Type II-like Biomarkers vs. ECM compositions (left to right): Coll I, Laminin, Fibronectin, Coll IV, Gelatin, Elastin, Coll IV-FN-L.

Figure 9A:
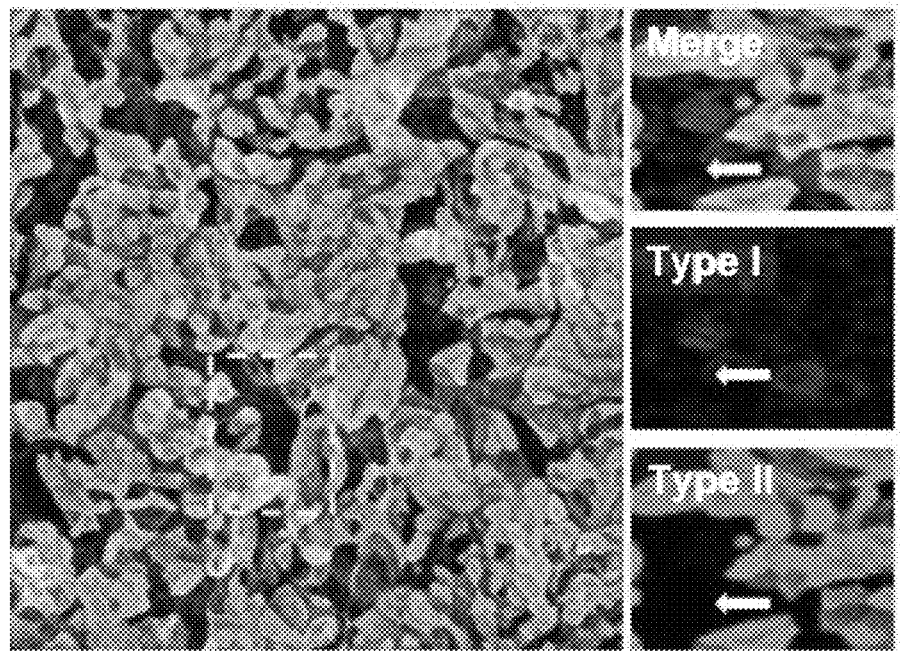
FIG. 9A-B A higher power view of immunofluorescent micrographs of cells showing Differential Cell Staining of HTI-56 (Type I-Like cells) and HTII-280 (Type II cells).
Figure 9B:
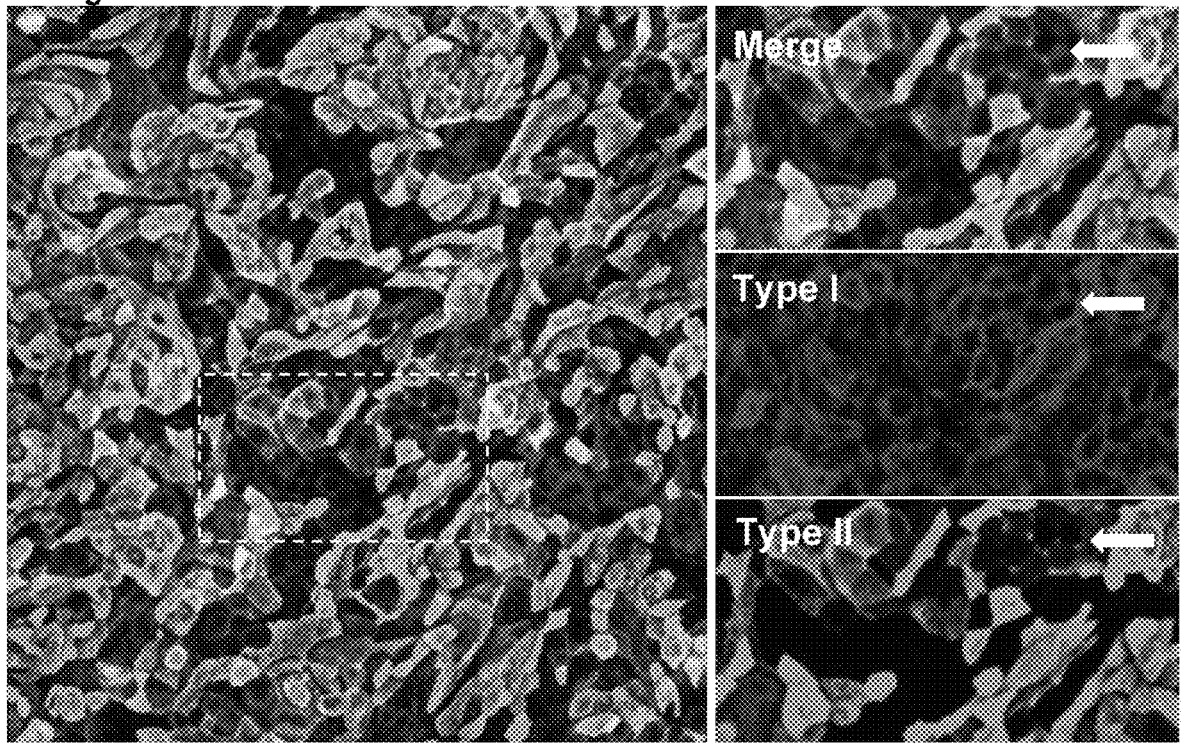

FIG. 9A-B A higher power view of immunofluorescent micrographs of cells showing Differential Cell Staining of HTI-56 (Type I-Like cells) and HTII-280 (Type II cells). Upper to lower boxes to the right of images show higher magnifications of the box outlined in dotted lines in the left hand image: Merge, Type I (red) and Type II (green).

FIG. 9A cells cultured on Collagen I coated surfaces show Irregular cell morphology and large Type I/Type II overlap area (yellow) indicate poor cell differentiation.

FIG. 9B cells cultured on Collagen IV-Fibronectin-Laminin promotes the segregation of both Type I/Type II cell markers on different cell populations.

Further, cells cultured on Collagen IV-Fibronectin-Laminin show more typical distributions, as compared to in vivo, of more flat Type I cells and more cuboidal-like Type II cells than observed in cultures grown on Collagen I.

Therefore, Coll IV, Fibronectin and Laminin was chosen as the best ECM for use in coating the surfaces for attaching alveolar cells to fluidic devices.

TABLE 1

Exemplary Gene and Protein BioMarkers For Lung Cells.

| Gene Marker | Marker For Alveolar Type I or Type II cells or transitional cells |
|---|---|
| Pdpn (Podoplanin) refers to a type-I integral membrane glycoprotein | Type I |
| HOPX (HOP homeobox) refers to a protein-coding gene having an atypical homeodomain | Type I |
| Aquaporin 5 (AQP5) refers to a small integral membrane water channel protein | Type I |
| Pro-surfactant B refers to a precursor protein of surfactant B, which in turn refers to an amphipathic protein that enhances the rate of spreading and increases the stability of surfactant monolayers in vitro | Type II |
| SP-C SP-C refers to a lipoprotein of protein of surfactant C, which in turn refers to an amphipathic protein that enhances the rate of spreading and increases the stability of surfactant monolayers in vitro | Type II |
| ABCA3 (ATP-binding cassette, sub-family A (ABC1) member 3) refers to a membrane-associated protein | Type II |
| TGF-B (transforming growth factor, beta1) refers to a member of the transforming growth factor beta (TGFB) family of cytokines | Epithelial to Mesenchymal Transition (EMT) |

E. Effect of Culture Medium Compositions on Cell Viability and Maintenance of Tissue-Specific Markers in Fluidic Devices.

Figure 10A:
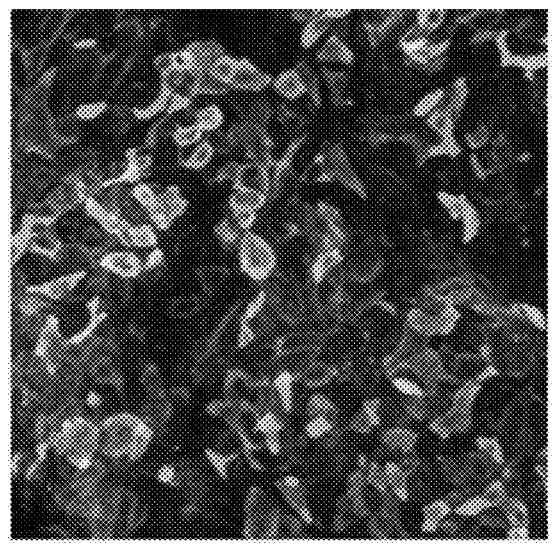

Immunofluorescence read-outs were also used to analyze HTI and HTII marker expression of lung cells cultured in fluidic devices under flow and stretch for a total of 12 days (5 days in submerged state and at least 7 days at air-liquid interface). Alveolar cells cultured in SAGM medium, known for supporting epithelial cells in culture, showed a peculiar distribution of HTI (Type I specific marker) and HTII (Type II specific marker) positive cells (FIG. 10A). SAGM is currently considered the gold standard medium for alveolar cell growth and differentiation.

Figure 10D:
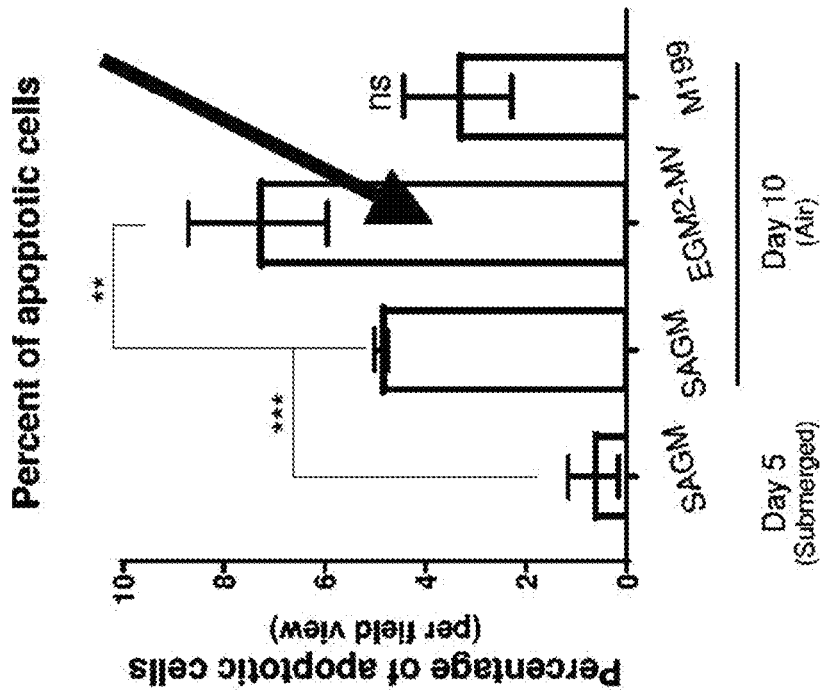
Figure 10C:
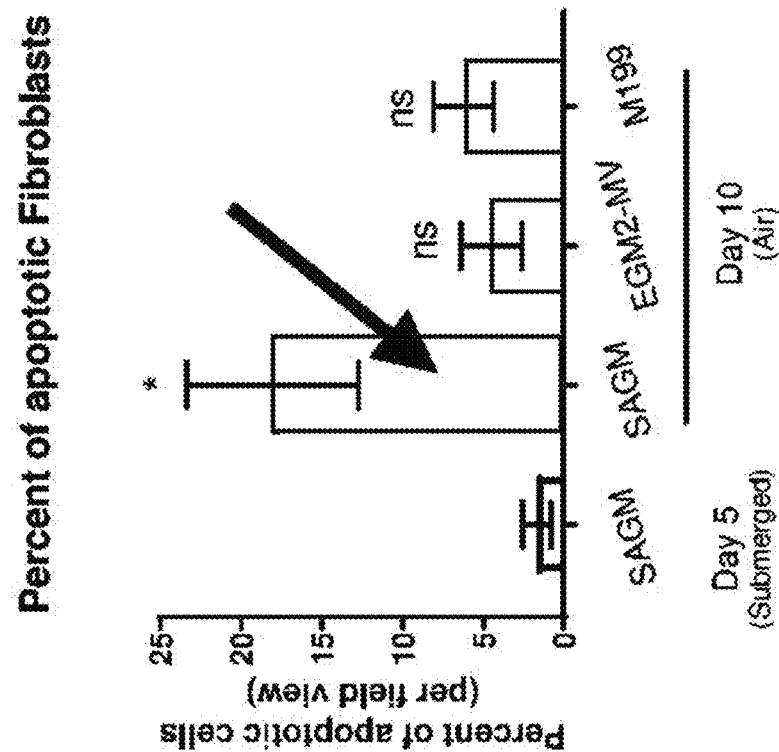

Unfortunately, the use of SAGM medium in the Open-Top fluidic device was precluded by its incompatibility with long-term survival of endothelial cells and fibroblasts (FIG. 10C). In fact, SAGM resulted to be extremely detrimental for fibroblast survival while both EGM-2MV and M199 generate similarly low level of apoptosis (FIG. 10C). In contrast, epithelial cells grown in SAGM medium showed low levels of apoptotic cells (FIG. 10D). Immunofluorescence images of epithelial cells, endothelial cells and fibroblasts cultured in SAGM are shown in FIGS. 11G vs. 11H vs. 11I, respectively.

Similarly, EGM-2MV medium is considered the gold standard for culturing microvascular endothelial cells. Unfortunately, EGM-2MV medium has a severely negative effect on the morphology and marker expression of the alveolar epithelial cells (shown in FIGS. 11D vs. 11A vs. 11G).

Similarly to the epithelial apoptosis trend, it evidenced that there is a general increase of apoptosis when primary fibroblasts are cultured for an extended period of time at ALI.

Therefore, in order to achieve a long-term co-culture of these three different cell types using a single medium during the air-liquid interface phase, a different medium was needed to allow, and ideally promote, survival and differentiation/function of all three of these primary cell types, pneumocytes (alveolar cells), fibroblasts and endothelial cells.

To achieve this goal of a universal medium, a series of media was created and tested in order to identify a new pneumocyte differentiation medium (ALI-M/M199) as the best compromise between the two gold standard culture mediums. In fact, one of the new mediums tested was a 50:50 mixture of the gold standard mediums, SAGM and EGM2-MV, however, as described herein, this mixture did not support viable/functional co-cultures.

A described herein, a successful ALI-M, air-liquid interface medium, also referred to as M199, was created and used as described herein. There is also a surprising additional advantage of using one instead of two different culture mediums, because one of the pod reservoirs, previously used for a culture medium, is needed for air during the ALI phase. Thus one of the reservoirs becomes unavailable for an additional medium. The use of one medium for the three cell types is advantages in light of the one reservoir available at that time.

A direct comparison of three culture mediums: ALI-M/M199, EGM-2MV and SAGM, at 7 days of culture, showed that ALI-M/M199 induces expression of both HTI, HTII biomarkers while maintaining endothelial coverage of the spiral channel along with apoptotic percentages of fibroblasts that were not significantly different than when using the gold standard for endothelial cells (EGM-2MV) and much less than when using the gold standard SAGM for epithelial cells.

Further, there appeared to be differences in distribution and amounts of Type II v. Type I cells when comparing alveolar cells growing in ALI-M vs. SAGM medium. Specifically there appeared to be a higher prevalence of HTII positive cells over HTI positive cells (FIG. 11A vs. FIG. 11G), more in line with in vivo histological observations of alveolar sacs. Moreover, the morphology of alveolar epithelial HTI and HTII positive cells look more regular and defined in regards to each phenotype in M199 compared to both SAGM and EGM-2MV (FIG. 11A vs. FIG. 11D vs. FIG. 11G).

In fact, some of the epithelial cells exposed at EGM-2MV for long time (7 days) showed severe alterations of the morphology with some of HTII positive cells assuming fibroblast-like morphology (FIG. 11D). Even further, an almost complete loss of HTI positive cells was observed when culturing with EGM-2MV medium (FIG. 11D).

Viability of the epithelial cells cultured in these different media was tested by caspase 3/7 staining of apoptotic dead or dying cells, shown as turquoise blue, in FIGS. 11C, 11F, and 11I with percentages of apoptotic fibroblast cells shown in FIG. 10C. This caspase staining showed that epithelial cells cultured for an extended period of time at ALI have a natural tendency to become apoptotic, however the apoptosis level is relatively lower in M199 medium when compared to both EGM-2MV and SAGM (FIG. 10C). Primary lung microvascular endothelial cells cultured in SAGM showed extended areas of cell death (dark areas in FIG. 11H) impacting severely on the integrity of the endothelial monolayer covering the bottom spiraled microfluidic channel. In contrast, both EGM-2MV and ALI-M/M199 medium are comparable regarding the level of cell coverage observed in the bottom spiraled microfluidic channel (FIGS. 11B and 11E).

FIG. 11A-I shows immunofluorescent images of cells stained for epithelium HTI Type I (colored red) and Type II HTII biomarkers (colored green); FIG. 11B, 11E, 11H endothelial cells (colored green) in addition to FIG. 11C, F, I fibroblast cells in the stroma area where nuclei are colored blue and turquoise colored apoptotic identified by anticaspase antibodies. FIG. 11A, 11B, 11C. ALI-M/M199. FIG. 11D, 11E, 11F EGM-2MV: gold standard for growing endothelial cells. FIG. 11G, 11H, 11I SAGM: gold standard for growing epithelial cells.

Figure 12A:
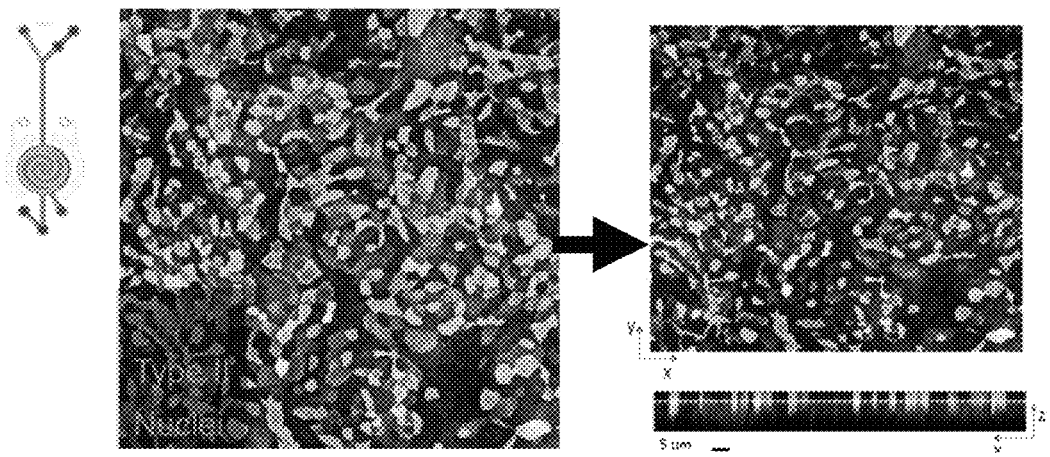
FIG. 12A shows an immunofluorescent image of a cross sectional z-stack through immunostained cell layers (upper image) in vitro showing green Type II cell markers generally in higher locations near the ALI due to their cubodial shape than the lower flatter red Type I cell biomarkers (FIG. 12A lower bar). Moreover, florescent intensity for each biomarker's signal distribution shifted when moving from the upper region (higher fluorescent intensity colored in green for Type I cells) to the lower region (higher (higher fluorescent intensity colored in red for Type I cells) (FIG. 12B). Cell nuclei are stained then colored blue.
Figure 12B:
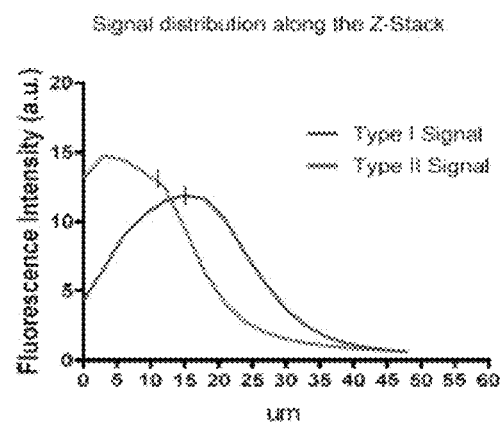

Further evaluation of Type II and Type I cell populations in open top fluidic devices cultured at an ALI in ALI-M/M199 showed general cell shape morphology and distribution of biomarkers corresponding to locations in lung biopsies (FIG. 12A). Specifically, an image of a cross sectional z-stack through immunostained cell layers in vitro show green Type II cell markers generally in higher locations near the ALI due to their cuboidal shape than the red Type I cell markers for flatter cells (FIG. 12A lower bar). Moreover, florescent intensity for each biomarker's signal distribution shifted when moving from the upper region (higher fluorescent intensity colored in green for Type I cells) to the lower region (higher (higher fluorescent intensity colored in red for Type I cells) (FIG. 12B).

Observational confirmation of Type I and Type II cell morphological cell types using scanning electron microscopy.

Figure 13:
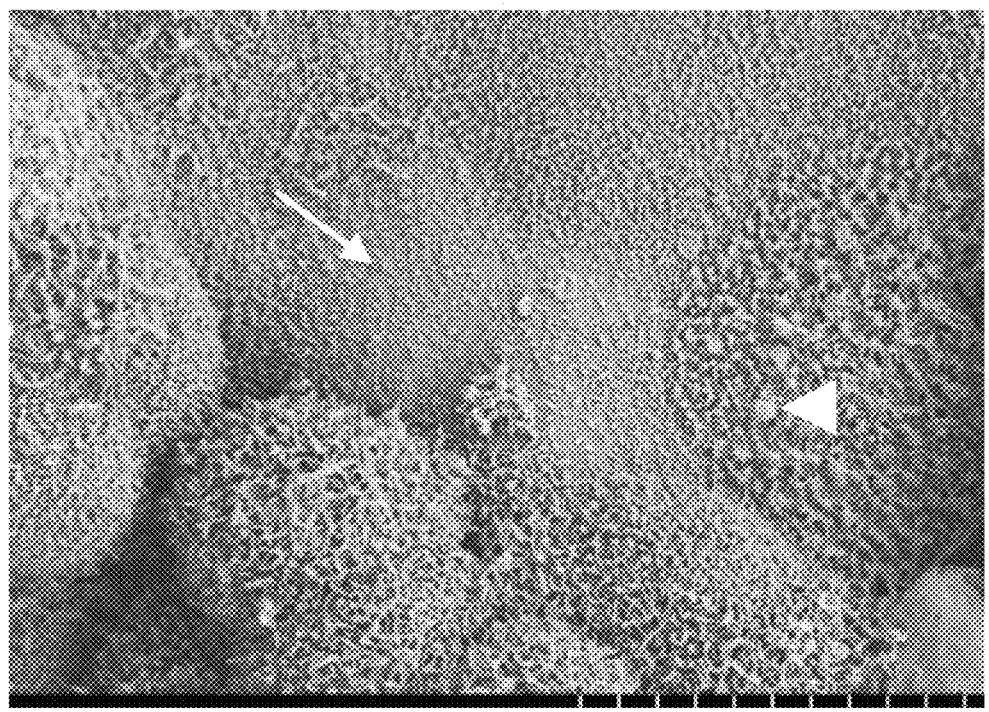
FIG. 13 shows a scanning electron microscope image of Type II-like raised cuboidal cells having numerous microvilli covered with possible remnants of surface surfactant protein (white arrowhead), see, lower cuboidal-like cells and cells to the left and right. The center and upper region of the image show flatter cells with few-short microvilli (white arrow) as typical of Type I cells.

FIG. 13 shows a scanning electron microscope image of Type II-like raised cuboidal cells having numerous microvilli and possible remnants of surface surfactant protein (white arrowhead), see, lower cuboidal-like cells and cells to the left and right. The center and upper region of the image show flatter cells with few-short microvilli (white arrow) as typical of Type I cells.

Observational confirmation of Type I and Type II cell morphological cell types using transmission electron microscopy.

FIG. 14 shows a transmission electron microscope image of Type II-like cells containing vesicles filled with presumable surfactant protein (black arrows) and numerous microvilli (white arrowheads). White arrow points to a tight junction between cells.

In order to further evaluate the level of maturation of the endothelial monolayer lining the microfluidic channel when cultured in ALI-M/M199 medium, biomarker expression by endothelial cells was evaluated by immunostaining and confocal fluorescence microscopy. Canonical endothelial staining for VWF, PECAM-1 (DC31) and VE-Cadherin showed an even level of maturation throughout the entire length of the microfluidic channel. Higher magnification images of the endothelial monolayer evidenced also an even distribution of intracellular junctions (VE-Cad and PECAM-1) and homogeneous distribution of VWF signal among cells after 10 days of flow, signs of a healthy endothelial monolayer. On a cellular level, VWF stained cytoplasmic areas, whereas PECAM-1 and VE-cadherin were expressed at cell junctions.

Figures 15A, 15B, 15C, 15D:
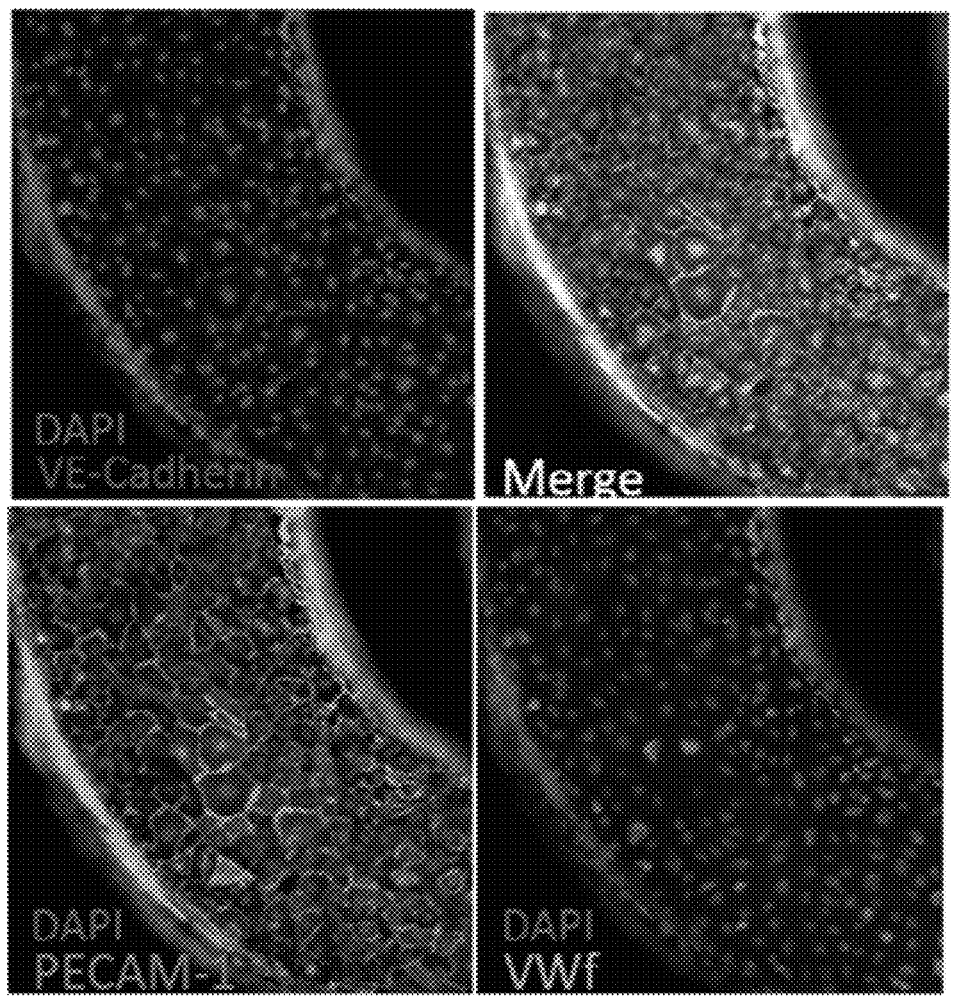
FIG. 15A-D shows fluorescent microscopy images of healthy endothelial cells forming a layer in the spiral fluidic channel.

FIG. 15A-D shows fluorescent microscopy images of healthy endothelial cells forming a layer in the spiral fluidic channel. FIG. 15A shows double staining for VE-Cadherin (red) and DAPI stained nuclei (blue). FIG. 15B shows double staining for PECAM-1 (DC31) (green) and DAPI stained nuclei (blue). FIG. 15C shows double staining for VWF (pink) and DAPI stained nuclei (blue). FIG. 15D shows a merged image of FIG. 15A-C showing endothelial cells with outlined by PECAM-1 (DC31) (green).

Furthermore, the use of ALI-M/M199 had even more advantages. Specifically, signs of fibroblast activation (yellow arrows) were detected in chips perfused with EGM2 for 10 days but not in case of ALI-M/M199 or SAGM which is desired for experiments using nonactivated fibroblasts. In preferred embodiments, fibroblasts within the stroma area of fluidic chips are desired to be nonactivated in order to observe effects of activation in contemplated inflammatory and immunological evaluations.

Figure 16A:
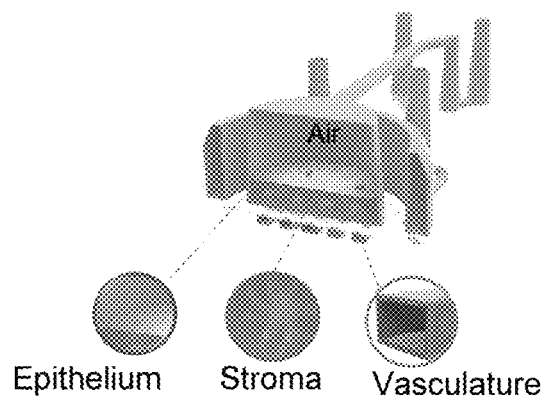
FIG. 16A schematic of open top chip showing an ALI (upper chamber) adjacent to an epithelial layer; a stroma area containing pink fibroblasts and an endothelial coated spiral channel.
Figure 16B:
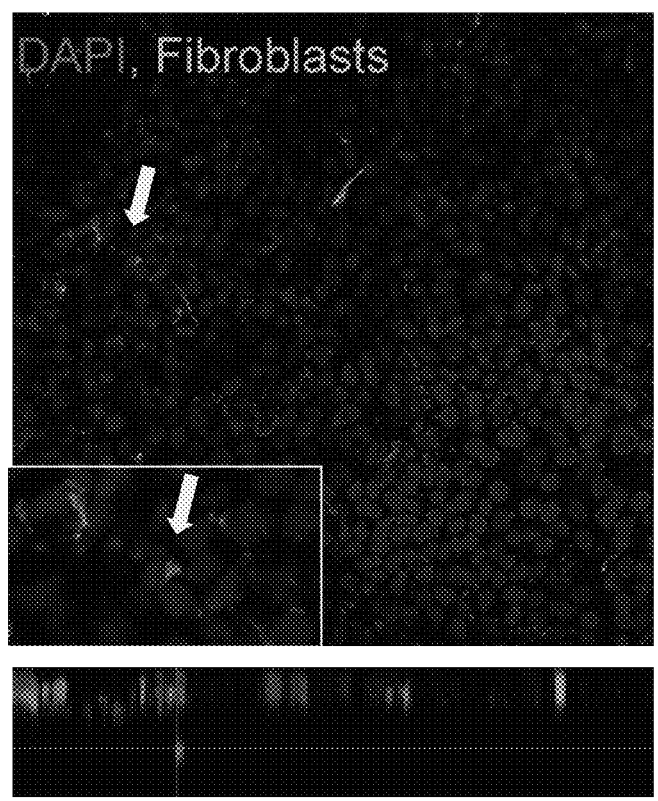
FIG. 16B-D Signs of fibroblast (yellow arrows) activation were detected in chips perfused with EGM2 for 10 days but not in case of SAGM or ALI-M/M199. Type I colored red and Type II cells colored green; fibroblasts colored pink; nuclei DAPI stained and colored blue.
Figure 16D:
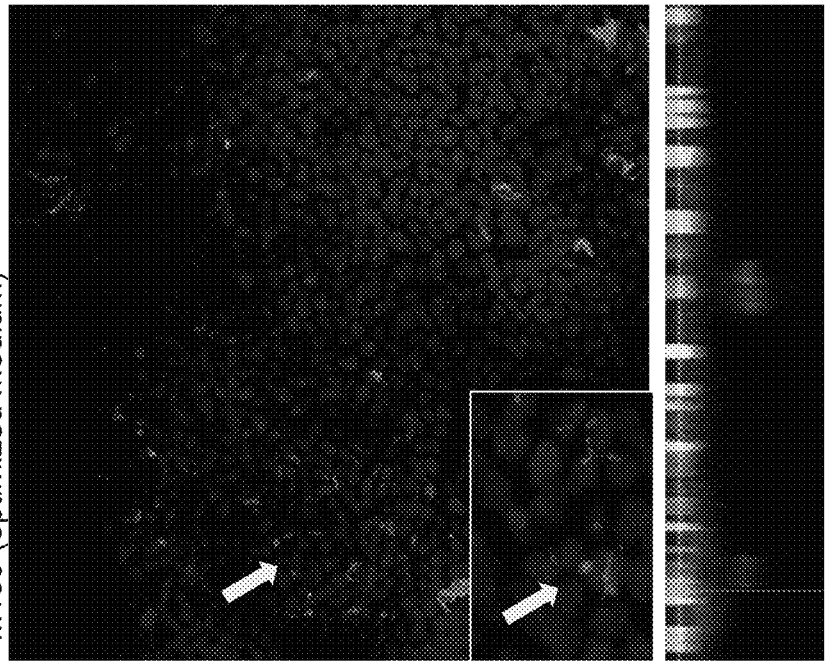
Figure 16C:
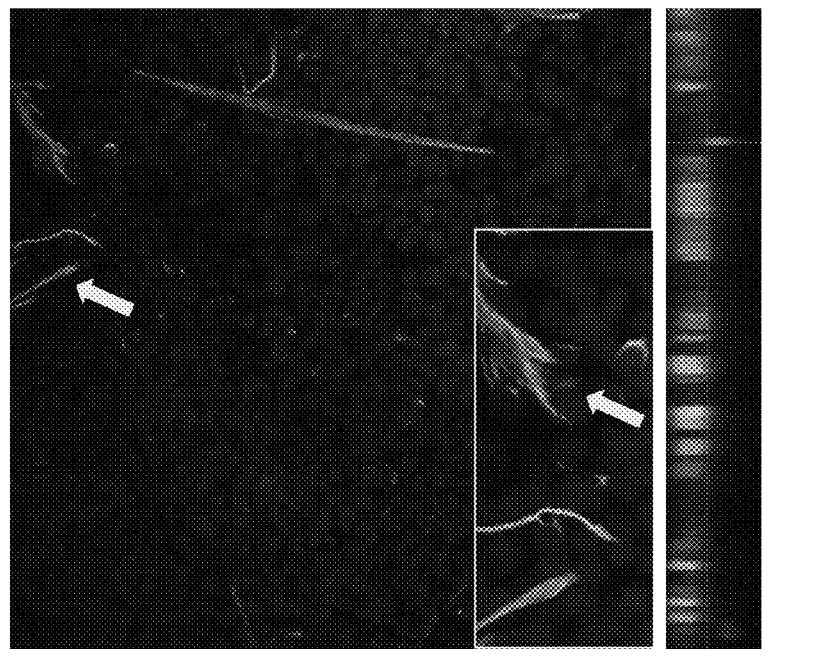

FIG. 16A schematic of open top chip showing an ALI (upper chamber) adjacent to an epithelial layer; a stroma area containing pink fibroblasts and an endothelial coated spiral channel. FIG. 16B-D Signs of fibroblast (yellow arrows) activation were detected in chips perfused with EGM2 for 10 days but not in case of SAGM or ALI-M/M199. Type I colored red and Type II cells colored green; fibroblasts colored pink; nuclei DAPI stained and colored blue. FIG. 16B shows fibroblasts cultured in SAGM. Lower inset shows a higher magnification of stained fibroblasts. The lower bar is a z-stack showing fibroblasts in the epithelial layer along with some Type II cells and few Type I cells. FIG. 16C shows fibroblasts cultured in EGM2. Inset shows a higher magnification of activated-elongated fibroblasts. The lower bar is a z-stack showing fibroblasts in the epithelial layer along with many Type II cells and few Type I cells. FIG. 16D shows fibroblasts cultured in ALI-M/M199. Inset shows a higher magnification of stained fibroblasts. The lower bar is a z-stack showing fibroblasts in the stroma area below many Type II cells and many Type I cells.

F. Contributions of Fibroblasts and Mechanical Stretching.

The contribution of lung fibroblasts to alveolar co-cultures was assessed at optical (observational), gene expression and protein levels.

Figure 17A:
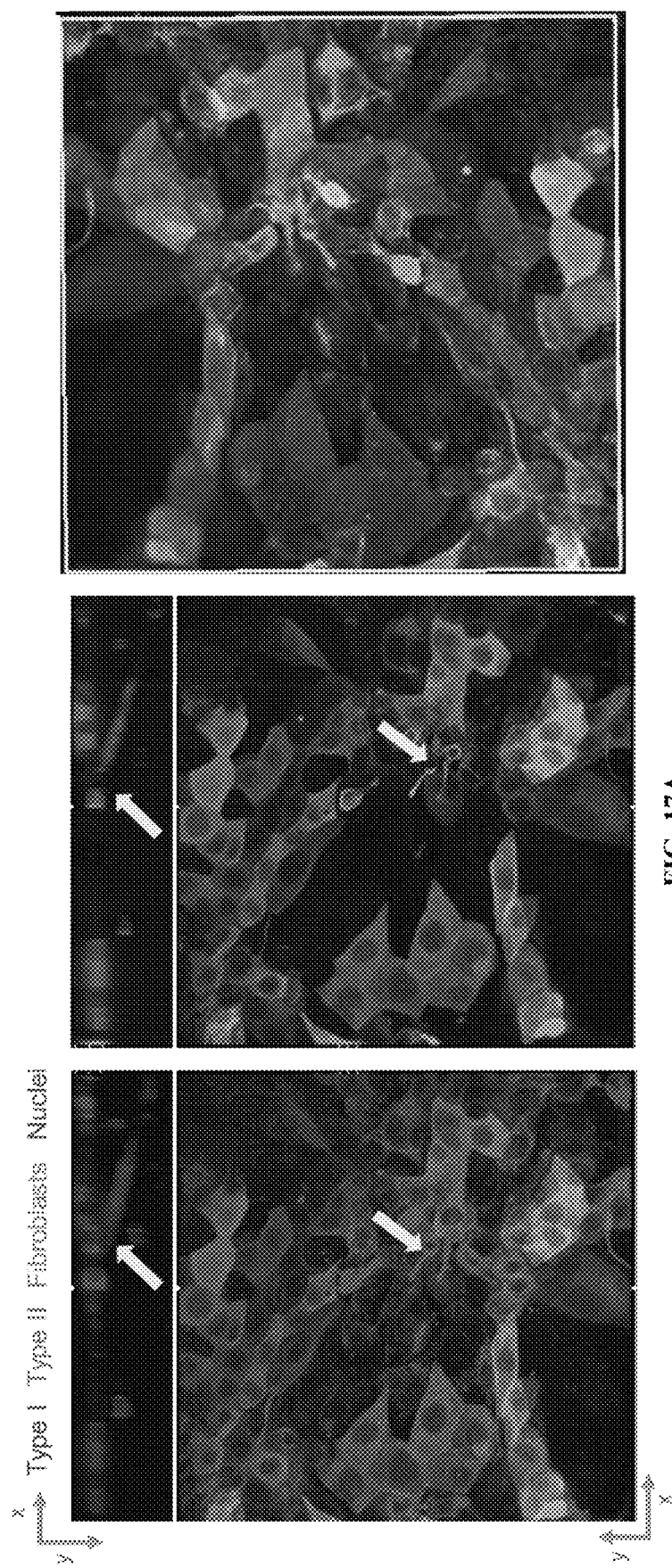
FIG. 17A-D Fibroblast co-cultures enhance gene expression of alveolar genes while stretching of the membrane enhances Type II biomarkers.

In particular a three dimensional optical reconstruction of the stroma-epithelium interface (FIG. 17B) revealed that some of the fibroblasts embedded in the hydrogel of the stroma area extended cellular processes toward the epithelium, see z-stacks of pink fibroblasts (yellow arrows) in FIG. 17A. In these images the fibroblasts appeared to physically touch the epithelial cells (FIG. 17A).

Figure 17B:
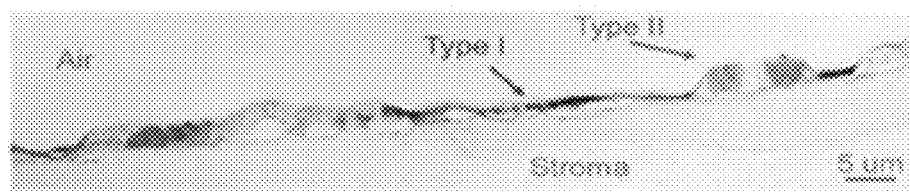
Figure 17C:
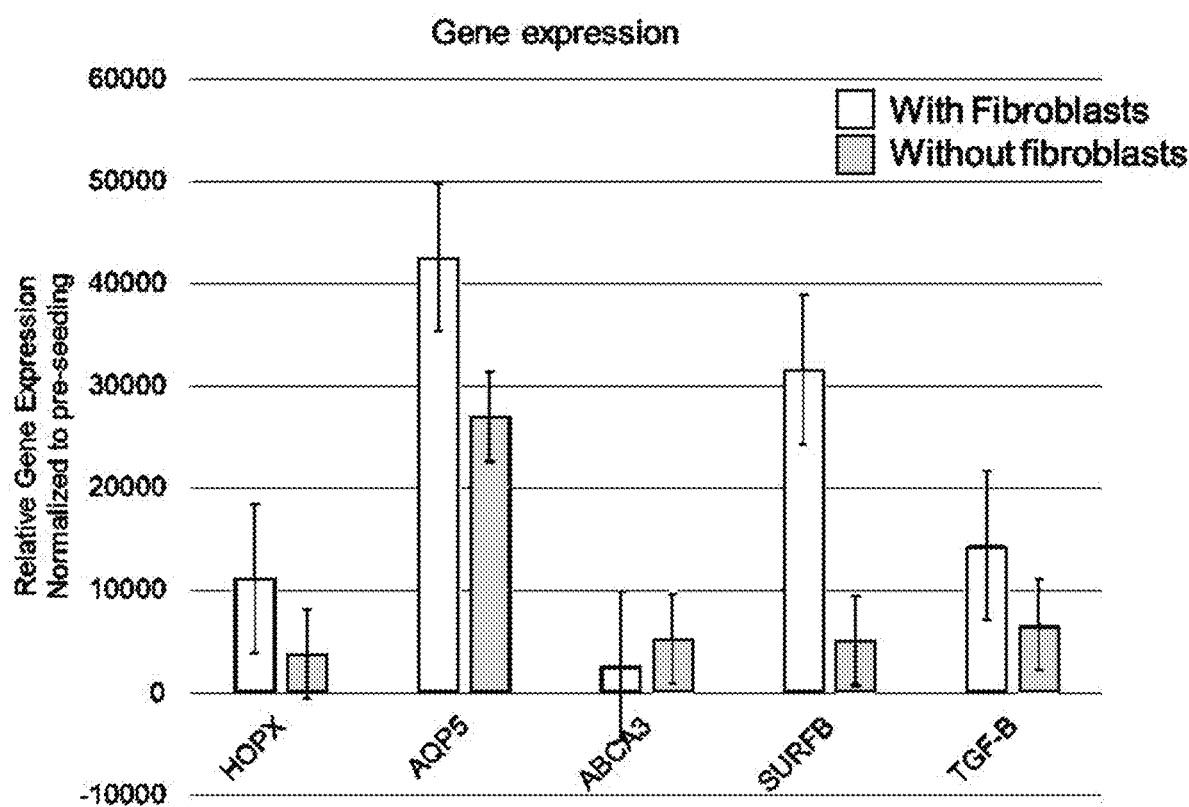

Surprisingly, we also found evidence that the presence of lung fibroblasts in the recreated lung stroma (a collagen I gel with embedded fibroblasts coated with Col IV-Fib-Lam) increases the expression of canonical pneumocyte genes such as HOPX, AQP5, ABCA3, SURFB, TGF-β (FIG. 17C).

FIG. 17A-D Fibroblast co-cultures enhance gene expression of alveolar genes while stretching of the membrane enhances Type II biomarkers. FIG. 17A Left: immunofluorescent image of a fibroblast cell (pink) in relation to Type I (red) cells. Type II cells are stained and colored green. Nuclei are stained and colored blue. The upper bar is a representative z-stack showing a fibroblast extending into the epithelial layer next to a Type I cells. Middle: the same image as on the left but with the red Type I cells removed showing fibroblasts next to nuclei of uncolored cells further supporting the observation that the fibroblasts are contacting mainly the Type I cells. Type II cells are stained green. Right: image from a Supplementary Movie 2: showing that fibroblasts protruding towards the alveolar epithelium. FIG. 17B shows a bright field image of an H&E stained cross section of an embedded epithelial layer showing a stoma area. FIG. 17C shows that relative gene expression of biomarkers for Type I and Type II cells are increased in co-cultures containing fibroblasts, including Type I biomarkers HOPX and AQP5 and surprisingly showing a major increase in Surfactant B expression of Type II cells.

Figure 17D:
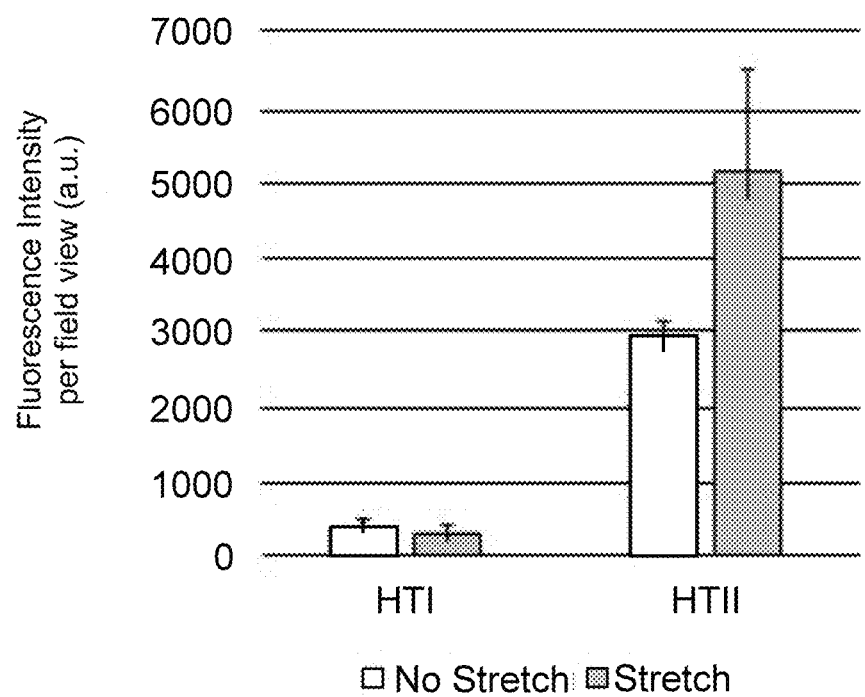

We investigated the effect of having lung fibroblasts within a simulated lung stroma area below primary human alveolar cells in an ALI of the microfluidic open top device undergoing three days of stretching/relaxation cycles of 5% strain 0.2 Hz. Under these conditions an increased fluorescence intensity signal for HTII positive cells but not HTI positive cells was observed. Therefore stretching conditions are contemplated to increase the presence (number or percentage) of type II pneumocytes. (FIG. 17D). FIG. 17D stretching of the membrane enhances Type II biomarkers but not Type I biomarkers.

Further observations showed that that fibroblasts have a preferential growth or migration in the region just underneath the epithelium, see FIG. 17A and FIG. 18A-B. The majority of these fibroblasts were viable cells demonstrating morphology of long individual cells, see FIG. 18C. FIG. 18A-B fluorescent micrographs show fibroblast morphology and viability in the stretchable open top device. FIG. 18A Schematic of open top device. Fluorescent micrographs of immunostained cells. Phalloidin (pink) staining of F-actin expressed by fibroblasts in the stroma area. FIG. 18B Type I-like cells (green). Stained nuclei colored blue. FIG. 18C live (green)/dead (red) staining of fibroblasts.

G. Fibroblasts Enhance Surfactant Production On-Chip.

An unexpected and surprising discovery was that the presence of fibroblasts enhances the production of surfactant in these stretchable open top microfluidic devices.

Figure 19A:
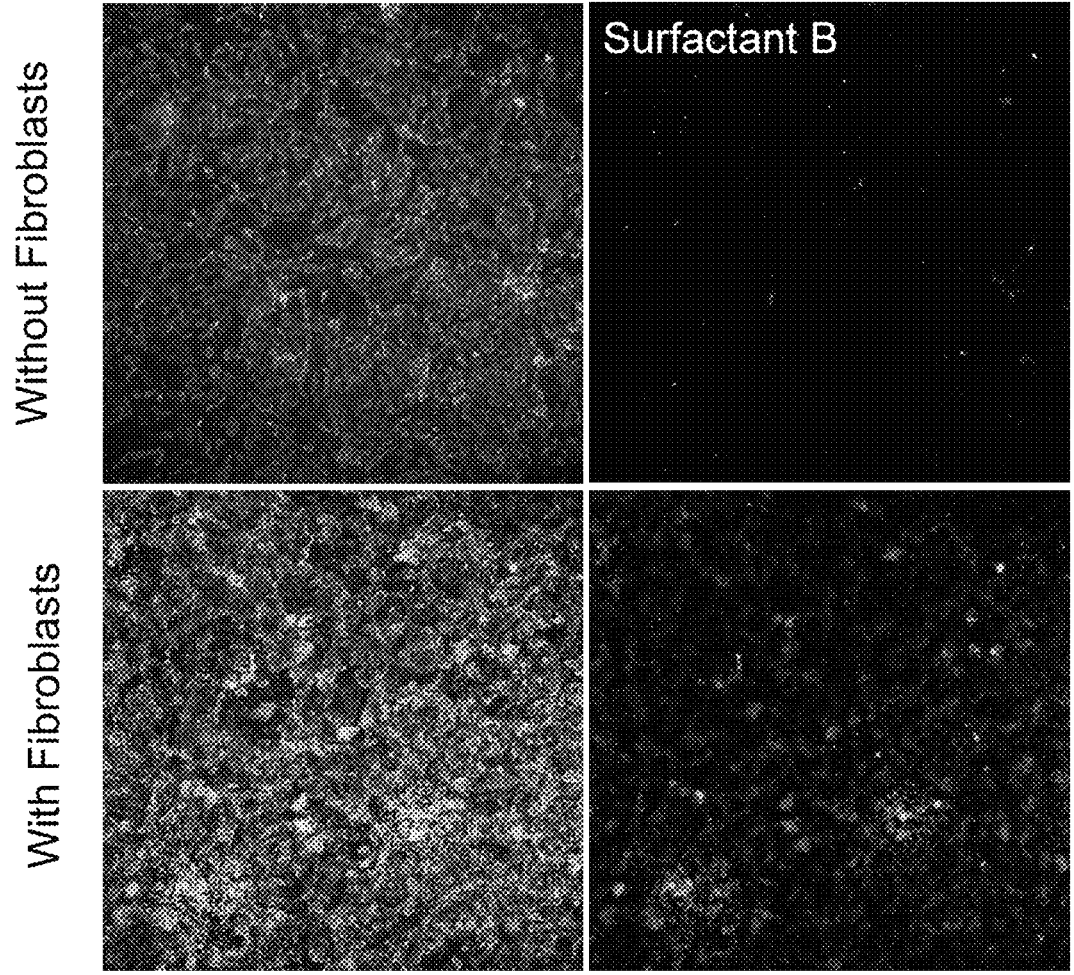
FIG. 19A-C Fibroblasts Enhance Surfactant Production On-Chip FIG. 19A. Lung-fibroblasts increase surfactant production of alveolar primary cells growing on-Chip as detected at both gene FIG. 19C and protein FIG. 19B expression levels.
Figures 19B, 19C:
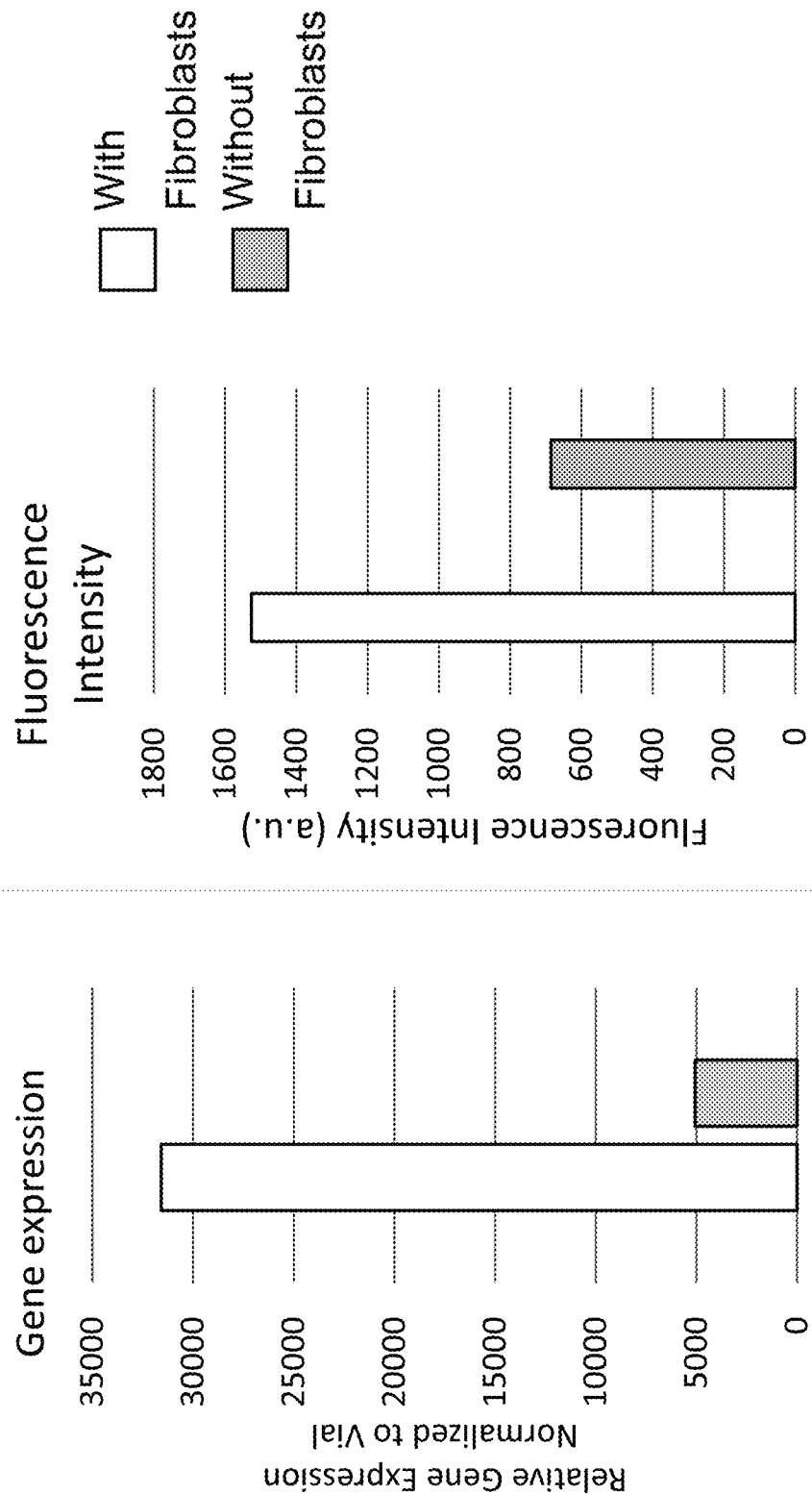

Surprisingly surfactant production was measured at the protein level as detected by immunofluorescence intensity of surfactant immunostaining of the primary alveolar cells (FIG. 19A-B; FIG. 20B). Surfactant protein secretion was supported by gene expression levels (FIG. 19C).

FIG. 19A-C Fibroblasts Enhance Surfactant Production On-Chip FIG. 19A. Lung-fibroblasts increase surfactant production of alveolar primary cells growing on-Chip as detected at both gene FIG. 19C and protein FIG. 19B expression levels.

In fact, there was surprisingly enough surfactant to measure surfactant C secretion in effluent from the open top Alveolar fluidic devices. Further, surfactant B was shown by immunostaining, along with surfactant C and other markers of alveolar cells. These devices were treated using the ALI-M/M199 following a KIAD boost method, i.e. incubating cells in SAGM-KIAD supplements.

Figure 20A:
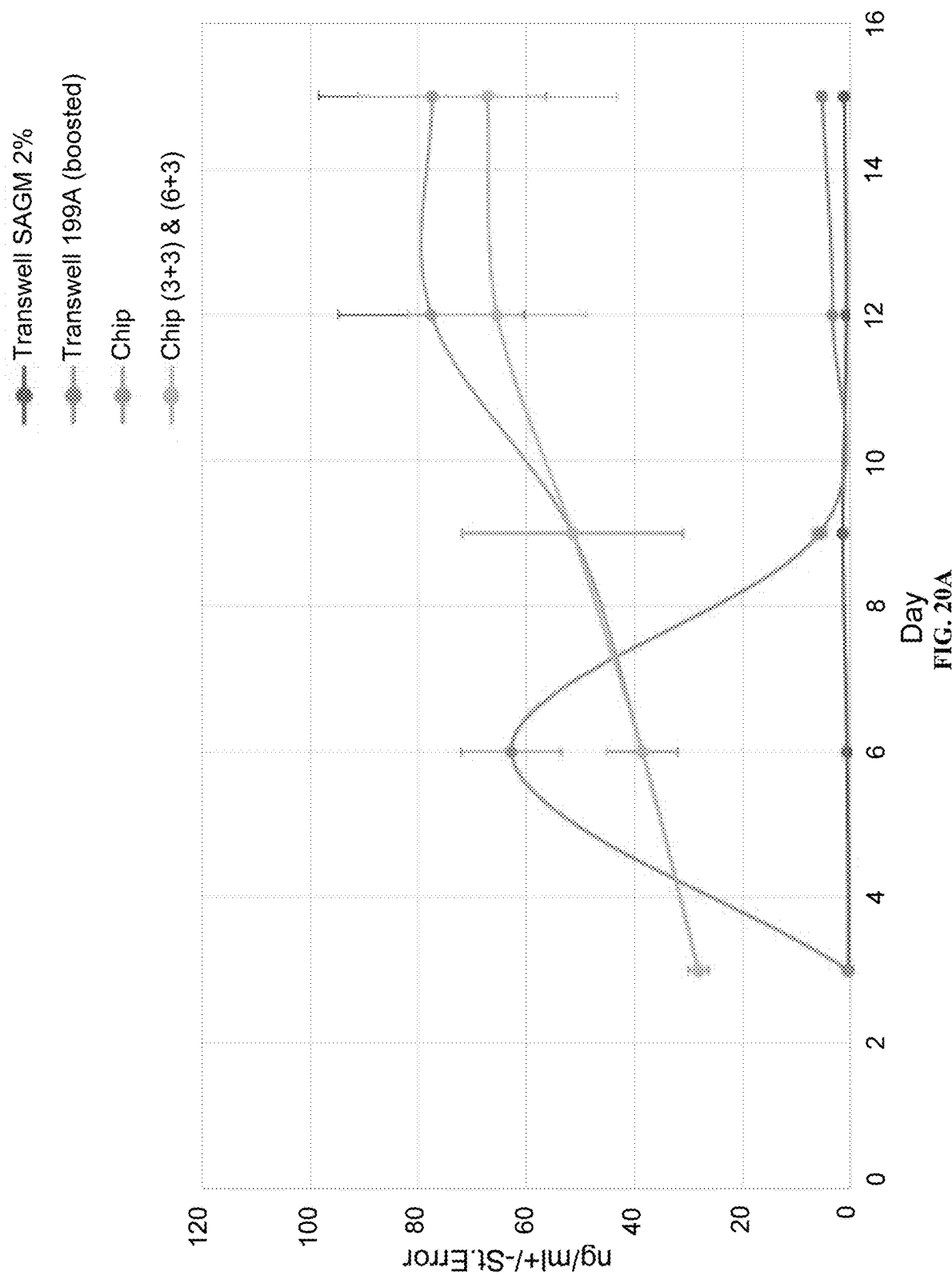
FIG. 20A-B surfactant C secretion over time in open top Alveolar-Chip fluidic device by HPLC, ng/ml in effluent or used culture fluid and florescent micrographs showing the presence of surfactant B and surfactant C in addition to other Alveolar biomarkers.
Figure 20B:
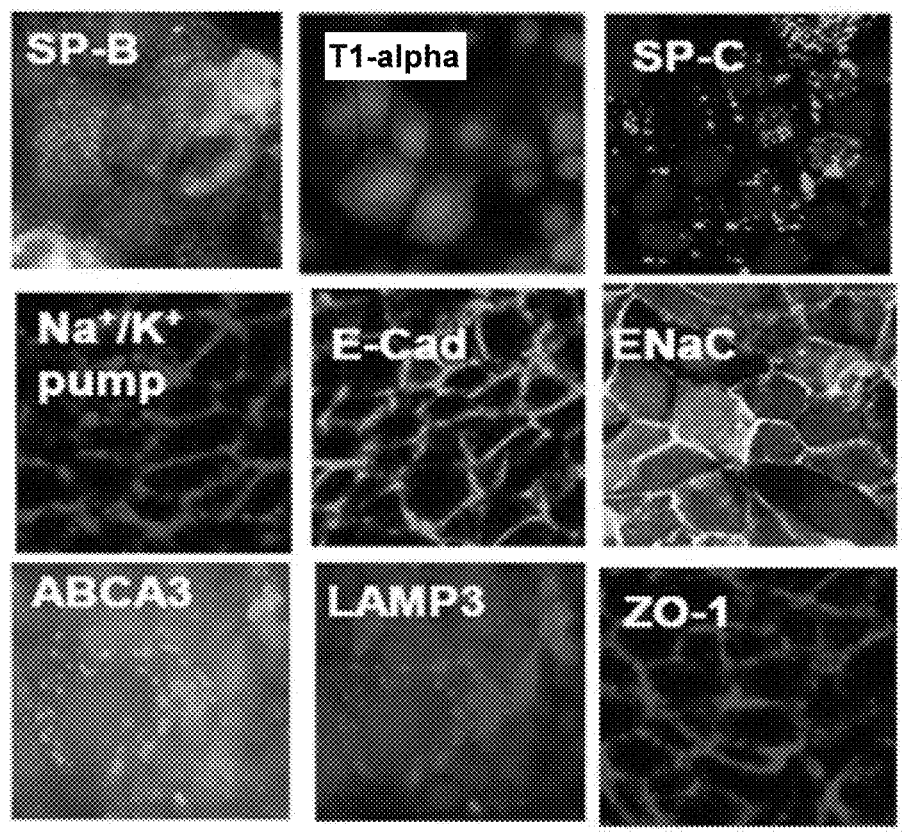

FIG. 20A-B surfactant C secretion over time in open top Alveolar-Chip fluidic device in ng/ml from effluent fluid washes of epithelial cells) or used culture fluid (measured by ELISA) and florescent micrographs showing the presence of surfactant B and surfactant C in addition to other alveolar biomarkers. FIG. 20A microfluidic device (chip) ALI-M/M199 (grey); and microfluidic device (chip) (3+3) & (6+3) (gold). Transwell cells incubated in SAGM with 2% fetal calf serum (blue); Transwell cells incubated in ALI-M/M199 (following a KIAD boost method) (orange).

Using a combined method of co-culturing fibroblast-lung epithelium; stretching; ALI-M/M199 medium and an ALI, resulted in functional alveolar cells identified by canonical alveolar markers (see, FIG. 20E) such as Surfactant B (Surf B; SP-B) and Surfactant C (Surf C; SP-C), which were detectable at the protein level by antibody staining in Type II cells; T1-α (Podoplanin; PDPN) a biomarker for Type I cells; Na$^+$/K$^+$-ATPase (Na$^+$/K$^+$ pump) a biomarker for Type II cells; Epithelial Cadherin an epithelial cell biomarker (E-Cad); epithelial sodium channel 1 Alpha Subunit protein (αENaC) a biomarker for Type II cells; ATP Binding Cassette Subfamily A Member 3 (ABCA3) protein associated with surfactant metabolism and transporting various molecules across extra- and intracellular membranes, a biomarker for Type II cells; Lysosomal Associated Membrane Protein 3 (LAMP3) a biomarker for type II alveolar epithelial cells associated with conditioning and/or the secretion of surfactant and often associated with lysosomes; and Tight Junction Protein 1: Zona Occludens 1 (ZO-1). Podoplanin refers to a mucin-type transmembrane glycoprotein expressed on the cell surface. Homologs of podoplanin (T1-α) are expressed in alveolar epithelial type I cells and inflammatory alveolar macrophages. ZO-1 refers to a member of the membrane-associated guanylate kinase (MAGUK) family of proteins, which acts as a tight junction adaptor protein that also regulates adherens junctions. Tight junctions regulate the movement of ions and macromolecules between endothelial and epithelial cells. Additional biomarkers that may find use in characterizing alveolar cell function include but are not limited to: NPHS2, Podocin (PDCN); Connexin 43; etc. FIG. 20B.

In some areas of the device the alveolar marker expression, though present, was not homogeneous. In fact, it was possible to find patchy areas where the level of marker expression significantly varied.

In general, the co-culturing method in a fluidic device described herein provided a lung tissue-tissue interface, i.e. epithelial layer derived from primary human lung tissue, including alveolar cells, interfaced with a stroma area (region: section(s) in fluidic contact with an endothelial layer (within a spiral channel) separated by a stretchable membrane, combined with fluid under flow; cyclic membrane stretching and an ALI. The conditions under which this lung tissue-tissue interface was created induced a significant increase in the number of pneumocytes that expressed canonical alveolar epithelial markers, which is a breakthrough for providing a lung chip for use in more accurate in vitro modeling with applications for biomedicine and the biomedical field. Further, this is the first reported system where primary human alveolar cells where growth (partially under fluid flow) then further cultured and maintained under an Air-Liquid interface on an artificial stroma for an extended period of time, wherein the endothelial cells are under fluid flow, and to which was applied cyclic stretching movements of the membrane separating the endothelium and stroma area, that caused movement of the overlaying epithelium.

FIG. 20B ALI-M/M199 (following a KIAD boost method) showing exemplary fluorescent microscope images of immunostained biomarkers of functional Type II cells: Surfactant protein B (SP-B) (red); T1-α (red); Surfactant protein C (SP-C) (green); Na+/K+ pump (red); E-cadherin (green); epithelial sodium channels (αENaC) (red) located on the apical membrane of epithelial cells; co-staining of one cell: ABCA3 left (green) and LAMP3 right (red); ZO-1 (tight junctions) (red). Nuclei are colored blue in some images.

Taken together, these results indicate that co-culture of pneumocytes and human lung microvascular endothelial cells in Open-Top microfluidic platform under flow and cyclic mechanical strain enable formation of organ-level function that more closely resembles the normal in vivo lung tissue-tissue interface of the alveolar epithelium-stroma-endothelial capillary wall. These combined characteristics were not provided using conventional cell-culture models, especially when compared to plate co-cultures.

Physiological cyclic deformations of the membrane also contributed to the maintenance or retaining of the alveolar differentiation markers and/or in the turnover/release of surfactants B and C.

Surfactant in general refers to a combination of lipoprotein, mainly dipalmitoyl-phosphatidylcholine and some glycoprotein components, secreted by functional Type II alveoli. Secreted surfactant then spreads out over the surface of the alveolar cell layer. Surfactant functions in maintaining the stability of pulmonary tissue by reducing the surface tension of fluids that contact the lung cells, i.e. lowering the surface tension at the air-liquid interface in the peripheral air spaces. Some forms of surfactant, but not surfactant C, are also secreted by lung cells other than alveoli. Surfactant is internalized by type II cells in a recycling pathway for re-incorporation into surface-active material.

There are at least 4 surfactant-associated proteins/proteins and apolipoproteins in the human lung: 2 small hydrophobic proteins (SPB: SP-B and SPC: SP-C) and 2 collagenous, carbohydrate-binding glycoproteins (SPA: SP-A and SPD: SP-D).

Each surfactant protein has distinct patterns of expression in a subset of respiratory epithelial cells that include the alveolar type II cell. SP-C is the most restricted of the surfactant proteins in expression by cell types being detected only in the surfactant producing type II cell in the adult lung while SP-A, B, and D are expressed in tracheal gland cells (SP-A) and the bronchiolar—Clara cell epithelial population as well as alveolar type II cells. Glasser, et al., Surfactant Protein-C in the Maintenance of Lung Integrity and Function." J Aller Ther S7:001 (8 pages), 2011.

Normal SP-B and SP-C are highly hydrophobic peptides that associate with the surfactant phospholipids providing stability and function of the alveolar surfactant film. SPB was shown to enhance the rate of spreading and increasing the stability of surfactant monolayers in vitro. Surfactant B is encoded by a surfactant protein B gene (SFTPB) in type 2 alveolar pneumocytes and nonciliated bronchiolar cells as a hydrophilic pro-surfactant protein B (pro-SFTPB) that is cleaved at the N and C terminus into the mature SFTPB form.

SP-B is then secreted into the alveolar space as an approximate 6.5-8-kDa protein. SP-B may have anti-inflammatory and anti-oxidant properties. Bronchoalveolar Clara cells also express pro-SP-B, but do not process it to the mature form. Instead, a proSP-B form is secreted into the alveolar space.

SP-C is a lipopeptide synthesized by alveolar type II pneumocytes as pro-SFTPC, cleaved then secreted into the alveolar space for stabilizing the alveolar surfactant film. After transport from the ER to the Golgi, the adjacent cysteines of the transmembrane domain are palmitoylated. This in turn initiates endocytic translocation to multivesicular bodies where sequential proteolysis steps eliminate the long C-terminal domain. Multivesicular bodies that coalesce into concentric membranous lamellae containing organelles. Upon condensation of the multivesicular bodies into densely packed lamellar bodies, the short N-terminal domain is proteolytically removed. These lamellar bodies serve as the intracellular storage form of surfactant. Native human lung surfactant protein C (SP-C) is a 4.2-kDa acylpeptide that associates with alveolar surfactant phospholipids.

Exocytosis of the lamellar body into the extracellular space results in a rapid unraveling and release of phospholipid rich materials that ultimately reorganizes into a monolayer across the surface of the alveolus. The compression and expansion of the phospholipids in the surfactant film lower surface tension and impart resistance to collapse during respiration. During repetitive breathing extracellular forms of surfactant are altered and depleted of SP-B/SP-C. Surfactant is internalized by type II cells in a recycling pathway for re-incorporation into surface-active material. Alveolar surfactant levels are also regulated by macrophages that phagocytose and degrade surfactant. Impaired surfactant catabolism results in a clearance disorder termed alveolar proteinosis where the alveolar lumens fill with surfactant material and alters respiratory function.

Fully palmitoylated SP-C has optimal surface-active properties and has been further shown to exhibit synergistic surface activity with SP-B.

Extracts of porcine and bovine surfactant are now used clinically to rescue neonatal respiratory distress. These surfactant extracts contain variable amounts of SP-B and are enriched in SP-C. Instillation of SPC-phospholipid preparations into the lungs of surfactant deficient animals improved the outcome of experimental RDS. Recombinant SP-C based preparations decreased injury in both a preterm animal model of pulmonary surfactant deficiency and animals with acute lung injury induced by lavage depletion of surfactant. A synthetic surfactant comprised of recombinant SP-C and synthetic phospholipids was tested in trials for adult RDS with limited efficacy. The poor outcome of the clinical trials may reflect the complex origins, advanced injury, and spectrum of disorders grouped into adult RDS, relative to the developmental deficiency that is newborn RDS.

Thus, in some embodiments, surfactant produced by, then harvested from, alveolar chips may be used for testing as a treatment for surfactant deficiencies in lungs, including but not limited to lung diseases, e.g. Respiratory distress syndrome (RDS).

In contrast, SP-A and SP-D are synthesized by alveolar type II cells and unciliated bronchial epithelial cells (Clara cells). SP-A and SP-D are aqueous soluble proteins that harbor collagen like domains and lectin-like binding domains and are thus commonly referred to as collectins. SP-A and SP-D proteins bind to microbial pathogens to enhance their clearance and prevent or reduce the severity of infection.

Surfactant has multiple functions including but not limited to lower the surface tension on the cell membranes; stabilizing alveolar size; reducing the work of breathing; etc. People with insufficient surfactant have difficulty breathing. Additional immunologic properties provided by SP-A and SP-D include macrophage activation, facilitation of chemotaxis, enhancement of respiratory burst activity, and inflammatory cytokine expression.

Primary intracellular storage site for surfactant is within in lamellar bodies of alveolar type II cells. Lamellar bodies are lysosomal-like organelles highly enriched in phospholipids, generally containing approximately 10 to 12 mg of phospholipid per mg of protein. A diversity of proteins are present in the lamellar bodies as identified by mass spectroscopy. The limiting membrane of the LB contains at least one ABC transporter, ABCA3, which plays a role in importing phospholipids into the LB. Mutations in the ABCA3 transporter block the formation of lamellar bodies and cause severe lung disease in newborn infants. Lipid composition of lamellar bodies is similar to that for surfactant isolated from lung lavage fluid. Active, fully processed SP-B and SP-C peptides are highly enriched in lamellar bodies and are co-secreted with phospholipids into the air space. Like ABCA3, mutations in the genes encoding SP-B and SP-C (SFTPB and SFTPC) cause severe lung disease in neonates and infants. Jeffrey A. Whitsett, in *Fetal and Neonatal Physiology* (Fifth Edition), 2017. Composition of Lamellar Bodies.

H. Transitional Human Alveolar Epithelium.

Conversion of differentiated type II epithelial cells into fibroblasts and myofibroblasts occurs normally during development, but in aberrant wound repair processes, epithelial-to-mesenchymal transition (EMT) may lead to fibrosis and scarring. In general EMT induces epithelial cells expressing mesenchymal features. Conversely, mesenchymal-to-epithelial transition (MET) may occur during development.

While Type I alveolar cells in vivo usually undergo cell death during natural turnover or after injury. Type II alveolar cells in vivo have a variety of biological responses, i.e. functions, including participating in proinflammatory responses, proliferation, functioning by differentiation into terminally differentiated type I epithelia.

On the other hand, Type II alveolar cells may also contribute in vivo to dysregulated repair, such as by EMT, inducing fibrosis and in the extreme, respiratory failure. While in vivo Type II alveolar cells undergo physiological stretching during breathing and bodily movement, high levels of stretching, such as induced by mechanical ventilation, may lead to induced epithelial injury. Thus, excessive epithelial cell stretch may lead to lung injury (VILI) associated with pulmonary edema, inflammation, and fibrosis, leading to respiratory failure and death.

Type II alveolar cells constitute the majority of alveolar epithelial cells. When injured Type II cells can undergo epithelial-Mesenchymal transition (EMT). EMT is indicated by a decrease in epithelial cell markers, such as E-cadherin, and an increase in Mesenchymal cell markers such as Vimentin and alpha-smooth muscle actin ($\alpha$-SMA). EMT is found in healthy tissue during embryogenesis and is observed in wound healing, but it has also been recognized as a source for myofibroblasts in fibrosis. Additionally, alveolar EMT was shown to occur in idiopathic pulmonary fibrosis.

In vitro, TGF-$\beta$1 induces human alveolar epithelial to mesenchymal cell transition (EMT) which may be detected by an increase in expression of alpha smooth muscle Actin (alpha-SMA).

Figure 21A:
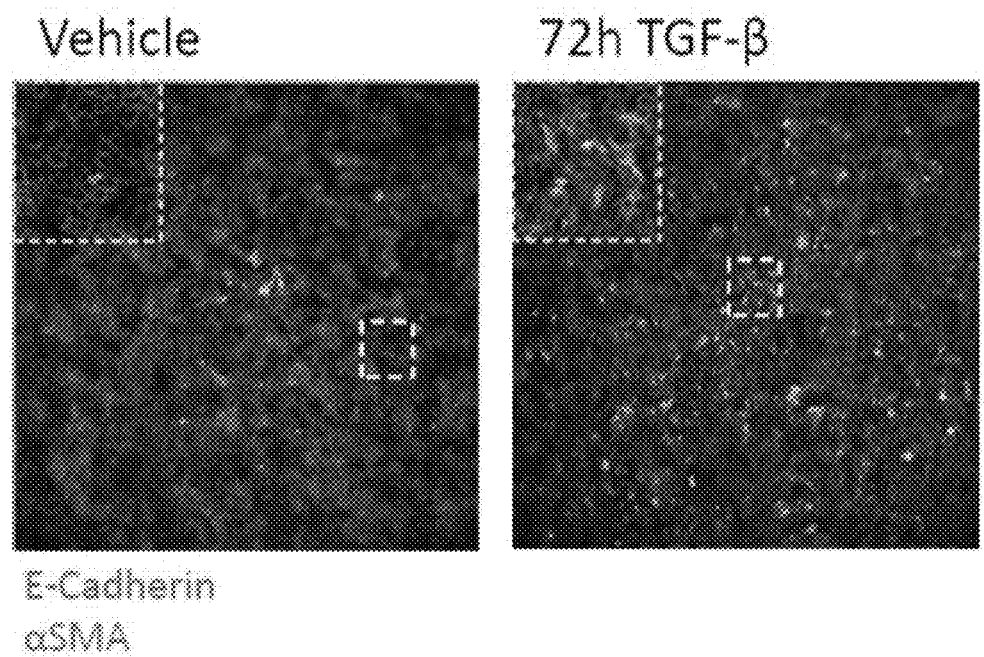
FIG. 21A-C shows one embodiment of a open top Alveolar-Chip fluidic device treated with TGF-β at 0.1, 1 or 10 ng/ml of TGF-B for 24 h or 72 h.
Figure 21C:
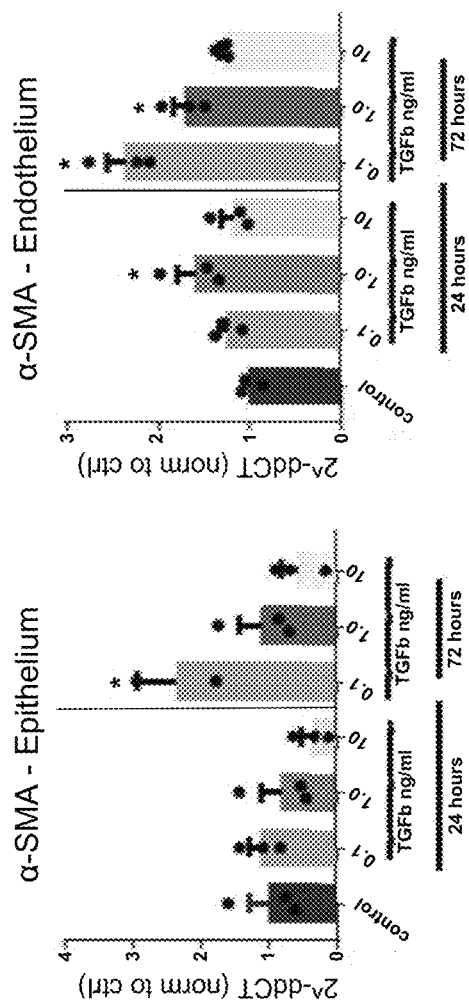
Figure 21B:
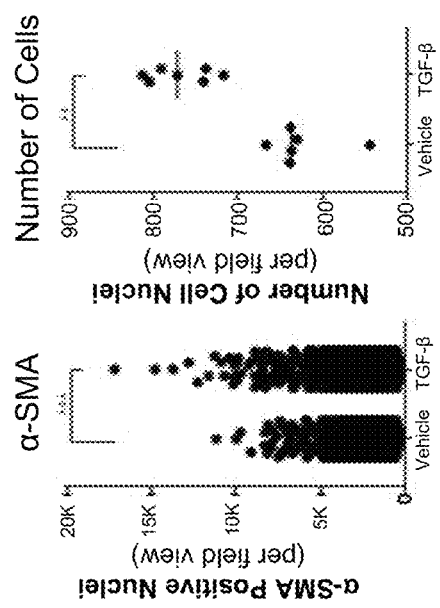

FIG. 21A-C shows one embodiment of a open top Alveolar-Chip fluidic device treated with TGF-$\beta$ for up to 72 hours showing in FIG. 21A (right panel) induction of alpha smooth muscle Actin (alpha-SMA) (green) and lack of ICAM-1 (red) compared to vehicle treatment (left panel). E-cadherin is shown in pink. FIG. 21B left chart shows quantitation of alpha-SMA+ nuclei between vehicle (left) and TGF-$\beta$1 induced (right). Right chart shows number of DAPI stained cells per field of view. FIG. 21C left chart shows $2^{\wedge}ddCT$ fold changes in alpha-SMA RNA expression measured by qRT-PCR (normalized to control) in relation to alpha-SMA+ nuclei in the epithelium at 24 and 72 hours over low amounts of TGF-$\beta$1. Right chart shows $2^{\wedge}ddCT$ fold changes (normalized to control) in relation to alpha-SMA+ nuclei in the endothelium at 24 and 72 hours over low amounts of TGF-$\beta$1.

Thus, we modeled ventilator-associated lung injury (VALI), an acute lung injury that develops during mechanical ventilation and is termed ventilator-induced lung injury (VILI) if it can be proven that the mechanical ventilation caused the acute lung injury. This cannot be achieved using conventional cell-culture models currently in use to study alveolar biology, because conventional models lack a fluidic endothelium-lined vascular compartment in direct contact with the stroma and alveolar epithelium. Thus, the microfluidic Open-Top Alveolus-chip platform could potentially facilitate future investigations into the molecular mechanisms of alveolar breathing in the normal and diseased states.

I. Lipopolysaccharide (LPS)-Induced Lung Inflammation.

Lipopolysaccharide (LPS) refers to a component of the cell wall of gram-negative bacteria. LPS is typically purchased commercially and used to induce inflammation as a simulation of part of the events during gram-negative bacteria infections. Further, LPS is considered a chemical stressor and known to induce a reversible disruption of the cellular monolayer after acute administration both in vivo and in vitro. Studies in static transwell demonstrated a dose dependent loss of barrier function as doses up to 100 ng/ml for LPS.

LPS used herein induced vascular expression of ICAM1 and secretion of pro-inflammatory cytokines in co-cultures of lung epithelial cells with endothelial cells, with or without fibroblasts, in open top fluidic devices, as described herein.

Figure 22A:
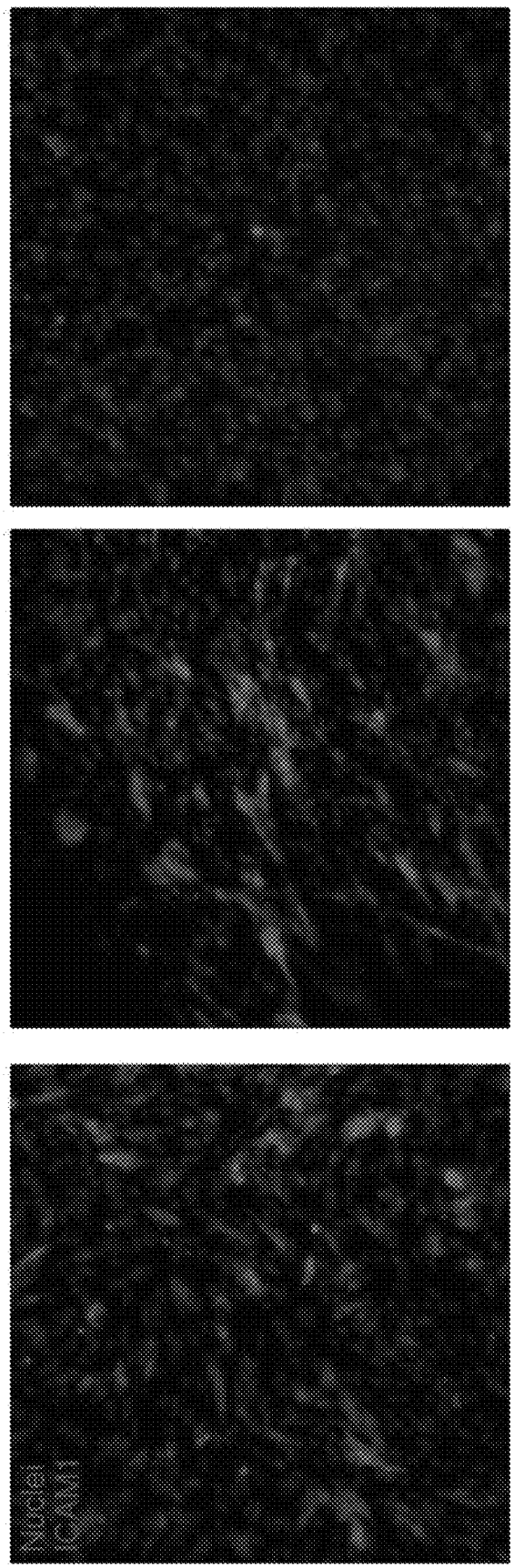
FIG. 22A-C shows one embodiment of an open top Alveolar-Chip fluidic device treated with LPS.
Figure 22B:
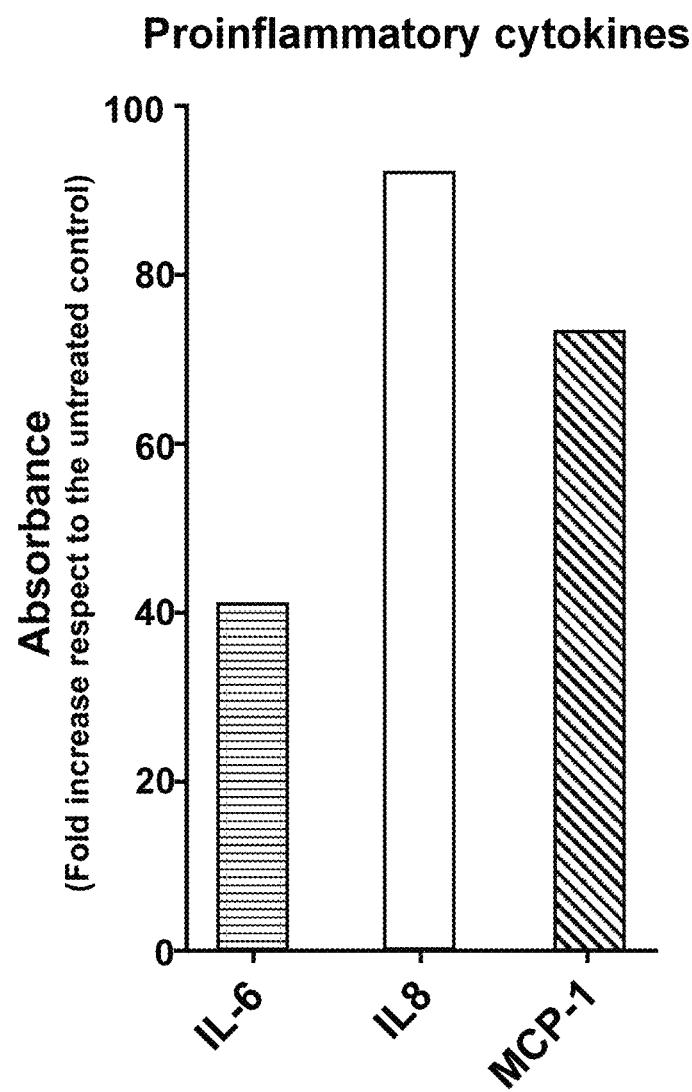
Figure 22C:
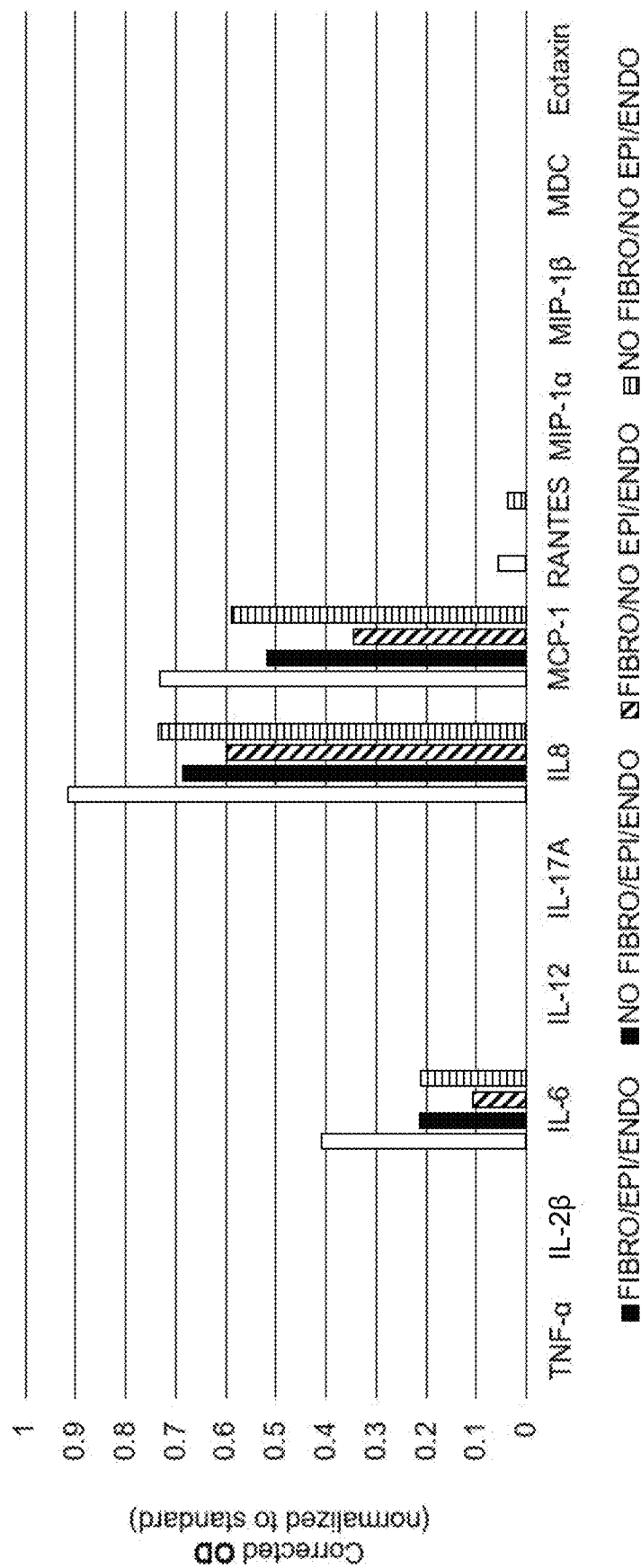

FIG. 22A-C shows one embodiment of an open top Alveolar-Chip fluidic device treated with LPS. FIG. 22A Effect of LPS on Vascular Expression of ICAM1. Left panel shows intercellular adhesion molecule-1 (ICAM1) (red) induction in co-cultures of Epithelium/Fibroblasts/Vasculature. Middle panel shows ICAM1 (red) induction in co-cultures of Epithelium/Vasculature. Right panel shows little ICAM1 (red) induction in co-cultures of Fibroblasts/Vasculature without epithelium. Representative images (20×) of endothelial cells (HMECs) lining the vascular surface of the Chip fixed and stained for ICAM1 (red) at 24 h post LPS treatment of the alveolar epithelial compartment. Nuclei are colored blue. FIG. 22B shows secretion of exemplary pro-inflammatory cytokines in the co-presence of epithelial cells. IL-6, il-8 and MCP-1 have 40-90 fold increases in relation to untreated controls. FIG. 22C Detection of exemplary Lung-Specific Cytokines and Chemokines, IL-6; IL-8; MCP-1 and RANTES, in response to LPS stimulation. Co-cultures of Epithelium/Fibroblasts/Vasculature induced higher levels of cytokines than co-cultures of Epithelium/Vasculature; Fibroblasts/Vasculature or Vasculature alone.

J. Functional Validation of the Vascular Compartment.

Figure 23:
FIG. 23 shows that blood perfusion of inflamed chip results in adhesion and aggregation of platelets. Left, schematic diagrams of the upper channels blue and ports blue dots, and spiral lower vascular endothelial channel red and ports red dots. Middle image shows one frame of blood flowing through the spiral channel. Right, shows one frame of platelets colored pink and DAPI stained blue nuclei flowing through the spiral channel. Larger pink areas represent aggregation of platelets and adhered platelets are observed at the lower sharp bend.

For further validation on the functionality of the endothelial compartment, the vascular compartment comprising an endothelial cell lining, was exposed to blood under flow. In one embodiment, an LPS pretreated microfluidic Alveolar-chip was perfused with blood, i.e. blood was flowed through the spiral channel. In one embodiment, a sample of human blood, e.g. 5 ml of whole blood isolated the same day from a healthy person (e.g. in citrate or heparin anticoagulation compounds) was perfused through the bottom spiraled channel with Ca2+ and Mg2+ to counteract the anticoagulation compounds, at 30 ml/hour. Blood perfusion of inflamed Alveolar-chip results in platelet adhesion and aggregation. FIG. 23 shows that blood perfusion of inflamed chip results in adhesion and aggregation of platelets. Left, schematic diagrams of the upper channels blue and ports blue dots, and spiral lower vascular endothelial channel red and ports red dots. Middle image shows one frame of blood flowing through the spiral channel. Right, shows one frame of platelets colored pink and DAPI stained blue nuclei flowing through the spiral channel. Larger pink areas represent aggregation of platelets and adhered platelets are observed at the lower sharp bend.

K. In Vitro Modeling of Pneumocyte Toxicity, Acute and Chronic Inflammation: Activation of the Nrf2 Pathway Protects the Alveolus-Chip from Acute-Stress-Induced injury.

Because there is limited availability of in vitro models that closely mimics human alveolar epithelium function and/or its disease states, we explored if the microfluidic Alveolus-Chip lined with the primary alveolar epithelial cell on an artificially created lung stroma with embedded primary lung fibroblasts and pulmonary microvascular endothelial cells would model a lung injury state.

To test this, we exposed the Alveolus-Chips to an acute damage generated by exposure to $H_2O_2$ under continuous infusion through the epithelium top channel, similarly to as it is orally administered in mice. One effect of $H_2O_2$ treatment is activating the Nrf2 pathway in alveolar cells. Nrf2 refers to a basic leucine zipper (bZIP) protein that regulates the expression of antioxidant proteins that in turn protect a cell against oxidative damage triggered by injury and inflammation.

Figure 24A:
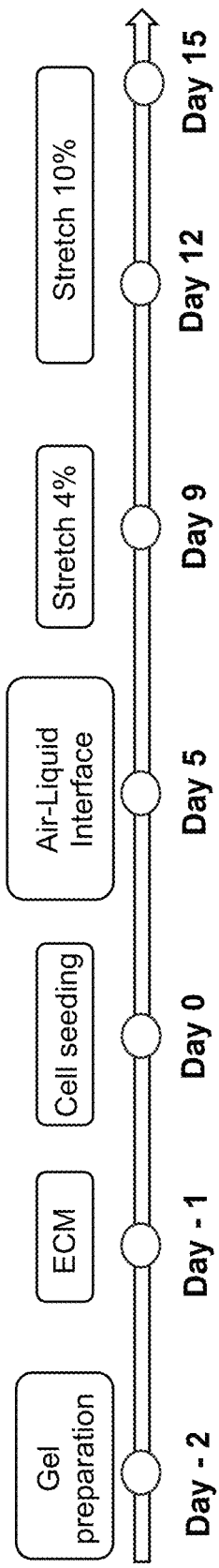
FIG. 24A-C shows exemplary schematics of one embodiment of a schematic timeline for providing a lung-chip (FIG. 24A) in addition to an exemplary timeline for testing compounds in the presence of $H_2O_2$ (e.g. 10 mM) (FIG. 24B) and an exemplary Nrf2 (Nuclear Factor Erythroid 2-Related Factor 2) signaling pathway triggered by $H_2O_2$ (FIG. 24C).
Figure 24B:
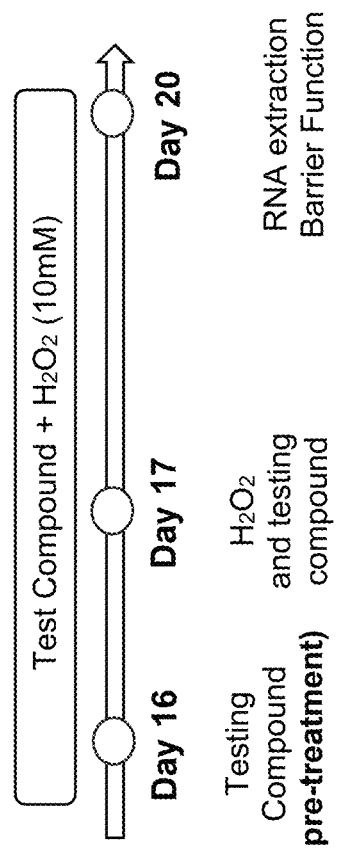
Figure 24C:
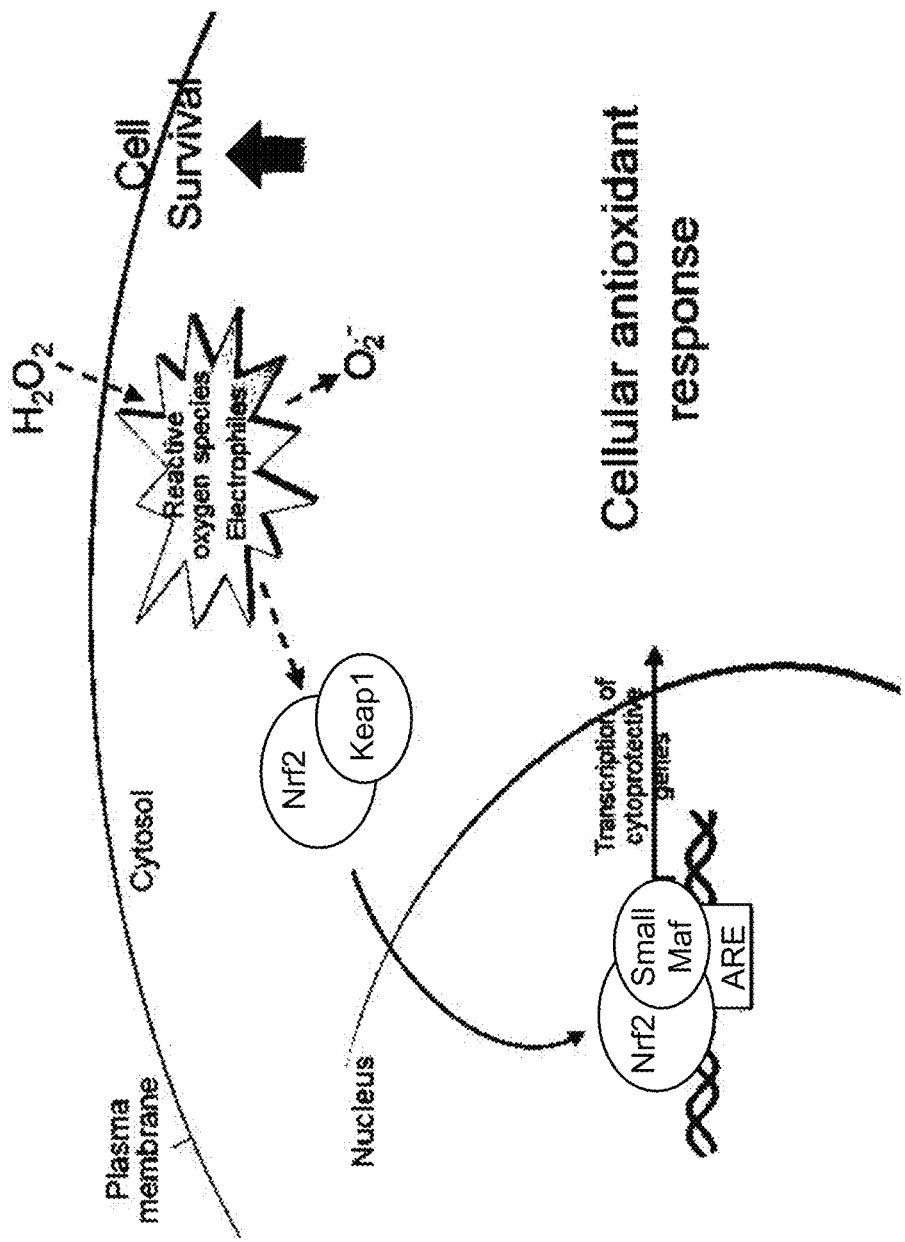

FIG. 24A-C shows exemplary schematics of one embodiment of a schematic timeline for providing a lung-chip (FIG. 24A) in addition to an exemplary timeline for testing compounds in the presence of $H_2O_2$ (e.g. 10 mM) (FIG. 24B) and an exemplary Nrf2 (Nuclear Factor Erythroid 2-Related Factor 2) signaling pathway triggered by $H_2O_2$ (FIG. 24C).

We studied interaction between different chip compartments by perturbating the system with biological and chemical stressors such as LPS, and $H_2O_2$ which are known to induce a reversible disruption of the cellular monolayer after acute administration both in vivo and in vitro. Studies in static transwell demonstrated a dose dependent loss of barrier function as doses up to 100 ng/ml for LPS (described above) and 10 mM for $H_2O_2$. To assess changes in the barrier function following the exposure to these insults, we added a fluorescent dies (Luciferase Yellow—Dextran-FITC) to the endothelial compartment which under control conditions, without the addition of activating compounds, demonstrated steps where the endothelium and epithelium form a barrier then becomes leaky while the cells die. The presence of a strong barrier is indirectly confirmed by the presence of continuous pattern of E-cad and VE-cad in the monolayer of Alveolar epithelial and endothelial cell, respectively. We found that treatment with LPS (10 ng/ml) and/or $H_2O_2$ (10 mM) causes barrier breakdown and disruption of intracellular junction which results in an influx of medium from the endothelial compartment to the epithelial compartment (detectable by visual eye observation or by barrier function analysis).

In one embodiment, a method is used for testing the effects of activating the Nrf2 system on pathological cell responses using an activating treatment, such as $H_2O_2$; LPS, etc. FIG. 25 shows exemplary fluorescent imaging of biomarker staining where $H_2O_2$ (48 h) treatment induces redistribution of E-Cadherin. Control left panel, $H_2O_2$ (10 mM) (48 h) treatment, right panel. E-cadherin (green) actin (pink) and nuclei blue.

To test the sensitivity of Alveolus-Chips to anti-radical treatment, we choose compounds, e.g. glycogen synthase kinase (GSK-3) thienotriazolodiazepine (JQ1), Bardoxolone (methyl), etc. representative for small molecules for testing in the alveolar chip. A dose response test system was used for determining whether there is a dependent correlation between the administration of a fixed concentration of $H_2O_2$ (10 mM) and different doses of a small molecule, e.g. GSK.

An exemplary result showed a significant loss of barrier function in presence of $H_2O_2$ (10 mM) alone while it showed different degree of barrier function loss that inversely correlated to the concentration of GSK. Specifically, lower to higher barrier function values were observed at 1 µM, 0.1 µM and 0.01 µM respectively.

Significant preventive effects on the barrier leakage were observed when the insult ($H_2O_2$) was co-administrated with a known antiradical small molecules such as Bardoxolone, GSK and JQ1 at clinically relevant concentrations of 50 nM for Bardoxolone, 0.01-1.0 µM, for GSK and 2 µM for JQ1. The remaining adherent pneumocytes exhibited retention of their normal phenotype with a "normal" distribution of the E-Cadherin.

Figure 26A:
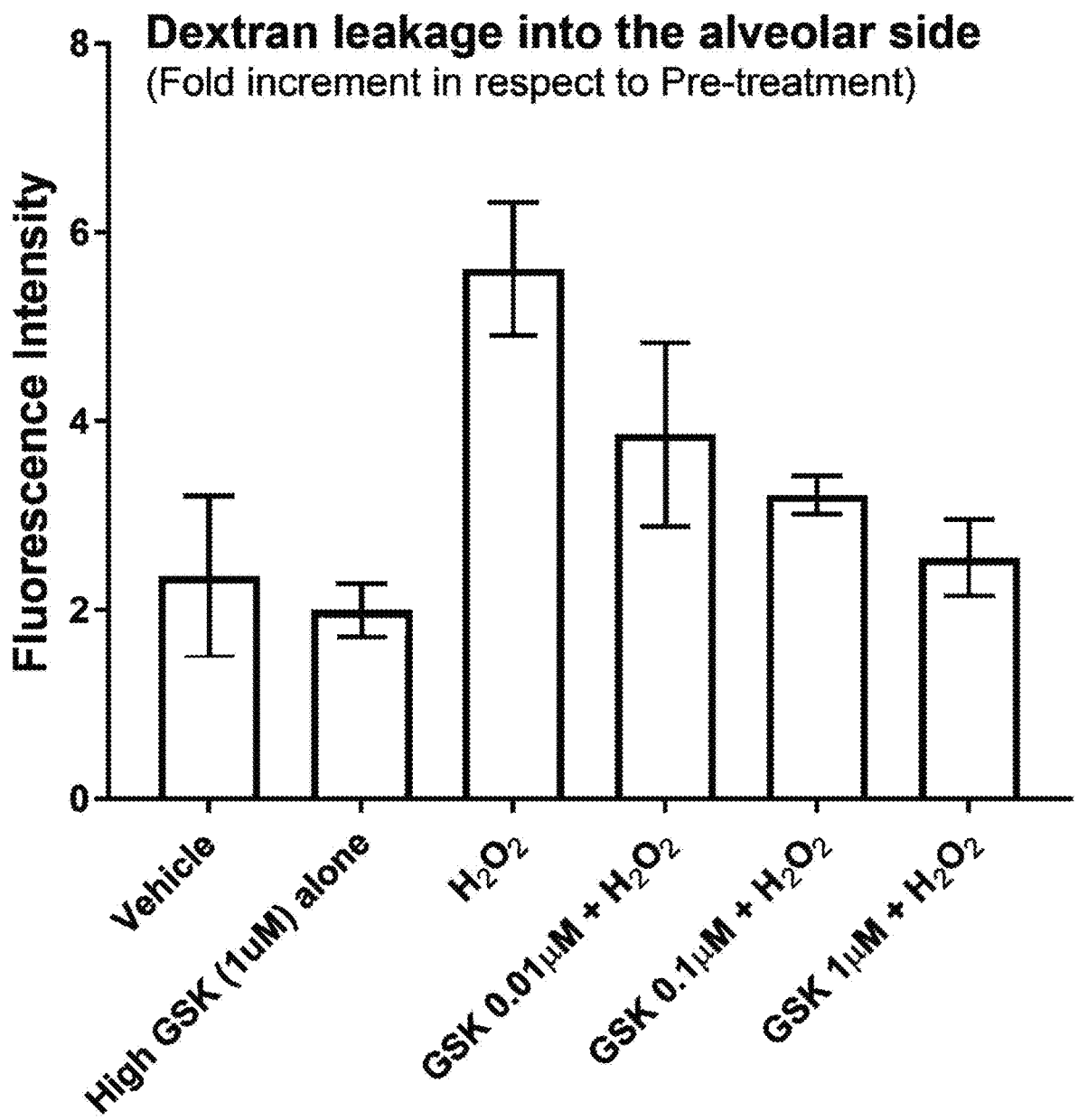
FIG. 26A-F effects of GSK alone or in combination with $H_2O_2$.
Figure 26B:
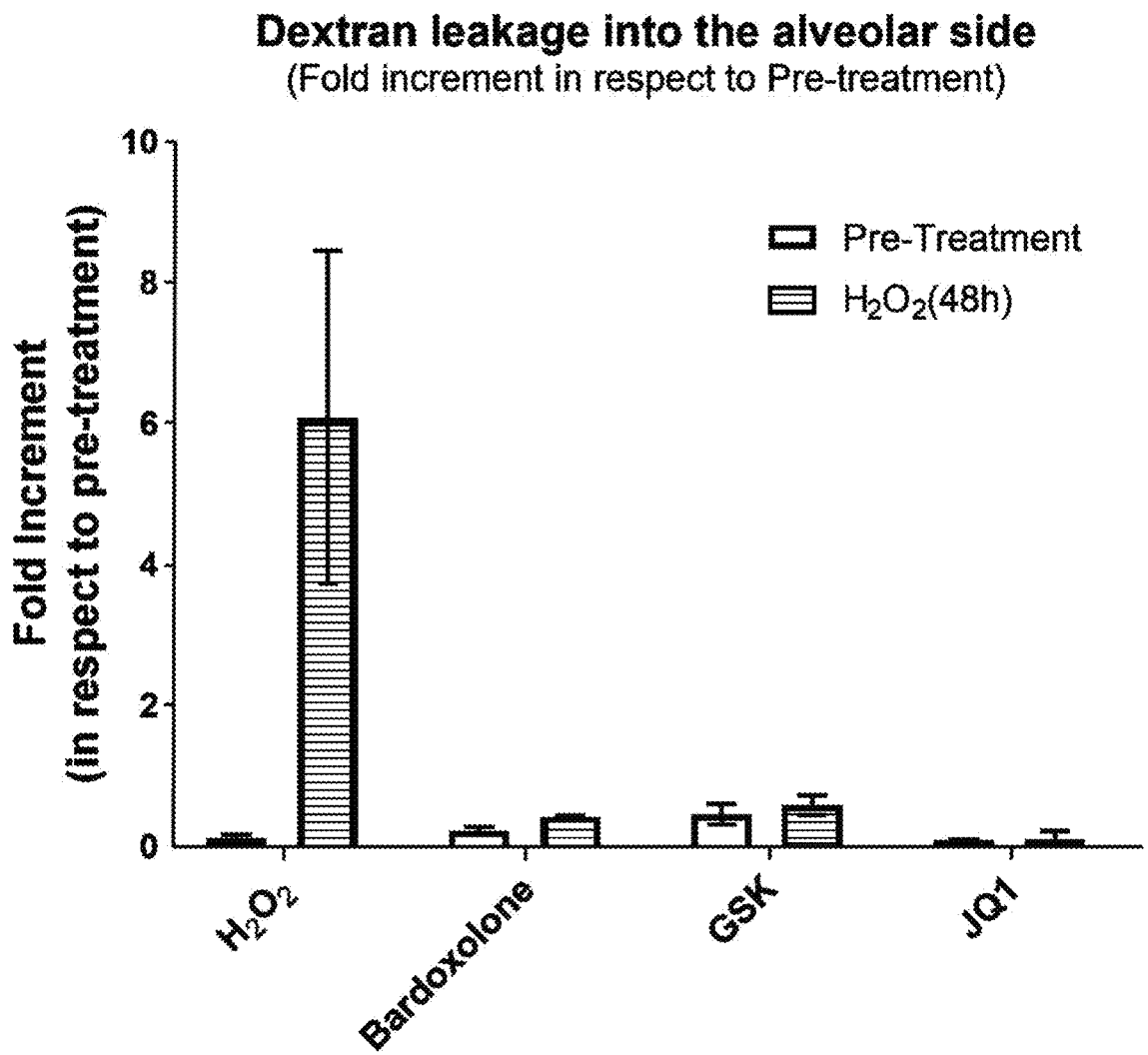
Figure 26C:
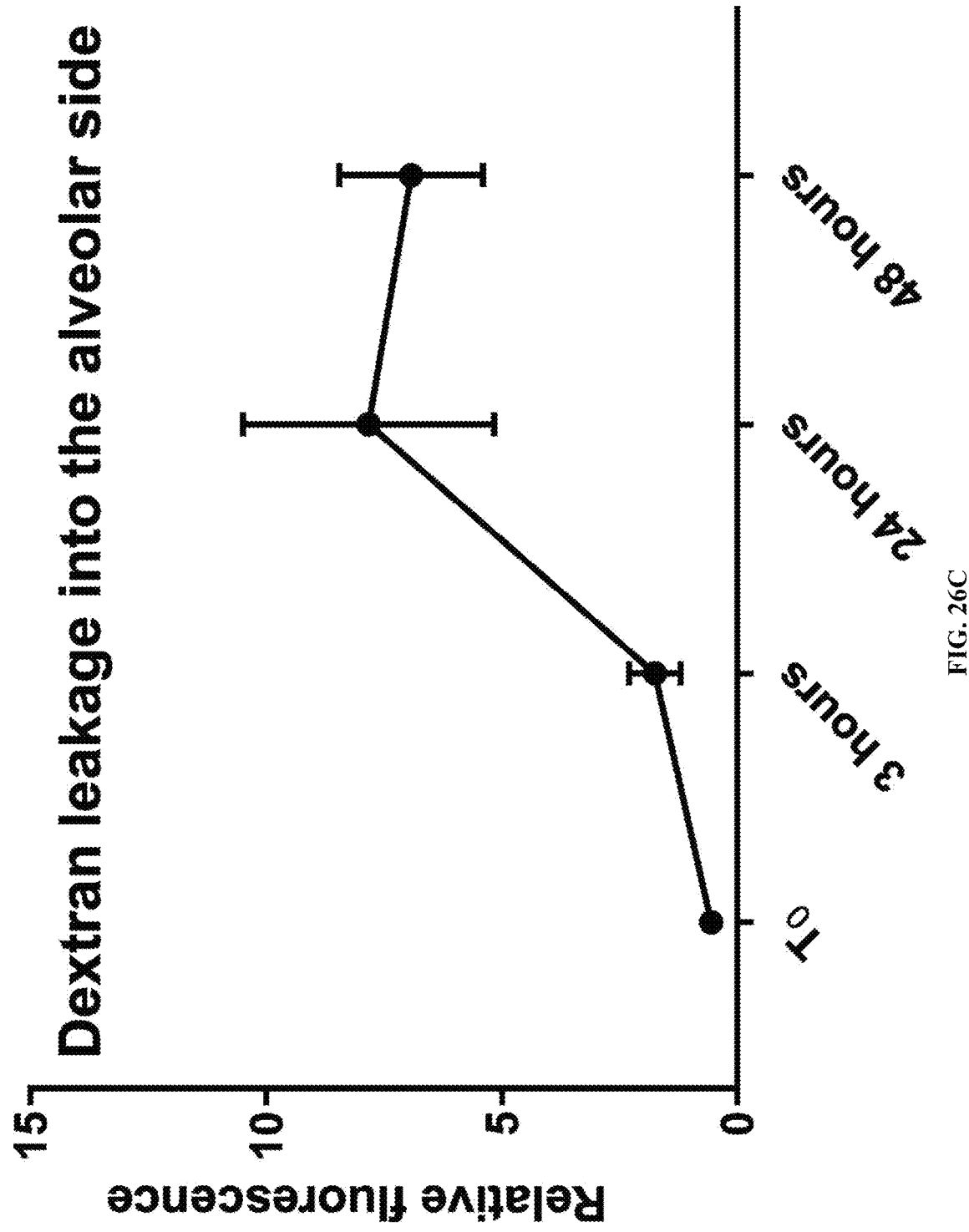
Figure 26D:
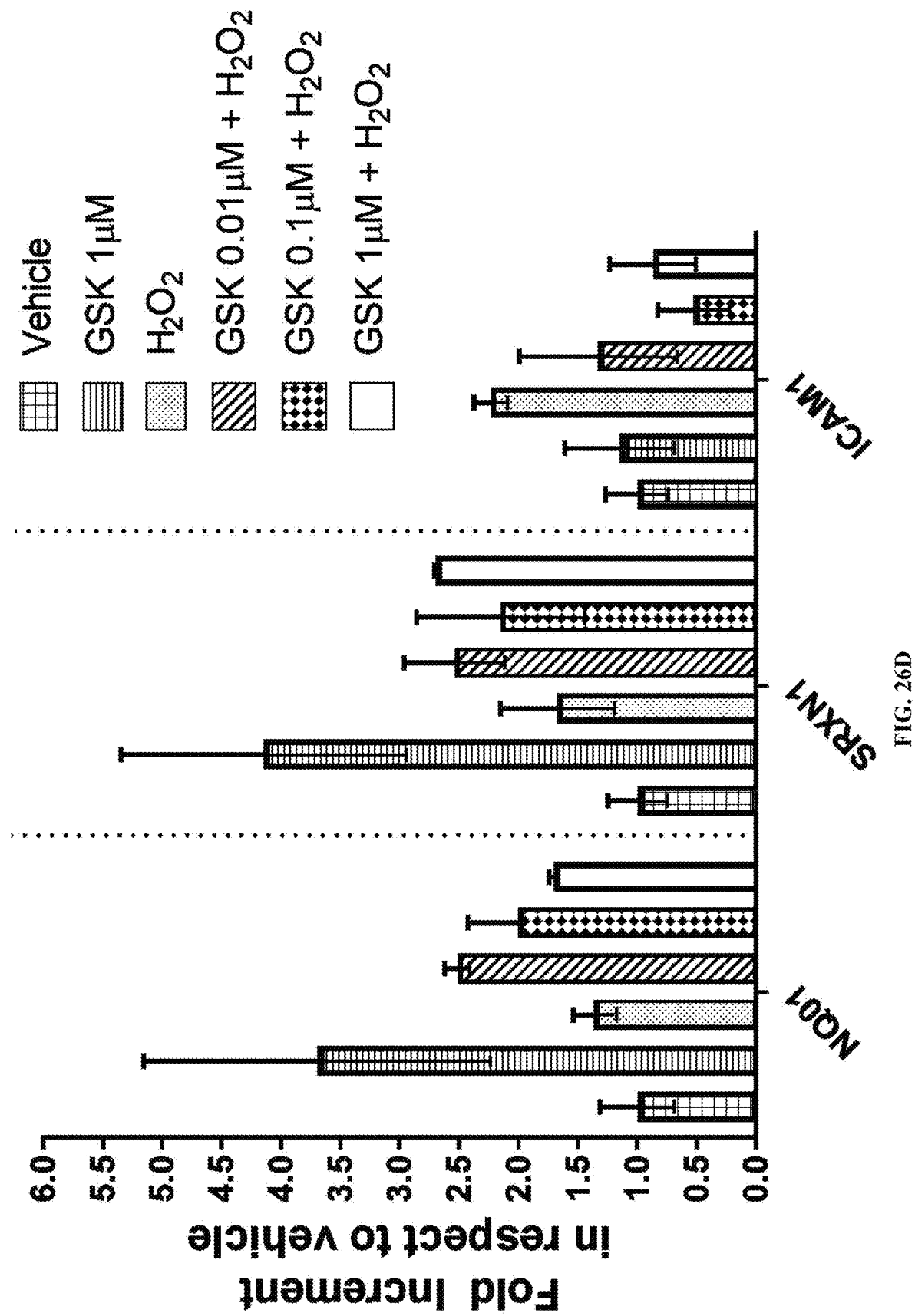
Figure 26E:
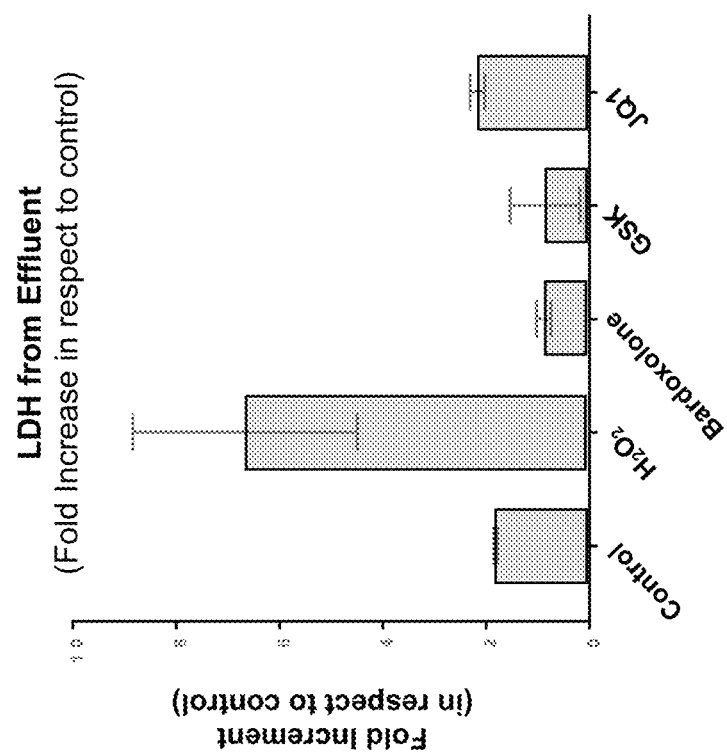
Figure 26F:
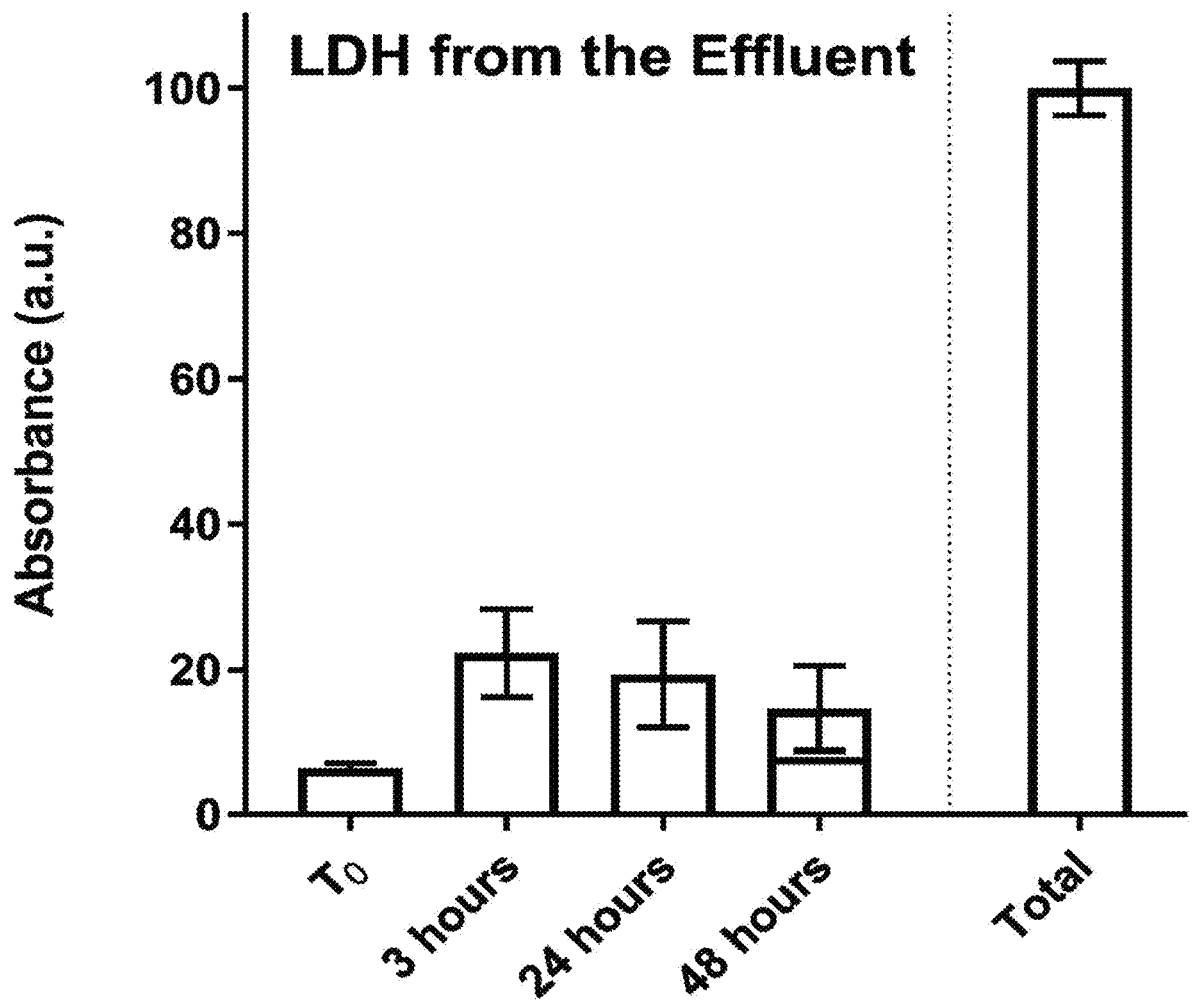

Embodiments of Alveolar chips were used for testing GSK alone, or in the presence of $H_2O_2$ for determining effects upon barrier functions along with gene changes in gene expression. FIG. 26A. FIG. 26A-F effects of GSK alone or in combination with $H_2O_2$. FIG. 26A Exemplary Dextrin leakage into the alveolar side in response to $H_2O_2$ 48 hours alone, GSK alone, or $H_2O_2$ in combination with GSK. FIG. 26B Exemplary Dextrin leakage into the alveolar side in response to $H_2O_2$ 48 hours in combination with one of the small molecules: GSK, JQ1 and Bardoxolone—pink bars. Pretreatment levels blue bars. FIG. 26C Exemplary Dextrin leakage into the alveolar side over time, 0-48 hours. FIG. 26D Exemplary $H_2O_2$ and GSK induced changes in gene expression of NQ01; SRXN1 and ICAM1. FIG. 26E Exemplary lactate dehydrogenase (LDH) release measured in effluent in response to $H_2O_2$ and small molecules: GSK, JQ1 and Bardoxolon. FIG. 26F Exemplary lactate dehydrogenase (LDH) release measured in effluent over time, 0-48 hours.

In summary, we further validated the capability of the system to predict human responses by testing several classes of pharmaceutical compounds such as small molecule (GSK, JQ1 and Bardoxolone), gluco-corticosteroid and cytokine (TGF-β) in a dose response fashion. The results described herein, using organ-chips suggest that this system more closely mimics the human lung organ-specific physiology contemplated to enable clinically relevant responses to drugs predictive of a response in vivo. This approach based on better mimicking a human lung microenvironment comprising enhanced alveolar cell differentiation and increased functions of the alveolus tissue in the fluidic device. We also contemplate that by improving tissue functions though application of the co-culture technology described herein, to other organs, such as skin, might enable the development of novel in vitro models. In vitro fluidic devices described herein, are contemplated to serve as replacements for animal use in drug discovery and toxin testing, which should further facilitate drug development and use in personalized-medicine applications.

Thus, in one embodiment, a method is used for activating the Nrf2 pathway for testing drug treatments. As one example, exemplary activation of the Nrf2 pathway protects the Alveolus-Chip from Acute-Stress-Induced injury. In some embodiments, an activated Nrf2 pathway in the Alveolus-Chip is used for determining pharmacology responses using an exemplary read out of dextran leakage into the alveolar side (Fold increment in respect to Pre-treatment).

Embodiments for Preparing an Open Top Alveolus-Chip.

Preparation of the Open-Top Alveolus-Chip is a multistep process that includes: preparation of the stromal compartment, coating with tissue-specific ECM proteins (Collagen IV, Fibronectin, Laminin), seeding of primary epithelial cells, seeding of primary lung-microvascular endothelial cells, establishment of air-liquid-interface (ALI), mechanical stretching.

The best differentiation of alveolar tissues occurs using both primary fibroblasts and alveolar epithelial cells that were not subjected to long-term passaging in culture. Thus, for some preferred embodiments, alveolar cells purchased commercially were directly seeded into fluidic chips, designated herein as passage 1 cells. In some embodiments, alveolar cells and lung cells undergoing additional passages are used. In some embodiments, alveolar cells are seeded into chips after undergoing isolation procedures for Type II progenitor cells derived from lung biopsies. In some preferred embodiments, alveolar cells are seeded into fluidic chips while in an active growth, i.e. replication, phase. In some embodiments, alveolar cells are seeded into fluidic chips prior to acquiring a more stem cell like phenotype. In some preferred embodiments, primary fibroblasts and primary endothelial cells are seeded into fluidic chips while in an active growth, i.e. replication. In some preferred embodiments, when previously cultured cells are used for seeding into chips, these cells should be harvested from sub-confluent cultures, during a growth phase, for best results.

To prepare the stroma equivalent, a solution of bovine type I collagen is typically used. Briefly, 8 volumes of collagen I gel solution 10 mg/ml is mixed on ice with 1 volume of 10×EMEM and 1 volume of 10× Reconstruction buffer while kept on ice to obtain a collagen solution at a final concentration of 8.0 mg/ml. This solution will have the appropriate consistency for making stroma equivalents compatible with Open-Top Chip applications. It requires a modest volume of NaOH to adjust the pH appropriately, typically 12 μl of NaOH for ml of collagen mixture. Proper pH can be accurately assessed in the final solution by the change in color of the collagen mixture from yellow to a light pink color.

Following the addition of NaOH Add 1 volume of fibroblast solution (0.5M/ml) and fully mix without introducing bubble. Introduction of bubbles during mixing of the collagen-fibroblast suspension should be avoided. Bubbles that eventually form in the collagen are not detrimental to alveolar differentiation, however they can create optical distortions or other types of visualization issue during chip imaging. Before seeding alveolar epithelial cells onto the stromal equivalents, it is important to coat the hydrogel surface with a coating of collagen IV, fibronectin and laminin to improve alveolar cell adherence and attachment. We find particular beneficial to slightly under seed the surface of the recreated stroma and allows the cells to grow an extra day before reaching confluence.

In one embodiment, after seeding fibroblast cells, alveolar cells and endothelial cells were seeded into fluidic devices at the same time using a 50:50 mixture of two types of culture medium, SAG and MDEM. However, this method resulted in elongated and strange phenotypes of many cells.

Thus, in a preferred embodiment, a "boost" culture medium, e.g. KIAD boost, is used in a method of "boosting" using a "boost" culture medium. In one embodiment, the use of a boost culture medium increases the induction of alveolar cell differentiation in co-cultures of epidermal alveolar cells, fibroblasts and endothelial cells, as shown by an increase "boost" in expression of Type I and/or Type II surface biomarkers. In one embodiment, the increased induction "boost" is observed during maturation in ALI-M/M199. In one embodiment, the "boost" results in a more differentiated Type I and/or Type II during culture in ALI-M/M199. In one embodiment, the "boost" method includes a step after seeding fibroblast cells, alveolar cells are seeded before endothelial cells and cultured in a "boost" epithelial medium, such as SAGM-KIAD, that promotes viability and function of alveolar cells. In some embodiments, an epithelial "boost" SAGM culture medium is SAGM further comprising KIAD supplements. In some embodiments, SAGM further comprising KIAD supplements and retinoic acid.

In the boost method, after confluence of the alveolar cells is reached, alveolar cells are kept submerged and treated with boosting KIAD and/or KIAD-retinoic acid (RA) supplements (i.e. SAGM-KIAD, SAGM-KIAD-RA) to induce alveolar cell differentiation. Alveolar cells are kept under this regime for 5 days. At day 4 HMVEC cells are seeded into the bottom spiraled channel with a double seeding procedure, as described herein, that guarantees an even coverage of the entire lumen of the bottom spiraled microfluidic channel with in EGM-2MV flowing through the lower channel for 24 hours, while the epithelium is kept submerged in KIAD supplemented medium. Typically, endothelial cells die in SAG medium, as shown herein.

One Embodiment of a Double Seeding

At day 5, EGM-2MV medium is switched to ALI-M (M199) prior to exposing epithelial cells to the air-liquid interface. After 4 days of culturing air-liquid interface stretching (defined as negative pressure cycle of 40 KPa corresponding at about 5% stain at a frequency of 0.2 hertz) is applied to the epithelium and recreated stroma for a total of 3 days. Stretching further stimulate maturation of the alveolar phenotype. Stretching profile is affected by the circular geometry of the stroma chamber therefore it results slightly uneven as it is possible to see in FIG. 6A. In some embodiments, the amount of serum is gradually lowered in order to avoid overcrowding. As a nonlimiting example, media comprising 5% serum is decreased to 2%, then lowered to 1%.

Another embodiment for providing an Alveolar fluidic chip device.

Two days before seeding lung cells into fluidic devices; prepare artificial lung stroma as hydrogels (e.g. 1% Col I) with embedded fibroblast cells by adding gel solutions and fibroblasts into exemplary molds as shown in FIG. 2G.

Chemically activate the middle stroma (stromal) surfaces of the fluidic device for allowing cross-linking between the biological component (Hydrogel) and the physical component (PDMS parts) of the Chip.

Insert the molded hydrogel-fibroblasts into fluidic device on the opposite side of the membrane from the spiral vascular channel. In some embodiments, the surfaces of the spiral channel are chemically activated for increasing endothelial cell attachment.

One day before seeding lung cells, in some embodiments, overlay hydrogel-fibroblasts with an ECM layer, e.g. collagen IV, fibronectin and laminin for increased expression of both Type I and Type II pneumocytes HI and HII genes, respectively, over other ECM components, see examples described herein.

Day 0: Seed alveolar cells, at subconfluent densities, onto the ECM layer of directly on top of the hydrogel surface. Day 0 Culture medium is SAGM additionally containing KIAD supplements. The presence of KIAD supplements encourages alveolar cell differentiation, e.g. induces alveolar cells towards a more differentiated phenotype when further cultured in ALI-M, under flow and stretch. Cells are kept under this regime for 5 days.

While at day 4, endothelial cells, e.g. HMVEC cells, are seeded into the bottom spiraled channel using a double seeding procedure. Endothelial cells are seeded using EGM-2MV media then cultured for 24 hours in EGM-2MV, while the epithelium is kept submerged in boost culture medium, e.g. SAGM-KIAD supplemented medium. During this time, staining for Type I and Type II-like cells shows both cell types are present.

After EGM-2MV medium incubation and boost, switch to ALI-M prior to exposing epithelial cells to the air-liquid interface. The upper channel of KIAD medium is also switched to ALI-M at this time. The lower channel is cultured under fluid flow.

Day 4: keep epithelial cells submerged until Day 5, then switch to an ALI. After 4 days of air-liquid interface then stretching (as negative pressure cycle of 40 KPa corresponding at about 5% stain at a frequency of 0.2 hertz) is applied to the epithelium and stroma. Using the timeline provided, FIG. 24A, no stretch was used for 5 days, then on Day 9 stretch at 4% was applied, increasing to 10% with the next 3 days so that on Day 12 stretch is at 10%. Stretching further stimulates maturation of the alveolar phenotype.

In summary, a method of forming a layer of differentiated pneumocytes in a fluidic device, comprises, seeding the epithelial cells on the top of the stroma (collagen I hydrogel with embedded fibroblasts) and differentiation in situ using the pneumocyte differentiation medium described herein, in the presence of fluid flow and stretch. Generating a combination of fluid flow and cyclic mechanical strain mimics physiological conditions present in the alveolar milieu.

Specifically, primary adult lung cells maintained in flat tissue culture containers were collected and seeded into fluidic devices where they underwent differentiation into functional cells under fluid flow in combination with mechanical strain. Alveolar cells cultured under these conditions expressed to a greater degree (or showed higher levels in the expression of) alveolar protein, e.g. surfactant, compared to alveolar cells not exposed to cyclic stretching. By comparison to control cultures, such as duplicate samples of adult primary lung cells differentiated in Transwell dishes, mechanical forces influence pneumocyte differentiation by enhancing expression of alveolar specific markers.

In addition, these co-cultured cells remained viable during culture over time in the microfluidic devices for at least two weeks of propagation, as measured by maintenance of flow levels of lactate dehydrogenase (LDH) release. These results demonstrate the possibility to maintain viable and differentiated for extended times in culture in the microfluidic devices human primary alveolar epithelial cell which could enable the application of this Organ-Chip approach also for patient-specific drug tolerance efficacy analyses in the future.

We created a tissue-tissue interface of the human alveolar epithelium-stroma-endothelial capillary wall on-chip by seeding alveolar cells directly on the recreated lung stroma (collagen I gel with embedded primary lung fibroblast from the same patient from which alveolar epithelial cell were collected) and by seeding primary lung microvascular endothelial cells in the lower spiraled channel in direct contact with the stroma.

To guarantee the survival and differentiation of all cell types a series of steps were performed sequentially. First the stromal layer was deposited into the chamber taking advantage of the open top configuration, gel were polymerized for 2 hours at 37° C. after which coated with a mixture of Fibronectin, Collagen IV and Laminin to recreate the basement membrane, which strongly enhanced pneumocyte attachment to the recreated stroma and stimulated alveolar marker expression (such as type I (ABCA3 and SURFB) and Type II (PDPN, HOPX and AQP5) markers).

KIAD differentiation medium "boost" or other culture media was administrated through the upper microfluidic channel to the pneumocytes on top of the artificial simulated stroma in the stroma compartment.

After 4 days of static culture, microvascular endothelial cells were seeded into the microfluidic device using microvascular endothelial medium EGM-2MV after which endothelial medium was perfused through the lower vascular channel lined by lung endothelial cells for 24 hours, at this point it was switched to special medium produced in house that enhances alveolar differentiation while keeping alive and differentiated endothelial cells.

Endothelial cells were seeded into the bottom spiraled channel in a double seeding procedure which guaranteed an even coverage of the microfluidic channel similarly to that described in other organ-on-chip papers. However differently from other reports, we noticed that Human Lung Microvascular Endothelial Cells (Lonza) undergoing prolonged cycle of stretching/relaxation cycle faded, therefore, to mitigate (or eliminate) this issue, we design the shape of the wall of the stroma compartment chamber to maximize the stretching at level of the epithelium monolayer and minimize the stress on endothelial compartment. Specifically, the stromal chamber wall was drafted with a 3 degrees angle to generate an anisotropic axial displacement of the hydrogel which maximize displacement at about 1 mm of the height of the chamber and drop to virtually zero (or is completely absent) at level of the membrane.

Endothelial cells were shown to replicate until complete confluence over the surface of the vascular channel. Endothelial cells undergoing shear stress from flowing liquid was recognized as a modulator of endothelial phenotype, including but not limited to morphology, gene expression, and differentiation. Therefore, the spiral-shape vascular channel is designed for generating a constant wall-shear-stress along the entire length of the vascular channel and, at the same time, to provide the overlying stromal compartment with sufficient nutrients to support fibroblasts and epithelial cell growth. Of note, the porous and elastic membrane interposed between the vascular and stromal chambers, allows cell-cell interaction and exchange of soluble factors between the two compartments. Live/dead staining performed on-chip have shown that pulmonary fibroblasts are alive after 15 days in culture (FIG. 18C).

Within the same time frame, epithelial cells lining the apical surface of the stromal compartment form a compact monolayer and express tissue-specific markers of type I-like and type II pneumocytes when exposed to air (air-liquid interface) for 8-10 days (FIG. 8A). Interestingly, cross section of the epithelial/stromal compartment obtained either via traditional tissue-processing techniques or confocal imaging, indicate that fibroblasts can migrate within the tridimensional extracellular matrix and eventually interact with the overlying epithelial cells (FIG. 17A).

While the significance of this observations for the current organ-chip model has yet to be investigated, a growing body of evidences support the hypothesis that the interaction of fibroblasts with epithelial cells is central for the development of physiological alveolar functions in healthy (Lo et al. 2017) and disease states (Sakai and Tager 2013)(Crosby and Waters 2010).

We found exemplary pneumocytes differentiated in the presence of both fluidic shear stress and exposed to 5% cyclic strain (0.2 Hz) in the bottom channels exhibited a significant increase in the intensity of surfactant B and C staining (FIG. 19A) and a higher release of cytoplasmic surfactant C ($P<0.05$) (FIG. 20B) compared to pneumocytes differentiated under either fluid flow alone or static (no cyclic strain), indicating that mechanical stimuli can induce higher level of pneumocyte maturation.

Development of a Universal Medium for Short-Term; Long-Term Use with an ALI.

Following the developmental paradigm described above, we first seeded dissociated alveolar cells and cultured them on a collagen I gel with embedded fibroblast coated with Laminin, Collagen IV Fibronectin ECM in submerged condition.

We selected KGF, cAMP, Dexamethasone and KGF (KIAD) based on previous genetic and immunological studies that showed that such factors were indispensable for the differentiation of pneumocytes and for the growth and differentiation of microvascular endothelial cells in in vitro systems. Therefore, after five days from the seeding, to promote differentiation into more mature alveolar cell, the pneumocyte were re-fed with medium containing KGM, Dexamethasone, IBMX and cAMP and cultured for at Air Liquid interface (ALI) a minimum of 10 days. This treatment-induced cell to expressed some of the characteristic alveolus mature cell markers.

Moreover, similar results were obtained with surfaces functionalized with Collagen IV, Fibronectin, and Laminin. These results indicate that laminin-Collagen IV-Fibronectin functionalized surfaces support the ability of soluble inductive factors to promote adhesion of alveolar cells and their further differentiation into the adult Type I, Type II alveolar cell.

Adult alveolar progenitor cells when exposed to air and treated with SAGM-KIAD supplements rapidly (within 4-5 days) acquired morphological features exhibited by adult lung pneumocytes including a cell body with a prominent nucleus and multiple lamellar-body like structure/vesicles. The larger size of the alveolar-cell obtained by this treatment was similar to the size of an immortalized podocyte cell line that was established previously from human lung A549. As pneumocytes become more differentiated during lung development, Surfactant C (or lamellar body) is shuttled/transported from ER/Golgi to the cytoplasm across the plasma membrane outside the cell. Therefore, the subcellular localization of pro-Surfactant C indicates the developmental status of pneumocytes.

Immunofluorescence microscopy analysis showed exemplary pro-Surfactant C more localized in the cytoplasm and on the plasma membrane of the Alveolar-cells compared to the immortalized cell-line A549, which exhibited primarily perinuclear staining. The A549 cells showed both nuclear and cytoplasmic expression of pro-Surfactant C. The A549 pneumocyte also showed enhanced release of Surfactant C, as determined by western blot/ELISA analysis, and deposited basement membrane collagen type IV, as detected by immunofluorescence microscopy. Together, these results demonstrate that methods developed and used herein along with an open top stretchable fluidic device induces pneumocyte differentiation efficiently for providing reproducible cultures of functional alveolar cells having morphological and molecular phenotypes that are consistent with mature alveolar pneumocytes.

Exemplary Cells And Culture Medium.

Examples of cells used during the development of the present inventions include but are not limited to human healthy cells isolated from patient biopsies, e.g. lung, airways or other bodily sources as chosen for certain studies, such as skin fibroblasts, vascular endothelial cells, etc., and healthy human cells-derived from patient lung biopsies that are maintained and/or cultured as undifferentiated or partially differentiated stock cell populations (Cryopreserved; plate culture, e.g., Petri, culture flasks, e.g. small T-25, larger T-75, etc.) Human Primary Alveolar Epithelial Cells isolated from normal human lung tissue (e.g., Cell Biologics Cat. (Catalog) #: H-6053; SAEC, Human Healthy Primary Small Airway Epithelial Cells isolated from normal human lung tissue in the distal portion of the lung in the 1 mm bronchiole area (Lonza Cat #: CC-2547 and CC-2547S); Human Pulmonary Alveolar Epithelial Cells (e.g., ScienCell Research Catalog #3200), Human Primary Lung Fibroblasts, including Human Lung Fibroblasts isolated from adult lung tissue, (e.g., Cell Biologics Cat. #: H-6013; Lonza Cat. #: CC-2512) and Human Lung Microvascular Endothelial Cells (e.g., Lonza Cat #: CC-2527). In some embodiments, cells were cultured in T-75 culture flasks in an atmosphere of 5% $CO_2$ at 37° C. according to the instructions provide by the manufacturers. Additionally, examples of diseased human lung fibroblasts may be isolated from human tissue and/or purchased commercially, for one nonlimiting example, D-HLF-COPD—Diseased Human Lung Fibroblast Cell (isolated from adult COPD donors: Lonza Catalog #: 00195277).

As one example, primary Alveolar epithelial cells (PI) (or other cell types during the development of the present inventions) were cultured in SAGM™ (modified) medium. SAGM™ modified medium refers to SABM™ Basal Medium with SAGM™ SingleQuots™ supplements: Lonza Cat. #: CC-4124). Thus, SAGM™ medium (SAGM) has a formula of 1×SABM Basal Medium (CC-3119) 500 mL+1× SAGM SingleQuots™ Supplement Pack (CC-4124).

Human Primary Lung Fibroblasts (PI) were cultured in DMEM/F-12 (e.g., Gibco™ Cat #: 11320082) containing 10% Heat Inactivated HyClone™ FetalClone™ II Serum (GE Healthcare Life Sciences, U.S.-sourced Cat #: SH30066.03); 1% penicillin-streptomycin (e.g., Gibco™ Cat #: 15140122) and 1% GlutaMAX™ (e.g., Gibco™ Cat #: 35050061).

Human Lung Microvascular Endothelial Cells were cultured in EGM™-2 MV Microvascular Endothelial Cell Growth Medium (EGM-2MV) (e.g., Lonza Cat. #: EBM™-2 Basal Medium (CC-3156) with EGM™-2 MV SingleQuots™ supplements (CC-4147).

Additional Culture Medium Formulations:

KIAD boost culture medium refers to a culture medium that has an addition of KIAD supplements. KIAD refers to a combination of Keratinocyte Growth Factor, Isobutylmethylxanthine, 8-bromo-cyclicAMP, and Dexamethasone). In one embodiment, KIAD also includes RA. In one embodiment, KIAD supplements for providing a "boost" culture medium was prepared by adding the following compounds to SAGM™ modified medium: Keratinocyte Growth Factor (KGF) (e.g., PromoCell: C-63821 KGF (Recombinant Human Fibroblast Growth Factor 7 (FGF-7), human recombinant (HEK: HEK cell-derived, for one example, HEK-293 refers to a cell line derived from human embryonic kidney cells initiated by the transformation and culturing of normal HEK cells with sheared adenovirus 5 DNA)) at final concentration of 10 ng/ml, Isobutylmethylxanthine (IBMX) (e.g., Sigma-Aldrich Cat #: 15879-100MG) at final concentration of 0.1 mM, cAMP (e.g., Sigma-Aldrich: B7880-250MG) at final concentration of 80 UM and Dexamethasone (e.g., Sigma-Aldrich: D2915-100MG). In one embodiment, KIAD boost culture medium further comprises retinoic acid, e.g. 15 ng/ml.

A mixture of KIAD compounds were added at final concentration of 200 nM to SABM™ Small Airway Epithelial Basal Medium (e.g., Lonza Inc.) supplemented with variable percentages of Heat Inactivated HyClone™ Fetal-Clone™ II Serum (GE Healthcare Life Sciences, U.S.-sourced), as described herein.

For "boosting" epithelial cells are submerged in "boost" culture medium on Day 5 for around 24 hours.

As used herein, "ALI-M" refers to a medium used for culturing cells either with or without an ALI.

Universal Medium (ALI-M/M199; differentiation medium): In some embodiments, a medium was created and used for culturing at least 3 primary cell types in fluidic devices, both short and long term cultures in addition for use with an Air-Liquid interface, i.e. ALI-M (medium) for flowing through the upper channel containing alveolar epithelial cells was prepared by adding 2% Heat Inactivated HyClone™ FetalClone™ II Serum, GlutaMax™ (e.g., Gibco™) at final concentration of 2 mM, Heparin sodium salt from porcine intestinal mucosa 2 Unit/ml, a growth factor that stimulates the proliferation of epidermal and epithelial cells: Epidermal Growth Factor (EGF) (e.g., rHu EGF, PromoCell Cat #: C-60170) at final concentration of 10 ng/ml, KGF (e.g., PromoCell: C-63821) at final concentration of 3 ng/ml, a stimulator of proliferation and survival of endothelial cells: e.g. VEGF-165, (Vascular Endothelial Cell Growth Factor, human recombinant VEGF-A alternatively spliced isoform provided by transformed *E. coli*) (e.g., PromoCell Cat #: C-64420) at final concentration of 1 ng/ml (concentration range of 0.5-8.0 ng/ml), cAMP (e.g., Sigma-Aldrich: 8-Bromoadenosine 3',5'-cyclic monophosphate sodium salt, B7880-250MG) at final concentration of 80 µM, and Dexamethasone (e.g., Sigma-Aldrich Cat #: D2915-100MG) at final concentration of 20 nM in Gibco™ Medium 199, no phenol red (with L-glutamine and without HEPES) (e.g., Gibco™ Cat #: 11043023, 500 ml).

In some embodiments, commercially obtained M199 comprises Earle's salts; vitamins, amino acids, inorganic salts and other components, exemplary components described in Table 2.

TABLE 2

Medium 199, no phenol red. Morgan, and Campbell, "The nutrition of animal tissues cultivated in vitro. I. A survey of natural materials as supplements to synthetic medium 199." J. Natl. Cancer Inst., 16: 557-657 (1955). Morgan, Morton, and Parker. "Nutrition of animal cells in tissue culture; initial studies on a synthetic medium." Proc. Soc. Exp. Biol. Med., 73: 1-8 (1950).

| Components | Molecular Weight | Concentration (mg/L) | mM |
|---|---|---|---|
| Amino Acids | | | |
| Glycine | 75.0 | 50.0 | 0.6666667 |
| L-Alanine | 89.0 | 25.0 | 0.28089887 |
| L-Arginine hydrochloride | 211.0 | 70.0 | 0.33175355 |
| L-Aspartic acid | 133.0 | 30.0 | 0.22556391 |
| L-Cysteine hydrochloride-H2O | 176.0 | 0.1 | 5.681818E−4 |
| L-Cystine 2HCl | 240.0 | 26.0 | 0.108333334 |
| L-Glutamic Acid | 147.0 | 75.0 | 0.5102041 |
| L-Glutamine | 146.0 | 100.0 | 0.6849315 |
| L-Histidine hydrochloride-H2O | 210.0 | 21.88 | 0.10419047 |
| L-Hydroxyproline | 131.0 | 10.0 | 0.07633588 |
| L-Isoleucine | 131.0 | 40.0 | 0.3053435 |
| L-Leucine | 131.0 | 60.0 | 0.45801526 |
| L-Lysine hydrochloride | 183.0 | 70.0 | 0.38251367 |
| L-Methionine | 149.0 | 15.0 | 0.10067114 |
| L-Phenylalanine | 165.0 | 25.0 | 0.15151516 |
| L-Proline | 115.0 | 40.0 | 0.3478261 |
| L-Serine | 105.0 | 25.0 | 0.23809524 |
| L-Threonine | 119.0 | 30.0 | 0.25210086 |
| L-Tryptophan | 204.0 | 10.0 | 0.04901961 |
| L-Tyrosine disodium salt dihydrate | 261.0 | 58.0 | 0.22222222 |
| L-Valine | 117.0 | 25.0 | 0.21367522 |
| Vitamins | | | |
| Ascorbic Acid | 176.0 | 0.05 | 2.840909E−4 |
| Biotin | 244.0 | 0.01 | 4.0983607E−5 |
| Choline chloride | 140.0 | 0.5 | 0.0035714286 |
| D-Calcium pantothenate | 477.0 | 0.01 | 2.096436E−5 |
| Folic Acid | 441.0 | 0.01 | 2.2675737E−5 |
| Menadione (Vitamin K3) | 172.0 | 0.01 | 5.8139532E−5 |
| Niacinamide | 122.0 | 0.025 | 2.0491803E−4 |
| Nicotinic acid (Niacin) | 123.0 | 0.025 | 2.0325204E−4 |
| Para-Aminobenzoic Acid | 137.0 | 0.05 | 3.6496352E−4 |
| Pyridoxal hydrochloride | 204.0 | 0.025 | 1.2254903E−4 |
| Pyridoxine hydrochloride | 206.0 | 0.025 | 1.21359226E−4 |
| Riboflavin | 376.0 | 0.01 | 2.6595744E−5 |
| Thiamine hydrochloride | 337.0 | 0.01 | 2.967359E−5 |
| Vitamin A (acetate) | 328.0 | 0.1 | 3.0487805E−4 |
| Vitamin D2 (Calciferol) | 397.0 | 0.1 | 2.5188917E−4 |
| alpha Tocopherol phos. Na salt | 554.7 | 0.01 | 1.8027762E−5 |
| i-Inositol | 180.0 | 0.05 | 2.7777778E−4 |
| Inorganic Salts | | | |
| Calcium Chloride (CaCl2) (anhyd.) | 111.0 | 200.0 | 1.8018018 |
| Ferric nitrate (Fe(NO3)—9H2O) | 404.0 | 0.7 | 0.0017326733 |
| Magnesium Sulfate (MgSO4) (anhyd.) | 120.0 | 97.67 | 0.8139166 |
| Potassium Chloride (KCl) | 75.0 | 400.0 | 5.3333335 |
| Sodium Bicarbonate (NaHCO3) | 84.0 | 2200.0 | 26.190475 |
| Sodium Chloride (NaCl) | 58.0 | 6800.0 | 117.24138 |
| Sodium Phosphate monobasic (NaH2PO4—H2O) | 138.0 | 140.0 | 1.0144928 |
| Other Components | | | |
| 2-deoxy-D-ribose | 134.0 | 0.5 | 0.0037313432 |
| Adenine sulfate | 404.0 | 10.0 | 0.024752475 |
| Adenosine 5'-phosphate | 347.0 | 0.2 | 5.763689E−4 |
| Adenosine 5'-triphosphate | 605.0 | 1.0 | 0.0016528926 |
| Cholesterol | 387.0 | 0.2 | 5.1679584E−4 |
| D-Glucose (Dextrose) | 180.0 | 1000.0 | 5.5555553 |
| Glutathione (reduced) | 307.0 | 0.05 | 1.6286645E−4 |
| Guanine hydrochloride | 188.0 | 0.3 | 0.0015957447 |
| Hypoxanthine Na | 136.0 | 0.4 | 0.0029411765 |
| Ribose | 150.0 | 0.5 | 0.0033333334 |
| Sodium Acetate | 82.0 | 50.0 | 0.6097561 |
| Thymine | 126.0 | 0.3 | 0.0023809525 |
| Tween 80 ® | | 20.0 | Infinity |
| Uracil | 112.0 | 0.3 | 0.0026785715 |
| Xanthine-Na | 152.0 | 0.34 | 0.0022368422 |

One example of a Recombinant Human EGF amino acid (AA) Sequence:

(SEQ ID NO: 1)
NSDSECPLSH DGYCLHDGVC MYIEALDKYA CNCVVGYIGE
RCQYRDLKWW ELR.

-continued

One example of a Human VEGF165 AA Sequence (monomer):

(SEQ ID NO: 2)
APMAEGGGQN HHEVVKFMDV YQRSYCHPIE TLVDIFQEYP

DEIEYIFKPS CVPLMRCGGC CNDEGLECVP TEESNITMQI

MRIKPHQGQH IGEMSFLQHN KCECRPKKDR ARQENPCGPC

SERRKHLFVQ DPQTCKCSCK NTDSRCKARQ LELNERTCRC

DKPRR.

Interconnectivity

Interconnectivity refers to the observation that adding a compound to the epithelial side may induce a cytokine mediated response in the endothelial side. For example, exposure to LPS on the epithelial compartment induces expression of ICAM on endothelial cells in the vascular compartment. Conversely, exposing endothelial cells directly to LPS does not induce expression of ICAM on these cells. Therefore this effect of interconnectivity does not happen in absence of epithelium. In other words, inflamed epithelial cells modulate function of the endothelial cells.

We studied interaction between different chip compartments by perturbating the system with biological and chemical stressors such as LPS, and $H_2O_2$ which are known to induce a reversible disruption of the cellular monolayer after acute administration both in vivo and in vitro. Studies in static transwell demonstrated a dose dependent loss of barrier function as doses up to 100 ng/ml for LPS and 10 mM for $H_2O_2$. To assess changes in the barrier function following the exposure to these insults, we added a fluorescent dye (e.g. Luciferase Yellow—Dextran-FITC) to the endothelial compartment, which is under control condition confirmed that the endothelium and epithelium form a barrier to the dies. The presence of a strong barrier is also indirectly confirmed by the presence of continuous pattern of E-cad and VE-cad in the monolayer of Alveolar epithelial and endothelial cell, respectively. We found that treatment of Alveolar chips with LPS (10 ng/ml) and/or $H_2O_2$ (10 mM) causes barrier breakdown and disruption of intracellular junction which results in an influx of medium from the endothelial compartment to the epithelial compartment (detectable by eye) and contemplated changes in barrier function analysis. Analysis of the medium effluent after 24 hours of exposure to LPS shows increases of lung specific cytokines such as IL-6, IL-8 and MCP-1 (FIGS. 22B and 22C), while no apparent correlation between releasing of IL-6, IL-8 and MCP-1 and exposure to $H_2O_2$ has been observed. We also decoupled the effect of single biological component to the inflammatory response by selectively removing them from the system in an integrated matrix. In the specific we cross-tested several cell combinations: full system including fibroblasts, endothelial and epithelial cell, system formed of endothelial and epithelial cell, system formed of fibroblast and endothelial cells, system formed of fibroblast and epithelial cells and fibroblast alone which evidenced that each component of the biological model responds to the insult differently and we identified epithelial cells as the main releaser of IL-6, while fibroblasts and endothelial cells gave little to no contribution to IL-6 release. Oppositely, epithelial and endothelial cells are similarly involved in the releasing of IL-8. Data also showed that each compartment epithelial, endothelial and stromal compartment contributes to the inflammatory response and that for some of the cytokines the cross talk between epithelial and endothelial cell amplifies the response. In fact, the recorded value of IL-6 and IL-8 is not the algebraic sum of the concentration of the factors released by the single cellular components. Endothelial cells lining the vascular surface of the chip stained for ICAM at 24 hours post LPS treatment making in evidence that LPS induces ICAM1 expression only in presence of epithelial cells, confirming some degree of interconnectivity between the endothelial and epithelial compartment, or at least, that some of the soluble factors released by epithelial cell can reach the endothelium through the recreated stroma. These results also suggest that some peculiar aspects of the inflammatory response cannot be modulated without the presence of multiple cell types. DD TGF-β Data if they make sense.

When we removed the LPS, $H_2O_2$ and TGF-β and cultured cells for an additional 2 days in fresh medium, we found that the barrier breakdown in our chip was reversable and the disrupted epithelial intracellular junctions re-formed resulting in a restoration (recovery) of the barrier function, however in some embodiments, we did not observe a similar degree of recovery of the endothelium.

However, we succeeded in reconstituting aspects of human alveolus-stroma-capillary interface that have, to our knowledge, never been modelled in vitro, and that might have a great impact on research and drug development. For example, our data demonstrated that this microfluidic model recapitulates the ability of the alveolar epithelial cells to retain essential alveolar proteins, such as surfactant B and C, ABCA3, etc.

We showed that the three compartments were in communication, i.e. interconnectivity, showing the ability of LPS, $H_2O_2$ and TGF-β1 to generate a cascade of event culminating in excreting smaller molecules/cytokines signaling inflammation in the circulation sector, which is one of the primary pathological events occurring at level of the alveolus barrier when under an acute toxicity or injury. In some embodiments, a toxic response to a test compound or drug results in one or more of increased Type II cell proliferation, Type II cell differentiation to Type I cells, Type II cell death, Type I cell death, decreased functioning of Type I and/or Type II cells, etc.

III. Modeling Human Airways Pathophysiology On-Chip

In some embodiments, lung chips described and/or referenced herein are contemplated to be used with stem cells for providing stem cell-based microfluidic lung chips.

Based on similar designs and microfabrication techniques used for the alveolus-on-a-chip, several on-chip platforms modeling various features of the human airways in health and disease were recently been developed (46, 101-103). For instance, a "small airway-on-a-chip" recapitulates the human bronchial and bronchiolar epithelium by supporting the full differentiation of a columnar, pseudostratified, mucociliary, bronchiolar epithelium composed of human primary airway epithelial cells isolated from normal or diseased patients. As in the alveolus model, the epithelium is underlined by a functional human pulmonary microvascular endothelium experiencing continuous fluid flow (46).

Human airway cells cultured on-chip at air liquid interface for three weeks reconstitute an in vivo-like epithelium composed of multi-ciliated cells with physiological cilia beating frequency as well as goblet cells secreting mucus into the lumen resulting in robust mucociliary clearance (46). Surprisingly, the proportion of ciliated, goblet and basal cells inside the mature small-airway-on-a-chip are in proportions strikingly similar to those found in human lung, suggesting that the reconstituted tissue closely recapitulates the morphology and functions of the human airway epithelium. Perfusion of the cells through the vascular channel with IL-13 to mimic a microenvironment enriched with inflammatory Type 2 T helper (Th2) cells resulted in significant airway remodeling with goblet cells hyperplasia, increase of pro-inflammatory cytokines, and reduction of cilia beating frequency. This phenotype was suppressed following incubation with Tofacitinib, a Jak inhibitor used as a therapeutic against rheumatoid arthritis (46). Using primary airway cells derived from COPD patients, the small-airway-on-a-chip was also leveraged to investigate exacerbations in COPD, and to measure human neutrophil recruitment to the activated endothelium following epithelial exposure to pro-inflammatory stimuli. In addition, because the small-airway-on-a-chip has a separate air channel, it is possible to circulate air-borne pollutants through the epithelial chamber and evaluate, for example, the response of epithelial cells to cigarette smoke (101).

Alternative on-chip platforms of the human airway epithelium include a triple channel chip design where an additional compartment containing fibroblasts is inserted between the epithelial and vascular channels (103, 104). This configuration, however, does not support full differentiation of the human primary airway epithelial cells but remains promising for investigating cross communication between the three different cell populations and their respective influence on each other growth and differentiation. In addition, inclusion of fibroblasts to this system may be useful for studying human airway diseases such as idiopathic pulmonary fibrosis. Using a markedly different design approach, Nesmith et al. built a human airway musculature-on-a-chip consisting of ECM cantilevers actuated by human bronchial smooth muscle cells (102). When stimulated with IL-13, increased cantilever curvature mimicked acetylcholine-induced hyper contractility observed in asthmatics, a response that could be reduced by a ROCK inhibitor.

To date, published Lung-on-a-Chip platforms rely on cancer cell lines or primary cells to reconstitute lung tissue in vitro. While cancer cell lines are cost efficient and enable high-throughput studies, they are progressively being replaced by primary cells isolated directly from human or animal tissue. Thus, the biological relevance of cancerous or otherwise immortalized cells is questioned (105).

Nevertheless, even the most advanced Organ-on-Chip model of the human lung fails to fully reconstitute the elements of a functional lung in vitro. Elements that are needed for recapitulating lung function include but are not limited to elements such as tissue-tissue interfaces (e.g. between epithelium-stroma-vascular endothelium), spatiotemporal gradients of nutrients and oxygen between simulated capillaries and an air surface, exposure to air while experiencing a mechanically active microenvironmental force acting on living cells. This combination of elements are believed to contribute to the function of living lung tissue. Therefore a more comprehensive 3D cell-culture model having a combination of environmental factors including co-cultures of living lung cells, would have advantages associated with Three-dimensional (3D)organotypic culture: a system where cells are grown within and/or over (on the surface of) or and/or under a three-dimensional scaffold made of natural extracellular matrix (ECM). In particular, leveraging microfabrication technologies from the microchip industry we created a microfluidic cell-culture microenvironment that supports alveolar cells viability, differentiation in addition to functional secretion of surfactant. Further, it has aspects of the in vivo alveolar tissue-tissue interfaces, spatiotemporal chemical gradients, and mechanical forces normally acting on the alveolar microenvironments such as mechanical stretch and fluidic shear stress. Nonlimiting examples of cancer cells include H1275 H1299 lung cancer cells. In some embodiments, cancer cells seeded onto alveolar cells are contemplated for or monitor effects of stretching, resistant to drugs, with or without breathing, and at different breathing cycles.

In some embodiments, different methods of seeding cancer cells, such as at the same time, sequential seedings of cancer cells, etc., are contemplated for determining cancer cell growth rates. As one example, concurrent seeding of cancer cells results in flatter morphology of cancer cells. In some embodiments, closed top chips are used for cancer experiments. In some embodiments, open top are used for cancer experiments.

A. Human Primary Alveolar Cells.

Primary cells offer a number of advantages compared to cell lines including recapitulation of original tissue characteristics, the ability to differentiate to in vivo-like tissue, preservation of donor disease phenotypes, increased predictiveness of human responses to drugs, control of cell source, and increased donor diversity.

Nonetheless, the use of primary cells has drawbacks. First, primary cells usually have a limited lifespan, although methods to prolong culture have been developed (106). Primary cells are also difficult and costly to genetically modify, as transfection efficiency can be very low. Finally, primary cell diversity can also be an obstacle to long term in vitro studies as cells from the same patients are hard to obtain and usually require complex ethical agreements.

However, as described herein, embodiments of a fluidic device, e.g. an open top chip was developed and a co-culture system was developed within the open top chip in combination with developing a culture media for supporting co-culturing of multiple cell types (e.g. ALI-M/199M), that overcame some of the limitations of using primary human lung cells, e.g. alveolar cells, e.g. for recapitulation of original tissue characteristics, the ability to differentiate to in vivo-like tissue, limited lifespan, etc. In fact, in some embodiments, an Alveolar-fluidic device as described herein, provides as readily replicated system for differentiating primary human lung cells, derived from adult lung biopsies, into a functional layer of alveolar cells in vitro for simulating alveolar cells in a lung air sac in vivo.

In Vitro Modelling of Pneumocyte Toxicity, Acute and Chronic Inflammation.

Given the limited availability of in vitro models that can closely mimic human alveolar epithelium function and/or its disease states, we explored whether a microfluidic Alveolus-Chip lined with the primary alveolar epithelial cells on an artificial lung stroma with embedded primary lung fibroblasts and pulmonary microvascular endothelial cells would model a lung injury state. To test this, we exposed the Alveolus-Chips to an acute damage generated by exposure to $H_2O_2$ under continuous infusion through the epithelium top channel, similarly to as it is orally administered in mice. Microscopy imaging revealed disruption of the pneumocyte monolayer with partial cell detachment from the recreated stroma. Quantification of E-Cadherin and phalloidin-stained cells confirmed pronounced loss and re-distribution of E-Cadherin into the epithelial monolayer (FIG. 25), and this correlated with decreasing in epithelial barrier as determined by the barrier function which consists in the quantification of the increased entry of a fluorescent compound at a fixed concentration (we used for this specific experiment 3000 KDa Dextran-FITC 100 µg/ml) from the endothelial to the epithelial compartment (values were normalized by chip and expressed as percentage of leakage of a fluorescent from the epithelial to the endothelial compartment.

Notably, significant preventive effect on the barrier leakage was observed when the insult ($H_2O_2$) was co-administrated with known antiradical small molecules such as Bardoxolone, GSK and JQ1. The remaining adherent pneumocytes exhibited retention of their normal phenotype with a "normal distribution of the E-Cadherin.

To test the sensitivity of Alveolus-Chips to anti-radical treatment, we choose a compound, specifically GSK, representative for the class of small molecules and investigate if there was a dose dependent correlation between the administration of a fixed concentration of $H_2O_2$ (10 mM) and different doses of GSK. Consistent with the previous observation, our biological system exhibited significant loss of barrier function in presence of $H_2O_2$ (10 mM) alone while it showed different degree of barrier function loss that inversely correlated to the concentration of GSK. Specifically, lower to higher barrier function values were observed at 1 µM, 0.1 µM and 0.01 µM respectively.

Human Stem Cells.

The use of human stem cells on the other hand can overcome some of these limitations of using primary cells in microfluidic chips. For instance, because adult stem cells can be maintained indefinitely and are easy to transform, functional gene studies are particularly straightforward and inexpensive. Stem cells from a single patient can also be used to recreate virtually any cell type. This possibility is exceedingly valuable when the primary tissue is difficult to isolate, such as biopsies containing alveolar epithelial cells. Stem cells are also advantageous when autologous co-cultures systems (i.e. cells obtained from the same patient) are needed, for instance to insure compatibility when culturing epithelial and T cells together.

Therefore, in one embodiment, it is contemplated to use stem cells for initiating on-chip differentiation into terminally differentiated cell types. Furthermore, by combining organs-on-chips with stem cell technology additional features would be enabled that are currently missing in published lung organoids and other stem cell-based systems. Exemplary features such as the recapitulation of dynamic physicochemical stem cells niches, access to luminal and vascular compartments, dynamic immune cells circulation, and controlled application of physiological mechanical cues.

Read-outs, exemplary nonlimiting readouts are described herein.

Immunostaining And Image Analysis.

Open-Top Organ-Chips were fixed in 10% neutral buffered formalin. Endothelial cells were stained inside the chip by performinutesg the immunofluorescence steps described below directly inside the microfluidic channel. Stroma equivalents were stained as described by the step below inside the chip or alternatively extracted from the chip and processed for immunohistochemistry analysis. For immunofluorescence staining cells were permeabilized using 0.3% Triton 100× solution for 20 minutes, followed by blockage of non-specific staining in blocking solution containing 1% bovine serum albumin (BSA), 5% donkey serum in Dulbecco's phosphate-buffered saline (PBS). After blocking, stroma equivalents were incubated overnight with primary antibodies (e.g. 1:100) at 4° C. overnight, followed by washing steps and sandwich labeling with appropriate secondary antibodies (e.g. 1:200) at 4° C. overnight, counter-stained with DAPI (4',6-diamidino-2-phenylindole typically a blue-fluorescent DNA stain) and imaged using a confocal laser fluorescent microscope. The primary antibodies used included ABCA3 (Abcam plc. Cambridge, Massachusetts, USA, ab24751), LAMP3 (Abcam plc. Cambridge, Massachusetts, USA, ab111090), Angiotensin receptor subtype AT1 mediates alveolar epithelial cell apoptosis (AT1-alpha); T1-α Anti-Podoplanin/gp36 antibody (Abcam PLC. Cambridge, Massachusetts, USA, ab128994), Anti-alpha 1 Sodium Potassium ATPase antibody (Na+/K+ pump) (Abcam plc. Cambridge, Massachusetts, USA, ab2872); Surfactant B (Abcam plc. Cambridge, Massachusetts, USA, ab40876), Connexin 43 (Abcam PLC. Cambridge, Massachusetts, USA, ab11370), ENaC (Abcam plc. Cambridge, Massachusetts, USA, ab115272), Anti HT1-56 (HTI) (Terrace Biotech, San Francisco, California, USA, TB-29AHT1-56) Human Lung Alveolar Type 1 Cells; the antibody binds to a partially characterized 56 kDa apical membrane protein specific to human Type 1 Cells; anti HT2-280 (HTII) (Terrace Biotech, San Francisco, California, USA, TB-27AHT2-280) Human Lung Alveolar Type 2 Cells; the antibody binds to a 280 kDa apical membrane antigen specific to human Type 2 Cells; E-Cadherin (Abcam plc. Cambridge, Massachusetts, USA, ab40772, ab1416, ab15148), ZO-1 (Invitrogen, 33-9100), podo PDCN: Podocin; Anti-NPHS2 antibody (Abcam plc. Cambridge, Massachusetts, USA, ab50339), VE-cadherin (Abcam plc. Cambridge, Massachusetts, USA, ab33168), PECAM-1 (Abcam plc. Cambridge, Massachusetts, USA, ab9498), VWF (Abcam plc. Cambridge, Massachusetts, USA, ab8822) and Surfactant C (Seven Hill, WRAB-9337). Donkey anti mouse or rabbit Alexa Fluor 488, Alexa Fluor 568, Alexa Fluor 647-conjugated antibodies (Abcam) and Goat anti-Mouse IgG1 Alexa Fluor 568 and anti-Mouse IgM Alexa Fluor 488 (Invitrogen) were used as secondary antibodies. DAPI (4',6-Diamidino-2-Phenylindole, Dihydrochloride) (ThermoFisher Cat #: D1306) and Alexa Fluor™ 647 Phalloidin (Invitrogen Cat #: A22287) were used for counterstaining nuclei and actin, respectively. Where no specific biomarker is named, the cells were labeled with either Anti HT1-56 (HTI) for Type I cells or anti HT2-280 (HTII) for Type II cells.

Immunostaining And Microscopy.

Bright field images were captured using an exemplary Zeiss microscope equipped with a Zeiss AxioCam. Microscope images were acquired with a Zeiss inverted microscope using a 40×/1.25 objective. Cell size measurements were determined using ImageJ software. Immunostaining was visualized with a fluorescence microscope Olympus equipped with a camera and imaging software. Confocal scanning electron microscope images, videos and co-localization measurements were collected with IMARIS software. Quantification of cell processes were performed using IMARIS software or Fiji for ImageJ.

Barrier Function Assay (Barrier Integrity Assay).

Air-Liquid interface was replaced by phenol red free MEM (GIBCO: 51200-038) and medium in the bottom fluidical spiraled channel substituted by one containing 1 mg/ml Lucifer Yellow CH, Lithium Salt (ThermoFisher: L453) or 0.1 mg/ml Dextran, Fluorescein, 3000 MW, Anionic, Lysine Fixable (ThermoFisher: D3306). Leakage of the fluorescent probe from the lumen of the spiraled channel to the epithelial compartment was collected from the outlet reservoirs after indicated hours of perfusion. The fluorescence intensity was measured with a 96-well fluorimeter at excitation/emission indicated by the manufacturer.

Quantitative Real-Time PCR.

RNA was purified using a RNeasy kit (Qiagen, Valencia, California, USA). qPCR was performed with the TaqMan Fast Advanced Master Mix (Cat #4444964, Thermo Fisher Scientific) and SuperScript™ IV first-strand synthesis system (Cat #18091050, 50 reactions) using a QuantStudio 3 Real-Time PCR system. Endogenous Control Genes for cDNA content (Human GAPDH: FAM/MGB probe, non-primer limited, Cat #4333764T; Eukaryotic 18S rRNA: FAM/MGB probe, non-primer limited, Cat #4333760T). Exemplary primers used for qPCR are listed in Tables 3 and 4.

ELISA.

The amount of Surfactant B and C was collected from chip epithelial cell surface by PBS washing and measured by Human SFTPB/Surfactant Protein B ELISA Kit (Sandwich ELISA)—LS-F4439 and Human SFTPC/Surfactant Protein C ELISA Kit (Sandwich ELISA)—LS-F12438 (LifeSpan-BioScience) following the manufacturer's protocol. The color reaction was measured at 450 nm with a photometer (specification). Samples were stored at −80° C. until analysis. Similarly, the presence of IL-6, IL-8 and MPC in medium samples was detected by Human TLR-induced Cytokines II: Microbial-induced Multi-Analyte ELISArray Kit (MEH-008A) (Qiogen) following the manufacturer's protocol. The color reaction was measured at 450 nm with a photometer (specification). Samples were stored at −80° C. until analysis.

Electron Microscopy.

Cells were differentiated into the Open-Top Chip (Emulate, Inc) by following protocols described above.

Transmission Electron Microscopy (TEM). Cells were fixed with 2.5% glutaraldehyde in 0.1 M sodium cacodylate buffer (Electron Microscopy Sciences) for 1 hour followed by 1% osmium tetroxide in 0.1 M sodium cacodylate (Electron Microscopy Sciences) for 1 hour and then dehydrated in ascending grades (30%, 50%, 70%, 80%, 90%, 95% and 100%) of ethanol. Tissues are gradually infiltrated with the propylene oxide mixture up to pure resin. Total time depends on tissue size and density of tissue. Tissues pieces are transferred to fresh 100% resin in capsules. Prepared blocks are placed in a hot oven at 60-70° C. overnight for polymerization (hardening) of the epoxy resin. Thin cross sections of epithelial layers sections were mounted onto grids. Tissue on grids are then stained with uranyl acetate followed by lead citrate to further enhance contrast of cellular organelles. Stained grids of tissue are observed using a transmission electron microscope with negatives developed and printed or digital photographs of representative areas taken and archived.

Scanning Electron Microscopy (SEM).

Some of the samples in 100% ethanol were processed for SEM imaging by chemical drying and sputter-coating. Starting in a 1:2 solution of Hexamethyldisilizane (HMDS) (Electron Microscopy Sciences): 100% ethanol for 20 minutes, transferring sample to a fresh solution of 2:1 HMDS: ethanol for 20 minutes, transferring sample into 100% HMDS for 20 minutes, then transferring into fresh 100% HMDS and leaving in a desiccator overnight. Before imaging, samples were mounted and sputter-coated with a thin layer of gold (for coverslip samples) or 5-nm layer of platinum-palladium (for microfluidic devices) and imaged using field emission scanning electron microscopy (FE-SEM) with a secondary detector which provides an SEM topography image of the sample surface with a large depth of field.

Liquid Chromatography and Mass Spectrometry

Exemplary analysis of surfactant, including but not limited to surfactant C, is described briefly as follows. In part, such surfactant analysis is contemplated to include but not limited to quantitative analysis; determination of the palmitoylation status of surfactant produced in fluidic devices described herein; for detecting modifications of surfactant production in fluidic devices compared to surfactant in vivo; for detecting modifications of surfactant production in fluidic devices for drug testing, etc. As one example, mature human lung SP-C is around 34 or 35 amino acid residues, and contains two palmitoylated cysteine residues near the N-terminal end. LC-MS/MS is used because the molecular mass of SP-C can be small (approximately 4 kDa).

Liquid chromatography was performed on an Agilent System equipped with an exemplary C-18 column at 25° C. column temperature. An exemplary mobile phase of (A) 0.05% formic acid/water and (B) 0.05% formic acid/methanol. for providing a gradient starting at 50% solvent B and linearly increased to 99% solvent B over 10 min.

LCMS (Liquid chromatography tandem mass spectrometry) LC-MS/MS analysis was performed on an Agilent triple quadrupole system equipped with a jet stream ESI source. MRM was performed in the positive ion mode. Exemplary MS is in the positive ion mode, with the spray voltage at 3,000 V, capillary temperature at 220° C., and vaporizer temperature at 450° C. For MS2 analyses, the collision gas was argon at 0.8 mTorr and the collision energy was 20, 30, 40, or 50 V. An exemplary 0.01 mg/ml solution of SP-C harvested from a fluidic device was infused post-column via a tee connector using a syringe pump at a flow rate of 5 µl/min. See, for examples, Harayama, et al., "Establishment of LC-MS methods for the analysis of palmitoylated surfactant proteins." J Lipid Res. 56(7): 1370-1379. (2015).

Statistical Analyses.

Analyses were done using Correlation Analysis in the GraphPad Prism software program (San Diego, CA). Means±SEM are listed. Analyses were done using Correlation Analysis in the GraphPad Prism software program (San Diego, CA). Means±SEM are listed.

IV. Human Embryonic and Induced Pluripotent Stem Cells for Human Lung Modeling On-Chip Differentiating stem cells off-chip (e.g. in microplate wells or culture dishes) is contemplated for use in seeding (placing) derivative lung (including progenitor) cells on-chip. In one embodiment, exemplary stem cells are placed on tissue culture surfaces off-chip, in microplate wells, tissue culture plates, for initiating lung cell differentiation. In some embodiments, stem cells undergo differentiation procedures for deriving terminally differentiated lung cells, e.g. alveolar cells, Types I and/or II, bronchial epithelial cells, goblet cells, etc., which are then seeded into microfluidic chips. In other embodiments, stem cell differentiation is initiated for providing cells not yet terminally differentiated for seeding into microfluidic chips for experimentation or for inducing differentiation protocols on-chip for inducing terminal differentiation. For example, stem cell differentiation is induced for providing a SOX17+ cell population where the SOX17+ cells are harvested then seeded into microfluidic chips. In some embodiments, a SOX9+ cell population is harvested then seeded into microfluidic chips. In some embodiments, a SOX2+ cell population is harvested then seeded into microfluidic chips. In some embodiments, a NKX2-1+ cell population is harvested then seeded into microfluidic chips. It is not meant to limit the cell marker for a lung epithelial progenitor cell, such that any cell marker identifying a cell population capable of differentiating into the desired lung cell, off-chip or on-chip, may be used.

A. Maintenance of Human Pluripotent Stem Cells

Human ESC and iPSC may be maintained on mitotically inactivated mouse embryonic fibroblast feeders in Knockout DMEM (GIBCO) with 15% Serum Replacement (GIBCO), Glutamax (Invitrogen), penicillin/streptomycin (GIBCO), 1 mM nonessential amino acids (GIBCO), 0.5 mM mercaptoethanol, and 10 ng/ml FGF2 (Peprotech).

B. Generation and Characterization of Human iPSC Lines.

Human skin fibroblasts may be commercially obtained or from a patient with informed consent. Fibroblasts may be isolated from a donor skin biopsy. By 4 weeks of reprogramming human skin fibroblasts, human ESC-like EGFP+ colony numbers may be enriched under puromycin selection before picking and expansion. CF-iPSC lines with ESC-like morphology may be further assessed for pluripotency marker expression (NANOG, TRA1-81, TRA1-60) by flow cytometry and immunofluorescence, and real-time qPCR to examine up-regulation of endogenous pluripotency genes (OCT4, SOX2, C-MYC and KLF4) and down-regulation of the exogenous retroviral transgenes. In addition, gene expression of other pluripotency markers DNMT3B, REX1, TERC, TERT may be assessed. Finally, iPSC lines may be subjected to in vitro embryoid body and in vivo teratoma assays for functional tests of pluripotency. See, Wong et al. 2012.

Lung cells derived from human pluripotent stem cells (PSCs), particularly human embryonic stem cells (ESCs) and induced pluripotent stem cells (iPSCs), hold great potential to build advanced in vitro models of human lung tissue and to further our understanding of lung physiology and disease. While numerous attempts were made to generate airway and distal lung epithelial cells from human PSCs, recently this type of undertaking gained significant traction. Initial studies first reported efficient embryonic induction into mesodermal and ectodermal lineages; however, maturation into the third endodermal germ layer remained limited (107). While recreation of posterior endoderm cell derivatives that give rise to organs such as the liver, intestine, and pancreas became possible (108-110), anterior foregut endoderm induction leading to lung tissues was unachievable until more recently. In 2011, a study elucidated a mechanism permitting stem cell differentiation into lung-specific endoderm precursor (Green, A. Chen, M.-C. Nostro, S. L. D'Souza, C. Schaniel, I. R. Lemischka, V. Gouon-Evans, G. Keller, H.-W. Snoeck, Generation of anterior foregut endoderm from human embryonic and induced pluripotent stem cells, *Nat. Biotechnol.* 29, 267-272 (2011)), thus leading to an effective strategy for ESC and iPSC generation of the lung.

C. Differentiating Stem Cells Off-Chip (e.g. in Microplate Wells or Culture Dishes) then Seeding (Placing) Derivative Lung Cells On-Chip.

1. One protocol for generation of lung progenitor cells from ESCs or iPSCs in vitro is accomplished through directed differentiation, a process where in vivo tissue developmental stages are mimicked using controlled sequences of endogenous signaling factors (Murry, G. Keller, "Differentiation of embryonic stem cells to clinically relevant populations: lessons from embryonic development." Cell 132, 661-80 (2008)). In brief, in one embodiment, Pluripotent stem cells are first directed into definitive endoderm through Activin-A simulation, followed by anterior foregut endoderm (AFE) induction through dual inhibition of bone morphogenic protein (BMP) and transforming growth factor (TGF-β) (Green, A. Chen, M.-C. Nostro, S. L. D'Souza, C. Schaniel, I. R. Lemischka, V. Gouon-Evans, G. Keller, H.-W. Snoeck, "Generation of anterior foregut endoderm from human embryonic and induced pluripotent stem cells." Nat. Biotechnol. 29, 267-272 (2011)). morphogenesis of the endoderm where the trachea and lung buds eventually emerge ventrally (Morrisey, B. L. M. Hogan, Preparing for the first breath: genetic and cellular mechanisms in lung development., Dev. Cell 18, 8-23 (2010)).

AFE ventralization may be achieved through WNT, BMP, and fibroblast growth factor (FGF) signaling (Lee, D. H. Bhang, A. Beede, T. L. Huang, B. R. Stripp, K. D. Bloch, A. J. Wagers, Y. Tseng, S. Ryeom, C. F. Kim, "Lung stem cell differentiation in mice directed by endothelial cells via a BMP4-NFATc1-thrombospondin-1 axis." Cell 156, 440-55 (2014); Green, A. Chen, M.-C. Nostro, S. L. D'Souza, C. Schaniel, I. R. Lemischka, V. Gouon-Evans, G. Keller, H.-W. Snoeck, "Generation of anterior foregut endoderm from human embryonic and induced pluripotent stem cells." Nat. Biotechnol. 29, 267-272 (2011)) yielding cells expressing transcription factor NKX2-1.

Thus, in one embodiment, NKX2-1+ cells refer to lung progenitor cells used to produce lung alveolar cells in vitro. NKX2-1 is one general marker for respiratory tissue fate, however is some cases NKX2-1 may be expressed on additional pluripotent cells capable of neural and/or thyroid tissue fate (Kimura, Y. Hara, T. Pineau, P. Fernandez-Salguero, C. H. Fox, J. M. Ward, F. J. Gonzalez, The T/ebp null mouse: thyroid-specific enhancer-binding protein is essential for the organogenesis of the thyroid, lung, ventral forebrain, and pituitary., Genes Dev. 10, 60-9 (1996)).

However, NKX2-1 positive cells as used herein, may merely represent an exemplary population of primordial lung epithelial progenitors capable of differentiate into proximal airway and distal lung bud lineages, cell populations defined by SOX2 or SOX9 expression, respectively (Mizuno, A. Sridharan, Y. Du, M. Guo, J. Tang, K. A. Wikenheiser-Brokamp, A.-K. T. Perl, V. A. Funari, J. J. Gokey, B. R. Stripp, J. A. Whitsett, "Single-cell RNA sequencing identifies diverse roles of epithelial cells in idiopathic pulmonary fibrosis." JCI Insight 1, 1-18 (2016).). Thus, terminal differentiation is then directed by further pathway signaling modification and determined by specific sets of markers. For example, distal lung markers of the alveoli include Surfactant Protein C (SFTPC), Surfactant Protein B and LAMP3/DC-LAMP for ATII cells, Podoplanin, Caveolin, and Aquaporin 5 for ATI cells, and bronchiolar markers include SCGB1A1/CC10 for Clara cells, P63 or Keratin 5 for basal cells, acetylated alpha tubulin for ciliated cells, and MUC5AC for goblet cells. Additional methods that may be used for specification (differentiation) to proximal airway or distal alveolar progenitors are discussed herein.

2. Recent Advances in Alveolar Generation.

Progress using exemplary NKX2-1 lung progenitors to generate human alveolar epithelial cells was made by leveraging strategies for maintaining human primary cells. The combination of glucocorticoid, growth factors, and cAMP effectors (dexamethasone, 8-br-cAMP, IBMX, and KGF/FGF7; collectively known as DCIK) (Gonzales, S. H. Guttentag, K. C. Wade, A. D. Postle, P. L. Ballard, Differentiation of human pulmonary type II cells in vitro by glucocorticoid plus CAMP., *Am. J. Physiol. Lung Cell. Mol. Physiol.* 283, L940-L951 (2002), Wade, S. H. Guttentag, L. W. Gonzales, K. L. Maschhoff, J. Gonzales, V. Kolla, S. Singhal, P. L. Ballard, Gene induction during differentiation of human pulmonary type II cells in vitro., *Am. J. Respir. Cell Mol. Biol.* 34, 727-37 (2006)) was shown to induce alveolar maturation through activation of PKA and CDP-choline pathways which upregulate lamellar body surfactant production (Andreeva, M. A. Kutuzov, T. A. Voyno-Yasenetskaya, "Regulation of surfactant secretion in alveolar type II cells." *Am. J. Physiol. Lung Cell. Mol. Physiol.* 293, L259-71 (2007)). Stimulation of two dimensional cultures of differentiated PSCs growing in 2D with DCIK, FGF10 and WNT activators led to expression of ATI and ATII markers, mature phenotypic characteristics of lamellar bodies, and functional surfactant uptake capability (Huang, M. D. Green, A. T. de Carvalho, M. Mumau, Y.-W. Chen, S. L. D'Souza, H.-W. Snoeck, The in vitro generation of lung and airway progenitor cells from human pluripotent stem cells., *Nat. Protoc.* 10, 413-25 (2015)).

Similarly, PSCs spheroid cultures also induce cell maturation of the alveoli epithelium. Surprisingly, 3D co-culture with human fetal lung fibroblasts and stimulation with DCIK yielded ATII specific markers and lamellar bodies formation, although functional maturity was not confirmed (120). Functional surfactant uptake was then confirmed by first generating PSC lung bud organoids, followed by Matrigel culture with a WNT activator (inducer), FGF10, KGF, BMP4 and RA in place of DCIK. ATII markers were found to be abundant in this protocol while ATI markers were minimally expressed (Chen, S. X. Huang, A. L. R. T. de Carvalho, S.-H. Ho, M. N. Islam, S. Volpi, L. D. Notarangelo, M. Ciancanelli, J.-L. Casanova, J. Bhattacharya, A. F. Liang, L. M. Palermo, M. Porotto, A. Moscona, H.-W. Snoeck, A three-dimensional model of human lung development and disease from pluripotent stem cells., Nat. Cell Biol. 19, 542-549 (2017)).

Long term expansion of alveolar epithelial cells, a challenge with distal lung cell cultures, was recently achieved using an organoid approach and a refined differentiation sequence after AFE induction (121). This sequence differs from previous protocols by incorporating a preconditioning step of WNT activation, DAPT notch inhibition, and FGF10 plus KGF supplementation, resulting in SFTPC gene expression, a marker of ATII cells, similar to levels found in the fetal lung. These cells were then matured using DCIK in organoids co-cultured with fibroblasts. Surprisingly, co-cultures with fetal lung fibroblasts lines resulted in SFTPC expressing cells, though variable (ranging from 2% to 51%), whereas incorporating a dermal fibroblast line showed no SFTPC induction. With passaging, the proportion of ATII cells in the culture increased to approximately 70%. Notably, induction of SFTPC expression was also achieved in fibroblast-free cultures using DCIK plus ROCK inhibition, WNT activation, and TGF-β inhibition, albeit at a lower efficiency of 23%.

3. Recent Advances in Proximal Lung Generation.

Protocols for proximal airway differentiation also advanced in the past few years. Differentiation of PSCs into airway epithelial cells was achieved in spheroids cultures using FGF10, KGF, WNT agonist and Notch inhibition (Konishi, S. Gotoh, K. Tateishi, Y. Yamamoto, Y. Korogi, T. Nagasaki, H. Matsumoto, S. Muro, T. Hirai, I. Ito, S. Tsukita, M. Mishima, Directed Induction of Functional Multi-ciliated Cells in Proximal Airway Epithelial Spheroids from Human Pluripotent Stem Cells, Stem Cell Reports 6, 18-25 (2016)).

More recently, proximal fate was efficiently induced by modifying WNT signaling in the directed differentiation strategy. Suppressing WNT signaling after ventralized AFE promoted proximal fate (McCauley, F. Hawkins, M. Serra, D. C. Thomas, A. Jacob, D. N. Kotton, Efficient Derivation of Functional Human Airway Epithelium from Pluripotent Stem Cells via Temporal Regulation of Wnt Signaling, *Cell Stem Cell* 20, 844 857.e6 (2017).), potentially explaining why previous studies encountered difficulty in maintaining airway epithelial markers in culture. To promote cilia development, Notch inhibition in organoids or air-liquid interface in 2D cultures is required (Wong, C. Bear, S. Chin, P. Pasceri, T. Thompson, L.-J. Huan, F. Ratjen, J. Ellis, J. Rossant, Directed differentiation of human pluripotent stem cells into mature airway epithelia expressing functional CFTR protein., *Nat. Biotechnol.* 30, 876-882 (2012).). For long term expansion of these cells, it may be possible to incorporate findings from human primary cell cultures. Specifically, inhibition of SMAD signaling pathways was recently found to enable the expansion of primary P63+ airway basal cells (Mou, V. Vinarsky, P. R. Tata, S. H. Choi, A. K. Crooke, B. Zhang, G. M. Solomon, B. Turner, H. Bihler, J. Harrington, A. Lapey, C. Channick, C. Keyes, A. Freund, S. Artandi, M. Mense, S. Rowe, J. F. Engelhardt, Y. Hsu, J. Rajagopal, Dual SMAD signaling inhibition enables long-term expansion of diverse epithelial basal cells, Cell Stem Cell 19, 217-231 (2017).) which are pathways that may also promote proximal lung regeneration in PSC cultures.

4. Another Example for Providing Cells for Use Herein, is Provided Below.

Differentiation of Human ESC and iPSC into Definitive Endoderm.

The following is a brief protocol for use in differentiation of human ESC or human iPSC into definitive endoderm (e.g. SOX17+ population). Pluripotent stem cells are harvested, gently triturating cells into single cell suspensions then seeded onto transwells (0.4 μm pore size, Corning) of microfluidic chips, whose well surface or membranes are pre-coated with human placental collagen Type IV. Cells are immediately treated with 100 ng/ml Activin-A and 25 ng/ml WNT3A (R&D Systems) for 4 consecutive days in Endoderm Differentiation Media comprising serum-free Knockout DMEM (Invitrogen) with Glutamax (Invitrogen), penicillin/streptomycin (GIBCO), 1 mM nonessential amino acids (GIBCO) and 0.5 mM mercaptoethanol. Subsequent differentiation steps were performed on the transwell cultures or microfluidic chips.

Differentiation of Definitive Endoderm into Anterior Foregut Endoderm Progenitors.

For anterior foregut endoderm differentiation and especially for providing embryonic lung progenitors, definitive endoderm cells (see above) were treated with 500 ng/ml FGF2 (Preprotech) and 50 ng/ml Sonic hedgehog (SHH, Cedarlane) for 5 days in Endoderm Differentiation Media.

Directed Differentiation of Foregut Endoderm into Mature Lung Cell Fates.

Anterior foregut endoderm progenitor cells were treated with 50 ng/ml FGF10, 50 ng/ml KGF (FGF7) and 5 ng/ml BMP4 (all R&D systems) for 5 days followed by 10 ng/ml FGF10, 10 ng/ml FGF7 and 10 ng/ml FGF18 (Sigma-Aldrich) for an additional 5 days. To differentiate the cells into mature airway epithelial cells, the cells were cultured in Bronchial Epithelial Growth Media (BEGM, Lonza) supplemented with FGF18 (10 ng/ml) for 10 days followed by Bronchial-Air Liquid interface (B-ALI, Lonza) media for an additional 15+ days. For transwell cultures, cells are "air-lifted" and B-ALI media was added to the bottom but not the top of the transwell. For anterior foregut endoderm progenitor cells treated on microfluidic chips, an air-liquid interfaces was established instead of air-lifting" cells.

Therefore, in some embodiments, differentiating lung cell populations include: progenitor cells deriving from SOX2+/

OCT4+ pluripotent stem cells (PSC) that may express the following markers in order of progression during differentiation: SOX17+/FOXA2+ cells; SOX2+/FOXA2+ cells; NKX2-1+ cells; SOX9+ distal (airway lung bud lineage) progenitors: Alveolar Type I (ATI) cells—Podoplanin, Caveolin (CAV1), and Aquaporin 5 (AQP5); Alveolar Type II (ATII) cells—characterized by Surfactant Protein C (SFTPC), Surfactant Protein B (SFTPB) HTII-280, ABCA3, and LAMP3/DC-LAMP for ATII cells in addition to cells' capacity of lamellar bodies to process surfactant proteins and produce dipalmitoylphosphatidylcholine (DPPC) surfactant phospholipid. Co-cultures and several passages with fetal lung fibroblasts lines induces higher percentages of SFTPC expressing cells along with ATI cells. In addition to an alternative differentiation pathway including SOX2+ proximal (airway lung bud lineage) progenitors resulting in terminally differentiated basal cells; club cells (Clara cells: bronchiolar exocrine cells having short microvilli); ciliated epithelial cells; goblet cells, etc.

Therefore, in some embodiments, nonlimiting markers for differentiating lung cells include: Progenitor cells deriving from SOX2+/OCT4+ pluripotent stem cells (PSC) in order of progression: SOX17+/FOXA2+ progenitor cells; SOX2+/FOXA2+ progenitor cells; NKX2-1+ progenitor cells; SOX9+ distal (airway lung bud lineage) progenitors: Alveolar Type I (ATI)—Podoplanin, Caveolin (CAV1), and Aquaporin 5 (AQP5) and Alveolar Type II (ATII)—characterized by Surfactant Protein C (SFTPC), Surfactant Protein B (SFTPB) HTII-280, ABCA3, and LAMP3/DC-LAMP for ATII cells in addition to cells' capacity of lamellar bodies to process surfactant proteins and produce dipalmitoylphosphatidylcholine (DPPC) surfactant phospholipid. Co-cultures and several passages with fetal lung fibroblasts lines induces higher percentages of SFTPC expressing cells along with ATI cells. In addition to SOX2+ proximal (airway lung bud lineage) progenitors: basal cells; club cells; ciliated epithelial cells; and goblet cells.

C. Cystic Fibrosis Stem Cells on Chips for Preclinical and Clinical Drug Tests.

This is an exemplary description of a Cystic fibrosis related ion channel function test for stem cells and organoids seeded into a microfluidic device as described herein.

In some embodiments, any one or more of cells in microfluidic devices described herein, are stem cells, such as stem cells, stem cell derived progenitor cells, terminally differentiated cells from stem cells, organoids, etc., derived from a cystic fibrosis patient or a patient suspected of or actually known to have cystic fibrosis genes in their cellular DNA, e.g. one or more mutated cystic fibrosis transmembrane conductance regulator (CFTR) genes, are added to microfluidic chips as described herein. Other microfluidic chips containing corresponding stem cells derived from people without cystic fibrosis symptoms, patients known to be free of particular cystic fibrosis genes or corresponding test cells treated with an ionophore are used for a control for comparison to a stem-cell based cystic fibrosis microfluidic chip.

Microfluidic chips containing these control and stem-cell derived cystic fibrosis cells and organoids may then be tested for ion channel function by the addition of an agent to cell cultures on microfluidic chips for use in a swelling test. A swelling test agent may be any agent that acts as to increase ion channel function, e.g. alters cyclic AMP-dependent protein kinase (protein kinase A or protein kinase C function. As one example of a test agent for ion channel function is an inducer of intracellular cyclic AMP (cyclic adenosine 3'-5'-monophosphate: cAMP), i.e. increases intracellular cyclic AMP (cAMP) in cells, e.g. Cyclic AMP, Cyclic AMP analogs, Forskolin, e.g. 12-24 µM, test drug compounds, small-molecule drugs, etc. Cells and organoids are stained with calcein green, and forskolin-induced swelling is monitored by confocal live cell microscopy at 37° C.

For example, organoids from a healthy individual (WT) and a diagnosed cystic fibrosis patient are added to chips, each on a separate chip or on different areas of the same chip. The WT organoids will show functioning ion channels by responding by swelling while CF organoids will show less swelling.

For CFTR inhibition, organoids may be preincubated for 1-3 hours with 75 mM CFTRinh-172 (B7; Cystic Fibrosis Foundation Therapeutics, Inc).

For CFTR inhibition, organoids were simultaneously incubated for 60 minutes with 10 µM-2 mM calcein-green (Invitrogen) and 50 µM CFTRinh-172 (Sigma), 50 µM GlyH-101 (Calbiochem) or combined treatment of 50 µM CFTRinh-172 and 50 µM GlyH-101. After 60 minutes of calcein-green treatment (with or without CFTR inhibition), of 5 µM forskolinb may be added and organoids directly analyzed by confocal live cell microscopy (LSM710, Zeiss, 5× objective). Organoid surface may be calculated by Volocity imaging software. It is contemplated that in vitro swell responses correlate with the clinical response to therapy. With the addition of an appropriate drug, the organoid of a cystic fibrosis patient will see similar swelling. Organoids on chips are monitored for an increase in size, i.e. area, at least every 5 minutes up to 30 minutes, up to 60 minutes, in order to capture any swelling before collapse of a swelling organoid. In some embodiments, area measurements are normalized to area measurements of control organoids then compared or graphed over time. In some embodiment, cholera toxin is used.

This assay provides a protocol for the identification of drug-responsive individuals, independent of their CFTR mutations and may also be instrumental in the development of future CFTR modulators.

Mean cell volume may be measured in cell suspensions by electronic cell sizing (Coulter Multisizer II, AccuComp software version 1.19, Hialeah, FL) using an 100-µm aperture. Cells in subconfluent culture may be harvested with minimal trypsin (0.05%), suspended in cell culture medium, centrifuged for 1 min at 1,000×g, resuspended in 3 ml of isotonic buffer, and incubated with gentle agitation for 30-45 min. Aliquots (approximately 500 µl) of cell suspension may be added to 20 ml of isotonic or hypotonic (40% less NaCl) buffer. Measurements of 20,000 cells on average at specified time points after exposure to isotonic or hypotonic buffer were compared with basal values in isotonic buffer (time 0). Changes in values may be expressed as relative volume normalized to the basal period.

D. Challenges.

Tracing a respiratory developmental path has provided insights into lung differentiation, yet the majority of our knowledge about lung development stems from mouse studies due to limited availability of human samples. Recently, new studies have been conducted examining human lung development using various gestational week human fetal lungs (126). The genetic transcriptome for mouse development was found to be remarkably similar to humans, however, differences between both may help identify targets and develop better strategies to advance human lung modeling. For instance, lung bud tip signaling is associated with BMP4 and Sonic hedgehog (Shh) in the mouse, yet BMP2, BMP7, and Indian hedgehog (IHH) were found to be expressed in human lung bud tips. Further, human pseudoglandular bud tips were found to initially express SOX2 and SOX9 rather than solely SOX9. Surprisingly, these bud tip cells were used successfully as stem cells for forming organoids under conventional FGF, WNT, BMP, and TGF-β signaling modifications without the need for mesenchymal cells (126).

Despite progress in mimicking in vivo developmental pathways through signaling factors, many mechanisms still require further investigation. For instance, incorporating WNT signaling inhibition earlier in combination with TGF-β and BMP inhibition increased NKX2-1 expression, suggesting ventral patterning may begin before AFE (127). Additionally, utilizing FGF2 and Sonic hedgehog (SHH) signaling for promoting AFE expressing NKX2-1 was successful, albeit with suboptimal efficiency (128). Removing FGF signaling to differentiate into ventralized AFE was also found to have no significant effect for human cultures, highlighting a need to explore the essential timing of FGF signaling (127).

While current differentiation protocols are effective for both ESCs and iPSC sources, high induction efficiency remains one of many challenges. The directed differentiation strategy results in heterogenous populations of NKX2-1 cells with efficiencies widely ranging from 20% to 87%, an outcome that led to the questioning of NKX2-1 as a lung origination marker, but was recently confirmed (120). Additional tools for purifying lung progenitor cells could ultimately provide the necessary supply for in vitro applications. Recently, this was accomplished with the discovery of highly specific cell surface markers CD47 (129) and Carboxypeptidase M (CPM). These markers allowed for live tracking and sorting resulting in an impressive ~90% purity of NKX2-1 cells when differentiating into ventralized AFE (121).

V. Rationale for Stem Cells-Derived Lung-On-Chips

One practical approach to help evolve lung models is by adding in some of the spatiotemporal dynamics and heterogeneity found in the lung. Chemical signals, structural cues, ECM, and additional cell types were shown to enhance maturation of lung epithelial PSCs: implantation into injured mice, scaffolding using decellularized lung matrix, or multi-culturing with lung mesenchyme and fibroblasts have led to the development of lung epithelia of all fates (34, 120, 127, 129-133). Furthermore, lung PSC culture systems utilize a 3D system to create advanced lung organoids. Likewise, the Lung-chip provides an increased complex and dynamic microenvironment, providing signals that are known to influence stem cell differentiation (134). By delicately trypsinizing organoids, it may be possible to seed matured lung PSCs on the surface of the ECM-coated porous membrane forming a monolayer within the chip channels, thus supplying cells with a microenvironment characterized by physiological ECM, air-liquid interface, stretch, and fluid shear, while enabling additional complexity from a vascular channel for additional cell types such as endothelial cells and fibroblasts. Further, fluid flow and apical/basal distinctions in the Lung-on-Chip can be utilized to finely tune the timing and distribution of signaling factors, and explore spatiotemporal responses to stimuli. The multitude of parameters organ-on-chip technology provides for recapitulating and also isolating dynamic and spatiotemporally heterogeneous aspects of in vivo physiology holds great potential in advancing lung PSCs and in vitro lung models.

VI. Exemplary Embodiments Describing Applications of Stem-Cell Based Human Lung-On-Chip in Disease Modeling and Drug Development Contemplated application of a stem-cell based human Lung-on-Chip include but are not limited to a range of diseases such as cystic fibrosis, congenital pediatric lung diseases, inflammatory diseases of the lung, pulmonary fibrosis, lung cancer, pulmonary infectious disease, in addition to emphysema, bronchitis, asthma, severe asthma, chronic bronchitis, etc.

A. Disease Modeling.

Human microphysiological systems, such as, organs-on-chips, promise to provide greater insight into pathogenesis of human tissues and enable screening of drugs efficacy and toxicity in a physiologically relevant in vitro platform. Combining Organs-on-Chips with human stem cells would offer the opportunity to test compounds that correct patient specific phenotypes associated with defined genotypes or genes mutations, thus creating predictive platforms for the field of personalized medicine (135). While maturation potential and genetic stability of embryonic stem (ES) cells remain superior (136), tissue-derived induced pluripotent stem (iPS) cells present advantages over ES, including renewable supply of patient-specific cells from individuals with acquired and genetic lung disease.

Recently, the first 100 lung disease-specific iPS cell lines were generated, including lines from individuals with cystic fibrosis and $\alpha_1$-antitrypsin deficiency, the two most common monogenic lung diseases (137). Immediate research applications of these disease-specific cell lines include probing the relative contribution of somatically acquired versus genetic risk factors, genetic engineering to induce or repair putative disease-causing mutations, the comparison of tissues derived from patients and their healthy relatives, and the study of both disease pathology in different genetic backgrounds and their response to drugs (138). Direct consequences for clinical research are imminent: Because stem cells are derived from a specific patient, analysis of their response to various stimuli or drugs should predict individual patient responses. For example, if a compound improves the function of a diseased human iPSC-derived tissues, the same result may be achieved in the patient. Conversely, if adverse drug effects are identified in human iPSC-derived tissues with a specific genetic backgrounds, it might predict drug failure in the clinical trial for this subset of patients.

In monoculture, iPS cells are most suitable for investigating monogenetic diseases that have complete penetrance and well-defined cellular phenotypes caused by the mutation (cell-autonomous disease), such as cystic fibrosis cells with mutations of the cystic fibrosis transmembrane conductance regulator (CFTR) gene which impair chloride ion transport in cells that express CFTR. However, by integrating multiple cell types, immune cells, and a dynamic mechanochemical environment, Organs-on-Chip technology provides the ability to also study non-cell-autonomous diseases such as asthma, in which environmental agents in interaction with airway and immune cells generate a diversity of phenotypes. Lastly, Lung-on-Chip platforms combined with iPS cells could facilitate affordable research in rare pulmonary diseases for which there are no preclinical disease models because of the lack of commercial incentives (139). In the following, we will discuss diseases that might benefit from stem cell-based Lung-on-Chip platform.

B. Cystic Fibrosis.

Cystic fibrosis (CF) disease is highly variable and human patients have a median life expectancy of approximately 40 years. Cystic fibrosis is caused by mutations in genes encoding transmembrane conductance regulator (CFTR) protein located in a cystic fibrosis (CF) locus (7q31.2 region of DNA) on the long (q) arm of human chromosome 7. Mutations in the CFTR gene cause cystic fibrosis in humans, a debilitating disease characterized by persistent airway infections and permanent damage to the lung resulting from changes in chloride ion transport, mucus rheology, inflammation and bacterial adherence (140). Over the past 20 years, there has been tremendous progress in alleviating the symptoms and even treating some of the underlying molecular causes of the disease, leading to a significance increase in life expectancy (141). However, the lack of suitable model systems hinders addressing the predominant cause of pulmonary decline in CF patients, the infection with biofilm-forming phenotypes of Pseudomonas aeruginosa that emerge in the CF lung (142). Mice with deletion of the CFTR gene do not develop the spontaneous lung disease or chronic bacterial infections seen in humans (143) and, unlike humans, CFTR mutant mice appear to have alternate chloride ion channels compensating for dysfunctional transport by CFTR (144). Recent development of pig and ferret models of CF alleviate some of these limitations and have been shown to recapitulate aspects of CF in humans, including persistent bacterial infection of the lung (145), however, these animal models do not replicate the highly specific association with P. aeruginosa seen in human patients, are unsuitable for high-throughput drug screening, and are unlikely to support genotype-phenotype studies for most of the 850 mutant CFTR alleles known to cause CF (146). Human Organs-on-Chips, whose vascular and interstitial flow channels support the controlled addition of circulating or resident immune cells as well as bacteria, are a promising new avenue for studying the interactions between microbes, epithelium, and immune system (147, 148). Recently, stem-cell derived gut organoids have been used as a bioassay to probe the disease phenotypes of different CFTR mutations and screen efficacy of CFTR-restoring compounds (149).

C. Congenital Pediatric Lung Diseases.

A range of pediatric lung diseases are due to mutations in genes encoding surfactant proteins (SP-C, SP-B) or factors required for surfactant trafficking (ABCA3), causing surfactant deficiency. Mouse models generated by gene deletion tend to recapitulate merely a subset of the clinical spectrum observed in human populations, likely because of different lung physiology, and no therapy has been developed thus far (151). Stem-cell based in vitro models of human lung development (34) provide a new platforms for studying etiology and pathogenesis of these and other pediatric congenital lung diseases, and might lead to novel therapeutic approaches.

D. Inflammatory Diseases of the Lung.

Chronic obstructive lung disease (COPD) and asthma are the most prevalent of all chronic respiratory diseases worldwide, and they rank among the top 20 conditions causing disability globally (152). Both conditions engender respiratory distress and chronic inflammation of the lung and are thought to result from environmental exposure in genetically susceptible individuals (153, 154). The symptoms can be further exacerbated by airborne particles, or viral and bacterial infection of the airways. Currently, there are limited treatment options for severe asthma and COPD, partly because of the lack of suitable preclinical model systems for dissecting the contributions and temporal dependencies between environmental factors, genetic predispositions, and acquired susceptibility. In fact, animal models do not naturally develop asthma (30), and even when they can be rendered sensitive to antigens, they fail to recapitulate all aspects of the human pathogenesis (155-157). This is likely due to well-known differences in airways physiology, anatomy and immunology a between animals and humans (158-160). For instance, secretory goblet cells are overabundant in COPD and asthmatic airways; this pathological hyperplasia is possibly mediated by Notch signaling-directing differentiation of basal cells, the stem cells of the large airway, towards a secretory fate (161). Mice, however, exhibit a much lower abundance of goblet cells than humans and therefore do not provide a good model for development and homeostasis of goblet cells in healthy and diseased human lungs. Further, whereas the role of inflammation and the innate immune system in asthma is well known (162), the spatiotemporal dynamics of this process cannot easily be studied in animal systems. Also, the origin of pathological inflammatory responses might be found in developmental events that are human or even patient-specific, such as in utero fetal programming of gene expression involved in lung development (163), or signaling from the microbiome during a responsive postnatal time window thought to promote immune tolerance (164). Human primary cell 3D models of the airways have demonstrated a new avenue towards addressing these and other questions in vitro (165, 166). In the future, human stem-cell based lung chip models that support the dynamic interaction with circulating immune cells, essential in asthma and COPD pathogenesis, could help elucidate the underlying inflammatory mechanisms, model exacerbation in vitro and lead to the development of new therapies and identify new treatment options.

E. Pulmonary Fibrosis.

Idiopathic pulmonary fibrosis (IPF), a chronic and irreversible disease associated with lung scarring and progressive decline in lung function, causes the death of 80,000 US Americans and Europeans each year (167). To date no therapy is available to reverse disease process. In the recent years, two pharmaco-therapeutic agents, pirfenidone and nintedanib, have been developed that can halt disease progression, however both drugs are associated with adverse effects (168). While the precise disease mechanisms are still unknown, it is believed that myofibroblasts and fibrosis progenitor cells are responsible for the fibrotic architectural remodeling in the lung (57, 169). Altered mucociliary properties could also contribute to the disease process by reducing clearance of noxious agents from the epithelium (170). Several genetic polymorphisms and mutations predispose to IPF but how the fibrotic process is initiated and sustained remains unclear, partly because no good mouse model of the disease exist, leading to poor preclinical to clinical translation and extensive clinical trial failure (171). Patient-specific in vitro models of the human alveolar epithelium are urgently needed to help elucidate pathogenesis and the role of genetic predisposition and environmental exposure in determining disease penetrance (169, 172). Specifically, on-chip model comprising the different cell types of the alveolar epithelium, ideally from the same patient, and recapitulating the cross talk between alveolar epithelial cells and the surrounding fibroblasts could reveal unknown mechanisms of pathogenesis and lead to new therapeutic targets. In addition, the ability to test the influence of physiological mechanical stretch on alveolar cells in vitro is another feature of Organs-on-Chips in modeling IPF.

F. Lung Cancer.

Lung cancer is the leading cause of cancer mortality and causes more than 160,000 deaths per year in the United States (173). Development of drug-resistant tumor cells and eventually fatal metastases is common despite aggressive treatment with surgery, radiation and chemotherapy, and long-term survival rates of lung cancer patients remain low (174). Clearly, new treatment strategies are needed. Approaches that elicit anti-tumor immune responses such as antibody-based immune therapy (175) and or enhanced T-cell activation using gene editing (175) have raised great hopes; however, in many cases preclinical efficacy does not translate to human trials. For example, in some cases, immunologic response was not correlated with survival (176). Perhaps more concerning, in recent phase II/III clinical trials, nearly 80% of all the studies failed (24) due to elevated levels of circulating immunosuppressive cytokines and various immunological checkpoints in humans that may not be present in animal models (25). Indeed, there is a lack of human-relevant model systems where tumor biology in response to treatment and immune responses can be observed and quantified. Conventional subcutaneous implants of tumor tissue in mouse models do not mimic organ-specific differences in cancer growth or responses to drugs observed in the clinic (177). Notably, human tumor xenografts implanted in mice at the corresponding organ site from which the tumors were derived are better at recapitulating physiological tumor growth and metastasis (178, 179). These results indicate the importance of the organ-specific microenvironment in determining tumor biology and drug response; however, the contributions and spatiotemporal dynamics of the tumor-organ interactions have remained a "black box" because of the difficulty to visualize and probe tumor development in vivo. Conventional 2D in vitro cancer cultures, on the other hand, are accessible to real time imaging and investigation but lack the organ-specific microenvironment and heterogeneous 3D architecture of real tumors which leads to different growth profiles and drug responses. Organ-on-chip models of human lung cancer provide an alternative approach by recapitulating the organ-specific 3D microenvironment, tissue-tissue interfaces, mechanochemical cues, vascular perfusion and potential interactions with immune cells while also enabling continuous monitoring of tumor evolution and tumor-organ interactions (100). Combining these approaches with stem-cell derived tumor tissues could aid in the development of patient-specific therapies and treatment strategies overcoming tumor drug-resistance (180).

Thus, in one embodiment, embodiments of Alveolus-Chip as an open top fluidic device seeded with primary cells, includes modeling cancer/tumor lung models. In fact, data generated during the development of the present inventions showed cancer cells growing on top of alveolar cells, in addition to cancer cells growing together with alveolar cells (in embodiments of sequential vs. embodiments of concurrent seedings of alveolar and cancer cells) with growth of cells for at least 2 weeks. In some embodiments, effects of co-culturing cancer-associated fibroblasts vs healthy fibroblasts are contemplated to explore signaling between cells in a tumor model. In some embodiments, results are readouts as comparisons of genomics of gene expression and proteomics of protein expression.

G. Pulmonary Infectious Disease.

Respiratory infections of the lung from a viral, bacterial or amoeboid source are a cause of human mortality worldwide. Second to cardiovascular disease in their effect on global health, lower respiratory infections constitute the most deadly communicable diseases, causing 3.2 million deaths in 2015 (185). Tuberculosis and other bacteria, together with influenza, as well as respiratory syncytial viruses, rhinoviruses, human metapneumovirus, parainfluenza virus adenoviruses and coronaviruses can cause life threatening diseases in healthy people, and complications in patients with pre-existing lung diseases such as asthma, COPD, bronchiectasis, chronic bronchitis, cystic fibrosis, or primary immunodeficiencies, and other conditions that alter immunologic mechanisms against microbial invasion (186). Susceptibility to infection as well as onset, duration and severity of symptoms is controlled by dynamic and patient-specific host-microbe interactions which, in addition to the rise in antibiotic resistance, has contributed to the difficulty of developing effective treatments (187-189). Lung homeostasis relies on a finely regulated balance between immune tolerance towards innocuous exogenous particles that continuously enter the lungs on the one hand, and defense mechanisms against infectious agents on the other hand. An imbalance in immune homeostasis of the lung can lead to exaggerated inflammatory responses such as allergies or "cytokines storm" following viral infections, causing ultimately extensive tissue damages (190). Respiratory infections pathogenesis is largely mediated by the interaction between the infected tissue and the host immune system, including lung resident and circulating immune cells. While most in vitro systems enable the study of isolated immune cells or epithelial cells in static conditions, human Lung-on-Chip are dynamic fluidic systems that offer the unprecedented possibility to investigate interaction of lung endothelium and epithelium with flowing immune cells in a dynamic fashion mimicking lung capillaries. This unique feature can be leveraged to dissect individual roles of infiltrating immune cells in lung infection, to probe the underlying disease mechanisms, and to identify new therapeutic targets or facilitate vaccines development. Disease phenotypes are also modulated by more subtle interactions with the patient's resident immune cells. For example, pathogenesis of tuberculosis agent *Mycobacterium tuberculosis* involves modification of core cell signaling pathways in immune cells, and patient-specific immune cell responses might be part of the reason why probability and course of infection are highly variable between patients (191, 192). Hence, both the development of novel, host-directed therapies as well as understanding the mechanisms of disease onset and progression in tuberculosis would benefit from patient-specific in vitro models of the dynamic interactions between bacteria, lung cells, and the immune system (193-195).

H. Pulmonary Drug And Toxicity Testing.

1. Pulmonary Drug Testing.

Preclinical drug discovery and development process involves testing of drug's safety, pharmacodynamics (also referred to as efficacy, i.e., mechanisms of action and dose-response relationships), and pharmacokinetics (including ADME, i.e., drug absorption, distribution, metabolism, and excretion, as well as potential drug-drug interactions). For the same reasons previously addressed, animal models, and particularly rodents, are limited in their ability to predict human responses. Stem-cell based organ-on-chips might complement or even replace animal studies in the preclinical phase of drug development.

2. Safety of Pulmonary Drugs.

Drug compounds can induce specific adverse effects in the lungs, and the lungs may be affected by general toxicity too. Several hundred medications, delivered by various routes, are known to cause drug-induced adverse responses and respiratory diseases (196). Because the clinical, radiologic, and histological symptoms are often non-specific, it can be difficult to diagnose lung-related adverse drug reactions, especially if the patient is taking multiple drugs, and hence pulmonary toxicity, estimated at approximately 3%, is likely under-diagnosed (197, 198). Adverse effects can be idiosyncratic or due to a toxic reaction of the drug or one of its metabolites, since the lungs metabolize certain substances. In addition, secondary mechanisms such as immune system responses can cause further damage. For example, drug-induced interstitial lung disease (DILD) is a common complication which can cause acute respiratory distress all the way to pulmonary fibrosis (characterized by proliferation of fibroblasts and extensive ECM deposition) (199, 200). DILD is thought to be caused by direct, dose-dependent cytotoxicity to bronchial epithelial cells or the alveolar capillary endothelium but also by a T-cell mediated immune response. While age, sex, existing lung disease, drug interactions, and drug dose are risk factors known to correlate with phenotype of DILD and other drug-induced respiratory diseases, a mechanistic understanding of factors influencing disease onset and progression is lacking. Human Lung-on-Chips could help isolate and query genetic predispositions of specific patient populations, detangle interdependencies of risk factors, predict safety risks, and identify safe drug dosing regimens.

3. Efficacy of Pulmonary Drugs.

For most chronic lung diseases the available treatments are aimed at providing symptomatic relief rather than curing underlying disease mechanisms (201). Further, most new drugs being developed are based on disease targets that were identified many years ago, and clinical trials are plagued by high failure rates, indicating that relevance, reproducibility and predictiveness of experimental models need to be improved. Lung-on-Chip models in particular could help identify preclinical endpoints that can be translated to the clinic, stratify diagnosis and therapeutic care based on molecular mechanisms, tailor treatments to patient subgroups, and design trial end-points that quantify drug efficacy. Indeed, in 2014, the Respiratory Expert Council (REC), a global team of research and clinical experts, presented recommendations for improving drug research and development for airway diseases (202), three of which human Lung-on-Chip models are poised to facilitate.

First, to capture and understand the heterogeneity of airway disease pathophysiology and clinical presentation, airway diseases need to be redefined based on molecular mechanisms and systems-biology-based strategies, particularly network analysis, to characterize variability due to patient to patient differences and due to progression of the disease through various stages (203). Categorizing the disease in this way could facilitate the design of patient-specific and stage-specific therapies and advance personalized respiratory medicine (204). In the simplest application, systems-biology-based disease definitions can help address questions such as whether a new drug should be developed and tested in a broad disease category, such as COPD, or focus on specific disease phenotypes. In particular, even if patients exhibit similar symptoms on the clinical level, the molecular factors driving disease progression can be different, and vice versa (205). Stem-cell based Lung-on-Chip models can provide a platform for studying genotype-phenotype relationships affecting drug responses in different patient populations. These pharmacogenomic insights could inform the design of clinical trials and determine the inclusion and exclusion criteria of patients to assure optimal drug targeting.

Second, preclinical studies need to take into account systemic manifestations of airway diseases, such as inflammation and immune system responses (206), and link them both to molecular and tissue-level disease symptoms as well as clinical endpoints. Vascularized Lung-on-Chip models provide the dynamic environment allowing for controlled and experimentally accessible interaction between local lung tissue and systemic factors, such as immune system components.

Third, new readouts of lung function are needed that can be translated between experimental models and the clinic. Of particular interest is to develop imaging markers and biomarkers that are sensitive to different stages of airway disease, demarcate early-stage lung disease, and group patients into distinct phenotype or endotype populations. Towards these goals, Lung-on-Chip models provide a platform to identify genetic and 'omics' markers associated with tissue-level disease phenotypes that could be integrated with clinical readouts from blood tests, biopsies, imaging, patient-reported outcomes and functional endpoints, such as forced expiratory volume in one second (FEV1). Such multi-scale disease signatures would then support the design of end-points that can be measured both in vitro and in the clinic and that are directly related to disease progression and drug efficacy (207, 208).

4. Pulmonary Drug Delivery.

Inhalation is one exemplary route for drug delivery because its large surface area (70-140 $m^2$ in adults), good vascularization, and thin alveolar epithelium offer the potential for rapid absorption of pharmaceuticals either for local deposition or for systemic delivery (209, 210). Indeed, inhalation is one of the fastest route for systemic drug delivery of small molecules (211). There is also great interest in the development of inhaled drugs for localized treatment of lung diseases, including pneumonia (212). However, achieving desired drug concentrations and localization after aerosol inhalation is not a trivial task because complex mechanical, chemical and biological pharmacokinetics (Pk) mechanisms are at play, including drug deposition, absorption, distribution, metabolism, and various clearance mechanisms.

The first step, drug deposition, depends mostly on the fluid-mechanics of lung morphology, breathing pattern, aerosol velocity, particle size and density. Merely part of the dose will reach the target site in the lung whereas some fraction will be deposited in the inhalation device or in the mouth and throat. Due to the large spatial scales involved, understanding and predicting initial drug deposition relies on computational models and perfused animal lungs (213, 214). Organ-on-chip models have the great potential, however, to mimic and quantify many aspects of drug fate following deposition in different regions of the lung. Specifically, for pulmonary absorption into tissue and blood circulation to occur, deposited drug particles have to (i) dissolve in the surface lining fluids, (ii) overcome various defense mechanisms by which the lung clears inhaled particles, including mechanical (i.e., mucociliary clearance), chemical (e.g., surfactant lipids, antiproteases), and immunological (e.g., phagocytosis) responses, (iii) pass the transepithelial air-blood barrier by passive diffusion or carrier-mediated active transport via paracellular or transcellular pathway, and (iv) withstand (or be activated by) the lung's metabolic activity (213). The relative role of these mechanisms in drug absorption vary depending on airway region. For example, the conducting airways (nasal cavity, sinuses, nasopharynx, oropharynx, larynx, trachea, bronchi, and bronchioles) are lined by ciliated cells and mucus-secreting cells, which together enable the mucociliary clearance of about 90% of inhaled particles, greatly reducing bioavailability of drug compounds (215). In the respiratory regions, on the other hand, which comprise about 95% of the total surface area and consist of respiratory bronchioles, alveolar ducts, and alveolar sacs, drug bioavailability is limited by absorption, transport across the pulmonary air-blood barrier, and metabolic and macrophage clearance (216). Because of the complexity of the lung morphology, the quantitative characterization of the in vivo interplay of all contributing factors either with in vitro assays or with in silico methods is an ongoing challenge. Briefly, rodents are generally exposed via nose inhalation, and hence the resulting plasma pharmacokinetics are a result of absorption from different regions of the lung, the nose, and the gastrointestinal tract (by means of swallowed mucus) (217). Modeling approaches of the pharmacokinetics of inhaled drugs either estimate Pk parameters based on the physico-chemical characteristics of the drug and on anatomical and physiological tissue properties. Such models can, for example, use general drug properties determined in vitro such as aqueous solubility and membrane permeability to predict routes of absorption and elimination. Another modeling approach is to estimate drug Pk parameters from clinical Pk data by means of correlation. Stem-cell based Lung-on-Chip models could complement these approaches and capture the currently invisible temporal dynamics and patient-specific Pk parameters of drug absorption by recapitulating organ-specific barrier functions such as endothelial cell junctions and electrical resistance, presence of specific membrane transporters and metabolic enzymes, genotypic variation, disease conditions, and drug-drug interactions. More general Pk parameters could also be probed with organs-on-chips approaches, including local drug dissolution, which, especially for lipophilic drugs, can represent the rate-limiting process for pulmonary absorption. Further, organs-on-chips could help quantify and scale the relative absorption across conducting airway epithelium and across alveolar epithelium.

Third, the effect of elimination processes such as mucociliary clearance on pulmonary bioavailability could be measured (218). Fourth, the flow environment of organs-on-chips enables the realistic test of time-dependent effects such as built-up of drug residue or drug carriers that can cause local toxicity (219). Lastly, the efficacy of drug delivery to specific lung cells in patient-specific tissues could be measured.

VII. Organs-On-Chips

The field of Organs-on-Chips derives from "miniaturized total chemical analysis systems" or µTAS, microscale chemical platforms directly inspired from the development and miniaturization efforts of the electronic industry in the second half of the twentieth century (75, 76). These µTAS, later regrouped under the name "lab-on-a-chip" systems, integrate fluidic microsystems into a single platform to perform several steps of a chemical assay (77, 78). Originally, these systems did not contain any living components. Adding living cells became possible when new methods to fabricate microscale fluidic channels were established as an alternatives to fused silica capillaries (79). Specifically, Organs-on-Chips emerged from the convergence of cellular micro-patterning methods designed to control cell shape and function with early miniaturized systems for electrophoresis (80, 81).

Micro-engineered cellular platforms were initially called "cells on chip" to illustrate the merger of cell biology with microfabrication methods adapted from the computer microchip industry (42, 43, 82). The more recent denomination "Organs-on-Chips" implies the modeling of complex physiological organ-level function in microfabricated biochips. However, in place of silicon, Organs-on-Chips are typically made from hydrogels (83) or a silicone elastomer called poly(dimethylsiloxane) (PDMS) which has played a central role in Organs-on-Chips sudden popularity (79, 84). PDMS offers numerous mechanical and chemical advantages over traditional micro-engineering materials such as glass and silicon (85).

First, PDMS is relatively inexpensive compared to silicon, allowing cheap prototyping. PDMS stiffness can also be easily modified by controlling the degree of cross-linking between the polymer chains, enabling the design of soft and stretchable surfaces similar to the mechanical environment of cells. Moreover, since PDMS forms a tight seal with glass and can be reversibly or irreversibly bound to plastic polymers, hybrid devices containing rigid parts can be constructed. Moreover, PDMS is easy to work with, and rapid prototyping methods involving soft lithography and replica molding permit the creation of inexpensive devices with complex flow channel designs (84, 86). Finally, PDMS is gas permeable, biocompatible and optically clear which makes it particularly well suited for growing living cells in enclosed microfluidic compartments and monitoring their behavior using various types of light microscopy.

Faced with the promises and challenges of tissue engineering, notably the need for cellular scaffolds and blood perfusion of in vitro tissue, researchers have started to adapt microfabrication approaches to culture human cells and engineer human tissues (82, 87, 88). Earliest attempts of cellular micro-patterning used PDMS microchannels sealed against a tissue-culture dish to support the alignment, perfusion, and growth of 3T3-J2 fibroblasts (81). Later, microfluidic designs modeled after blood capillaries supported the culture of human endothelial cells (89), quickly followed by other cell types, including liver (90-92), muscles (93), bones (94), brain (95), gut (96), and kidney (97, 98).

While Organ-on-Chips were originally developed to solve challenges encountered in the field of tissue engineering, their potential to recapitulate complex human organ-level functions became rapidly evident and led to an array of advanced models of human lung tissue, such as the "lung-on-a-chip", "alveolus-on-a-chip" and "small airway-on-a-chip" (42, 46, 68, 69, 99). Recent applications include the modeling of alveolar tissue-tissue interaction and inflammatory processes (42), responses of the alveolar epithelium to drugs, mechanical stresses (45, 99), and pulmonary thrombotic events (69), as well as lung cancer (100). Most recently, a functional microfluidic model of human airways comprising well differentiated airway epithelial cells at air-liquid interface has been developed. Moreover, the airway epithelium interacts with a continuously perfused pulmonary microvascular endothelium under physiological shear stress allowing circulation of immune cells. This model has been leveraged to model human obstructive respiratory diseases and test novel therapeutics (46).

VIII. Exemplary Embodiments for Use with Lung Cell Differentiation

The following describe embodiments for use with differentiation protocols. In some embodiments, at least partial induced differentiation of stem cells occurs off-chip for subsequent use of differentiated cells seeded into microfluidic chips. In some embodiments, a stem cell terminally differentiated into a lung cell occurs off chips for subsequent use seeded into microfluidic chips.

In some embodiments, at least partial stem cell differentiation into respiratory system tissues and cells, including lung, occurs on-chip. In some embodiments, stem cell differentiation into terminally differentiated respiratory system tissues and cells, including lung, occurs on-chip.

Merely as a non-limiting example, in some embodiments, a device used for stem cell differentiation into a respiratory tissue on-chip is a closed-top device. In some embodiments, a device used for stem cell differentiation into lung-on-chip is a closed-top device. In some embodiments, a device used for stem cell differentiation into a respiratory tissue on-chip is an open top device. In some embodiments, a device used for stem cell differentiation into lung-on-chips an open top device. In some embodiments, stem cell differentiation into a respiratory tissue on-chip does not include a gel. In some embodiments, organoid-on-Lung-Chip includes a gel. In some embodiments, stem cell differentiation into lung-on-chip does not include a gel. In some embodiments, stem cell differentiation into lung-on-chip includes a gel. Merely as a nonlimiting example, organoids on Lung-Chips are contemplated for use in providing organoid alveolus-on-chip and organoid small airway-on-chip. In some embodiments, a device used for organoid-on-Lung-Chip is a closed-top device. In some embodiments, a device used for organoid-on-Lung-Chip is an open-top Lung-Chip. In some embodiments, an organoid-on-Lung-Chip does not include a gel. In some embodiments, an organoid-on-Lung-Chip includes a gel.

A. Organs-On-Chips Technology.

Recent advances in microphysiological systems engineering have made it possible to create biomimetic microfluidic cell-culture platforms, known as Organs-on-Chips that contain continuously perfused microchannels lined by living human cells. This design reconstitutes functional and microenvironmental features of whole organs including tissue-tissue interfaces, mechanical forces, fluid flow and biochemical gradients (42-46). Organs-on-Chips have been shown to reproduce complex integrated organ-level responses to pathogens and inflammatory cytokines, as well as nanoparticles and pharmaceuticals; they can also effectively mimic disease states and complex pathophysiological responses. Mechanically active Organ-on-Chips microdevices populated with human cells may therefore expand the capabilities of cell culture models and provide low-cost alternatives to animal and clinical studies for disease modeling, drug screening and toxicology applications (47). As discussed in the following, Organs-on-Chips recreate the complex, dynamic state in which living cells function within the native human organ, including interactions with the substrate (extracellular matrix), tissue-tissue interface, mechanical forces, immune cells (and blood components), and biochemical microenvironment, which contribute to lung health and disease.

Extracellular Matrix. The ECM is the non-cellular component of a tissue that provides the structural scaffolding and biochemical and biomechanical support to the surrounding cells. In the lung and other organs, the ECM gives the tissue its physical and mechanical properties, and contributes to tissue development, morphology, and function (48). In the lungs, the ECM influences fundamental processes including cell signaling pathways (49), cell shape and function (50), cytoskeletal organization and differentiation (51), organogenesis (52), and wound healing (53). The ECM composition is specific to each organ in addition to having unique characteristics when compared between different sections of a tissue. Merely for examples, the lungs, which have a relatively soft ECM overall, alveoli ECM is composed of a mix of collagen III, IV, V, laminin, fibronectin and elastin (54) while the ECM of the upper airways includes collagens I, II (cartilage), V, laminin and fibronectin (55). Further, extensive ECM remodeling is associated with, or forms the basis of, many physiological and pathophysiological processes such as wound healing and pulmonary fibrosis (56). Therefore, the ECM composition used in a model of the lungs must carefully be determined and will depend on the region and the disease state one seeks to model.

Tissue-Tissue Interface. While lung ECM scaffolding dictates the tissue architecture and precisely compartmentalizes lung cell populations, neighboring cellular compartments constantly interact. Interaction can happen through direct cell-to-cell contact, such as airway epithelial cells and fibroblasts during fibrosis (57) and alveolar macrophages and pneumocytes in health and disease (58), or through soluble factors, such as in epithelial-endothelial cross talk during influenza virus-induced cytokine storms (59), endothelial influence on epithelial differentiation (21), and mesenchymal cells influence on epithelial development (13). Cross-compartment communication can modulate tissue growth, differentiation, and cell activation which mediates the recruitment of immune cells during inflammation (60) in vivo ref. Such multi cell type interactions can also be recapitulated in Organs-on-Chips; for instance, co-culture of differentiated human primary airway epithelial cells and endothelium in close proximity results in cross-communication between both tissues following treatment with a pro-inflammatory stimulus (46). Similarly, stimulation of the epithelium with a pro-inflammatory agent results in activation of the underlying endothelium, as indicated by overexpression of adhesion molecules such as ICAM-1, VCAM-1 and E-Selectin (46, 61).

Mechanical Forces. During breathing movements, lungs undergo dynamic deformation estimated to cause 4% stretch distension of the basement membrane (62, 63). These mechanical forces strongly influence lung cells, including effects on growth and repair, surfactant release, injury, inflammation (64-66), as well as tissue development from fetal to adult stage (64, 67). Additional mechanical forces that influence cell function and development include the shear stresses induced by the blood flow in the capillaries and the air flow in the lumen of the conducting airways. Organs-on-Chips offer the possibility to apply and control physiological biomechanical forces, including breathing movements (61, 68) and shear stresses, (45, 69) that cells experiences in vivo. Therefore, Organs-on-Chips provide a platform to study tissue biology in a relevant physical and biomechanical micro-environment. See U.S. Pat. No. 8,647,861, hereby incorporated by reference.

Biochemical microenvironment. The biochemical surroundings of cells are composed of elements that are secreted or transported through the tissue. These include growth factors, hormones, dissolved gases, and small molecules such as salts and nutrients. In the lungs, biochemical mediators are central to processes ranging from tissue development and homeostasis (ref) to inflammation and injury resolution (ref). Lung cells also play a significant role in the metabolism of xenobiotics and endogenous hormones such as serotonin, leading to degradation as well as activation of biologic properties (70). Xenobiotic-metabolizing cytochrome P450 enzymes expressed in bronchial and bronchiolar epithelium, Clara cells, type II pneumocytes, and alveolar macrophages in human lung activate environmental chemicals, modifying cell biochemical microenvironment and contributing to pathologies such as cancer and COPD (71). Precise control of biochemical microenvironment mimicking in vivo biochemical cues during tissue development is also fundamental to stem cell differentiation protocol. Because Organs-on-Chips offer the possibility to accurately control the regional and temporal biochemical microenvironment of cells through controlled perfusion of growth medium and gases, they could be applied to improve stem cell differentiation methods.

Immune Cells and Blood Components.

Circulating and resident immune cells are actors of inflammation and play a central role in the pathogenesis and resolution of respiratory diseases. Together with airway epithelial cells, lung resident and circulating immune cells, such as dendritic cells and macrophages initiate and set the tone of immune responses (72). The fluidic nature of Organs-on-Chips allows dynamic supply of nutrients and gases, in addition to enabling perfusion of immune cells through the system in a manner that replicates physiological parameters, such as shear stress present in microvessels (61, 73). This unique feature enables visualization and real time monitoring of interacting perfused freshly isolated immune cells with lung endothelial and epithelial cells (46, 61). Whole human blood can also be perfused through Organs-on-Chips to mimic thrombotic events and assess drug delivery, toxicity, and efficacy (69, 74).

B. Practical Approach to Micro-Engineer Lung-On-Chips.

Microengineering of the Lung-on-Chip means to recapitulate the essential structure-function relationships governing healthy and disease states of the organ (221). Because of the inherited complexity of the human airway, it is difficult to encapsulate organ-level functions in one system, and the prevailing strategy is instead to model fundamental tissue-level functions with reduced complexity and readouts. Specifically, Lung-on-Chip models aim to recapitulate the characteristic cellular composition and tissue architecture of individual functional tissue units of the lung and measure their specific function, such as gas exchange, maintenance of air-liquid interface, and oxygenation of blood in the alveoli, and mucociliary barrier function in the small airways. To achieve these goals, the following aspects in particular need to be carefully evaluated when deciding on the design of a Lung-on-Chip.

Tissue-level synergism on-chip. Biological mechanisms regulating organ homeostasis in vivo often rely on the ability of eukaryotic cells to communicate and respond collectively to a variety of stimuli. This "tissue-level synergism" achieved in vivo is an essential characteristics of animal tissues and is central to the establishment of Organs-on-Chips. Engineering a Lung-on-Chip hence requires incorporation of different cell types, together with well-defined biochemical and mechanical cues and boundaries, in order to reconstitute the tissue-level-synergism that cells develop in vivo. Accordingly, given that generation of a functional epithelial-endothelial interface is central to the development of the lung blood-air barrier (222, 223)(and maintenance of the air-liquid interface, epithelial and endothelial cells are frequently the first two cell types to be introduced on-chip. To support growth and differentiation of both cell populations, a semi-permeable membrane composed of silicone (PDMS) or plastic polymer (polyethylene, polycarbonate) coated with ECM is used in Lung-on-Chips platforms (46, 61). Both membrane material as well as pore size are parameters for achieving a healthy cell culture. Previous work demonstrated that PDMS membranes with 7 µm-diameter pores, or polyethylene membranes with 0.4 µm-diameter pores were suitable for cell attachment, growth and differentiation of alveolar and primary airway epithelial cells, respectively (224).

While challenging, one can establish optimal in vitro conditions supporting cell growth and function of multiple cell types that share the same biochemical environment (including cell culture medium and extracellular matrix). While limited in physiological relevancy, cell lines are quite permissive and a number of studies have already identified viable co-culture conditions (225, 226) that support the formation of an epithelial-endothelial interface, typically using Transwell inserts. Primary cells and PSC-derived cells need comparatively more demanding culture protocols and specific biochemical stimuli including hormones and extracellular matrix components are required to support appropriate cell maturation and differentiation. Moreover, reconstitution of the cell-cell interactions at the alveolar capillary interface may represents one element for the establishment of an iPSc-derived lung chip. In fact, endothelial cells have been shown to drive tissue morphogenesis (227) and maturation of pulmonary tissue (228). Noteworthy, in vivo mechanical and physical cues regulate different aspects of lung physiology. Pulmonary cells express a vast repertoire of receptors and biochemical pathways that allow mechanotransduction in order to sense the mechanical cues associated with breathing motion and blood flow (229, 230). These aspects, almost completely neglected and inaccessible in traditional static cell culture, are central to the development of the Lung-on-Chip in which appropriate mechanical cues, including shear flow and tissue strain, can be incorporated by mechanically deforming the flexible PDMS chip, using for example vacuum-driven tensile strain of the membrane (refs).

In some embodiments, Extracellular Matrix (ECM) proteins are used for stem cell derived lung cell differentiation. The extracellular matrix (ECM) plays a substantial role in maintaining proper adhesion, proliferation, orientation, and differentiation of various cell types (231). The ECM provides physical support and mechanical cues but it is also a biochemically active environment. Together, the mechanical and chemical signals of the ECM help orchestrate cellular responses, and reversely, the cells can remodel and reshape the ECM by deposition and break-down of ECM components as part of physiological and pathophysiological responses. Therefore, modelling of specific lung developmental steps and functions requires the use of appropriate ECM components, such as collagen IV and laminin. For instance, during the development of the alveolar sac, gradual changes in the ECM composition guide septation (232) and mediate maturation of Type-I and Type-II pneumocytes (233). Also, maturation of the mucociliary barrier responsible for clearance of the airway mucosa requires formation of epithelial tight junctions and apical cilia, a biochemical processes driven by epithelial cell interaction with the ECM (234). Notably, aberrant accumulation of collagen-I rich ECM in the lung parenchyma results in tissue stiffening and a progressive decline in lung function (235), eventually leading to lung fibrosis (56, 236). Given the growing body of evidence linking disease conditions (such as fibrosis and COPD) to changes in the ECM composition (237), in vitro disease modelling of the Lung-on-Chip should leverage the use of specific ECM components to model these pathophsyiological mechanisms and improve the relevancy of the disease model.

In some embodiments, a stem cells from a variety of sources are contemplated for use in stem cell derived lung cell differentiation. Choosing an appropriate cell source is a step toward building a functional Lung-on-Chip. The ideal cell source is reliable, i.e. reproducible results can be generated across multiple lots. Cell lines are considered the most reliable among the commercially available options. However, since cell lines are frequently derived from tumors or are immortalized via transfection with animal viruses, they most often have altered geno- and phenotypes compared to the desired cell type. For example, many of the immortalized epithelial cell lines do not correctly express crucial components of intercellular junctions (238).

Therefore, the use of cell lines for generating physiological relevant model of human organs can be questionable. For instance, the commercially available cell line A549, a human lung adenocarcinoma cell line, has been frequently used as model of lung surfactant producing cell. However, this cell line expresses lower amount of phospholipids when compared to primary human Type II alveolar cells (239), does not produce surfactant A and does not generate a tightly connected monolayer unless stimulated with dexamethasone (239).

On the other hand, primary cells, which can more close mimic physiologically relevant lung-functions and patient-specific disease states, often lack reproducibility because no renewable isogenic cell source is available. Specifically, the donor-to-donor variability represents a significant challenge that may be mitigated using narrow criteria for donor selection. In addition, not all cell types can be consistently isolated, expanded and matured in vitro using currently available protocols. In particular, maintaining the phenotype of primary lung cells in vitro is a well-recognized challenge in the field. Optimization of the biochemical environment, including ECM and media components, is needed to ensure the maintenance of the original phenotype and exclude loss of cell functions. As discussed earlier, PSC-derived lung cells are a recent and promising alternative that, by providing a renewable, isogenic, and patient-specific cell source, is designated to overcome many of the limitations associated with either cell lines or primary cells. Recently, protocols to differentiate human iPSCs into pulmonary cells have been introduced, and although additional efforts are required to generate fully functional alveolar cells expressing markers of the adult and mature organ, PSC-derived cells are prone to become a powerful source for in vitro models of the human lung (240).

Thus, a variety of cell sources for providing stem cells for use as described herein, include but are not limited to stem cells obtained from respiratory tissue biopsies, lung biopsies, respiratory system biopsies, embryonic stem cells (ESCs), pluripotentent stem cells, induced pluripotentent stem cells (iPSCs), organ-restricted adult stem cells (aSCs), organoids derived from primary cells, organoids derived from stem cells and organoids derived from iPS cells, in addition to other types of stem cells as described herein. Stem cell sources further include but are not limited to organoids derived from one or more cell types, (i.e. created using) including but not limited to primary cells; primary respiratory tissues; primary lung tissues; stem cells; embryonic stem cells (ESCs); or induced pluripotent stem cells (iPS cells). iPSC derived specialized organoids, may be known as tracheospheres, bronchospheres, and pneumospheres (or alveolospheres), etc. For descriptions and examples of methods that may find use for providing lung organoids, such as organoids representing the distal airways ("alveolospheres") containing both cell types in the same organoid, derived from single type I as well as type 2 alveolar cells, including co-culture with non-epithelial cells (e.g., mouse lung fibroblasts); early bronchiolar lung organoid culture protocol, involving Matrigel supplemented with EGF, e.g. Single basal cells isolated from the trachea grew into "tracheospheres" consisting of a pseudostratified epithelium with basal cells and ciliated luminal cells, see Clevers "Modeling Development and Disease with Organoids." Cell, 165(7):1586-1597 (2016).

In some embodiments, mechanical forces are used for stem cell derived lung cell differentiation. Mechanical forces. Breathing is a unique feature of the lung and the extent of mechanical deformation in the alveolus affects the functionality of the alveolus in a number of ways, including by controlling surfactant release, permeability, inflammation, and cell injury and repair (241). It was estimated that already during gestation the surface area of the distal human lung is stretched by 5%, due to fetal breathing movements (242). The resulting mechanical strain is known to induce proliferation of fetal epithelial cells and maturation of type-II pneumocytes (64, 67). However, the field is still lacking a comprehensive characterization of the human adult alveolar epithelial cells and, specifically, appropriate in vitro conditions for the growth of adult type II cells on elastic membrane for testing the effects of mechanical stretch have not yet been developed. In general, the use of adult human alveolar cells for in vitro studies is quite limited as they quickly flatten and rapidly lose their cell function, including their ability to produce surfactant, when grown in standard static cell culture conditions (243-245). Based on the evidence mentioned above, it is possible that incorporation of mechanical strain during culture may promote proliferation and differentiation of alveolar cells. Additionally, the use of appropriate parameters, including amplitude and frequency of mechanical strain, may help maturation of iPSc-derived lung cells. In fact, several lines of evidence indicate that mechanical strain of the alveolar compartment, which in vivo ranges from 5% to 25% (246-248), induces Ca2+ influx, in turn promoting surfactant secretion (249) and proliferation of type-II pneumocytes. Surprisingly, the cyclic stretching produced by breathing can also affect endothelial cell metabolism. Multiple studies have reported that mechanical stress improves endothelial tissue barrier function (250) and expression of physiological relevant soluble factors (251). Modelling the alveolar epithelium will therefore necessitate a Lung-on-Chip design and material composition that can be actuated to perform elastic stretching of the tissue. However, when modelling a section of the lungs which does not experience stretch, such as the proximal airway epithelium, simpler chip designs and rigid materials can be used.

Moreover, endothelial cells are also able to sense and adapt to variation in the blood-flow. In fact, by virtue of its location, the vascular wall serves as an interface between the blood and tissue and can respond to hemodynamic cues. The physiological shear stresses acting on the vascular wall have been show to modulate gene expression, cell morphology, and cell metabolism (252-254) of endothelial cells. Because of the central role that mechanical forces have in maintenance of the lung-tissue homeostasis in vivo, these parameters may be considered in the design of the lung-chip. Appropriate ranges of vascular fluidic flow rate and shear stresses as well as mechanical strain of the tissue could provide new opportunity for disease modelling, including pulmonary hypertension (255) and mechanical ventilation induced injury (256, 257), which are nearly impossible to mimic with classic plate culture or transwell inserts.

DETAILED DESCRIPTION OF THE INVENTION

I. Embodiments for Organ-On-Chip.

Organ-on-chip cultures as described herein, are contemplated to show physiological and morphological changes in epithelial cell layers directly related to the source of or differentiation stage or functions status of derived cells. Accordingly, some embodiments described herein relate to devices for simulating a function of epithelial tissue (also referred to as "organ-on-a-chip device"). The organ-on-a-chip microfluidic devices described herein can be used to simulate at least one or more (e.g., 1, 2, 3, 4, 5 or more) phenotypes and/or functions of a variety of tissues.

FIG. 1A-1B illustrates a perspective view of one embodiment of a microfluidic device in accordance with some embodiments described herein. For example, as shown in FIGS. 1A-1B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is merely exemplary and not limited to the configuration shown in FIGS. 1A-1B. While operating channels 252 (e.g., as a pneumatics means to actuate the membrane 208, see below for information on membrane 208 and see the International Appl. No. PCT/US2009/050830, the content of which is herein incorporated by reference in its entirety, for further details of the operating channels, are shown in FIGS. 1A-1B, they are not required in all of the embodiments described herein. In some embodiments, the devices do not comprise operating channels on either side of the microchannel. In other embodiments, the devices described herein can be configured to provide other means to actuate the membrane, e.g., as described in the International Pat. Appl. No. PCT/US2014/071570, the content of which is herein incorporated by reference in its entirety.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are herein incorporated by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof.

As used herein, the term "rigid" refers to a material that is stiff and does not bend easily, or maintains very close to its original form after pressure has been applied to it.

The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure.

In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof.

As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally or alternatively, at least a portion of the first structure 204 and/or second structure 206 can be made of non-flexible or rigid materials like glass, silicon, hard plastic, metal, or any combinations thereof.

The device in FIG. 1A can comprise a plurality of access ports 205. In addition, the branched configuration 203 can comprise a tissue-tissue interface simulation region or regions (such as a region on the membrane 208 in FIG. 1B) where cell behavior and/or passage of gases, chemicals, molecules, particulates and cells are monitored. FIG. 1B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204 and 206 when the portions 204 and 206 are mounted onto one another to form the overall body.

The microchannel(s) in the microfluidic devices can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 1B illustrates an exploded view of the device in accordance with an embodiment. As shown in FIG. 1B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 1B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

A Membrane Located in Between the First Structure and Second Structure.

In one embodiment, the membrane 208 is oriented along a plane between the first chamber 204 and the second chamber 206. It should be noted that although one membrane 208 is shown, more than one membrane 208 can be configured in devices which comprise more than two chambers.

The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass through. In some embodiments, a selectively-permeable membrane can allow certain cell types to pass through but not other cell types.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell-binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In some embodiments, cells are cultured on and/or under the membrane under flow conditions. In some embodiments, there is a steady-state perfusion of the cells. In other embodiments described herein, the devices can comprise a flowing culture medium in the first chamber and/or the second chamber, wherein the flowing culture medium generates a shear stress. Based on the viscosity of the culture medium and/or dimensions of the chambers, one of skill in the art can determine appropriate flow rates of culture medium through the chambers to achieve desired shear stress. In some embodiments, the flow rate of the culture medium through the first chamber can range from about 5 µL/hr to about 50 µL/hr. In some embodiments, the flow rate of the culture medium through the second chamber can range from about 15 µL/hr to about 150 µL/hr. Thus, in one embodiment, fluidic shear forces are generated.

Optional Vacuum Channels.

Fluidic channels in devices of the present inventions are optionally flanked by two vacuum channels that allow the pneumatically actuated stretching forces mimicking peristalsis, for a non-limiting example, bronchial spasms. In some embodiments, stretching forces are for stretching an epithelial layer. In one embodiment, mechanical forces are generated.

Exemplary Devices for Simulating a Function of a Tissue.

Some embodiments described herein relate to devices for simulating a function of a tissue, in particular an epithelial tissue. In one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

ECM Coating.

To determine optimum conditions for cell attachment, the surface-treated material (e.g., APTES-treated or plasma-treated PDMS) can be coated with an ECM coating of different extracellular matrix molecules at varying concentrations (based on the resulting cell morphology and attachment).

ECM Overlay.

The ECM overlay is typically a "molecular coating," meaning that it is done at a concentration that does not create a bulk gel. In some embodiments, an ECM overlay is used. In some embodiments, an ECM overlay is left in place throughout the co-culturing. In some embodiments, an ECM overlay is removed, e.g. when before seeding additional cells into a microfluidic device. In some embodiments, the ECM layer is provided by the cells seeded into the microfluidic device.

Although cells described for use in an organ-on-chip make their own ECM, it is contemplated that ECM in predisease and diseased states may contribute to inflammatory states. Further, the protein microenvironment provided by ECM also affects cells. Thus it is contemplated that tissue-derived ECM may carry over a disease state. Therefore, in addition to the ECM described herein, ECM used in microfluidic devises of the present inventions may be tissue-derived (native) ECM. In one embodiment, a device comprising tissue-derived ECM may be used as described herein, to identity contributions to healthy or disease states affected by native ECM. For example, ECM may be isolated from biopsies of healthy, non-disease and disease areas as tissue-derived ECM. Isolates for use may include cells within or attached or further processed to remove embedded cells for use in the absence of the cells. Additional examples of ECM materials include but are not limited to Matrigel®, Cultrex®, ECM harvested from humans, etc.

Matrigel® is a trade name for a solubilized basement membrane preparation extracted from the Engelbreth-Holm-Swarm (EHS) mouse sarcoma, a tumor rich in such ECM proteins as laminin (a primary component), collagen IV, heparin sulfate proteoglycans, entactin/nidogen, and a number of growth factors as produced and marketed by Corning Life Sciences. Matrigel® gels to form a reconstituted basement membrane. Versions of Matrigel® include BD Matrigel® (Basement Membrane) Matrix, offered as Standard, Growth Factor Reduced, Growth Factor Reduced-High Concentration (HC) and Growth Factor Reduced-Phenol Red-Free formulations, BD Matrigel® hESC-qualified Matrix, by BD Biosciences.

Trevigen, Inc. markets other ECM versions of BME harvested as a soluble form of basement membrane purified from Engelbreth-Holm-Swarm (EHS) tumor cells under the trade name Cultrex® Basement Membrane Extract (BME). Cultrex® extract gels at 37° C. to form a reconstituted basement membrane. Primary components of Cultrex® BME include laminin, collagen IV, entactin, and heparin sulfate proteoglycan. Several forms Cultrex® are offered by Trevigen as: Cultrex® Reduced Growth Factor Basement Membrane Extract, Type R1. Type R1 matrix provides a proprietary formulation that has higher tensile strength when compared to other Cultrex® products, i.e. Cultrex® BME, Cultrex® BME Type 2 and Cultrex® BME Type 3. Type R1 has a higher concentration of entactin, one of the BME components that connect laminins and collagens reinforcing the hydrogel structure. Cultrex® BME Type R1 has been specifically designed to culture tissue organoids. BME type R1 supports culture of organoids. In a Tube formation assay—BME type R1 promotes formation of capillary-like structures by human (HBMVEC; HUVEC). Under a Cultrex® Organoid Qualified BME, Type 2 designation, several formulations of Cultrex® BME are described for organiod culture, Cultrex® Reduced Growth Factor Basement Membrane Extract. Additional products that might find use include but are not limited to Cultrex® 3-D Culture Matrix® Reduced Growth Factor Basement Membrane Extract, Cultrex® Basement Membrane Extract, Type 3, PathClear®. The PathClear® designation means that in addition to standard sterility, endotoxin and MAP testing, the basement membrane extract is tested by PCR and is clear of 31 pathogens and viruses, including lactate dehydrogenase elevating virus (LDEV). Cultrex® BME Type 2 provides a formulation with a higher in tensile strength when compared to the original BME, while Cultrex® BME Type 3 is physiologically aligned with the in vivo solid tumors environment.

II. Closed Top Chips.

The present disclosure relates to organ-on-chips, such as fluidic devices comprising one or more cells types for the simulation one or more of the function of epithelial components. Accordingly, the present disclosure additionally describes closed-top organ-on-chips, see, e.g. schematics in FIG. 1A-B.

FIG. 1A illustrates an exploded view of the device in accordance with an embodiment. As shown in FIG. 1A, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 1B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), air flow, and/or cell culture media into the first chamber 204.

The device 200 can also comprise an outlet channel 227 connecting an outlet fluid port 212 to the first chamber 204. The outlet channels and outlet ports can also be used to introduce cells, agents (e.g., but not limited to, stimulants, drug candidate, particulates), air flow, and/or cell culture media into the first chamber 204.

Although the inlet and outlet apertures 211, 215 are shown on the top surface of the first structure 204 and are located perpendicular to the inlet and outlet channels 225, 227, one or more of the apertures 211, 215 can be located on one or more lateral surfaces of the first structure and/or second structure such that at least one of the inlet and outlet apertures 211, 215 can be in-plane with the inlet and/or outlet channels 225, 227, respectively, and/or be oriented at an angle from the plane of the inlet and/or outlet channels 225, 227.

In another embodiment, the fluid passing between the inlet and outlet fluid ports can be shared between the first chamber 204 and second chamber 206. In either embodiment, characteristics of the fluid flow, such as flow rate, fluid type and/or composition, and the like, passing through the first chamber 204 can be controllable independently of fluid flow characteristics through the second chamber 206 and vice versa.

In some embodiments, while not necessary, the first structure 204 can include one or more pressure inlet ports 214 and one or more pressure outlet ports 216 in which the inlet ports 214 are in communication with corresponding apertures 217 located on the outer surface of the device 200. Although the inlet and outlet apertures are shown on the top surface of the first structure 204, one or more of the apertures can alternatively be located on one or more lateral sides of the first structure and/or second structure. In operation, one or more pressure tubes (not shown) connected to an external force source (e.g., pressure source) can provide positive or negative pressure to the device via the apertures 217. Additionally, pressure tubes (not shown) can be connected to the device 200 to remove the pressurized fluid from the outlet port 216 via the apertures 223. It should be noted that the device 200 can be set up such that the pressure port 214 is an outlet and pressure port 216 is an inlet. It should be noted that although the pressure apertures 217, 223 are shown on the top surface of the first structure 204, one or more of the pressure apertures 217, 223 can be located on one or more side surfaces of the first structure 204.

Referring to FIG. 1B, in some embodiments, the second structure 206 can include one or more inlet fluid ports 218 and one or more outlet fluid ports 220. As shown in FIG. 1B, the inlet fluid port 218 is in communication with aperture 219 and outlet fluid port 220 is in communication with aperture 221, whereby the apertures 219 and 221 are located on the outer surface of the second structure 206. Although the inlet and outlet apertures are shown on the surface of the second structure, one or more of the apertures can be alternatively located on one or more lateral sides of the second structure.

As with the first outer body portion or first structure 204 described above, one or more fluid tubes connected to a fluid source can be coupled to the aperture 219 to provide fluid to the device 200 via port 218. Additionally, fluid can exit the device 200 via the outlet port 220 and outlet aperture 221 to a fluid reservoir/collector or other component. It should be noted that the device 200 can be set up such that the fluid port 218 is an outlet and fluid port 220 is an inlet.

In some embodiments, the second outer body portion and/or second structure 206 can include one or more pressure inlet ports 222 and one or more pressure outlet ports 224. In some embodiments, the pressure inlet ports 222 can be in communication with apertures 227 and pressure outlet ports 224 are in communication with apertures 229, whereby apertures 227 and 229 are located on the outer surface of the second structure 206. Although the inlet and outlet apertures are shown on the bottom surface of the second structure 206, one or more of the apertures can be alternatively located on one or more lateral sides of the second structure. Pressure tubes connected to an external force source (e.g., pressure source) can be engaged with ports 222 and 224 via corresponding apertures 227 and 229. It should be noted that the device 200 can be set up such that the pressure port 222 is an outlet and fluid port 224 is an inlet.

In an embodiment, the membrane 208 is mounted between the first structure 204 and the second structure 206, whereby the membrane 208 is located within the first structure 204 and/or second structure 206 of the device 200 (see, e.g., FIG. 1B). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, the membrane 208 in one embodiment can be made of a material which allows the membrane 208 to undergo stress and/or strain in response to an external force (e.g., cyclic stretching or pressure). In one embodiment, the membrane 208 can be made of a material which allows the membrane 208 to undergo stress and/or strain in response to pressure differentials present between the first chamber 204, the second chamber 206 and the operating channels 252. Alternatively, the membrane 208 is relatively inelastic or rigid in which the membrane 208 undergoes minimal or no movement.

An exemplary schematic of one embodiment of a closed top chip is shown in FIG. 1C. FIG. 1C shows cells in relation to device parts, e.g. upper and lower channels and optional vacuum chamber. 1. Air channel; 2. Vascular channel (lower); 3. Lung tissue (e.g. epithelial cells); 4. Capillaries (e.g. endothelial cells); 5. Membrane; and 6. Vacuum Channels.

A. Closed Top Microfluidic Chips Without Gels.

In one embodiment, closed top organ-on-chips do not contain gels, either as a bulk gel or a gel layer. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips With Gels.

In one embodiment, closed top organ-on-chips do contain gels, such as a gel layer, including but not limited to a gel matrix, hydrogel, bulk gels, etc. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips With Simulated Lumens.

A closed top organ-on-chip comprising a gel-lined simulated lumen may be used for generating a more physiological relevant model of epithelial tissue. In some embodiments, closed top organ-on-chips further comprise a gel simulated three-dimensional (3-D) lumen. In other words, a 3-D lumen may be formed using gels (e.g. viscous fingers) and/or mimicking tissue folds. In a preferred embodiment, the gel forms a lumen, i.e. by viscous fingering patterning.

Using viscous fingering techniques, e.g. viscous fingering patterning, a simulated lumen may be formed. As one example, viscous fingers may be formed and used to mimic epithelial projections in the respiratory system.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning." J Lab Autom. 2012 April; 17(2): 96-103. Author manuscript; available in PMC 2012 Jul. 16, herein incorporated by reference in its entirety. In one example of a viscous finger patterning method for use with microfluidic organ-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium.

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated lumens.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular microenvironment, (e.g. MATRIGEL®. In some embodiments, the first and second permeable matrixes can each independently comprise a polymer matrix. Methods to create a permeable polymer matrix are known in the art, including, e.g. but not limited to, particle leaching from suspensions in a polymer solution, solvent evaporation from a polymer solution, sold-liquid phase separation, liquid—liquid phase separation, etching of specific "block domains" in block co-polymers, phase separation to block-co-polymers, chemically cross-linked polymer networks with defined permabilities, and a combination of two or more thereof.

Another example for making branched structures using fluids with differing viscosities is described in "Method And System For Integrating Branched Structures In Materials" to Katrycz, Publication number US20160243738, herein incorporated by reference in its entirety.

Regardless of the type of lumen formed by a gel and/or structure, cells can be attached to theses structures either to lumen side of the gel and/or within the gel and/or on the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, LPDCs may be added within the gel, or below the gel, on the opposite side of the lumen. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Microfluidic Chips.

The present disclosure relates to organ-on-chips, such as fluidic devices comprising one or more cells types for the simulation one or more of the function of organ components.

Accordingly, the present disclosure additionally describes open-top organ-on-chips, see, e.g. schematic in FIGS. 2A-I. FIG. 2B shows an exemplary exploded view of one embodiment of an open-top chip device 1800, wherein a membrane 1840 resides between the bottom surface of the first chamber 1863 and the second chamber 1864 and the at least two spiral microchannels 1851, as shown in FIG. 2A. FIG. 2D shows optional vacuum chambers 4. Open top microfluidic chips include but are not limited to chips having removable covers, such as removable plastic covers.

Inlet and outlet ports, fluidic connectivity, etc. are provided, as described herein.

Fabrication and Assembly of One Embodiment of an Organ-Chip Platform.

Several nonlimiting examples of schematics of stretchable Open-Top platforms are shown in the figures. In one embodiment, a chip was fabricated by soft lithography/replica molding of polydimethylsiloxane (PDMS).

Briefly, the platform comprises four parts made of poly (dimethylsiloxane) (PDMS): a bottom spiraled shaped microfluidic channel (e.g. FIG. 2A), a membrane (e.g. 1840 membrane in FIG. 2B), a circular stroma chamber (e.g. 2 in FIG. 2B), and a top microfluidic channel (e.g. blue in FIG. 2C). The bottom spiraled shaped microfluidic channel, circular stromal chamber and top fluidic channel were fabricated by replica molding of polydimethylsiloxane (PDMS), using a 3D printer for printing a mold. A membrane was fabricated by casting poly(dimethylsiloxane) (PDMS) over a photolithographically prepared master that contained a positive relief of parallel microchannels organized in a pattern. The weight ratio of PDMS base to curing agent was 10:1. Pressure was applied constantly to the master during curing of PDMS to ensure intimate contact and penetration of PDMS through the silane-coated master while being cured at 65° C. overnight. This process produced 50-µm-thick PDMS membranes with circular through-holes (e.g. pores).

PDMS Parts.

Bottom spiraled shaped microfluidic channel components; membranes and a circular stroma chamber were carefully aligned and then bonded together by oxygen plasma treatment. Irreversible bonding was achieved by curing the PDMS parts at 65° ° C. overnight for bonding together the bottom spiraled shaped microfluidic channel, membrane and round stroma chamber.

Open-Top Technical Features And Applications.

The platform consists of a top microfluidic channel 200 µm×600 µm with variable geometry, a bottom spiraled shaped microfluidic channel 400 µm×600 µm, a circular chamber surrounded by two curved shaped hollow chambers on either sides of the central stromal chamber and separated by a porous flexible PDMS membrane (50 µm thick and 7 µm diameter pores with 40 µm spacing). The membrane acts as a support structure for the organotypic culture while allowing efficient transport of nutrients, metabolites and compounds. Its pore size was selected to prevent undesired cell migration through it. The lower compartment (called the endothelial compartment) comprises a spiraled shaped microfluidic channel surmounted by the porous membrane. The spiral channel is connected to an inlet and an outlet port. Channels are used to perfuse the tissue with culture media, blood or other fluids.

The middle compartment (called a stroma compartment for stromal tissues) comprises a 3 mm deep round PDMS chamber drafted with a 3 degrees angle and is surrounded by two curved shaped hollow vacuum chambers (4). The round chamber after a chemical activation is loaded with hydrogel(s) to form what we define: recreated stroma. One step in preparing a stroma chamber is chemical activation of PDMS chamber to cross-link together (or permanently integrate together) the biological component (Hydrogel) and the physical component (PDMS parts) of the Chip. Cylindrical 3D printed molds are made of resin (ProtoLab) for use in direct casting of hydrogels to a specific height. The two curved shaped hollow chambers (4) are used to generate a cyclic deformation of the PDMS chamber that transfers to the hydrogel (stretching) while the 3 degrees drafted chamber design helps to maximize the stretching at level of the epithelium and minimize the stress on endothelial compartment. The stroma compartment is surmounted by the top microfluidic channel that is connected to an inlet and an outlet effluent port.

The top microfluidic channel has several applications, including as a means of perfusion of culture media over the top of the cells, either for static incubation, intermittent flow or continuous flow, and/or for infusion of specific air/gas mixtures, with or without test contaminants or aerosolized drugs, for initiation and/or maintenance of an ALI; for air/gas ventilation, etc. An air-liquid interface (ALI) is provided on the apical side of the epithelial tissue, including for furthering maturation of alveolar lung cells.

Furthermore, blood sample, PBMCs or other white blood cells, e.g. immune cells can be perfused through the bottom channel, with or without a lining of endothelial cells.

In some embodiments, the top microfluidic channel is an active part of the system, as a microfluidic channel. However, the top microfluidic channel can be removed to allow direct access to the stroma chamber. Thus, in some embodiments, the top microfluidic channel merely serves as a lid of the stromal chamber.

The assembled microfluidic platform has a 35 mm×17 mm format with tissue culture and diffusion areas of 0.32 cm$^2$. The Open-Top Organ-Chip platform is compatible with a bioreactor. In some embodiments, a bioreactor instrument allows to simultaneously culture up to 12 fluidic Chips.

Each fluidic compartment has dedicated inlets and outlets that are used for perfusion of culture media, other liquids, or gaseous mixtures.

Special cylindrical mold 2 mm tall are designed to enabling direct casting of hydrogels after being deposited on the support membrane. Molds were 3D printed in resin, e.g. by ProtoLab, with optional micropatterning.

Open-Top platform part, tubing and fittings were sterilized, e.g. by plasma at 100 W for 1 min. The assembled microfluidic platform has a 35 mm×17 mm format with tissue culture and diffusion areas of 0.32 cm2. The inlet ports of the lower compartments of the organ-on-chip device were connected to 2-stop SC0320 PharMed® Ismaprene tubings (Cole-Parmer GmbH, Germany) mounted on an Ismatec® IPCN-12 peristaltic pump (Cole-Parmer GmbH, Germany) to supply the culture media or the receiver solution to each unit.

One Embodiment of a Bioreactor Compatible Fluidic Device.

The self-locking lids were fabricated in polycarbonate using a 3D printer. The lid and the insets have a cylindrical body and four thin teeth (0.6 mm thick, 1.7 mm wide) protruding 1.9 mm from its lateral surface, perpendicularly to the cylinder axis. The lid's body is a full cylinder while the inset's body is a hollow cylinder (FIGS. 2*c*, 2E and 2F). Each chip's locking station comprises four docking slots for the teeth of the lid/inset. Each slot has a vertical entrance and a lateral locking chamber (1 mm high) for the tooth. Gasket annuli are placed under the lids and the insets. The lids and inset are assembled to the chip by inserting their teeth in the locking stations' vertical entrances, applying a gentle pressure on them and rotating them to lock the teeth in the lateral slots. Once mounted on the chip, the lid or inset compresses the gasket, hence sealing the system and keeping the inset in place according to the same principle described in Alberti et al. [23].

Lids, insets, interconnection modules (e.g. parts of the bioreactor and platform were sterilized e.g. by plasma at 100 W for 1 min.; or UV (15 G) treatment. Tubing and fittings were sterilized in autoclave before assembling.

The assembled microfluidic platform has a 35 mm×17 mm format with tissue culture and diffusion areas of 0.32 cm². In one embodiment of a bioreactor configuration, the interconnection modules (POD), have capacities of up to 6 ml reservoir and flow volumes of 60 μL.

Chip Activation.

Open-Top Organ-Chip platform was chemically activated by sulfu sampo/buffer, such as HEPES, treatment (Emulate, Inc). Briefly, sulfu sampo and buffer were mixed together as specified by the instructions and added to the bottom spiraled shaped microfluidic channel and circular stromal chamber. The platform was then UV treated for 20 minutes using UV oven (e.g. 365 nm light and the bulb that generate the UV light are 9 Watt).

A. Chip Activation Compounds.

In one embodiment, bifunctional crosslinkers are used to attach one or more extracellular matrix (ECM) proteins. A variety of such crosslinkers are available commercially, including (but not limited to) the following compounds:

ANB-NOS
(N-5-azido-2-nitrobenzoyloxysuccinimide)

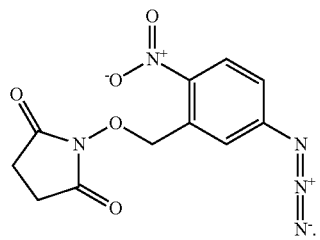

Sulfo-SAND (sulfosuccinimidyl 2-[m-azido-o-nitrobenzamido]ethyl-1,3'-dithiopropionate)

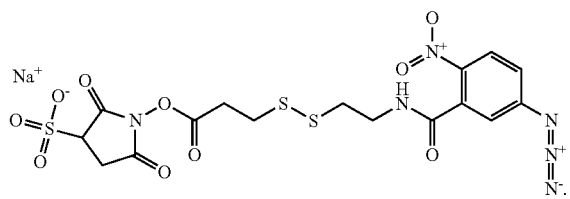

SANPAH (N-succinimidyl-6-[4'-azido-2'-nitrophenylamino]hexanoate)

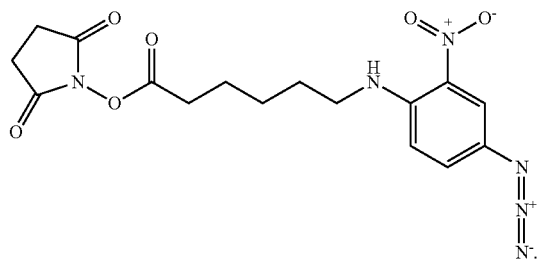

Sulfo-SANPAH (sulfosuccinimidyl-6-[4'-azido-2'-nitrophenylamino]hexanoate)

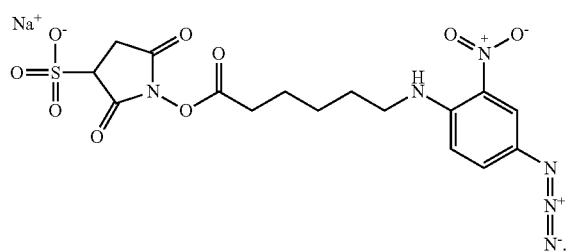

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—NH₂) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary Methods of Chip Activation.
1. Prepare and sanitize hood working space
2. S-1 Chip Handling—Use aseptic technique, hold Chip using Carrier
   a. Use 70% ethanol spray and wipe the exterior of Chip package prior to bringing into hood
   b. Open package inside hood
   c. Remove Chip and place in sterile Petri dish (6 Chips/Dish)
   d. Label Chips and Dish with respective condition and Lot #
3. Surface Activation with Chip Activation Compound (light and time sensitive)
   a. Turn off light in biosafety hood
   b. Allow vial of Chip Activation Compound powder to fully equilibrate to ambient temperature (to prevent condensation inside the storage container, as reagent is moisture sensitive)
   c. Reconstitute the Chip Activation Compound powder with ER-2 solution
      i. Add 10 ml Buffer, such as HEPES, into a 15 ml conical covered with foil
      ii. Take 1 ml Buffer from above conical and add to chip Activation Compound (5 mg) bottle, pipette up and down to mix thoroughly and transfer to same conical
      iii. Repeat 3-5 times until chip Activation Compound is fully mixed
      iv. NOTE: Chip Activation Compound is single use only, discard immediately after finishing Chip activation, solution cannot be reused
   d. Wash channels
      i. Inject 200 μl of 70% ethanol into each channel and aspirate to remove all fluid from both channels
      ii. Inject 200 μl of Cell Culture Grade Water into each channel and aspirate to remove all fluid from both channels
      iii. Inject 200 μl of Buffer into each channel and aspirate to remove fluid from both channels
   e. Inject Chip Activation Compound Solution (in buffer) in both channels
      i. Use a P200 and pipette 200 ul to inject Chip Activation Compound/Buffer into each channel of each chip (200 ul should fill about 3 Chips (Both Channels))
      ii. Inspect channels by eye to be sure no bubbles are present. If bubbles are present, flush channel with Chip Activation Compound/Buffer until bubbles have been removed
   f. UV light activation of Chip Activation Compound Place Chips into UV light box
      i. UV light treat Chips for 20 min
      ii. While the Chips are being treated, prepare ECM Solution.
      iii. After UV treatment, gently aspirate Chip Activation Compound/Buffer from channels via same ports until channels are free of solution
      iv. Carefully wash with 200 ul of Buffer solution through both channels and aspirate to remove all fluid from both channels
      v. Carefully wash with 200 ul of sterile DPBS through both channels
      vi. Carefully aspirate PBS from channels and move on to: ECM-to-Chip VI. ECM-to-Chip
A. Calculate total volume of ECM solution needed to coat Chips or hydrogel surfaces, these are exemplary ECM materials, as laminin may also be used with one or more ECM materials.
   1. Volume required per Chip=50 ul/Channel
   2. ECM diluent: PBS, prepared on ice
   3. Stock Concentrations for ECM coating:
      a. Collagen IV: 1 mg/ml (200 ul aliquots in −20° C.)
      b. Fibronectin: 1 mg/ml (50 ul aliquots in 4° C.)
      c. Matrigel: 10 mg/ml (200 ul aliquots in −20° C.)
   4. Working Concentrations for ECM coating:
      a. Collagen IV: 200 ug/ml
      b. Fibronectin: 30 ug/ml
   5. Top Channel Coating: 50 ul Collagen IV (200 ug/ml) and Matrigel (100 ug/ml)
   6. Bottom Channel Coating: 50 ul Collagen IV (200 ug/ml) and Fibronectin (30 ug/ml)
B. Load Channels with ECM solution.
   1. Place Chips in hood
   2. Pipette 50 μl of Top Channel Coating into Top Channel—keep the pipette plunger depressed until you see fluid come out opposite end of the channel, then take another pipette tip (200 μl tip) to close the outlet port. Once closed off, carefully remove the pipette tip, leaving the tip in the inlet port.
   3. Aspirate excess fluid from the surface of Chip (avoid direct contact with the port)
   4. Repeat 2b-2c, but with Bottom Channel Coating into Bottom Channel
   5. Incubate at 37 C for a minimum of 2 hours up to overnight
C. Exemplary Matrigel Coating
   1. Thaw Matrigel on ice and keep chilled to prevent solidification.
   1. Prepare Matrigel
      a. Matrigel Stock Concentration: 10 mg/ml
      a. Matrigel Final Concentration: 250 μg/ml
      a. Determine the volume of Matrigel needed to coat 50 μl of each Top Channel and resuspend accordingly in cell culture media
         a. Transfer the seeded Chips into the hood
         b. Wash both channels of each chip twice with 200 ul media
      a. Before inserting the tips, add a drop of media to prevent formation of bubbles
      b. Leave 50 ul media in bottom channel (Tips inserted)
      c. Add 50 ul 250 ug/ml matrigel to top channel (Tips inserted)
      d. Incubate at 37 C overnight
V. Cells-to-Chip—Chip Preparation.
   1. Transfer the ECM coated Chips into the hood
      a. Gently wash Chips after ECM coating
   2. Pipette 200 μl of DPBS into bottom channel inlet port—keep the pipette plunger depressed until you see fluid come out opposite end of channel and aspirate outflow
   3. Repeat the same procedure to wash top channel
   4. Pipette 200 μl of DPBS into top channel inlet port—keep the pipette plunger depressed until you see fluid come out opposite end of the channel, then take another pipette tip (200 μl) to close the outlet port. Once closed off, carefully remove the pipette tip, leaving the tip in the inlet port
   5. Repeat the same with the bottom channel Place back in incubator until cells are ready.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

2D Cell Culture—Flat Bottom Culture Dishes/Containers.

The following are exemplary cells purchased from commercial sources then culture prior to seeding into fluidic devices. Human Primary Alveolar Epithelial Cells (Cell Biologics Cat. #: H-6053), Human Primary Lung Fibroblasts (Cell Biologics Cat. #: H-6013) and Human Lung Microvascular Endothelial Cells (Lonza Cat #: CC-2527) were grown in T-75 culture flasks in an atmosphere of 5% $CO_2$ at 37° C. according to the instructions provided by the manufacturers.

Specifically, Primary Alveolar Epithelial Cells (PI) were cultured in SAGM medium (SAGM Lonza Cat. #: CC-4124). Human Primary Lung Fibroblasts (PI) were cultured in DMEM/F-12 (GIBCO Cat #: 11320082) containing 10% Heat Inactivated HyClone™ FetalClone™ II Serum (U.S.) (GE Healthcare Life Sciences Cat #: SH30066.03) and 1% penicillin-streptomycin (GIBCO Cat #: 15140122) and 1% GlutaMAX (GIBCO Cat #: 35050061). Human Lung Microvascular Endothelial Cells were cultured in EGM-2MV (Lonza Cat. #: CC-3202).

Generation of Stroma Equivalents and 3D Culture Steps.

The culture process of full-thickness stroma comprises several phases: generation of the stroma equivalent, epithelial cell seeding, and culturing on stroma equivalent, and the culture at the air-liquid interface (ALI).

Full-thickness stroma was generated using a collagen 1-based ECM (Fibricol, Advanced Biomatrix Cat #: 5133-20ML). Specifically, 8 volumes of Fibricol were mixed with 1 volume of 10× reconstruction buffer, 1 volume of 10×EMEM (Lonza) and 1 volume of fibroblast cell suspension containing $0.5 \times 10^6$ cells. Collagen I hydrogel with embedded fibroblasts were poured in the stromal chamber of the Open-Top Chip, casted using a special cylindrical mold 2 mm tall and incubated at 37° ° C. for 60 minutes. After polymerization gel surface and bottom spiraled channel were coated with a solution of collagen IV, Fibronectin and Laminin (1200 µl of 1 mg/ml solution+300 µl of 1 mg/ml solution+30 µl of 1 mg/ml) for 2-4 hours at 37° C., 5% $CO_2$.

After coating full-thickness equivalent was submerged in DMEM/F12 GlutaMax supplemented with 10% Heat Inactivated HyClone™ FetalClone™ II Serum (U.S.) (GE Healthcare Life Sciences cat #: SH30066.03) and kept in this submerged status for 24/48 hours to let fibroblasts recover from the embedding procedure.

Two days after the generation of the stromal equivalent Human Primary Alveolar Epithelial Cells (Cell Biologics Cat. #: H-6053) were detached from the T-75 flask using TrypLe (Gibco), collected in 15 ml conical containing SAGM 10% Heat Inactivated HyClone™ FetalClone™ II Serum, centrifuged at 1,200 r.p.m. for 5 minutes and re-suspended in SAGM (Lonza) 10% Heat Inactivated HyClone™ FetalClone™ II Serum at a concentration of 2 million cell/ml. 50 µl of a 2 million cell/ml solution (equivalent at about 100,000 cells) were added per chip on the stromal equivalent and let attach for at least 1 hour before being washed.

In the following 5 days, serum content was sequentially decreased from 10% to 5%, 2%, 1% and 0% while KIAD supplements were added to the SAGM medium. KIAD treatment was kept for the 5 days before the introduction of the Air-Liquid interface. (KIAD culture boost: KGF (Promocell cat #: C-63821) final concentration of 3 ng/ml, IBMX (Sigma Cat #: 15879-100MG) at final concentration, cAMP (Sigma: B7880-250MG) final concentration of 80 µM, Dexamethasone (Sigma cat #: D2915-100MG) final concentration of 200 nM.

On day 4, Human Lung Microvascular Endothelial Cells (Lonza Cat. #: CC-2527) were detached from the T75 flask using TrypLE (Gibco Cat #: A1285901) and seeded to the bottom spiraled shaped microfluidic channel. Two sequential seedings were performed, a first seeding where chips were flipped to allow endothelial cells attachment to the membrane side and a second seeding were chips were seeded to allow endothelial cells attachment to the bottom of the spiraled shaped microfluidic channel. Chips were performed for 24 hours using EGM-2MV medium (Lonza), while Human Primary Alveolar Epithelial Cells were kept submerged in SAGM (Lonza) 0% serum with added KIAD supplements.

On day 6, Human Primary Alveolar Epithelial Cells were exposed at Air-Liquid Interface (ALI) and the bottom channel was perfused at 60 µl/hour with differentiation medium 199A (Emulate, Inc proprietary) supplemented with 2% Heat Inactivated HyClone™ FetalClone™ II Serum. Chips were cultured using this condition until sacrificed for analysis (generally 10-15 days). Depending on the experiment goal, on day 9 was applied stretching.

Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated organ tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein, including but not limited to Eye-On-Chip, etc.

An exemplary schematic of one embodiment of an open top chip as a 3D Alveolus Lung On-Chip is shown in FIG. 2B. FIG. 2B An exemplary schematic shows one embodiment of a 3D Alveolus Lung On-Chip demonstrating an air layer on top of an alveolar epithelium layer overlaying a stromal area, including fibroblasts, in an upper channel with microvascular endothelial cells in a lower channel, e.g. showing a cut away view of multiple areas as part of one spiral channel.

Figures 3A, 3B:
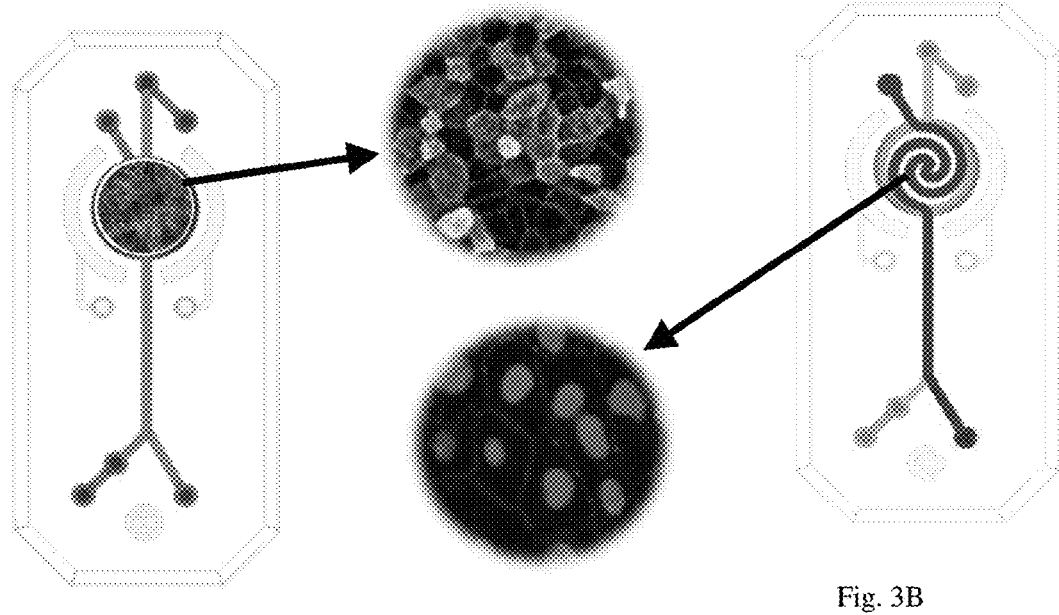
FIGS. 3A-C show an exemplary schematic of one embodiment a 3D Alveolus Lung On-Chip demonstrating locations of ports and input channels leading into the main growing chamber in relation to cell layers.
Figure 3C:
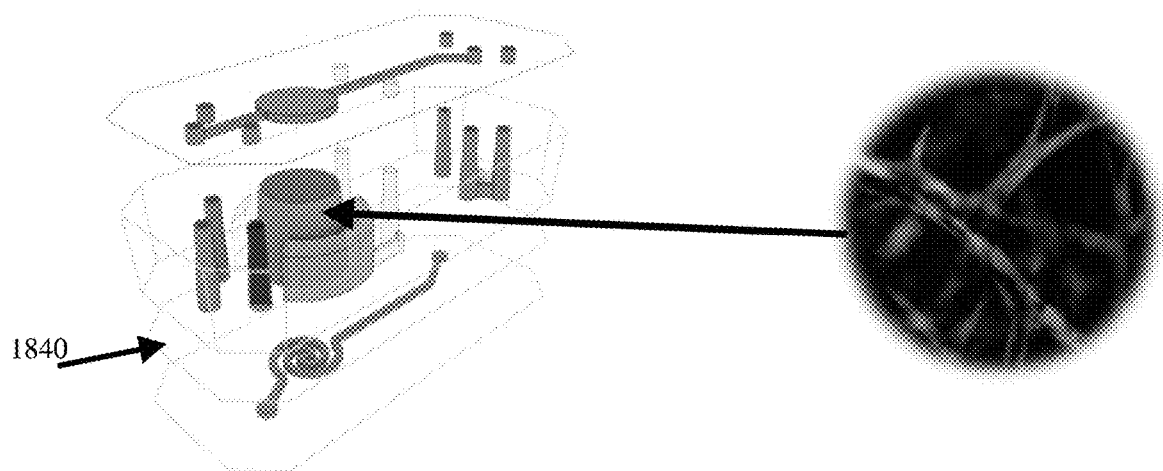
Figure 4A:
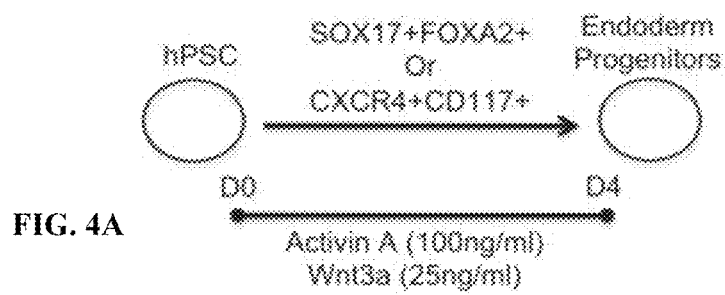
FIG. 4A Shows an exemplary schematic of a hPSC culture timeline and added agents, e.g. Activin A and Wnt3a, for generating endoderm progenitor cells expressing exemplary biomarkers for use with microfluidic stem cell based chips, e.g. stem cell based lung-on-chip. See, Wong, et al., 2012.
Figure 4B:
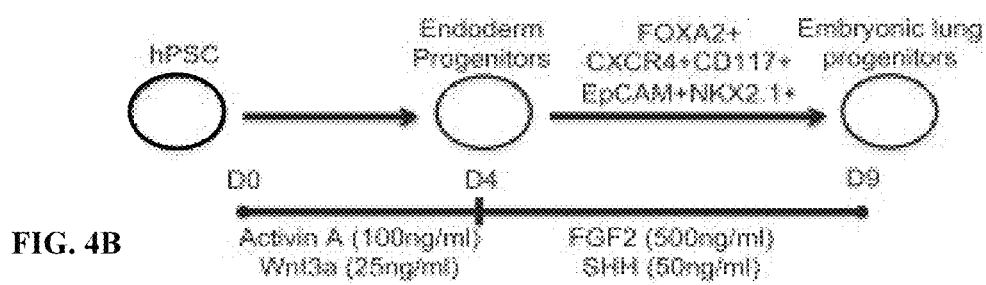
FIG. 4B Shows an exemplary schematic of a hPSC culture timeline and added agents for generating endoderm progenitor cells and then further differentiation with agents, e.g. FGF2 and SHH, for generating embroynic lung progenitor cells for use other microfluidic stem cell based chips, e.g. stem cell based lung-on-chip. See, Wong, et al., 2012.
Figure 4C:
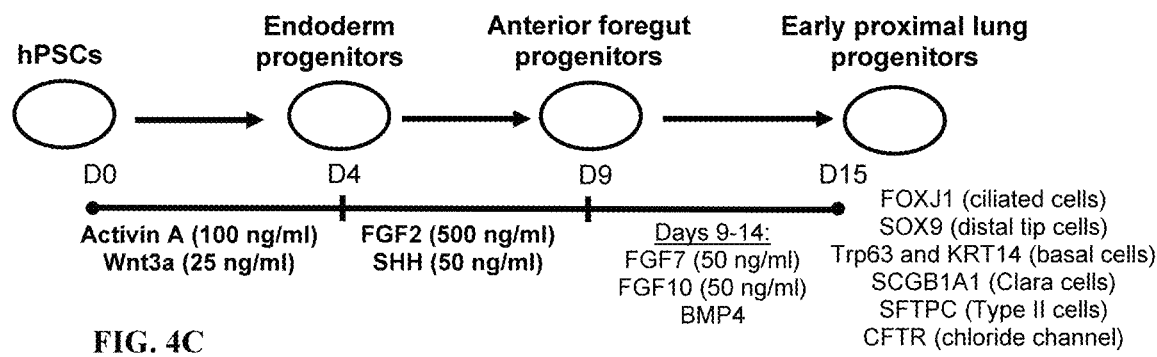
FIG. 4C Shows an exemplary schematic of a hPSC culture timeline and added agents for generating endoderm progenitor cells; further differentiation for generating embryonic lung progenitor cells; with continued differentiation using FGF7 and FGF10 with BMP4 for generating early proximal lung progenitor cells for use with microfluidic stem cell based chips, e.g. stem cell based lung-on-chip, for additional details, see, Wong, et al., 2012. Such early proximal lung progenitor cells may undergo further maturation either off chips or on-chips.

FIG. 3A-C An exemplary schematic shows one embodiment of a 3D Alveolus Lung On-Chip demonstrating locations of ports and input channels leading into the main growing chamber in relation to cell layers. FIG. 3A Overview of Epithelial surface (upper channel) showing exemplary primary adult human alveolar epithelial cells seeded on ECM made of Collagen IV, Fibronectin and Laminin. FIG. 3B Overview of Vascular compartment (lower channel) showing exemplary primary adult microvascular endothelial cells are seeded on ECM made of Collagen IV and Fibronectin. FIG. 3C An expanded side view of Tridimensional stroma showing exemplary primary adult human fibroblasts embedded within the stromal compartment.

In some embodiments, cells are cultured on and/or under the membrane under flow conditions. In some embodiments, there is a steady-state perfusion of the cells. In other embodiments described herein, the devices can comprise a flowing culture medium in the first chamber and/or the second chamber, wherein the flowing culture medium generates a shear stress. Based on the viscosity of the culture medium and/or dimensions of the chambers, one of skill in the art can determine appropriate flow rates of culture medium through the chambers to achieve desired shear stress. In some embodiments, the first chamber, the second chamber or both may comprise or be in communication with one or more fluidic channels. Such channels may allow, for example, the perfusion, the delivery or removal of reagents, and/or the collection of samples from one or both of the chambers. Such channels may provide independent fluidic access to each chamber, and correspondingly, to either side of the membrane. Additionally, an open top microfluidic chip may also be described herein, and in WO 2017173066 published Oct. 5, 2017, herein incorporated by reference in its entirety.

A. Open Top Microfluidic Chips Without Gels.

In one embodiment, open top organ-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips With Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel. In one embodiment, the open-top microfluidic device does contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or one gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips.

Thus, in some embodiments, open top microfluidic chips comprise lumens formed by viscous fingering described herein for closed top chips.

Lumen gel structures may be used in several types of embodiments for open top microfluidic chips, e.g. epithelial cells can be attached to outside of the gel, or within the gel. In some embodiments, stromal cells are added within the gel. In some embodiments, stromal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels.

III. Summary

By merging at least two technologies to engineer 1) patient-specific stem-cells with 2) Lung-on-Chips for providing patient-specific stem-cell Lung-on-Chips, we will amplify their respective advantages. Furthermore, patient-specific stem-cell Lung-on-Chip will enable the design of in vitro human Pk/Pd models for predicting efficacy and adverse effects in addition to drug-drug interactions; dosing protocols in specific genetic backgrounds, etc.

The need for in vitro human patient-specific stem-cell Lung-on-Chip differentiation models; in vitro human Pk/Pd models, etc., is continuously growing, given the current ban on animal testing for development of consumer products expected to expand from Europe (European Union Directive 76/768/EEC) into North America and worldwide, combined with a pressing need for more predictive preclinical platforms for developing new respiratory drugs. To enable such applications, however, Lung-on-Chip stem cell based models should be held to stringent and uniform criteria in order to be qualified and then validated for drug testing (259). The present invention contemplates, providing a less variable and more consistent stem cell based system for use with a standard microfluidic device system. Thus at least one variability challenge is to overcome may be solved, at least in part, to balance the trade-off between increasing the biological complexity of the chip on one hand, and maintaining scalability of fabrication, and ease of use on the other hand.

In general, a greater degree of biological complexity will extend the range of functions that can be studied and are physiologically relevant, but might conversely impair economic factors, such as fabrication steps per sample, reproducibility of results, ease of use, and volume of cells and reagents needed. To address this hurdle, US American funding agencies have started an initiative towards consolidating development of Organs-on-Chips and achieving robustness and replicability. Specifically, the National Institutes of Health (NIH), in partnership with the Defense Advanced Research Projects Agency (DARPA), the FDA, and more recently with the pharmaceutical industry, has invested in academic investigators to develop Organs-on-Chips technology suitable for industry applications. Further, the National Center for Advancing Translational Sciences (NCATS) has created centralized Tissue Chip Testing Centers (TCTCs) where investigators can submit their chips for standardized quality control testing. Further, the Center for Advancement of Science in Space (CASIS) is funding efforts towards dramatically simplifying and automating Organs-on-Chip technology (260).

The present invention contemplates an improved human lung model that can provide both large-scale screens of molecular level analysis of cell-cell interactions, and at the same time provide a platform to study or treat lung disorders with a personalized medicine approach.

Organs-on-Chips (OOC) are contemplated to assist in improving stem cells differentiation efficacy into lung cells and help develop more physiologically relevant in vitro platform of lung tissue to study biological mechanisms of healthy and diseased tissue, and test drug toxicity and efficacy.

Conclusion and Perspectives

Organs-on-Chips are considered a great technology to recapitulate the dynamic physiological micro-environment of human tissue. Stem cells are considered a great technology for use as an easy/practical method for application to patient specific studies, contemplated to provide a huge potential for personalized medicine and next generation biomedical research. Therefore, a combination of both technologies are contemplated for use to develop a stem cell-based lung model. Furthermore, the use of OOC offers the opportunity to break down whole organs into functional units or tissue regions and dissect the specific role/influences of each individual components. Additionally, a body-on-a-chip initiative (see, for example, Williamson, et al., "The Future of the Patient-Specific Body-on-a-Chip." Lab Chip, 13(18):3471-3480 (2013)) is contemplated to be adapted to include a stem cell based lung-on-chip may find use by linking: specific parts of the lungs, e.g. bronchi chip, bronchiole chip and alveolus chip to other relevant chips such as a nasal chip, a trachea chip, etc., to recreate in vitro an entire respiratory tract. In other words, there is a need to design and create relevant and useful models of stem cell based Lung-on-chips to increase our understanding of fundamental pathophysiological processes of the lung, discover new therapeutic targets and test drug efficacy and toxicity, etc. Thus, stem cell based lung-on-chip microfluidic devices are contemplated to meet at least one of these needs.

TABLE 3

Exemplary PCR primers for use in identifying cell populations expressing designated genes. Wong et al., 2012.

| SEQ ID NOS: | Gene | Forward primer (5'→3') | Reverse primer (5'→3') |
|---|---|---|---|
| 3, 4 | KRT5 | GGAGTTGGACCAGTCAACATC | TGGAGTAGTAGCTTCCACTGC |
| 5, 6 | MUC5AC | CCATTGCTATTATGCCCTGTGT | TGGTGGACGGACAGTCACT |
| 7, 8 | NKX2.1 | ACCAGGACACCATGAGGAAC | CGCCGACAGGTACTTCTGTT |
| 9, 10 | FOXJ1 | GAGCGGCGCTTTCAAGAAG | GGCCTCGGTATTCACCGTC |
| 11, 12 | SFTPC | CACCTGAAACGCCTTCTTATCG | TGGCTCATGTGGAGACCCAT |

TABLE 3-continued

Exemplary PCR primers for use in identifying cell populations expressing designated genes. Wong et al., 2012.

| SEQ ID NOS: | Gene | Forward primer (5'→3') | Reverse primer (5'→3') |
|---|---|---|---|
| 13, 14 | SCGB1A1 | TTCAG CGTGTCATCGAAACCCC | ACAGTGAGCTTTGGGCTATTTTT |
| 15, 16 | FOX A 2 | AGGAGGAAAACGGGAAAGAA | CAACAACAGCAATGGAGGAG |
| 17, 18 | BACT | CTGGAACGGTGAAGGTGACA | AAGGGACTTCCTGTAACAATGCA |
| 19, 20 | SOX 17 | AAGGGCGAGTCCCGTATC | TTGTAGTTGGGGTGGTCCTG |
| 21, 22 | TG | AGAAGAGCCTGTCGCTGAAA | TTGGACCAGAAGGAGCAGTC |
| 23, 24 | NKX6.1 | ATTCGTTGGGGATGACAGAG | C G AGTCCTG CTTCTTCTTG G |
| 25, 26 | PDX1 | CCCATGGATGAAGTCTACC | GTCCTCCTCCT T T T T CCAC |
| 27, 28 | AFP | TGGGACCCGAACTTTCCA | GGCCACATCCAGGACTAGTTTC |
| 29, 30 | CFTR | CTATGACCCGGATAACAAGGAGG | CAAAAATGGCTGGGTGTAGGA |
| 31, 32 | NANOG | TGATTTGTGGGCCTGAAGAAA | GAGGCATCTCAGCAGAAGACA |
| 33, 34 | Trp63 | ACTTCACGGTGTGCCACCCT | GAGCTGGGGTTTCTACGAAACGCT |
| 35, 36 | DNMT3B | TGAGCCTGAGACCCCAGCCC | TGTCTCCCTTCATGCTTTCCAAGC |
| 37, 38 | REX1 | AGTGCTCACAGTCCAGCAGGTGT | TGCCTTGCCTGGGCTTAGCC |
| 39, 40 | TERC | GACACTGCCTCCCTTCCTGCAAC | TGGCGGTTCCGGGGAGTTCTAG |
| 41, 42 | TERT | ACGCGAAAACCTTCCTCAGCTATGC | AGCCTTGAAGCCGCGGTTGAA |
| 43, 44 | CDX2 | CTGGAGCTGGAGAAGGAGTTTC | AT T T T AACCTGCCTCTCAGAGAGC |
| 45, 46 | SOX2 | GCACATGAAGGAGCACCCGGATTA | CGGGCAGCGTGTACTTATCCTTCTT |
| 47, 48 | FOXG1 | CTCCGTCAACCTGCTCGCGGF | CTGGCGCTCATGGACGTGCT |
| 49, 50 | PAX9 | TGGTTATGTTGCTGGACATGGGTG | GGAAGCCGTGACAGAATGACTACCT |
| 51, 52 | SOX9 | GAGGAAGTCGGTGAAGAACG | CCAACATCGAGACCTTCGAT |
| 53, 54 | PAX6 | TCTTTGCTTGGGAAATCCG | CTGCCCGTTCAACATCCTTAG |
| 55, 56 | OTX2 | GTGGGCTACCCGGCCACCC | GCACCCTCGACTCGGGCAAG |
| 57, 58 | KRT15 | GGCTGGAGAACTCACTGGC | CAGGCTGCGGTAAGTAGCG |
| 59, 60 | KRT16 | GACCGGCGGAGATGTGAAC | CTGCTCGTACTGGTCACGC |
| 61, 62 | MUC16 | CCAGTCCTACATCTTCGGTTGT | AGGGTAGTTCCTAGAGGGAGTT |
| 63, 64 | Pdpn | GTCCACGCGCAAGAACAAAG | G GTCACTGTTGA CAAAC CATCT |
| 65, 66 | P2X7 | TATGAGACGAACAAAGTCACTCG | GCAAAGCAAACGTAGGAAAAGAT |
| 67, 68 | FOXA1 | CTCGCCTTACGGCTCTACG | TACACACCTTGGTAGTACGCC |
| 69, 70 | FOXP2 | AATCTGCGACAGAGACAATAAGC | TCCACTTGTTTGCTGCTGTAAA |
| 71, 72 | FOXE1 | CACGGTGGACTTCTACGGG | GGACACGAACCG ATCTATCCC |
| 73, 74 | PITX1 | CTAGAGGCCACGTTCCAGAG | TGGTTACG CTCGCGCTTAC |
| 75, 76 | DLX3 | CTCGCCCAAGTCGGAATATAC | CTGGTAGCTGGAGTAGATCGT |
| 77, 78 | MUC2 | AG GATG ACA CCATCTACCTCAC | CATCG CTCTTCTC AATG AG C A |
| 79, 80 | PAX1 | TTGACTGCCGTACCCTCCTCACAA | AGGAAGGGAAAGAGAAAGGGAAGGA |
| 81, 82 | TBX1 | CGGCTCCTACGACTATTGCCC | GGAACGTATTCCTTGCTTGCCCT |

TABLE 4

Additional Exemplary PCR primers for use in identifying cell populations expressing designated genes. CatNumber 4331182 refers to a TTaqMan ™ Gene Expression Assay (FAM).

|  |  | CatNumber | ID |
|---|---|---|---|
| House Keeper | GAPDH | 4331182 | Hs02786624_g1 |
|  | 18s | 4331182 | Hs03003631_g1 |
| Type I | Aqp5 | 4331182 | Hs00387048_m1 |
|  | Pdpn | 4331182 | Hs00366766_m1 |
|  | Hopx | 4351372 | Hs04188695_m1 |
|  | Nkx2-1 | 4331182 | Hs04408121_m1 |
| Type II | Lamp3 | 4331182 | Hs00180880_m1 |
|  | SftpB | 4331182 | Hs00167036_m1 |
|  | SftpC | 4331182 | Hs00161628_m1 |
|  | Abca3 | 4331182 | Hs00184543_m1 |
| Junctions | Ocln | 4331182 | Hs00170162_m1 |
|  | ZO1 | 4331182 | Hs01551861_m1 |
|  | Ecadherin | 4331182 | Hs01023895_m1 |
| EMT | Ncadherin | 4331182 | Hs00983056_m1 |
|  | AlphaSMA | 4331182 | Hs00909449_m1 |
|  | TGF-beta |  | Hs00820148_g1 |
|  | Vimentin | 4331182 | Hs00958111_m1 |
| ROS and Inflamation | NFE2L2 (nrf2) | 4331182 | Hs00975960_m1 |
|  | Gabpa | 4331182 | Hs01022023_m1 |
|  | Nq01 | 4331182 | Hs00168547_m1 |
|  | Srxn1 | 4331182 | Hs00607800_m1 |

TABLE 4-continued

Additional Exemplary PCR primers for use in identifying cell populations expressing designated genes. CatNumber 4331182 refers to a TTaqMan ™ Gene Expression Assay (FAM).

|  |  | CatNumber | ID |
|---|---|---|---|
|  | Icam1 | 4331182 | Hs00164932_m1 |
|  | SOD1 |  | Hs00533490_m1 |
|  | glutathione peroxidase 2 (GPX2) |  | Hs01591589_m1 |
|  | Hmox1 | 4331182 | Hs01110250_m1 |
| Molecular Transporters | OCTN2 |  | Hs00929869_m1 |
|  | SLC15A2/PEPT2 |  | Hs01113665_m1 |
|  | SLCO2A1/OATP2A1 |  | Hs01114926_m1 |
|  | SLCO2B1/OATP2B1 |  | Hs01030343_m1 |
|  | ABCB1/P-gp |  | Hs00184500_m1 |
|  | ABCG2/BCRP |  | Hs01053790_m1 |
|  | MDM4/MRP-1 |  | Hs00159092_m1 |
|  | ABCA1 |  | Hs01059137_m1 |
| Possible Cancer Target | Folr1 | 4331182 | Hs01124177_m1 |

TABLE 5

Exemplary Antibodies, and sources for use in identifying designated cell populations. Wong et at., 2012

| Antigen | Company | Clone/Catalog # | Marker |
|---|---|---|---|
| SOXI7-APC | R&D | IC1924A | Endoderm, ciliated cells |
| FOXA2 | Abcam | Ab40874 | Endoderm, epithelial cells |
| FOXJ1 | Abcam | Ab40869 | Ciliated cells |
| CCSP(SCGBIAI) | Millipore | 07-623 | Clara cells |
| AFP | R&D | MAB1368 | Endoderm, liver cells |
| PanCK | Abcam | Ab80826 | Epithelial cells |
| TRAI-60 | Zymed | 41-1000 | Pluripotent stem cells |
| TRA1-81 | Zymed | 41-1100 | Pluripotent stem cells |
| SFTPC (proform) | Lifespan Biosciences | LS-C38457 | Type II alveolar cells |
| NKX2.1 (TTF1) | Abcam | Ab76013 | Lung progenitors |
| CXCR4-PECy7 | BD Biosciences | 560669 | Endoderm |
| CD117-FITC | BD Biosciences | 553354 | Endoderm |
| CD24-FITC | BD Biosciences | 555427 | Ciliated cells |
| CFTR | R&D | MAB1660 | R-domain |
| CFTR | Abcam | Ab4067 | NBD2 |
| CFTR | Abcam | Ab2916 | — |
| NANOG-PE | BD Biosciences | 560483 | Pluripotent stem cells |
| P63 | Abcam | Ab32353 | Basal cells |
| Thyroglobulin | Santa Cruz | Sc-51708 | Thyroid |
| HPdl | Stemgent | 09-0046 | Pancreatic duct |
| ZO-1 | Abcam | Ab59720 | Tight junction |
| ZO-1 | Invitrogen | 33-9100 | Tight junction |
| LHS28 | Abcam | Ab14373 | Basal bodies of cilia |
| MUC16 | Abcam | Ab115978 | Tracheal epithelia |
| MUC1 | Abcam | Ab28081 | Glandular epithelial cells |
| KRT14 | Abeam | Ab7800 | Basal cells |
| KRT16 | Novus Biologicals | NB110-62105 | Tracheal epithelium |
| Acetylated TUBA 1A | Abcam | Ab24610 | Cilia |
| B3 Tubulin | Millipore | MAB1637 | Neurons |
| SMA | Invitrogen |  | Smooth muscle cells |
| Beta Tubulin IV | Abcam | Ab15568 | Cilia |
| MUC5AC | Abcam | Ab3649 | Mucin, Goblet cells |
| CFTR antibody #450 | Courtesy of JR Riordan | — | www.unc.edu/~tjjensen/CFA/DP |

The following references are herein incorporated by reference for their entirety:
1. G. M. Green, G. J. Jakab, R. B. Low, G. S. Davis, Defense mechanisms of the respiratory membrane., *Am. Rev. Respir. Dis.* 115, 479-514 (1977).
2. WHO, World Health Statistics 2011, (2011) (available a www.who.int/whosis/whostat/2011/en/).
3. World Health Organization, Global Alliance against Chronic Respiratory Disease (2005) (available at www.who.int/gard/news_events/1-3.%0AGARD-06-07-K1.pdf).
4. Forum of International Respiratory Societies, *Respiratory diseases in the world Realities of Today—Opportunities for Tomorrow* (2013; www.ersnet.org/pdf/publications/firs-world-report.pdf).
5. P. J. Landrigan, R. Fuller, N. J. R. Acosta, O. Adeyi, R. Arnold, N. Basu, A. B. Baldé, R. Bertollini, S. Bose-O'Reilly, J. I. Boufford, P. N. Breysse, T. Chiles, C. Mahidol, A. M. Coll-Seck, M. L. Cropper, J. Fobil, V. Fuster, M. Greenstone, A. Haines, D. Hanrahan, D. Hunter, M. Khare, A. Krupnick, B. Lanphear, B. Lohani, K. Martin, K. V. Mathiasen, M. A. McTeer, C. J. L. Murray, J. D. Ndahimananjara, F. Perera, J. Potočnik, A. S. Preker, J. Ramesh, J. Rockström, C. Salinas, L. D. Samson, K. Sandilya, P. D. Sly, K. R. Smith, A. Steiner, R. B. Stewart, W. A. Suk, O. C. P. van Schayck, G. N. Yadama, K. Yumkella, M. Zhong, The Lancet Commission on pollution and health, *Lancet* 6736 (2017), doi: 10.1016/S0140-6736(17)32345-0.
6. H.-W. Snoeck, Modeling human lung development and disease using pluripotent stem cells., *Development* 142, 13-6 (2015).
7. C. G. A. Persson, Con: mice are not a good model of human airway disease., *Am. J. Respir. Crit. Care Med.* 166, 6-7; discussion 8 (2002).
8. R. R. Driskell, J. F. Engelhardt, in *Handbook of Stem Cells*, (Elsevier, 2004), pp. 547-554.
9. R. Barrios, in (2008), pp. 144-149.
10. S. N. Bhatia, D. E. Ingber, Microfluidic organs-on-chips., *Nat. Biotechnol.* 32, 760-772 (2014).
11. M. Ghaedi, L. E. Niklason, J. C. Williams, Development of Lung Epithelium from Induced Pluripotent Stem Cells, *Curr. Transplant. Reports* 2, 81-89 (2015).
12. T. J. Franks, T. V. Colby, W. D. Travis, R. M. Tuder, H. Y. Reynolds, A. R. Brody, W. V. Cardoso, R. G. Crystal, C. J. Drake, J. Engelhardt, M. Frid, E. Herzog, R. Mason, S. H. Phan, S. H. Randell, M. C. Rose, T. Stevens, J. Serge, M. E. Sunday, J. A. Voynow, B. M. Weinstein, J. Whitsett, M. C. Williams, Resident Cellular Components of the Human Lung: Current Knowledge and Goals for Research on Cell Phenotyping and Function, *Proc. Am. Thorac. Soc.* 5, 763-766 (2008).
13. M. J. Evans, L. S. Van Winkle, M. V Fanucchi, C. G. Plopper, The attenuated fibroblast sheath of the respiratory tract epithelial-mesenchymal trophic unit., *Am. J. Respir. Cell Mol. Biol.* 21, 655-7 (1999).
14. J. E. Boers, a W. Ambergen, F. B. Thunnissen, Number and proliferation of clara cells in normal human airway epithelium., *Am. J. Respir. Crit. Care Med.* 159, 1585-91 (1999).
15. C. L. Ordoñez, R. Khashayar, H. H. Wong, R. Ferrando, R. Wu, D. M. Hyde, J. A. Hotchkiss, Y. Zhang, A. Novikov, G. Dolganov, J. V Fahy, Mild and moderate asthma is associated with airway goblet cell hyperplasia and abnormalities in mucin gene expression., *Am. J. Respir. Crit. Care Med.* 163, 517-23 (2001).
16. M. Saetta, G. Turato, S. Baraldo, A. Zanin, F. Braccioni, C. E. Mapp, P. Maestrelli, G. Cavallesco, A. Papi, L. M. Fabbri, Goblet cell hyperplasia and epithelial inflammation in peripheral airways of smokers with both symptoms of chronic bronchitis and chronic airflow limitation, *Am. J. Respir. Crit. Care Med.* 161, 1016-1021 (2000).
17. H. B. Barkauskas C E, Cronce M J, Rackley C R, Bowie E J, Keene D R, Stripp B R, Randell S H, Noble P W, Type 2 alveolar cells are stem cells in adult lung, *J Clin Invest* 123, 3025-3036 (2013).
18. A. Iwasaki, E. F. Foxman, R. D. Molony, Early local immune defences in the respiratory tract, *Nat. Rev. Immunol.* 17, 7-20 (2016).
19. S. J. Hirst, Airway smooth muscle as a target in asthma., *Clin. Exp. Allergy* 30 Suppl 1, 54-9 (2000).
20. C. Ramos, M. Montaño, J. García-Alvarez, V. Ruiz, B. D. Uhal, M. Selman, A. Pardo, Fibroblasts from idiopathic pulmonary fibrosis and normal lungs differ in growth rate, apoptosis, and tissue inhibitor of metalloproteinases expression., *Am. J. Respir. Cell Mol. Biol.* 24, 591-8 (2001).
21. J. Lee, D. H. Bhang, A. Beede, T. L. Huang, B. R. Stripp, K. D. Bloch, A. J. Wagers, Y. Tseng, S. Ryeom, C. F. Kim, Lung stem cell differentiation in mice directed by endothelial cells via a BMP4-NFATc1-thrombospondin-1 axis., *Cell* 156, 440-55 (2014).
22. R. Greek, A. Menache, Systematic reviews of animal models: Methodology versus epistemology, *Int. J. Med. Sci.* 10, 206-221 (2013).
23. M. Leist, T. Hartung, Inflammatory findings on species extrapolations: humans are definitely no 70-kg mice., *ALTEX* 30, 227-30 (2013).
24. C. Ogi, A. Aruga, Immunological monitoring of anti-cancer vaccines in clinical trials., *Oncoimmunology* 2, e26012 (2013).
25. K. Yaddanapudi, R. A. Mitchell, J. W. Eaton, C. Ogi, A. Aruga, Cancer vaccines: Looking to the future., *Oncoimmunology* 2, e23403 (2013).
26. J. M. Pilewski, R. A. Frizzell, Role of CFTR in airway disease., *Physiol. Rev.* 79, S215-55 (1999).
27. J. Bella, M. G. Rossmann, Review: rhinoviruses and their ICAM receptors., *J. Struct. Biol.* 128, 69-74 (1999).
28. A. L. Rasmussen, V. R. Racaniello, Selection of rhinovirus 1A variants adapted for growth in mouse lung epithelial cells, *Virology* 420, 82-88 (2011).
29. L. G. Byrd, G. a Prince, Animal models of respiratory syncytial virus infection., *Clin. Infect. Dis.* 25, 1363-8 (1997).
30. A. M. Holmes, R. Solari, S. T. Holgate, Animal models of asthma: value, limitations and opportunities for alternative approaches., *Drug Discov. Today* 16, 659-70 (2011).
31. M. A. Lancaster, J. A. Knoblich, Organogenesis in a dish: Modeling development and disease using organoid technologies, *Science (80-.).* 345, 1247125-1247125 (2014).
32. J. R. Rock, M. W. Onaitis, E. L. Rawlins, Y. Lu, C. P. Clark, Y. Xue, S. H. Randell, B. L. M. Hogan, Basal cells as stem cells of the mouse trachea and human airway epithelium., *Proc. Natl. Acad. Sci. U.S.A* 106, 12771-5 (2009).
33. P. R. Tata, H. Mou, A. Pardo-Saganta, R. Zhao, M. Prabhu, B. M. Law, V. Vinarsky, J. L. Cho, S. Breton, A. Sahay, B. D. Medoff, J. Rajagopal, Dedifferentiation of committed epithelial cells into stem cells in vivo, *Nature* 503, 218-223 (2013).

34. Y.-W. Chen, S. X. Huang, A. L. R. T. de Carvalho, S.-H. Ho, M. N. Islam, S. Volpi, L. D. Notarangelo, M. Ciancanelli, J.-L. Casanova, J. Bhattacharya, A. F. Liang, L. M. Palermo, M. Porotto, A. Moscona, H.-W. Snoeck, A three-dimensional model of human lung development and disease from pluripotent stem cells., *Nat. Cell Biol.* 19, 542-549 (2017).

35. A. Fatehullah, S. H. Tan, N. Barker, Organoids as an in vitro model of human development and disease., *Nat. Cell Biol.* 18, 246-254 (2016).

36. T. E. Gray, K. Guzman, C. W. Davis, L. H. Abdullah, P. Nettesheim, Mucociliary differentiation of serially passaged normal human tracheobronchial epithelial cells, *Am. J. Respir. Cell Mol. Biol.* 14, 104-112 (1996).

37. M. L. Fulcher, S. Gabriel, K. a Burns, J. R. Yankaskas, S. H. Randell, Well-differentiated human airway epithelial cell cultures., *Methods Mol. Med.* 107, 183-206 (2005).

38. R. G. Crystal, S. H. Randell, J. F. Engelhardt, J. Voynow, M. E. Sunday, Airway epithelial cells: current concepts and challenges., *Proc. Am. Thorac. Soc.* 5, 772-7 (2008).

39. A. Livraghi, S. H. Randell, Cystic fibrosis and other respiratory diseases of impaired mucus clearance., *Toxicol. Pathol.* 35, 116-29 (2007).

40. N. K. Malavia, C. B. Raub, S. B. Mahon, M. Brenner, R. a Panettieri, S. C. George, Airway epithelium stimulates smooth muscle proliferation., *Am. J. Respir. Cell Mol. Biol.* 41, 297-304 (2009).

41. M. N. Matrosovich, T. Y. Matrosovich, T. Gray, N. A. Roberts, H. D. Klenk, Human and avian influenza viruses target different cell types in cultures of human airway epithelium, *Proc. Natl. Acad. Sci. U.S.A* 101, 4620-4624 (2004).

42. D. Huh, B. D. Matthews, A. Mammoto, M. Montoya-Zavala, H. Y. Hsin, D. E. Ingber, Reconstituting organ-level lung functions on a chip., *Science* 328, 1662-8 (2010).

43. D. Huh, G. A. Hamilton, D. E. Ingber, From 3D cell culture to organs-on-chips, *Trends Cell Biol.* 21, 745-754 (2011).

44. D. Huh, Y. Torisawa, G. A. Hamilton, H. J. Kim, D. E. Ingber, Microengineered physiological biomimicry: Organs-on-Chips, *Lab Chip* 12, 2156 (2012).

45. D. Huh, D. C. Leslie, B. D. Matthews, J. P. Fraser, S. Jurek, G. a Hamilton, K. S. Thorneloe, M. A. McAlexander, D. E. Ingber, A human disease model of drug toxicity-induced pulmonary edema in a lung-on-a-chip microdevice., *Sci. Transl. Med.* 4, 159ra147 (2012).

46. K. H. Benam, R. Villenave, C. Lucchesi, A. Varone, C. Hubeau, H.-H. Lee, S. E. Alves, M. Salmon, T. C. Ferrante, J. C. Weaver, A. Bahinski, G. A. Hamilton, D. E. Ingber, Small airway-on-a-chip enables analysis of human lung inflammation and drug responses in vitro, *Nat. Methods* (2015), doi:10.1038/nmeth.3697.

47. E. W. Esch, A. Bahinski, D. Huh, R. Greek, A. Menache, L. G. Griffith, M. A. Swartz, D. Huh, H. J. Kim, J. P. Fraser, D. E. Shea, M. Khan, A. Bahinski, G. a Hamilton, D. E. Ingber, Capturing complex 3D tissue physiology in vitro., *Nat. Rev. Mol. cell Biol.* 14, 2135-57 (2013).

48. S. E. Dunsmore, D. E. Rannels, Extracellular matrix biology in the lung., *Am. J. Physiol.* 270, L3-27 (1996).

49. D. P. Bottaro, A. Liebmann-Vinson, M. A. Heidaran, Molecular signaling in bioengineered tissue microenvironments., *Ann. N. Y. Acad. Sci.* 961, 143-53 (2002).

50. A. I. Alford, D. E. Rannels, Extracellular matrix fibronectin alters connexin43 expression by alveolar epithelial cells., *Am. J. Physiol. Lung Cell. Mol. Physiol.* 280, L680-8 (2001).

51. R. A. Clark, R. J. Mason, J. M. Folkvord, J. A. McDonald, Fibronectin mediates adherence of rat alveolar type II epithelial cells via the fibroblastic cell-attachment domain., *J. Clin. Invest.* 77, 1831-40 (1986).

52. J. A. DeQuach, V. Mezzano, A. Miglani, S. Lange, G. M. Keller, F. Sheikh, K. L. Christman, Simple and high yielding method for preparing tissue specific extracellular matrix coatings for cell culture., *PLOS One* 5, e13039 (2010).

53. G. Serini, M. L. Bochaton-Piallat, P. Ropraz, A. Geinoz, L. Borsi, L. Zardi, G. Gabbiani, The fibronectin domain ED-A is crucial for myofibroblastic phenotype induction by transforming growth factor-beta1., *J. Cell Biol.* 142, 873-81 (1998).

54. R. R. Mercer, J. D. Crapo, Spatial distribution of collagen and elastin fibers in the lungs., *J. Appl. Physiol.* 69, 756-65 (1990).

55. J. L. Balestrini, L. E. Niklason, Extracellular Matrix as a Driver for Lung Regeneration, *Ann. Biomed. Eng.* 43, 568-576 (2015).

56. I. P. Tomos, A. Tzouvelekis, V. Aidinis, E. D. Manali, E. Bouros, D. Bouros, S. A. Papiris, Extracellular matrix remodeling in idiopathic pulmonary fibrosis. It is the "bed" that counts and not "the sleepers"., *Expert Rev. Respir. Med.* 11, 299-309 (2017).

57. N. Sakai, A. M. Tager, Fibrosis of two: Epithelial cell-fibroblast interactions in pulmonary fibrosis, *Biochim. Biophys. Acta—Mol. Basis Dis.* 1832, 911-921 (2013).

58. T. Hussell, T. J. Bell, Alveolar macrophages: Plasticity in a tissue-specific context, *Nat. Rev. Immunol.* 14, 81-93 (2014).

59. J. R. Teijaro, K. B. Walsh, S. Cahalan, D. M. Fremgen, E. Roberts, F. Scott, E. Martinborough, R. Peach, M. B. A. Oldstone, H. Rosen, Endothelial cells are central orchestrators of cytokine amplification during influenza virus infection., *Cell* 146, 980-91 (2011).

60. C. Blume, R. Reale, M. Held, M. Loxham, T. M. Millar, J. E. Collins, E. J. Swindle, H. Morgan, D. E. Davies, Cellular crosstalk between airway epithelial and endothelial cells regulates barrier functions during exposure to double-stranded RNA, *Immunity, Inflamm. Dis.* 5, 45-56 (2017).

61. D. Huh, B. D. Matthews, A. Mammoto, M. Montoya-Zavala, H. Y. Hsin, D. E. Ingber, Reconstituting Organ-Level Lung Functions on a Chip, *Science* (80-.). 328, 1662-1668 (2010).

62. J. Forrest, The effect of changes in lung volume on the size and shape of alveoli, *J. Physiol.* 210, 533-547 (1970).

63. J. J. Fredberg, R. D. Kamm, STRESS TRANSMISSION IN THE LUNG: Pathways from Organ to Molecule, *Annu. Rev. Physiol.* 68, 507-541 (2006).

64. J. Sanchez-Esteban, L. A. Cicchiello, Y. Wang, S. W. Tsai, L. K. Williams, J. S. Torday, L. P. Rubin, Mechanical stretch promotes alveolar epithelial type II cell differentiation., *J. Appl. Physiol.* 91, 589-95 (2001).

65. Y. S. Edwards, Stretch stimulation: its effects on alveolar type II cell function in the lung., *Comp. Biochem. Physiol. A. Mol. Integr. Physiol.* 129, 245-60 (2001).

66. S. P. Arold, E. Bartolák-Suki, B. Suki, Variable stretch pattern enhances surfactant secretion in alveolar type II cells in culture., *Am. J. Physiol. Lung Cell. Mol. Physiol.* 296, L574-81 (2009).

67. M. Liu, a K. Tanswell, M. Post, Mechanical force-induced signal transduction in lung cells., *Am. J. Physiol.* 277, L667-83 (1999).

68. A. O. Stucki, J. D. Stucki, S. R. R. Hall, M. Felder, Y. Mermoud, R. A. Schmid, T. Geiser, O. T. Guenat, A lung-on-a-chip array with an integrated bio-inspired respiration mechanism, *Lab Chip* 15, 1302-1310 (2015).
69. A. Jain, R. Barrile, A. D. van der Meer, A. Mammoto, T. Mammoto, K. De Ceunynck, O. Aisiku, M. A. Otieno, C. S. Louden, G. A. Hamilton, R. Flaumenhaft, D. E. Ingber, Primary Human Lung Alveolus-on-a-chip Model of Intravascular Thrombosis for Assessment of Therapeutics., *Clin. Pharmacol. Ther.* (2017), doi:10.1002/cpt.742. 70. A. B. Fisher, Normal and pathologic biochemistry of the lung, *Environ. Health Perspect.* Vol. 16, 3-9 (1976).
71. J. Hukkanen, O. Pelkonen, J. Hakkola, H. Raunio, Expression and regulation of xenobiotic-metabolizing cytochrome P450 (CYP) enzymes in human lung., *Crit. Rev. Toxicol.* 32, 391-411 (2002).
72. M. Kopf, C. Schneider, S. P. Nobs, The development and function of lung-resident macrophages and dendritic cells., *Nat. Immunol.* 16, 36 44 (2015).
73. J. Seo, D. Conegliano, M. Farrell, M. Cho, X. Ding, T. Seykora, D. Qing, N. S. Mangalmurti, D. Huh, A microengineered model of RBC transfusion-induced pulmonary vascular injury, *Sci. Rep.* 7 (2017), doi: 10.1038/s41598-017-03597-w.
74. A. Jain, A. D. van der Meer, A.-L. Papa, R. Barrile, A. Lai, B. L. Schlechter, M. A. Otieno, C. S. Louden, G. A. Hamilton, A. D. Michelson, A. L. Frelinger, D. E. Ingber, Assessment of whole blood thrombosis in a microfluidic device lined by fixed human endothelium., *Biomed. Microdevices* 18, 73 (2016).
75. A. Manz, H. M. Widmers, N. Graber, Miniaturized total chemical analysis systems: A novel concept for chemical sensing, *Sensors Actuators B Chem.* 1, 244-248 (1990).
76. A. van den Berg, P. Bergveld, *Proceedings of the µTAS*, 1994 (1995).
77. M. U. Kopp, A. J. De Mello, A. Manz, Chemical Amplification: Continuous flow PCR on a chip, *Science (80-.).* 280, 1046-1048 (1998).
78. R. Daw, J. Finkelstein, Lab on a chip, *Nature* 442, 367-367 (2006).
79. D. C. Duffy, J. C. McDonald, O. J. A. Schueller, G. M. Whitesides, Rapid prototyping of microfluidic systems in poly(dimethylsiloxane), *Anal. Chem.* 70, 4974-4984 (1998).
80. A. Folch, M. Toner, Microengineering of Cellular Interactions, *Annu. Rev. Biomed. Eng.* 2, 227-256 (2000).
81. A. Folch, a Ayon, O. Hurtado, M. a Schmidt, M. Toner, Molding of deep polydimethylsiloxane microstructures for microfluidics and biological applications., *J. Biomech. Eng.* 121, 28-34 (1999).
82. J. El-Ali, P. K. Sorger, K. F. Jensen, Cells on chips, *Nature* 442, 403-411 (2006).
83. D. J. Beebe, J. S. Moore, J. M. Bauer, Q. Yu, R. H. Liu, C. Devadoss, B.-H. Jo, Functional hydrogel structures for autonomous flow control inside microfluidic channels: Abstract: Nature, *Nature* 404, 588-590 (2000).
84. G. M. Whitesides, E. Ostuni, S. Takayama, X. Jiang, D. E. Ingber, Soft lithography in biology and biochemistry., *Annu. Rev. Biomed. Eng.* 3, 335-73 (2001).
85. S. R. Quake, From Micro- to Nanofabrication with Soft Materials, *Science (80-.).* 290, 1536-1540 (2000).
86. J. C. McDonald, G. M. Whitesides, Poly (dimethylsiloxane) as a Material for Fabricating Microfluidic Devices, *Acc. Chem. Res.* 35, 491-499 (2002).
87. R. Langer, J. P. Vacanti, Tissue engineering, *Science (80-.).* 260, 920-926 (1993).
88. A. Khademhosseini, G. C. Bong, Microscale technologies for tissue engineering, 2009 *IEEE/NIH Life Sci. Syst. Appl. Work. LiSSA* 2009 103, 56-57 (2009).
89. J. T. Borenstein, H. Terai, K. R. King, E. J. Weinberg, M. R. Kaazempur-Mofrad, J. P. Vacanti, Microfabrication Technology for Vascularized Tissue Engineering, *Biomed. Microdevices* 4, 167-175 (2002).
90. M. J. Powers, K. Domansky, M. R. Kaazempur-Mofrad, A. Kalezi, A. Capitano, A. Upadhyaya, P. Kurzawski, K. E. Wack, D. B. Stolz, R. Kamm, L. G. Griffith, A microfabricated array bioreactor for perfused 3D liver culture, *Biotechnol. Bioeng.* 78, 257-269 (2002).
91. E. Leclerc, Y. Sakai, T. Fujii, Cell culture in 3-dimensional microfluidic structure of PDMS (polydimethylsiloxane), *Biomed. Microdevices* 5, 109-114 (2003).
92. P. J. Lee, P. J. Hung, L. P. Lee, An artificial liver sinusoid with a microfluidic endothelial-like barrier for primary hepatocyte culture., *Biotechnol. Bioeng.* 97, 1340-6 (2007).
93. M. T. Lam, Y.-C. Huang, R. K. Birla, S. Takayama, Microfeature guided skeletal muscle tissue engineering for highly organized 3-dimensional free-standing constructs., *Biomaterials* 30, 1150-5 (2009).
94. K. Jang, K. Sato, K. Igawa, U. Chung, T. Kitamori, Development of an osteoblast-based 3D continuous-perfusion microfluidic system for drug screening., *Anal. Bioanal. Chem.* 390, 825-32 (2008).
95. J. W. Park, B. Vahidi, A. M. Taylor, S. W. Rhee, N. L. Jeon, Microfluidic culture platform for neuroscience research., *Nat. Protoc.* 1, 2128-36 (2006).
96. G. J. Mahler, M. B. Esch, R. P. Glahn, M. L. Shuler, Characterization of a gastrointestinal tract microscale cell culture analog used to predict drug toxicity., *Biotechnol. Bioeng.* 104, 193-205 (2009).
97. R. Baudoin, L. Griscom, M. Monge, C. Legallais, E. Leclerc, Development of a Renal Microchip for In Vitro Distal Tubule Models, *Biotechnol. Prog.* 23, 0-0 (2007).
98. K.-J. Jang, K.-Y. Suh, A multi-layer microfluidic device for efficient culture and analysis of renal tubular cells., *Lab Chip* 10, 36-42 (2010).
99. N. J. Douville, P. Zamankhan, Y.-C. Tung, R. Li, B. L. Vaughan, C.-F. Tai, J. White, P. J. Christensen, J. B. Grotberg, S. Takayama, Combination of fluid and solid mechanical stresses contribute to cell death and detachment in a microfluidic alveolar model, *Lab Chip* 11, 609-619 (2011).
100. B. A. Hassell, G. Goyal, E. Lee, A. Sontheimer-Phelps, O. Levy, C. S. Chen, D. E. Ingber, Human Organ Chip Models Recapitulate Orthotopic Lung Cancer Growth, Therapeutic Responses, and Tumor Dormancy In Vitro, *Cell Rep.* 21, 508-516 (2017).
101. K. H. Benam, R. Novak, J. Nawroth, R. Villenave, M. Hirano-Kobayashi, C. Lucchesi, T. C. Ferrante, Y.-J. Choe, R. Prantil-Braun, J. C. Weaver, K. K. Parker, A. Bahinski, D. E. Ingber, Matched-comparative modeling of normal and COPD human airway responses to inhaled smoke in vitro, *Cell Syst.* (2016).
102. A. P. Nesmith, A. Agarwal, M. L. McCain, K. K. Parker, Human airway musculature on a chip: an in vitro model of allergic asthmatic bronchoconstriction and bronchodilation, *Lab Chip* 14, 3925-3936 (2014).
103. K. L. Sellgren, E. J. Butala, B. P. Gilmour, S. H. Randell, S. Grego, A biomimetic multicellular model of the airways using primary human cells., *Lab Chip,* 3349-3358 (2014).
104. L. J. Barkal, C. L. Procknow, Y. R. Álvarez-García, M. Niu, J. A. Jiménez-Torres, R. A. Brockman-Schneider, J.

105. P. Hughes, D. Marshall, Y. Reid, H. Parkes, C. Gelber, The costs of using unauthenticated, over-passaged cell lines: how much more data do we need?, *Biotechniques* 43, 575, 577-8, 581-2 passim (2007).
106. C. R. Butler, R. E. Hynds, K. H. C. Gowers, D. D. H. Lee, J. M. Brown, C. Crowley, V. H. Teixeira, C. M. Smith, L. Urbani, N. J. Hamilton, R. M. Thakrar, H. L. Booth, M. A. Birchall, P. De Coppi, A. Giangreco, C. O'Callaghan, S. M. Janes, Rapid Expansion of Human Epithelial Stem Cells Suitable for Airway Tissue Engineering, *Am. J. Respir. Crit. Care Med.* 194, 156-168 (2016).
107. R. S. Kadzik, E. E. Morrisey, Directing lung endoderm differentiation in pluripotent stem cells., *Cell Stem Cell* 10, 355-61 (2012).
108. K. A. D'Amour, A. G. Bang, S. Eliazer, O. G. Kelly, A. D. Agulnick, N. G. Smart, M. A. Moorman, E. Kroon, M. K. Carpenter, E. E. Baetge, Production of pancreatic hormone-expressing endocrine cells from human embryonic stem cells, *Nat. Biotechnol.* 24, 1392-1401 (2006).
109. J. R. Spence, C. N. Mayhew, S. a Rankin, M. F. Kuhar, J. E. Vallance, K. Tolle, E. E. Hoskins, V. V Kalinichenko, S. I. Wells, A. M. Zorn, N. F. Shroyer, J. M. Wells, Directed differentiation of human pluripotent stem cells into intestinal tissue in vitro., *Nature* 470, 105-9 (2011).
110. J. Cai, Y. Zhao, Y. Liu, F. Ye, Z. Song, H. Qin, S. Meng, Y. Chen, R. Zhou, X. Song, Y. Guo, M. Ding, H. Deng, Directed differentiation of human embryonic stem cells into functional hepatic cells., *Hepatology* 45, 1229-39 (2007).
111. M. D. Green, A. Chen, M.-C. Nostro, S. L. D'Souza, C. Schaniel, I. R. Lemischka, V. Gouon-Evans, G. Keller, H.-W. Snoeck, Generation of anterior foregut endoderm from human embryonic and induced pluripotent stem cells, *Nat. Biotechnol.* 29, 267-272 (2011).
112. C. E. Murry, G. Keller, Differentiation of embryonic stem cells to clinically relevant populations: lessons from embryonic development., *Cell* 132, 661-80 (2008).
113. E. E. Morrisey, B. L. M. Hogan, Preparing for the first breath: genetic and cellular mechanisms in lung development., *Dev. Cell* 18, 8-23 (2010).
114. S. Kimura, Y. Hara, T. Pineau, P. Fernandez-Salguero, C. H. Fox, J. M. Ward, F. J. Gonzalez, The T/ebp null mouse: thyroid-specific enhancer-binding protein is essential for the organogenesis of the thyroid, lung, ventral forebrain, and pituitary., *Genes Dev.* 10, 60-9 (1996).
115. Y. Xu, T. Mizuno, A. Sridharan, Y. Du, M. Guo, J. Tang, K. A. Wikenheiser-Brokamp, A.-K. T. Perl, V. A. Funari, J. J. Gokey, B. R. Stripp, J. A. Whitsett, Single-cell RNA sequencing identifies diverse roles of epithelial cells in idiopathic pulmonary fibrosis, *JCI Insight* 1, 1-18 (2016).
116. L. W. Gonzales, S. H. Guttentag, K. C. Wade, A. D. Postle, P. L. Ballard, Differentiation of human pulmonary type II cells in vitro by glucocorticoid plus cAMP., *Am. J. Physiol. Lung Cell. Mol. Physiol.* 283, L940-L951 (2002).
117. K. C. Wade, S. H. Guttentag, L. W. Gonzales, K. L. Maschhoff, J. Gonzales, V. Kolla, S. Singhal, P. L. Ballard, Gene induction during differentiation of human pulmonary type II cells in vitro., *Am. J. Respir. Cell Mol. Biol.* 34, 727-37 (2006).
118. A. V Andreeva, M. A. Kutuzov, T. A. Voyno-Yasenetskaya, Regulation of surfactant secretion in alveolar type II cells., *Am. J. Physiol. Lung Cell. Mol. Physiol.* 293, L259-71 (2007).
119. S. X. L. Huang, M. D. Green, A. T. de Carvalho, M. Mumau, Y.-W. Chen, S. L. D'Souza, H.-W. Snoeck, The in vitro generation of lung and airway progenitor cells from human pluripotent stem cells., *Nat. Protoc.* 10, 413-25 (2015).
120. S. Gotoh, I. Ito, T. Nagasaki, Y. Yamamoto, S. Konishi, Y. Korogi, H. Matsumoto, S. Muro, T. Hirai, M. Funato, S. I. Mae, T. Toyoda, A. Sato-Otsubo, S. Ogawa, K. Osafune, M. Mishima, Generation of alveolar epithelial spheroids via isolated progenitor cells from human pluripotent stem cells, *Stem Cell Reports* 3, 394 403 (2014).
121. Y. Yamamoto, S. Gotoh, Y. Korogi, M. Seki, S. Konishi, S. Ikeo, N. Sone, T. Nagasaki, H. Matsumoto, S. Muro, I. Ito, T. Hirai, T. Kohno, Y. Suzuki, M. Mishima, Long-term expansion of alveolar stem cells derived from human iPS cells in organoids, *Nat. Methods* 14, 1097-1106 (2017).
122. S. Konishi, S. Gotoh, K. Tateishi, Y. Yamamoto, Y. Korogi, T. Nagasaki, H. Matsumoto, S. Muro, T. Hirai, I. Ito, S. Tsukita, M. Mishima, Directed Induction of Functional Multi-ciliated Cells in Proximal Airway Epithelial Spheroids from Human Pluripotent Stem Cells, *Stem Cell Reports* 6, 18-25 (2016).
123. K. B. McCauley, F. Hawkins, M. Serra, D. C. Thomas, A. Jacob, D. N. Kotton, Efficient Derivation of Functional Human Airway Epithelium from Pluripotent Stem Cells via Temporal Regulation of Wnt Signaling, *Cell Stem Cell* 20, 844-857.e6 (2017).
124. A. Wong, C. Bear, S. Chin, P. Pasceri, T. Thompson, L.-J. Huan, F. Ratjen, J. Ellis, J. Rossant, Directed differentiation of human pluripotent stem cells into mature airway epithelia expressing functional CFTR protein., *Nat. Biotechnol.* 30, 876-882 (2012).
125. H. Mou, V. Vinarsky, P. R. Tata, S. H. Choi, A. K. Crooke, B. Zhang, G. M. Solomon, B. Turner, H. Bihler, J. Harrington, A. Lapey, C. Channick, C. Keyes, A. Freund, S. Artandi, M. Mense, S. Rowe, J. F. Engelhardt, Y. Hsu, J. Rajagopal, Dual SMAD signaling inhibition enables long-term expansion of diverse epithelial basal cells, *Cell Stem Cell* 19, 217-231 (2017).
126. M. Z. Nikolić, O. Caritg, Q. Jeng, J.-A. Johnson, D. Sun, K. J. Howell, J. L. Brady, U. Laresgoiti, G. Allen, R. Butler, M. Zilbauer, A. Giangreco, E. L. Rawlins, Human embryonic lung epithelial tips are multipotent progenitors that can be expanded in vitro as long-term self-renewing organoids, *Elife* 6, 1-33 (2017).
127. S. X. L. Huang, M. N. Islam, J. O'Neill, Z. Hu, Y.-G. Yang, Y.-W. Chen, M. Mumau, M. D. Green, G. Vunjak-Novakovic, J. Bhattacharya, H.-W. Snoeck, Efficient generation of lung and airway epithelial cells from human pluripotent stem cells., *Nat. Biotechnol.* 32, 84-91 (2014).
128. A. A. P. Wong, C. C. E. Bear, S. Chin, P. Pasceri, T. T. O. Thompson, L.-J. L.-J. Huan, F. Ratjen, J. Ellis, J. Rossant, Directed differentiation of human pluripotent stem cells into mature airway epithelia expressing functional CFTR protein., *Nat. Biotechnol.* 30, 876-882 (2012).
129. F. Hawkins, P. Kramer, A. Jacob, I. Driver, D. C. Thomas, K. B. McCauley, N. Skvir, A. M. Crane, A. A. Kurmann, A. N. Hollenberg, S. Nguyen, B. G. Wong, A. S. Khalil, S. X. L. Huang, S. Guttentag, J. R. Rock, J. M. Shannon, B. R. Davis, D. N. Kotton, Prospective isolation of NKX2-1-expressing human lung progenitors derived from pluripotent stem cells, *J. Clin. Invest.* 127, 2277-2294 (2017).

130. M. Ghaedi, E. A. Calle, J. J. Mendez, A. L. Gard, J. Balestrini, A. Booth, P. F. Bove, L. Gui, E. S. White, L. E. Niklason, Technical advance Human iPS cell—derived alveolar epithelium repopulates lung extracellular matrix, *J. Clin. . . .* 123, 4950 (2013).

131. B. R. Dye, D. R. Hill, M. A. Ferguson, Y.-H. Tsai, M. S. Nagy, R. Dyal, J. M. Wells, C. N. Mayhew, R. Nattiv, O. D. Klein, E. S. White, G. H. Deutsch, J. R. Spence, In vitro generation of human pluripotent stem cell derived lung organoids, *Elife* 4, 1-25 (2015).

132. B. R. Dye, P. H. Dedhia, A. J. Miller, M. S. Nagy, E. S. White, L. D. Shea, J. R. Spence, A bioengineered niche promotes in vivo engraftment and maturation of pluripotent stem cell derived human lung organoids, *Elife* 5, 1-18 (2016).

133. C. E. Barkauskas, M.-I. Chung, B. Fioret, X. Gao, H. Katsura, B. L. M. Hogan, Lung organoids: current uses and future promise, *Development* 144, 986-997 (2017).

134. K. H. Vining, D. J. Mooney, Mechanical forces direct stem cell behaviour in development and regeneration, *Nat. Rev. Mol. Cell Biol.* 18, 728-742 (2017).

135. F. Hawkins, D. N. Kotton, Embryonic and induced pluripotent stem cells for lung regeneration., *Ann. Am. Thorac. Soc.* 12 Suppl 1, S50-3 (2015).

136. D. A. Robinton, G. Q. Daley, The promise of induced pluripotent stem cells in research and therapy., *Nature* 481, 295-305 (2012).

137. A. Somers, J.-C. Jean, C. A. Sommer, A. Omari, C. C. Ford, J. A. Mills, L. Ying, A. G. Sommer, J. M. Jean, B. W. Smith, R. Lafyatis, M.-F. Demierre, D. J. Weiss, D. L. French, P. Gadue, G. J. Murphy, G. Mostoslavsky, D. N. Kotton, Generation of transgene-free lung disease-specific human induced pluripotent stem cells using a single excisable lentiviral stem cell cassette., *Stem Cells* 28, 1728-40 (2010).

138. M. Bellin, M. C. Marchetto, F. H. Gage, C. L. Mummery, Induced pluripotent stem cells: the new patient?, *Nat. Rev. Mol. Cell Biol.* 13, 713-26 (2012).

139. P. Spagnolo, R. M. du Bois, V. Cottin, Rare lung disease and orphan drug development., *Lancet. Respir. Med.* 1, 479-87 (2013).

140. J. S. Elborn, Cystic fibrosis., *Lancet* (London, England) 388, 2519-2531 (2016).

141. A. Jaffé, A. Bush, Cystic fibrosis: review of the decade., *Monaldi Arch. chest Dis.=Arch. Monaldi per le Mal. del torace* 56, 240-7 (2001).

142. G. B. Pier, The challenges and promises of new therapies for cystic fibrosis., *J. Exp. Med.* 209, 1235-9 (2012).

143. F. Ratjen, G. Döring, Cystic fibrosis., *Lancet* (London, England) 361, 681-9 (2003).

144. R. Rozmahel, M. Wilschanski, A. Matin, S. Plyte, M. Oliver, W. Auerbach, A. Moore, J. Forstner, P. Durie, J. Nadeau, C. Bear, L. C. Tsui, Modulation of disease severity in cystic fibrosis transmembrane conductance regulator deficient mice by a secondary genetic factor., *Nat. Genet.* 12, 280-7 (1996).

145. G. M. Lavelle, M. M. White, N. Browne, N. G. McElvaney, E. P. Reeves, Animal Models of Cystic Fibrosis Pathology: Phenotypic Parallels and Divergences, *Biomed Res. Int.* 2016, 1-14 (2016).

146. J. Zielenski, Genotype and phenotype in cystic fibrosis., *Respiration.* 67, 117-33 (2000).

147. D. Konar, M. Devarasetty, D. V Yildiz, A. Atala, S. V Murphy, Lung-On-A-Chip Technologies for Disease Modeling and Drug Development., *Biomed. Eng. Comput. Biol.* 7, 17-27 (2016).

148. D. (Dan) Huh, A Human Breathing Lung-on-a-Chip, *Ann. Am. Thorac. Soc.* 12, S42-S44 (2015).

149. J. F. Dekkers, C. L. Wiegerinck, H. R. de Jonge, I. Bronsveld, H. M. Janssens, K. M. de Winter-de Groot, A. M. Brandsma, N. W. M. de Jong, M. J. C. Bijvelds, B. J. Scholte, E. E. S. Nieuwenhuis, S. van den Brink, H. Clevers, C. K. van der Ent, S. Middendorp, J. M. Beekman, A functional CFTR assay using primary cystic fibrosis intestinal organoids, *Nat. Med.* 19, 939-945 (2013).

151. J. A. Whitsett, S. E. Wert, T. E. Weaver, Alveolar surfactant homeostasis and the pathogenesis of pulmonary disease., *Annu. Rev. Med.* 61, 105-19 (2010).

152. GBD 2015 Chronic Respiratory Disease Collaborators, Global, regional, and national deaths, prevalence, disability-adjusted life years, and years lived with disability for chronic obstructive pulmonary disease and asthma, 1990-2015: a systematic analysis for the Global Burden of Disease Study 2015., *Lancet. Respir. Med.* 5, 691-706 (2017).

153. R. Balkissoon, S. Lommatzsch, B. Carolan, B. Make, Chronic obstructive pulmonary disease: a concise review., *Med. Clin. North Am.* 95, 1125-41 (2011).

154. J. T. Olin, M. E. Wechsler, Asthma: pathogenesis and novel drugs for treatment., *BMJ* 349, g5517 (2014).

155. M. M. Epstein, Do Mouse Models of Allergic Asthma Mimic Clinical Disease? *Int. Arch. Allergy Immunol.* 133, 84-100 (2004).

156. Y. S. Shin, K. Takeda, E. W. Gelfand, Understanding asthma using animal models *Allergy, Asthma Immunol. Res.* 1, 10-18 (2009).

157. J. H. T. Bates, M. Rincon, C. G. Irvin, Animal models of asthma., *Am. J. Physiol. Lung Cell. Mol. Physiol.* 297, L401-10 (2009).

158. B. J. Canning, J. L. Wright, Animal models of asthma and chronic obstructive pulmonary disease., *Pulm. Pharmacol. Ther.* 21, 695 (2008).

159. H. Fehrenbach, Animal models of pulmonary emphysema: A stereologist's perspective *Eur. Respir. Rev.* 15, 136-147 (2006).

160. J. G. Martin, D. Ramos-Barbón, Airway smooth muscle growth from the perspective of animal models., *Respir. Physiol. Neurobiol.* 137, 251-261 (2003).

161. J. S. Guseh, S. A. Bores, B. Z. Stanger, Q. Zhou, W. J. Anderson, D. A. Melton, J. Rajagopal, Notch signaling promotes airway mucous metaplasia and inhibits alveolar development., *Development* 136, 1751-9 (2009).

162. M. J. Holtzman, D. E. Byers, J. Alexander-Brett, X. Wang, The role of airway epithelial cells and innate immune cells in chronic respiratory disease., *Nat. Rev. Immunol.* 14, 686-98 (2014).

163. S. Sharma, D. Chhabra, A. T. Kho, L. P. Hayden, K. G. Tantisira, S. T. Weiss, The genomic origins of asthma., *Thorax* 69, 481-7 (2014).

164. L. T. Stiemsma, S. E. Turvey, Asthma and the microbiome: defining the critical window in early life, *Allergy, Asthma Clin. Immunol.* 13, 3 (2017).

165. J. Parker, S. Sarlang, S. Thavagnanam, G. Williamson, D. O'donoghue, R. Villenave, U. Power, M. Shields, L. Heaney, G. Skibinski, A 3-D well-differentiated model of pediatric bronchial epithelium demonstrates unstimulated morphological differences between asthmatic and nonasthmatic cells., *Pediatr. Res.* 67, 17-22 (2010).

166. K. H. Benam, R. Villenave, C. Lucchesi, A. Varone, C. Hubeau, H.-H. Lee, S. E. Alves, M. Salmon, T. C. Ferrante, J. C. Weaver, A. Bahinski, G. A. Hamilton, D. E. Ingber, Small airway-on-a-chip enables analysis of human lung inflammation and drug responses in vitro., *Nat. Methods* 13, 151-7 (2016).

167. J. P. Hutchinson, T. M. Mckeever, A. W. Fogarty, V. Navaratnam, R. B. Hubbard, Increasing global mortality from idiopathic pulmonary fibrosis in the twenty-first century., *Ann. Am. Thorac. Soc.* 11, 1176-85 (2014).

168. F. J. Martinez, H. R. Collard, A. Pardo, G. Raghu, L. Richeldi, M. Selman, J. J. Swigris, H. Taniguchi, A. U. Wells, Idiopathic pulmonary fibrosis., *Nat. Rev. Dis. Prim.* 3, 17074 (2017).

169. J. H. Ryu, T. Moua, C. E. Daniels, T. E. Hartman, E. S. Yi, J. P. Utz, A. H. Limper, Idiopathic pulmonary fibrosis: evolving concepts., *Mayo Clin. Proc.* 89, 1130-42 (2014).

170. E. Renzoni, V. Srihari, P. Sestini, Pathogenesis of idiopathic pulmonary fibrosis: review of recent findings., *F1000 Prime Rep.* 6, 69 (2014).

171. F. Varone, G. Montemurro, F. Macagno, M. Calvello, E. Conte, E. Intini, B. Iovene, P. M. Leone, P.-V. Mari, L. Richeldi, Investigational drugs for idiopathic pulmonary fibrosis., *Expert Opin. Investig. Drugs* 26, 1019-1031 (2017).

172. P. W. Noble, C. E. Barkauskas, D. Jiang, Pulmonary fibrosis: patterns and perpetrators., *J. Clin. Invest.* 122, 2756-62 (2012).

173. A. Jemal, T. Murray, E. Ward, A. Samuels, R. C. Tiwari, A. Ghafoor, E. J. Feuer, M. J. Thun, Cancer statistics, 2005., *CA. Cancer J. Clin.* 55, 10-30.

174. M. Shanker, D. Willcutts, J. A. Roth, R. Ramesh, Drug resistance in lung cancer., *Lung Cancer* (Auckland, N.Z.) 1, 23-36 (2010).

175. L. E. Raez, S. Fein, E. R. Podack, Lung Cancer Immunotherapy, *Clin. Med. Res.* 3, 221-228 (2005).

176. J. Nemunaitis, D. Sterman, D. Jablons, J. W. Smith, B. Fox, P. Maples, S. Hamilton, F. Borellini, A. Lin, S. Morali, K. Hege, Granulocyte-macrophage colony-stimulating factor gene-modified autologous tumor vaccines in non-small-cell lung cancer., *J. Natl. Cancer Inst.* 96, 326-31 (2004).

177. I. J. Fidler, C. Wilmanns, A. Staroselsky, R. Radinsky, Z. Dong, D. Fan, Modulation of tumor cell response to chemotherapy by the organ environment., *Cancer Metastasis Rev.* 13, 209-22 (1994).

178. J. J. Killion, R. Radinsky, I. J. Fidler, Orthotopic models are necessary to predict therapy of transplantable tumors in mice., *Cancer Metastasis Rev.* 17, 279-84.

179. S. E. Gould, M. R. Junttila, F. J. de Sauvage, Translational value of mouse models in oncology drug development., *Nat. Med.* 21, 431-9 (2015).

180. F. Weeber, S. N. Ooft, K. K. Dijkstra, E. E. Voest, Tumor Organoids as a Pre-clinical Cancer Model for Drug Discovery., Cell *Chem. Biol.* 24, 1092-1100 (2017).

185. WHO, The top 10 causes of death: Fact sheet N°310 World Heal. Organ. (2013) (available at www.who.in/mediacentre/factsheets/fs310/en/).

186. B. Alvarez, J. Arcos, M. L. Fernández-Guerrero, Pulmonary infectious diseases in patients with primary immunodeficiency and those treated with biologic immunomodulating agents., *Curr. Opin. Pulm. Med.* 17, 172-9 (2011).

187. S. M. Bhavnani, C. M. Rubino, J. P. Hammel, A. Forrest, N. Dartois, C. A. Cooper, J. Korth-Bradley, P. G. Ambrose, Pharmacological and patient-specific response determinants in patients with hospital-acquired pneumonia treated with tigecycline., *Antimicrob. Agents Chemother.* 56, 1065-72 (2012).

188. L. Pirofski, A. Casadevall, The damage-response framework of microbial pathogenesis and infectious diseases., *Adv. Exp. Med. Biol.* 635, 135-46 (2008).

189. H. M. Kling, G. J. Nau, T. M. Ross, T. G. Evans, K. Chakraborty, K. M. Empey, J. L. Flynn, Challenges and Future in Vaccines, Drug Development, and Immunomodulatory Therapy, *Ann. Am. Thorac. Soc.* 11, S201-S210 (2014).

190. C. Chiu, P. J. Openshaw, Antiviral B cell and T cell immunity in the lungs, *Nat. Immunol.* 16, 18-26 (2015).

191. R. N. Mahon, R. Hafner, Immune Cell Regulatory Pathways Unexplored as Host-Directed Therapeutic Targets for *Mycobacterium tuberculosis*: An Opportunity to Apply Precision Medicine Innovations to Infectious Diseases., *Clin. Infect. Dis.* 61 Suppl 3, S200-16 (2015).

192. T. R. Hawn, A. I. Matheson, S. N. Maley, O. Vandal, Host-Directed Therapeutics for Tuberculosis: Can We Harness the Host?, *Microbiol. Mol. Biol. Rev.* 77, 608-627 (2013).

193. R. S. Wallis, R. Hafner, Advancing host-directed therapy for tuberculosis., *Nat. Rev. Immunol.* 15, 255-63 (2015).

194. K. L. Fonseca, P. N. S. Rodrigues, I. A. S. Olsson, M. Saraiva, Experimental study of tuberculosis: From animal models to complex cell systems and organoids., *PLOS Pathog.* 13, e1006421 (2017).

195. T. R. Lerner, S. Borel, M. G. Gutierrez, The innate immune response in human tuberculosis, *Cell. Microbiol.* 17, 1277-1285 (2015).

196. D. B. Flieder, W. D. Travis, Pathologic characteristics of drug-induced lung disease., *Clin. Chest Med.* 25, 37-45 (2004).

197. D. B. Coultas, R. E. Zumwalt, W. C. Black, R. E. Sobonya, The epidemiology of interstitial lung diseases., *Am. J. Respir. Crit. Care Med.* 150, 967-72 (1994).

198. B. Nemery, A. Bast, J. Behr, P. J. Borm, S. J. Bourke, P. H. Camus, P. De Vuyst, H. M. Jansen, V. L. Kinnula, D. Lison, O. Pelkonen, C. Saltini, Interstitial lung disease induced by exogenous agents: factors governing susceptibility., *Eur. Respir. J.* Suppl. 32, 30 s-42 s (2001).

199. O. Matsuno, Drug-induced interstitial lung disease: mechanisms and best diagnostic approaches., *Respir. Res.* 13, 39 (2012).

200. M. Schwaiblmair, Drug Induced Interstitial Lung Disease, *Open Respir. Med. J.* 6, 63-74 (2012).

201. K. Ask, M. R. J. Kolb, Drug development for chronic lung disease—mission impossible?, *Respirology* 20, 13-4 (2015).

202. S. Holgate, A. Agusti, R. M. Strieter, G. P. Anderson, R. Fogel, E. Bel, T. R. Martin, T. F. Reiss, Drug development for airway diseases: looking forward., *Nat. Rev. Drug Discov.* 14, 367-8 (2015).

203. D. Diez, A. Agustí, C. E. Wheelock, Network analysis in the investigation of chronic respiratory diseases. From basics to application., *Am. J. Respir. Crit. Care Med.* 190, 981-8 (2014).

204. A. Agustí, J. M. Antó, C. Auffray, F. Barbé, E. Barreiro, J. Dorca, J. Escarrabill, R. Faner, L. I. Furlong, J. Garcia-Aymerich, J. Gea, B. Lindmark, E. Monsó, V. Plaza, M. A. Puhan, J. Roca, J. Ruiz-Manzano, L. Sampietro-Colom, F. Sanz, L. Serrano, J. Sharpe, O. Sibila, E. K. Silverman, P. J. Sterk, J. I. Sznajder, Personalized respiratory medicine: exploring the horizon, addressing the 205. L. E. G. W. Vanfleteren, J. W. H. Kocks, I. S. Stone, R. Breyer-Kohansal, T. Greulich, D. Lacedonia, R. Buhl, L. M. Fabbri, I. D. Pavord, N. Barnes, E. F. M. Wouters, A. Agusti, Moving from the Oslerian paradigm to the post-genomic era: are asthma and COPD outdated terms?, *Thorax* 69, 72-9 (2014).

206. E. F. M. Wouters, N. L. Reynaert, M. A. Dentener, J. H. J. Vernooy, Systemic and local inflammation in asthma and chronic obstructive pulmonary disease: is there a connection?, *Proc. Am. Thorac. Soc.* 6, 638-47 (2009).

207. G. Raghu, H. R. Collard, K. J. Anstrom, K. R. Flaherty, T. R. Fleming, T. E. King, F. J. Martinez, K. K. Brown, Idiopathic pulmonary fibrosis: clinically meaningful primary endpoints in phase 3 clinical trials., *Am. J. Respir. Crit. Care Med.* 185, 1044-8 (2012).

208. S. D. Nathan, K. C. Meyer, IPF clinical trial design and endpoints., *Curr. Opin. Pulm. Med.* 20, 463-71 (2014).

209. I. Gonda, Systemic delivery of drugs to humans via inhalation., *J. Aerosol Med.* 19, 47-53 (2006).

210. I. Gonda, The ascent of pulmonary drug delivery., *J. Pharm. Sci.* 89, 940-5 (2000).

211. J. S. Patton, C. S. Fishburn, J. G. Weers, The lungs as a portal of entry for systemic drug delivery., *Proc. Am. Thorac. Soc.* 1, 338-44 (2004).

212. A. Safdar, S. A. Shelburne, S. E. Evans, B. F. Dickey, Inhaled therapeutics for prevention and treatment of pneumonia, *Expert Opin. Drug Saf.* 8, 435-449 (2009).

213. X. Liu, L. Jin, J. W. Upham, M. S. Roberts, The development of models for the evaluation of pulmonary drug disposition., *Expert Opin. Drug Metab. Toxicol.* 9, 487-505 (2013).

214. A. Tsuda, F. S. Henry, J. P. Butler, in *Comprehensive Physiology*, (John Wiley & Sons, Inc., Hoboken, NJ, USA, 2013), pp. 1437-1471.

215. S. Gizurarson, The effect of cilia and the mucociliary clearance on successful drug delivery., *Biol. Pharm. Bull.* 38, 497-506 (2015).

216. R. H. Hastings, H. G. Folkesson, M. A. Matthay, Mechanisms of alveolar protein clearance in the intact lung., *Am. J. Physiol. Lung Cell. Mol. Physiol.* 286, L679-89 (2004).

217. B. Forbes, B. Asgharian, L. A. Dailey, D. Ferguson, P. Gerde, M. Gumbleton, L. Gustavsson, C. Hardy, D. Hassall, R. Jones, R. Lock, J. Maas, T. McGovern, G. R. Pitcairn, G. Somers, R. K. Wolff, Challenges in inhaled product development and opportunities for open innovation., *Adv. Drug Deliv. Rev.* 63, 69-87.

218. J. M. Borghardt, B. Weber, A. Staab, C. Kloft, Pharmacometric Models for Characterizing the Pharmacokinetics of Orally Inhaled Drugs, *AAPS J.* 17, 853-870 (2015).

219. A. J. Hickey, L. Garcia-Contreras, Immunological and toxicological implications of short-term studies in animals of pharmaceutical aerosol delivery to the lungs: relevance to humans., *Crit. Rev. Ther. Drug Carrier Syst.* 18, 387-431 (2001).

220. X. Liu, Z. Yan, M. Luo, J. F. Engelhardt, Species-Specific Differences in Mouse and Human Airway Epithelial Biology of Recombinant Adeno-Associated Virus Transduction, *Am. J. Respir. Cell Mol. Biol.* 34, 56-64 (2006).

221. A. K. Capulli, K. Tian, N. Mehandru, A. Bukhta, S. F. Choudhury, M. Suchyta, K. K. Parker, Approaching the in vitro clinical trial: engineering organs on chips, *Lab Chip* 14, 3181 (2014).

222. R. Lucas, A. D. Verin, S. M. Black, J. D. Catravas, Regulators of endothelial and epithelial barrier integrity and function in acute lung injury, *Biochem. Pharmacol.* 77, 1763-1772 (2009).

223. S. Sukriti, M. Tauseef, P. Yazbeck, D. Mehta, Mechanisms Regulating Endothelial Permeability, *Pulm. Circ.* 4, 535-551 (2014).

224. D. Huh, H. J. Kim, J. P. Fraser, D. E. Shea, M. Khan, A. Bahinski, G. a Hamilton, D. E. Ingber, Microfabrication of human organs-on-chips., *Nat. Protoc.* 8, 2135-57 (2013).

225. S. Dekali, C. Gamez, T. Kortulewski, K. Blazy, P. Rat, G. Lacroix, Assessment of an in vitro model of pulmonary barrier to study the translocation of nanoparticles, *Toxicol. Reports* 1, 157-171 (2014).

226. M. I. Hermanns, R. E. Unger, K. Kehe, K. Peters, C. J. Kirkpatrick, Lung epithelial cell lines in coculture with human pulmonary microvascular endothelial cells: development of an alveolo-capillary barrier in vitro, *Lab. Investig.* 84, 736-752 (2004).

227. S. K. Smith, G. Giannopoulos, Influence of pulmonary endothelial cells on fetal lung development., *Pediatr. Pulmonol.* 1, S53-9.

228. S. K. Ramasamy, A. P. Kusumbe, R. H. Adams, Regulation of tissue morphogenesis by endothelial cell-derived signals, *Trends Cell Biol.* 25, 148-157 (2015).

229. W. Mitzner, in *Comprehensive Physiology*, (John Wiley & Sons, Inc., Hoboken, NJ, USA, 2011).

230. H. R. Wirtz, L. G. Dobbs, The effects of mechanical forces on lung functions, *Respir. Physiol.* 119, 1-17 (2000).

231. D. M. Bryant, K. E. Mostov, From cells to organs: building polarized tissue, *Nat. Rev. Mol. Cell Biol.* 9, 887-901 (2008).

232. E. Bancalar, The Newborn Lung: *Neonatology Questions and Controversies* (2012).

233. P. Lu, K. Takai, V. M. Weaver, Z. Werb, Extracellular Matrix Degradation and Remodeling in Development and Disease, *Cold Spring Harb. Perspect. Biol.* 3, a005058-a005058 (2011).

234. T. Seeger-Nukpezah, E. A. Golemis, The extracellular matrix and ciliary signaling, *Curr. Opin. Cell Biol.* 24, 652-661 (2012).

235. J. Bourbon, O. Boucherat, B. Chailley-Heu, C. Delacourt, Control Mechanisms of Lung Alveolar Development and Their Disorders in Bronchopulmonary Dysplasia, *Pediatr. Res.* 57, 38R-46R (2005).

236. M. W. Parker, D. Rossi, M. Peterson, K. Smith, K. Sikström, E. S. White, J. E. Connett, C. A. Henke, O. Larsson, P. B. Bitterman, Fibrotic extracellular matrix activates a profibrotic positive feedback loop, *J. Clin. Invest.* 124, 1622-1635 (2014).

237. J. K. Burgess, T. Mauad, G. Tjin, J. C. Karlsson, G. Westergren-Thorsson, The extracellular matrix—the under-recognized element in lung disease?, *J. Pathol.* 240, 397-409 (2016).

238. H. Wan, H. L. Winton, C. Soeller, G. A. Stewart, P. J. Thompson, D. C. Gruenert, M. B. Cannell, D. R. Garrod, C. Robinson, Tight junction properties of the immortalized human bronchial epithelial cell lines Calu-3 and 16HBE14o-., *Eur. Respir. J.* 15, 1058 68 (2000).

239. R. J. Swain, S. J. Kemp, P. Goldstraw, T. D. Tetley, M. M. Stevens, Assessment of Cell Line Models of Primary Human Cells by Raman Spectral Phenotyping, *Biophys. J.* 98, 1703-1711 (2010).
240. A. Jacob, M. Morley, F. Hawkins, K. B. McCauley, J. C. Jean, H. Heins, C.-L. Na, T. E. Weaver, M. Vedaie, K. Hurley, A. Hinds, S. J. Russo, S. Kook, W. Zacharias, M. Ochs, K. Traber, L. J. Quinton, A. Crane, B. R. Davis, F. V. White, J. Wambach, J. A. Whitsett, F. S. Cole, E. E. Morrisey, S. H. Guttentag, M. F. Beers, D. N. Kotton, Differentiation of Human Pluripotent Stem Cells into Functional Lung Alveolar Epithelial Cells, *Cell Stem Cell* 21, 472-488.e10 (2017).
241. L. M. Crosby, C. M. Waters, Epithelial repair mechanisms in the lung., *Am. J. Physiol. Lung Cell. Mol. Physiol.* 298, L715-31 (2010).
242. J. A. Kitterman, The effects of mechanical forces on fetal lung growth., *Clin. Perinatol.* 23, 727-40 (1996).
243. L. G. Dobbs, Isolation and culture of alveolar type II cells., *Am. J. Physiol.* 258, L134-47 (1990).
244. S. R. Bates, L. W. Gonzales, J.-Q. Tao, P. Rueckert, P. L. Ballard, A. B. Fisher, Recovery of rat type II cell surfactant components during primary cell culture., *Am. J. Physiol. Lung Cell. Mol. Physiol.* 282, L267-76 (2002).
245. I. R. Witherden, E. J. Vanden Bon, P. Goldstraw, C. Ratcliffe, U. Pastorino, T. D. Tetley, Primary human alveolar type II epithelial cell chemokine release: effects of cigarette smoke and neutrophil elastase., *Am. J. Respir. Cell Mol. Biol.* 30, 500-9 (2004).
246. C. E. Perlman, J. Bhattacharya, Alveolar expansion imaged by optical sectioning microscopy., *J. Appl. Physiol.* 103, 1037-44 (2007).
247. H. Bachofen, S. Schurch, M. Urbinelli, E. R. Weibel, Relations among alveolar surface tension, surface area, volume, and recoil pressure., *J. Appl. Physiol.* 62, 1878-87 (1987).
248. E. Roan, C. M. Waters, What do we know about mechanical strain in lung alveoli?, *Am. J. Physiol. —Lung Cell. Mol. Physiol.* 301, L625-L635 (2011).
249. J. A. Gutierrez, R. F. Gonzalez, L. G. Dobbs, Mechanical distension modulates pulmonary alveolar epithelial phenotypic expression in vitro., *Am. J. Physiol.* 274, L196-202 (1998).
250. K. Fujiwara, Mechanical stresses keep endothelial cells healthy: beneficial effects of a physiological level of cyclic stretch on endothelial barrier function, *Am. J. Physiol.—Lung Cell. Mol. Physiol.* 285, L782-L784 (2003).
251. C. D. Ochoa, H. Baker, S. Hasak, R. Matyal, A. Salam, C. A. Hales, W. Hancock,
D. A. Quinn, Cyclic Stretch Affects Pulmonary Endothelial Cell Control of Pulmonary Smooth Muscle Cell Growth, *Am. J. Respir. Cell Mol. Biol.* 39, 105-112 (2008).
252. P. F. Davies, C. F. Dewey, S. R. Bussolari, E. J. Gordon, M. A. Gimbrone, Influence of hemodynamic forces on vascular endothelial function. In vitro studies of shear stress and pinocytosis in bovine aortic cells., *J. Clin. Invest.* 73, 1121-1129 (1984).
253. M. J. Levesque, R. M. Nerem, E. A. Sprague, Vascular endothelial cell proliferation in culture and the influence of flow., *Biomaterials* 11, 702-7 (1990).
254. P. F. Davies, Flow-mediated endothelial mechanotransduction., *Physiol. Rev.* 75, 519-60 (1995).
255. Y. Tanabe, M. Saito, A. Ueno, M. Nakamura, K. Takeishi, K. Nakayama, Mechanical stretch augments PDGF receptor beta expression and protein tyrosine phosphorylation in pulmonary artery tissue and smooth muscle cells., *Mol. Cell. Biochem.* 215, 103-13 (2000).
256. K. G. Birukov, Cyclic Stretch, Reactive Oxygen Species, and Vascular Remodeling, *Antioxid. Redox Signal.* 11, 1651-1667 (2009).
257. D. DREYFUSS, G. SAUMON, Ventilator-induced Lung Injury, *Am. J. Respir. Crit. Care Med.* 157, 294-323 (1998).
258. J. F. Dekkers, G. Berkers, E. Kruisselbrink, A. Vonk, H. R. de Jonge, H. M. Janssens, I. Bronsveld, E. A. van de Graaf, E. E. S. Nieuwenhuis, R. H. J. Houwen, F. P. Vleggaar, J. C. Escher, Y. B. de Rijke, C. J. Majoor, H. G. M. Heijerman, K. M. de Winter-de Groot, H. Clevers, C. K. van der Ent, J. M. Beekman, Characterizing responses to CFTR-modulating drugs using rectal organoids derived from subjects with cystic fibrosis, *Sci. Transl. Med.* 8, 344ra84-344ra84 (2016).
259. No Title (available at www.fda.gov/Food/NewsEvents/ConstituentUpdates/ucm551503.htm).
260. No Title (available at).europepmc.org/articles/pmc5504483).

EXAMPLES

The following examples illustrate some embodiments and Embodiments described herein. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Maintenance of Human Pluripotent Stem Cells.

Human ESC and iPSC may be maintained on mitotically inactivated mouse embryonic fibroblast feeders in Knockout DMEM (GIBCO) with 15% Serum Replacement (GIBCO), Glutamax (Invitrogen), penicillin/streptomycin (GIBCO), 1 mM nonessential amino acids (GIBCO), 0.5 mM mercaptoethanol, and 10 ng/ml FGF2 (Peprotech).

Generation and Characterization of Human iPSC Lines.

Human skin fibroblasts may be commercially obtained or from a patient with informed consent. Fibroblasts may be isolated from a donor skin biopsy. By 4 weeks of reprogramming human skin fibroblasts, human ESC-like EGFP+ colony numbers may be enriched under puromycin selection before picking and expansion. CF-iPSC lines with ESC-like morphology may be further assessed for pluripotency marker expression (NANOG, TRA1-81, TRA1-60) by flow cytometry and immunofluorescence, and real-time qPCR to examine up-regulation of endogenous pluripotency genes (OCT4, SOX2, C-MYC and KLF4) and down-regulation of the exogenous retroviral transgenes. In addition, gene expression of other pluripotency markers DNMT3B, REX1, TERC, TERT may be assessed. Finally, iPSC lines may be subjected to in vitro embryoid body and in vivo teratoma assays for functional tests of pluripotency. See, Wong et al. 2012.

Example A—Differentiating Stem Cells Off-Chip (e.g. in Microplate Wells or Culture Dishes) then Seeding (Placing) Derivative Lung Cells On-Chip 1. One protocol for generation of lung progenitor cells from ESCs or iPSCs in vitro is accomplished through directed differentiation, a process where in vivo tissue developmental stages are mimicked using controlled sequences of endogenous signaling factors (Murry, G. Keller, "Differentiation of embryonic stem cells to clinically relevant populations: lessons from embryonic development." Cell 132, 661-80 (2008)). In brief, in one embodiment, Pluripotent stem cells are first directed into definitive endoderm through Activin-A simulation, followed by anterior foregut endoderm (AFE) induction through dual inhibition of bone morphogenic protein (BMP) and transforming growth factor (TGF-β) (Green, A. Chen, M.-C. Nostro, S. L. D'Souza, C. Schaniel, I. R. Lemischka, V. Gouon-Evans, G. Keller, H.-W. Snoeck, "Generation of anterior foregut endoderm from human embryonic and induced pluripotent stem cells." Nat. Biotechnol. 29, 267-272 (2011)). morphogenesis of the endoderm where the trachea and lung buds eventually emerge ventrally (Morrisey, B. L. M. Hogan, Preparing for the first breath: genetic and cellular mechanisms in lung development., Dev. Cell 18, 8-23 (2010)).

AFE ventralization may be achieved through WNT, BMP, and fibroblast growth factor (FGF) signaling (Lee, D. H. Bhang, A. Beede, T. L. Huang, B. R. Stripp, K. D. Bloch, A. J. Wagers, Y. Tseng, S. Ryeom, C. F. Kim, "Lung stem cell differentiation in mice directed by endothelial cells via a BMP4-NFATc1-thrombospondin-1 axis." Cell 156, 440-55 (2014); Green, A. Chen, M.-C. Nostro, S. L. D'Souza, C. Schaniel, I. R. Lemischka, V. Gouon-Evans, G. Keller, H.-W. Snoeck, "Generation of anterior foregut endoderm from human embryonic and induced pluripotent stem cells." Nat. Biotechnol. 29, 267-272 (2011)) yielding cells expressing transcription factor NKX2-1.

Thus, in one embodiment, NKX2-1+ cells refer to lung progenitor cells used to produce lung alveolar cells in vitro. NKX2-1 is one general marker for respiratory tissue fate, however is some cases NKX2-1 may be expressed on additional pluripotent cells capable of neural and/or thyroid tissue fate (Kimura, Y. Hara, T. Pineau, P. Fernandez-Salguero, C. H. Fox, J. M. Ward, F. J. Gonzalez, The T/ebp null mouse: thyroid-specific enhancer-binding protein is essential for the organogenesis of the thyroid, lung, ventral forebrain, and pituitary., Genes Dev. 10, 60-9 (1996)).

However, NKX2-1 positive cells as used herein, may merely represent an exemplary population of primordial lung epithelial progenitors capable of differentiate into proximal airway and distal lung bud lineages, cell populations defined by SOX2 or SOX9 expression, respectively (Mizuno, A. Sridharan, Y. Du, M. Guo, J. Tang, K. A. Wikenheiser-Brokamp, A.-K. T. Perl, V. A. Funari, J. J. Gokey, B. R. Stripp, J. A. Whitsett, "Single-cell RNA sequencing identifies diverse roles of epithelial cells in idiopathic pulmonary fibrosis." JCI Insight 1, 1-18 (2016).). Thus, terminal differentiation is then directed by further pathway signaling modification and determined by specific sets of markers. For example, distal lung markers of the alveoli include Surfactant Protein C (SFTPC), Surfactant Protein B and LAMP3/DC-LAMP for ATII cells, Podoplanin, Caveolin, and Aquaporin 5 for ATI cells, and bronchiolar markers include SCGB1A1/CC10 for Clara cells, P63 or Keratin 5 for basal cells, acetylated alpha tubulin for ciliated cells, and MUC5AC for goblet cells. Additional methods that may be used for specification (differentiation) to proximal airway or distal alveolar progenitors are discussed herein.

2. Recent Advances in Alveolar Generation.

Progress using exemplary NKX2-1 lung progenitors to generate human alveolar epithelial cells was made by leveraging strategies for maintaining human primary cells. The combination of glucocorticoid, growth factors, and cAMP effectors (dexamethasone, 8-br-cAMP, IBMX, and KGF/FGF7; collectively known as DCIK) (Gonzales, S. H. Guttentag, K. C. Wade, A. D. Postle, P. L. Ballard, Differentiation of human pulmonary type II cells in vitro by glucocorticoid plus CAMP., Am. J. Physiol. Lung Cell. Mol. Physiol. 283, L940-L951 (2002), Wade, S. H. Guttentag, L. W. Gonzales, K. L. Maschhoff, J. Gonzales, V. Kolla, S. Singhal, P. L. Ballard, Gene induction during differentiation of human pulmonary type II cells in vitro., Am. J. Respir. Cell Mol. Biol. 34, 727-37 (2006)) was shown to induce alveolar maturation through activation of PKA and CDP-choline pathways which upregulate lamellar body surfactant production (Andreeva, M. A. Kutuzov, T. A. Voyno-Yasenetskaya, "Regulation of surfactant secretion in alveolar type II cells." Am. J. Physiol. Lung Cell. Mol. Physiol. 293, L259-71 (2007)). Stimulation of two dimensional cultures of differentiated PSCs growing in 2D with DCIK, FGF10 and WNT activators led to expression of ATI and ATII markers, mature phenotypic characteristics of lamellar bodies, and functional surfactant uptake capability (Huang, M. D. Green, A. T. de Carvalho, M. Mumau, Y.-W. Chen, S. L. D'Souza, H.-W. Snoeck, The in vitro generation of lung and airway progenitor cells from human pluripotent stem cells., Nat. Protoc. 10, 413-25 (2015)).

Similarly, PSCs spheroid cultures also induce cell maturation of the alveoli epithelium. Surprisingly, 3D co-culture with human fetal lung fibroblasts and stimulation with DCIK yielded ATII specific markers and lamellar bodies formation, although functional maturity was not confirmed (120). Functional surfactant uptake was then confirmed by first generating PSC lung bud organoids, followed by Matrigel culture with a WNT activator, FGF10, KGF, BMP4 and RA in place of DCIK. ATII markers were found to be abundant in this protocol while ATI markers were minimally expressed (Chen, S. X. Huang, A. L. R. T. de Carvalho, S.-H. Ho, M. N. Islam, S. Volpi, L. D. Notarangelo, M. Ciancanelli, J.-L. Casanova, J. Bhattacharya, A. F. Liang, L. M. Palermo, M. Porotto, A. Moscona, H.-W. Snoeck, A three-dimensional model of human lung development and disease from pluripotent stem cells., Nat. Cell Biol. 19, 542-549 (2017)).

Long term expansion of alveolar epithelial cells, a challenge with distal lung cell cultures, was recently achieved using an organoid approach and a refined differentiation sequence after AFE induction (121). This sequence differs from previous protocols by incorporating a preconditioning step of WNT activation, DAPT notch inhibition, and FGF10 plus KGF supplementation, resulting in SFTPC gene expression, a marker of ATII cells, similar to levels found in the fetal lung. These cells were then matured using DCIK in organoids co-cultured with fibroblasts. Surprisingly, co-cultures with fetal lung fibroblasts lines resulted in SFTPC expressing cells, though variable (ranging from 2% to 51%), whereas incorporating a dermal fibroblast line showed no SFTPC induction. With passaging, the proportion of ATII cells in the culture increased to approximately 70%. Notably, induction of SFTPC expression was also achieved in fibroblast-free cultures using DCIK plus ROCK inhibition, WNT activation, and TGF-β inhibition, albeit at a lower efficiency of 23%.

3. Recent Advances in Proximal Lung Generation.

Protocols for proximal airway differentiation also advanced in the past few years. Differentiation of PSCs into airway epithelial cells was achieved in spheroids cultures using FGF10, KGF, WNT agonist and Notch inhibition (Konishi, S. Gotoh, K. Tateishi, Y. Yamamoto, Y. Korogi, T. Nagasaki, H. Matsumoto, S. Muro, T. Hirai, I. Ito, S.

Tsukita, M. Mishima, Directed Induction of Functional Multi-ciliated Cells in Proximal Airway Epithelial Spheroids from Human Pluripotent Stem Cells, *Stem Cell Reports* 6, 18-25 (2016)).

More recently, proximal fate was efficiently induced by modifying WNT signaling in the directed differentiation strategy. Suppressing WNT signaling after ventralized AFE promoted proximal fate (McCauley, F. Hawkins, M. Serra, D. C. Thomas, A. Jacob, D. N. Kotton, Efficient Derivation of Functional Human Airway Epithelium from Pluripotent Stem Cells via Temporal Regulation of Wnt Signaling, *Cell Stem Cell* 20, 844-857.e6 (2017).), potentially explaining why previous studies encountered difficulty in maintaining airway epithelial markers in culture. To promote cilia development, Notch inhibition in organoids or air-liquid interface in 2D cultures is required (Wong, C. Bear, S. Chin, P. Pasceri, T. Thompson, L.-J. Huan, F. Ratjen, J. Ellis, J. Rossant, Directed differentiation of human pluripotent stem cells into mature airway epithelia expressing functional CFTR protein., *Nat. Biotechnol.* 30, 876-882 (2012).). For long term expansion of these cells, it may be possible to incorporate findings from human primary cell cultures. Specifically, inhibition of SMAD signaling pathways was recently found to enable the expansion of primary P63+ airway basal cells (Mou, V. Vinarsky, P. R. Tata, S. H. Choi, A. K. Crooke, B. Zhang, G. M. Solomon, B. Turner, H. Bihler, J. Harrington, A. Lapey, C. Channick, C. Keyes, A. Freund, S. Artandi, M. Mense, S. Rowe, J. F. Engelhardt, Y. Hsu, J. Rajagopal, Dual SMAD signaling inhibition enables long-term expansion of diverse epithelial basal cells, *Cell Stem Cell* 19, 217-231 (2017).) which are pathways that may also promote proximal lung regeneration in PSC cultures.

4. Another Example for Providing Cells for Use Herein, is Provided Below. Differentiation of Human ESC and iPSC into Definitive Endoderm.

The following is a brief protocol for use in differentiation of human ESC or human iPSC into definitive endoderm (e.g. SOX17+ population). Pluripotent stem cells are harvested, gently triturating cells into single cell suspensions then seeded onto transwells (0.4 μm pore size, Corning) of microfluidic chips, whose well surface or membranes are pre-coated with human placental collagen Type IV. Cells are immediately treated with 100 ng/ml Activin-A and 25 ng/ml WNT3A (R&D Systems) for 4 consecutive days in Endoderm Differentiation Media comprising serum-free Knockout DMEM (Invitrogen) with Glutamax (Invitrogen), penicillin/streptomycin (GIBCO), 1 mM nonessential amino acids (GIBCO) and 0.5 mM mercaptoethanol. Subsequent differentiation steps were performed on the transwell cultures or microfluidic chips.

Differentiation of Definitive Endoderm into Anterior Foregut Endoderm Progenitors.

For anterior foregut endoderm differentiation and especially for providing embryonic lung progenitors, definitive endoderm cells (see above) were treated with 500 ng/ml FGF2 (Preprotech) and 50 ng/ml Sonic hedgehog (SHH, Cedarlane) for 5 days in Endoderm Differentiation Media. Directed Differentiation of Foregut Endoderm into Mature Lung Cell Fates.

Anterior foregut endoderm progenitor cells were treated with 50 ng/ml FGF10, 50 ng/ml KGF (FGF7) and 5 ng/ml BMP4 (all R&D systems) for 5 days followed by 10 ng/ml FGF10, 10 ng/ml FGF7 and 10 ng/ml FGF18 (Sigma-Aldrich) for an additional 5 days. To differentiate the cells into mature airway epithelial cells, the cells were cultured in Bronchial Epithelial Growth Media (BEGM, Lonza) supplemented with FGF18 (10 ng/ml) for 10 days followed by Bronchial-Air Liquid interface (B-ALI, Lonza) media for an additional 15+ days. For transwell cultures, cells are "air-lifted" and B-ALI media was added to the bottom but not the top of the transwell. For anterior foregut endoderm progenitor cells treated on microfluidic chips, an air-liquid interfaces was established instead of air-lifting" cells.

Therefore, in some embodiments, differentiating lung cell populations include: progenitor cells deriving from SOX2+/OCT4+ pluripotent stem cells (PSC) that may express the following markers in order of progression during differentiation: SOX17+/FOXA2+ cells; SOX2+/FOXA2+ cells; NKX2-1+ cells; SOX9+ distal (airway lung bud lineage) progenitors: Alveolar Type I (ATI) cells—Podoplanin, Caveolin (CAV1), and Aquaporin 5 (AQP5); Alveolar Type II (ATII) cells—characterized by Surfactant Protein C (SFTPC), Surfactant Protein B (SFTPB) HTII-280, ABCA3, and LAMP3/DC-LAMP for ATII cells in addition to cells' capacity of lamellar bodies to process surfactant proteins and produce dipalmitoylphosphatidylcholine (DPPC) surfactant phospholipid. Co-cultures and several passages with fetal lung fibroblasts lines induces higher percentages of SFTPC expressing cells along with ATI cells. In addition to an alternative differentiation pathway including SOX2+ proximal (airway lung bud lineage) progenitors resulting in terminally differentiated basal cells; club cells (Clara cells: bronchiolar exocrine cells having short microvilli); ciliated epithelial cells; goblet cells, etc.

Example B—Differentiating Stem Cells into Lung Cells On-Chip

Exemplary stem cells for use in seeding chips include but are not limited to stem cell sources described herein, including organoids derived (i.e. created) starting from one or more cell types, including but not limited to primary lung tissues, primary cells; stem cells; embryonic stem cells (ESCs); or induced pluripotent stem cells (iPS cells), or other cells as described herein. iPSC organoids may be known as tracheospheres, bronchospheres, and pneumospheres (or alveolospheres), etc., according to the lung or respiratory tissue they most closely represent.

As another example, a microfluidic chip as described herein, may be seeded by cells that were partially differentiated, i.e. not yet terminally differentiated, e.g. as one or more populations comprising SOX17+/FOXA2+, SOX2+/FOXA2+, NKX2-1+, SOX9+ distal progenitor cells, etc., for undergoing further differentiation stages on-chip, resulting in terminally differentiated stem cell based alveolar lung-on-chip. As another example, a microfluidic chip as described herein, may be seeded by cells that were partially differentiated, i.e. not yet terminally differentiated, e.g. as one or more cell populations comprising SOX17+/FOXA2+ cells, SOX2+/FOXA2+ cells, NKX2-1+ cells, SOX2+ proximal progenitor cells, etc., for undergoing further differentiation stages on-chip, resulting in terminally differentiated stem cell based small-airway-on-chip. Such stem cell based small-airway-on-chip may included basal cells; club cells; ciliated cells; goblet cells, etc.

As another example, a microfluidic chip as described herein, may be seeded with a population of stem cells, such as any one or more populations described herein, e.g. iPS cells, EPS cells, etc. As an exemplary protocol, such stem cells may be treated with factors for inducing SOX17+/FOXA2+ cells, SOX2+/FOXA2+ cells, NKX2-1+ cells, then either inducing a predominant distal progenitor cells, e.g. SOX9+ or proximal progenitor cells, e.g. SOX2+ for undergoing terminal differentiation into alveolar cells or bronchial/tracheal cells, respectively.

As another example, a microfluidic chip as described herein and in cited publications herein incorporated by reference, may be seeded with organoids capable of differentiating into respiratory cells, lung cells, etc. In one contemplative embodiment, organoids seeded into chips may be whole, e.g. as lifted off of the tissue culture surface. In another contemplative embodiment, organoids seeded into chips may be partial, e.g. lifted off of the tissue culture surface then mechanically disrupted (e.g. vortexed), for seeding organoids as pieces. In yet other embodiments, organoids may be disrupted or sorted into single cells suspensions, e.g. filtering, flow cytometry sorting for specific markers, such as one or more of SOX2+/FOXA2+ cells, NKX2-1+ cells, SOX2+ proximal progenitor cells, etc., for seeding onto stem cell based microfluidic lung chips.

In yet other embodiments, a microfluidic chip as described herein and in cited publications herein incorporated by reference, may be used to generate lung organoids for use herein either to further differentiate on-chip or for harvesting for use in seeding a a microfluidic chip as described herein for providing a stem cell based lung-on-chip. In particular, in some embodiments, lung organoids derived from starting iPS cells involved a last stage air-liquid interphase culture that may be induced on-chip (for an example of one protocol that may used on-chip (for e.g. see, Wong, A. P., Bear, C. E., Chin, S., Pasceri, P., Thompson, T. O., Huan, L. J., Ratjen, F., Ellis, J., and Rossant, J. (2012). "Directed differentiation of human pluripotent stem cells into mature airway epithelia expressing functional CFTR protein." Nat. Biotechnol. 30, 876-882.).

In yet other embodiments, such microfluidic organoid cultures on-chips may be used for assays to screen for factors controlling generation of a particular cell type, such as alveolar type 1 vs. type II, multiciliated cells vs. percentages of secretory and basal cells.

In some embodiments, human ESC are treated with Activin A and WNT3a for 4 days then seeded onto collagen Type IV matrix in tissue culture plates. This method is known to generate table and reproducible definitive endoderm progenitor cells with >85% of the cells co-expressing CXCR4 and CD117 (cKit). The majority of the cells also co-stained for SOX17 and FOXA2. See, Wong, et al 2012. In some embodiments, cells generated with this method may instead be transferred to microfluidic devices as described herein, for subsequent additions of differentiation and maturation agents on-chips having collagen Type IV matrix coated membranes.

In some embodiments, adding high levels of FGF2 coupled with adding SHH for an additional 5 days may be used to induce definitive endoderm cells (such as SOX17+ cells) into lung progenitor (NKX2.1-expressing) cell fate. In some embodiments, after addition of FGF2 and SHH, expression of definitive endoderm marker SOX17 was down-regulated. In some embodiments, after addition of FGF2 and SHH, there may be up-regulation of anterior foregut endoderm transcription factors SOX2 and NKX2.1+. In some embodiments, progenitor cells express NKX2.1+ FOXA2+ and EpCAM. Progenitor cells obtained with this method are referred to as embryonic lung progenitors.

In some embodiments, adding FGF7 (50 ng/ml) and FGF10 (50 ng/ml) may increase expression of lung endoderm NKX2.1 and FOXA2 gene expression from embryonic lung progenitors.

CFTR proteins control anion negatively charged particles (i.e. negatively charged ion such as a Chlorine anion: Cl−) movement through the cell membrane in addition to regulating the function of other cell membrane channels, such as those transporting cation positively charged particles (e.g. sodium ions: Na+) across cell membranes. Thus CFTR proteins affect water secretion and absorption in epithelial tissues by maintaining fluid and electrolyte homeostasis at epithelial surfaces of many organs, including lung, airways, trachea, nasal areas, pancreas, sweat glands and intestine.

Considered an autosomal-recessive genetic disorder, loss-of-function mutations in CFTR genes, encoding CFTR proteins, cause altered ion and fluid transport. More specifically, a disease related mutation in a CFTR protein is associated with decreased chloride ion conductance across the apical membrane of the epithelial cells. Decreased chloride ion conductance results in accumulation of viscous mucus in the pulmonary and gastrointestinal tract. This viscous mucus is associated with bacterial infections, aberrant inflammation and malnutrition. Over 1500 mutations have been described mostly mutations that change single protein building blocks (i.e. amino acids) in the CFTR protein or delete a small amount of DNA from the CFTR gene.

The majority of genetic mutations found in human CF patients are a dominant mutation (approximately 67% of total mutant alleles worldwide) corresponding to a deletion of three base pairs of nucleotides in a CFTR resulting in a corresponding loss of phenylalanine at position 508 (CFTR-delF508) in the encoded CFTR protein (Kere, et al., "Identification of the Cystic Fibrosis Gene: Genetic Analysis." This deletion causes misfolding, endoplasmic reticulum (ER)-retention and thus early degradation of the CFTR protein that prevents it from reaching the external cell membrane. Other mutations in the CFTR gene that have been found in CF patients also impair protein folding or impair protein production, gating, conductance, splicing and/or interactions with other proteins (Riordan, et al., "Identification of the cystic fibrosis gene: cloning and characterization of complementary DNA", Science, vol. 245, 1989, pages 1066-1073, 1989). In other words, disease-causing mutations in the CFTR gene alter the production, structure, or stability of the chloride channel.

Changes in CFTR protein function are associated with rhinosinusitis, a chronic inflammation of the tissues that line the sinuses. This condition causes sinus pain and pressure, headache, fever, and nasal congestion or drainage. Other respiratory problems, including several conditions that partially block the airways and interfere with breathing, are also associated with CFTR mutations. These conditions include bronchiectasis, which damages the passages leading from the windpipe to the lungs (the bronchi), and allergic bronchopulmonary responses to fungi, which results from hypersensitivity to a certain types of fungal infection, e.g. Aspergillosis spp.

Example—C. Cystic Fibrosis

This is an exemplary description of a Cystic fibrosis related ion channel function test for stem cells and organoids seeded into a microfluidic device as described herein.

In some embodiments, any one or more of cells in microfluidic devices described herein, are stem cells, such as stem cells, stem cell derived progenitor cells, terminally differentiated cells from stem cells, organoids, etc., derived from a cystic fibrosis patient or a patient suspected of or actually known to have cystic fibrosis genes in their cellular DNA, e.g. one or more mutated cystic fibrosis transmembrane conductance regulator (CFTR) genes, are added to microfluidic chips as described herein. Other microfluidic chips containing corresponding stem cells derived from people without cystic fibrosis symptoms, patients known to be free of particular cystic fibrosis genes or corresponding test cells treated with an ionophore are used for a control for comparison to a stem-cell based cystic fibrosis microfluidic chip.

Microfluidic chips containing these control and stem-cell derived cystic fibrosis cells and organoids may then be tested for ion channel function by the addition of an agent to cell cultures on microfluidic chips for use in a swelling test. A swelling test agent may be any agent that acts as to increase ion channel function, e.g. alters cyclic AMP-dependent protein kinase (protein kinase A or protein kinase C function. As one example of a test agent for ion channel function is an inducer of intracellular cyclic AMP (cyclic adenosine 3'-5'-monophosphate: cAMP), i.e. increases intracellular cyclic AMP (cAMP) in cells, e.g. Cyclic AMP, Cyclic AMP analogs, Forskolin, e.g. 12-24 μM, test drug compounds, small-molecule drugs, etc. Cells and organoids are stained with calcein green, and forskolin-induced swelling is monitored by confocal live cell microscopy at 37° C.

For example, organoids from a healthy individual (WT) and a diagnosed cystic fibrosis patient are added to chips, each on a separate chip or on different areas of the same chip. The WT organoids will show functioning ion channels by responding by swelling while CF organoids will show less swelling.

For CFTR inhibition, organoids may be preincubated for 1-3 hours with 75 mM CFTRinh-172 (B7; Cystic Fibrosis Foundation Therapeutics, Inc).

For CFTR inhibition, organoids were simultaneously incubated for 60 minutes with 10 μM-2 mM calcein-green (Invitrogen) and 50 μM CFTRinh-172 (Sigma), 50 μM GlyH-101 (Calbiochem) or combined treatment of 50 μM CFTRinh-172 and 50 μM GlyH-101. After 60 minutes of calcein-green treatment (with or without CFTR inhibition), of 5 μM forskolinb may be added and organoids directly analyzed by confocal live cell microscopy (LSM710, Zeiss, 5× objective). Organoid surface may be calculated by Volocity imaging software. It is contemplated that in vitro swell responses correlate with the clinical response to therapy. With the addition of an appropriate drug, the organoid of a cystic fibrosis patient will see similar swelling. Organoids on chips are monitored for an increase in size, i.e. area, at least every 5 minutes up to 30 minutes, up to 60 minutes, in order to capture any swelling before collapse of a swelling organoid. In some embodiments, area measurements are normalized to area measurements of control organoids then compared or graphed over time. In some embodiment, cholera toxin is used.

This assay provides a protocol for the identification of drug-responsive individuals, independent of their CFTR mutations and may also be instrumental in the development of future CFTR modulators.

Mean cell volume may be measured in cell suspensions by electronic cell sizing (Coulter Multisizer II, AccuComp software version 1.19, Hialeah, FL) using an 100-μm aperture. Cells in subconfluent culture may be harvested with minimal trypsin (0.05%), suspended in cell culture medium, centrifuged for 1 min at 1,000×g, resuspended in 3 ml of isotonic buffer, and incubated with gentle agitation for 30-45 min. Aliquots (approximately 500 μl) of cell suspension may be added to 20 ml of isotonic or hypotonic (40% less NaCl) buffer. Measurements of 20,000 cells on average at specified time points after exposure to isotonic or hypotonic buffer were compared with basal values in isotonic buffer (time 0). Changes in values may be expressed as relative volume normalized to the basal period.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method, comprising: a) providing a microfluidic device comprising functional Type II lung parenchyma cells and a stroma area or layer comprising fibroblast cells; and b) culturing said functional Type II lung parenchyma cells and said fibroblast cells such that said functional Type II lung parenchyma cells secrete surfactant C in amounts between 30-100 ng/ml, wherein said amounts are secreted daily from day 9 to day 15 of culture.

2. The method of claim 1, further comprising the step of c) detecting said surfactant C at the protein level.

3. The method of claim 2, wherein said detecting is by antibody staining.

4. The method of claim 1, wherein said microfluidic device comprises a surface of a microfluidic channel, said microfluidic channel in fluid communication with a source of fluid.

5. The method of claim 1, wherein said functional Type II lung parenchyma cells are exposed to an air-liquid interface.

6. The method of claim 1, wherein said microfluidic device comprises a surface of a chamber, said chamber comprising said stroma area or layer.

7. The method of claim 6, wherein said stroma area or layer is located adjacent to a spiral channel, wherein said stroma area or layer is separated from the spiral channel by a stretchable membrane.

8. The method of claim 7, wherein said spiral channel comprises a confluent layer of endothelial cells.

9. A method, comprising: a) providing a microfluidic device comprising functional Type II lung parenchyma cells and a stroma area or layer, wherein each of said stroma area or layer comprises fibroblast cells; and b) culturing said functional Type II lung parenchyma cells and said fibroblast cells such that said functional Type II lung parenchyma cells secrete surfactant C in amounts between 30-100 ng/ml, wherein said surfactant C is secreted in an amounts greater than where said functional Type II lung parenchyma cells are cultured in the absence of said fibroblast cells, wherein said amounts are secreted daily from day 9 to day 15 of culture after introducing said functional Type II lung parenchyma cells into said microfluidic device.

10. The method of claim 9, further comprising the step of c) detecting said surfactant C at the protein level.

11. The method of claim 10, wherein said detecting is by antibody staining.

12. The method of claim 9, wherein said microfluidic device comprises a surface of a microfluidic channel, said microfluidic channel in fluid communication with a source of fluid.

13. The method of claim 9, wherein said functional Type II lung parenchyma cells are exposed to an air-liquid interface.

14. The method of claim 9, wherein said microfluidic device comprises a surface of a chamber, said chamber comprising said stroma area or layer.

15. The method of claim 9, wherein said microfluidic device comprises a stretchable membrane.

16. The method of claim 15, wherein said stroma area or layer is located adjacent to a spiral channel, wherein said stroma area or layer is separated from the spiral channel by said stretchable membrane.

17. The method of claim 16, wherein said spiral channel comprises a confluent layer of endothelial cells.

18. The method of claim 16, further comprising stretching said membrane.

19. A method, comprising:
   a) providing: i) a microfluidic device comprising a surface and ii) a population of living cells, wherein at least a portion of said living cells have the capability to differentiate into functional Type II lung parenchyma cells;
   b) introducing said living cells into said microfluidic device such that said living cells are positioned on said surface of said microfluidic device so as to create positioned cells; and
   c) exposing said positioned cells to conditions that cause at least a portion of said positioned cells to differentiate into functional Type II lung parenchyma cells secreting surfactant C in amounts between 30-100 ng/ml, wherein said amounts are secreted daily from day 9 to day 15 of culture after introducing said living cells into said microfluidic device.

20. The method of claim 19, further comprising the step of d) detecting said surfactant C at the protein level.

21. The method of claim 20, wherein said detecting is by antibody staining.

22. The method of claim 19, wherein said surface of said microfluidic device comprises a surface of a microfluidic channel, said microfluidic channel in fluid communication with a source of fluid.

23. The method of claim 19, wherein in step c) said positioned cells are exposed to an air-liquid interface.

* * * * *

SEQUENCE LISTING

```
<160> NUMBER OF SEQ ID NOS: 82

<210> SEQ ID NO 1
<211> LENGTH: 53
<212> TYPE: PRT
<213> ORGANISM: Homo sapiens

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 165
```

```
<212> TYPE: PRT
<213> ORGANISM: Homo sapiens

<400> SEQUENCE: 2

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65              70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
ggagttggac cagtcaacat c                                       21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
tggagtagta gcttccactg c                                       21

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ccattgctat tatgccctgt gt                                      22

<210> SEQ ID NO 6
<211> LENGTH: 19
<212> TYPE: DNA
<213> ORGANISM: Artificial Sequence
```

<220> FEATURE:
<223> OTHER INFORMATION: Synthetic

<400> SEQUENCE: 6
tggtggacgg acagtcact                                                  19

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
accaggacac catgaggaac                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cgccgacagg tacttctgtt                                                 20

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
gagcggcgct ttcaagaag                                                  19

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
ggcctcggta ttcaccgtc                                                  19

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
cacctgaaac gccttcttat cg                                              22

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tggctcatgt ggagacccat                                                 20

```
<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
ttcagcgtgt catcgaaacc cc                                              22

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
acagtgagct ttgggctatt ttt                                             23

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aggaggaaaa cgggaaagaa                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
caacaacagc aatggaggag                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ctggaacggt gaaggtgaca                                                 20

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
aagggacttc ctgtaacaat gca                                             23

<210> SEQ ID NO 19
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 19
aagggcgagt cccgtatc                                                    18

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ttgtagttgg ggtggtcctg                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
agaagagcct gtcgctgaaa                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ttggaccaga aggagcagtc                                                  20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
attcgttggg gatgacagag                                                  20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cgagtcctgc ttcttcttgg                                                  20

<210> SEQ ID NO 25
<211> LENGTH: 19
<212> TYPE: DNA
<213> ORGANISM: Artificial Sequence
<220> FEATURE:
<223> OTHER INFORMATION: Synthetic

<400> SEQUENCE: 25
cccatggatg aagtctacc                                                   19

<210> SEQ ID NO 26
```

```
<211> LENGTH: 19
<212> TYPE: DNA
<213> ORGANISM: Artificial Sequence
<220> FEATURE:
<223> OTHER INFORMATION: Synthetic

<400> SEQUENCE: 26
gtcctcctcc tttttccac                                                    19

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
tgggacccga actttcca                                                     18

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
ggccacatcc aggactagtt tc                                                22

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
ctatgacccg gataacaagg agg                                               23

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
caaaaatggc tgggtgtagg a                                                 21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
tgatttgtgg gcctgaagaa a                                                 21

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
```

```
gaggcatctc agcagaagac a                                            21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
acttcacggt gtgccaccct                                              20

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
gagctggggt ttctacgaaa cgct                                         24

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tgagcctgag accccagccc                                              20

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
tgtctccctt catgctttcc aagc                                         24

<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
agtgctcaca gtccagcagg tgt                                          23

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
tgccttgcct gggcttagcc                                              20

<210> SEQ ID NO 39
<211> LENGTH: 23
<212> TYPE: DNA
```

```
<213> ORGANISM: Artificial Sequence
<220> FEATURE:
<223> OTHER INFORMATION: Synthetic

<400> SEQUENCE: 39
gacactgcct cccttcctgc aac                                            23

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
tggcggttcc ggggagttct ag                                             22

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
acgcgaaaac cttcctcagc tatgc                                          25

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
agccttgaag ccgcggttga a                                              21

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
ctggagctgg agaaggagtt tc                                             22

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
attttaacct gcctctcaga gagc                                           24

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
gcacatgaag gagcacccgg atta                                           24
```

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
cgggcagcgt gtacttatcc ttctt                                    25

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
ctccgtcaac ctgctcgcgg                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ctggcgctca tggacgtgct                                          20

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
tggttatgtt gctggacatg ggtg                                     24

<210> SEQ ID NO 50
<211> LENGTH: 25
<212> TYPE: DNA
<213> ORGANISM: Artificial Sequence
<220> FEATURE:
<223> OTHER INFORMATION: Synthetic

<400> SEQUENCE: 50
ggaagccgtg acagaatgac tacct                                    25

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
gaggaagtcg gtgaagaacg                                          20

<210> SEQ ID NO 52
<211> LENGTH: 20
<212> TYPE: DNA
<213> ORGANISM: Artificial Sequence
<220> FEATURE:

<223> OTHER INFORMATION: Synthetic

<400> SEQUENCE: 52
ccaacatcga gaccttcgat                                           20

<210> SEQ ID NO 53
<211> LENGTH: 19
<212> TYPE: DNA
<213> ORGANISM: Artificial Sequence
<220> FEATURE:
<223> OTHER INFORMATION: Synthetic

<400> SEQUENCE: 53
tctttgcttg ggaaatccg                                            19

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
ctgcccgttc aacatcctta g                                         21

<210> SEQ ID NO 55
<211> LENGTH: 19
<212> TYPE: DNA
<213> ORGANISM: Artificial Sequence
<220> FEATURE:
<223> OTHER INFORMATION: Synthetic

<400> SEQUENCE: 55
gtgggctacc cggccaccc                                            19

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gcaccctcga ctcgggcaag                                           20

<210> SEQ ID NO 57
<211> LENGTH: 19
<212> TYPE: DNA
<213> ORGANISM: Artificial Sequence
<220> FEATURE:
<223> OTHER INFORMATION: Synthetic

<400> SEQUENCE: 57
ggctggagaa ctcactggc                                            19

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
caggctgcgg taagtagcg                                            19

```
<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
gaccggcgga gatgtgaac                                                19

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
ctgctcgtac tggtcacgc                                                19

<210> SEQ ID NO 61
<211> LENGTH: 22
<212> TYPE: DNA
<213> ORGANISM: Artificial Sequence
<220> FEATURE:
<223> OTHER INFORMATION: Synthetic

<400> SEQUENCE: 61
ccagtcctac atcttcggtt gt                                            22

<210> SEQ ID NO 62
<211> LENGTH: 22
<212> TYPE: DNA
<213> ORGANISM: Artificial Sequence
<220> FEATURE:
<223> OTHER INFORMATION: Synthetic

<400> SEQUENCE: 62
agggtagttc ctagagggag tt                                            22

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gtccacgcgc aagaacaaag                                               20

<210> SEQ ID NO 64
<211> LENGTH: 22
<212> TYPE: DNA
<213> ORGANISM: Artificial Sequence
<220> FEATURE:
<223> OTHER INFORMATION: Synthetic

<400> SEQUENCE: 64
ggtcactgtt gacaaaccat ct                                            22

<210> SEQ ID NO 65
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 65
tatgagacga acaaagtcac tcg                                          23

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
gcaaagcaaa cgtaggaaaa gat                                          23

<210> SEQ ID NO 67
<211> LENGTH: 19
<212> TYPE: DNA
<213> ORGANISM: Artificial Sequence
<220> FEATURE:
<223> OTHER INFORMATION: Synthetic

<400> SEQUENCE: 67
ctcgccttac ggctctacg                                               19

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68
tacacacctt ggtagtacgc c                                            21

<210> SEQ ID NO 69
<211> LENGTH: 23
<212> TYPE: DNA
<213> ORGANISM: Artificial Sequence
<220> FEATURE:
<223> OTHER INFORMATION: Synthetic

<400> SEQUENCE: 69
aatctgcgac agagacaata agc                                          23

<210> SEQ ID NO 70
<211> LENGTH: 22
<212> TYPE: DNA
<213> ORGANISM: Artificial Sequence
<220> FEATURE:
<223> OTHER INFORMATION: Synthetic

<400> SEQUENCE: 70
tccacttgtt tgctgctgta aa                                           22

<210> SEQ ID NO 71
<211> LENGTH: 19
<212> TYPE: DNA
<213> ORGANISM: Artificial Sequence
<220> FEATURE:
<223> OTHER INFORMATION: Synthetic

<400> SEQUENCE: 71
cacggtggac ttctacggg                                               19

<210> SEQ ID NO 72
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 72
ggacacgaac cgatctatcc c                                              21

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ctagaggcca cgttccagag                                                20

<210> SEQ ID NO 74
<211> LENGTH: 19
<212> TYPE: DNA
<213> ORGANISM: Artificial Sequence
<220> FEATURE:
<223> OTHER INFORMATION: Synthetic

<400> SEQUENCE: 74
tggttacgct cgcgcttac                                                 19

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
ctcgcccaag tcggaatata c                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic

<400> SEQUENCE: 76
ctggtagctg gagtagatcg t                                              21

<210> SEQ ID NO 77
<211> LENGTH: 22
<212> TYPE: DNA
<213> ORGANISM: Artificial Sequence
<220> FEATURE:
<223> OTHER INFORMATION: Synthetic

<400> SEQUENCE: 77
aggatgacac catctacctc ac                                             22

<210> SEQ ID NO 78
<211> LENGTH: 21
<212> TYPE: DNA
<213> ORGANISM: Artificial Sequence
<220> FEATURE:
<223> OTHER INFORMATION: Synthetic

<400> SEQUENCE: 78
```

```
catcgctctt ctcaatgagc a                                              21

<210> SEQ ID NO 79
<211> LENGTH: 25
<212> TYPE: DNA
<213> ORGANISM: Artificial Sequence
<220> FEATURE:
<223> OTHER INFORMATION: Synthetic

<400> SEQUENCE: 79
ttagactgcc gtaccctcct cacaa                                          25

<210> SEQ ID NO 80
<211> LENGTH: 26
<212> TYPE: DNA
<213> ORGANISM: Artificial Sequence
<220> FEATURE:
<223> OTHER INFORMATION: Synthetic

<400> SEQUENCE: 80
aggaagggaa agagaaaggg aaggga                                         26

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
cggctcctac gactattgcc c                                              21

<210> SEQ ID NO 82
<211> LENGTH: 23
<212> TYPE: DNA
<213> ORGANISM: Artificial Sequence
<220> FEATURE:
<223> OTHER INFORMATION: Synthetic

<400> SEQUENCE: 82
ggaacgtatt ccttgcttgc cct                                            23
```